US010267799B2

(12) United States Patent
Watnick

(10) Patent No.: US 10,267,799 B2
(45) Date of Patent: Apr. 23, 2019

(54) SAPOSIN-A DERIVED PEPTIDES AND USES THEREOF

(75) Inventor: Randolph Watnick, Newton, MA (US)

(73) Assignee: Children's Medical Center Corporation, Boston, MA (US)

(*) Notice: Subject to any disclaimer, the term of this patent is extended or adjusted under 35 U.S.C. 154(b) by 0 days.

(21) Appl. No.: 13/516,511

(22) PCT Filed: Dec. 17, 2010

(86) PCT No.: PCT/US2010/061007
§ 371 (c)(1),
(2), (4) Date: Nov. 21, 2012

(87) PCT Pub. No.: WO2011/084685
PCT Pub. Date: Jul. 14, 2011

(65) Prior Publication Data
US 2013/0072425 A1 Mar. 21, 2013

Related U.S. Application Data

(63) Continuation of application No. 12/640,788, filed on Dec. 17, 2009, which is a continuation-in-part of application No. PCT/US2008/067899, filed on Jun. 23, 2008.

(60) Provisional application No. 60/936,792, filed on Jun. 22, 2007.

(51) Int. Cl.
A61K 38/10 (2006.01)
G01N 33/574 (2006.01)
C07K 14/475 (2006.01)
A61K 45/06 (2006.01)
A61K 38/17 (2006.01)
A61K 38/00 (2006.01)
A61K 48/00 (2006.01)

(52) U.S. Cl.
CPC ....... G01N 33/574 (2013.01); A61K 38/1709 (2013.01); A61K 45/06 (2013.01); C07K 14/475 (2013.01); A61K 38/00 (2013.01); A61K 48/00 (2013.01); G01N 2800/56 (2013.01)

(58) Field of Classification Search
None
See application file for complete search history.

(56) References Cited

U.S. PATENT DOCUMENTS

| 5,565,332 | A | * | 10/1996 | Hoogenboom | C07K 16/18 435/235.1 |
| 5,696,080 | A | | 12/1997 | O'Brien et al. | |
| 5,700,909 | A | | 12/1997 | O'Brien | |
| 5,714,459 | A | | 2/1998 | O'Brien et al. | |
| 5,817,752 | A | * | 10/1998 | Yu | C07K 1/12 530/317 |
| 6,500,431 | B1 | | 12/2002 | Gill | |
| 6,590,074 | B1 | * | 7/2003 | O'Brien | A61K 9/0019 530/350 |
| 6,638,911 | B1 | | 10/2003 | Blaschuk et al. | |
| 7,166,691 | B2 | | 1/2007 | Koochekpour et al. | |
| 7,341,730 | B1 | | 3/2008 | Gill | |
| 2002/0177551 | A1 | | 11/2002 | Terman | |
| 2004/0120961 | A1 | | 6/2004 | Koochekpour et al. | |
| 2004/0219609 | A1 | | 11/2004 | Day et al. | |
| 2004/0229799 | A1 | | 11/2004 | Qi | |
| 2006/0275274 | A1 | | 12/2006 | Onichtchouk et al. | |
| 2007/0099251 | A1 | * | 5/2007 | Zhang et al. | 435/7.23 |
| 2009/0269373 | A1 | | 10/2009 | Qi | |
| 2010/0144603 | A1 | | 6/2010 | Watnick | |
| 2013/0072425 | A1 | | 3/2013 | Watnick | |

FOREIGN PATENT DOCUMENTS

| WO | WO 95/03821 A1 | 2/1995 |
| WO | WO-99/12559 | 3/1999 |
| WO | WO 00/02902 A1 | 1/2000 |
| WO | WO 02/24952 A1 | 3/2002 |
| WO | WO 2004/084930 A1 | 10/2004 |
| WO | WO 2004/096159 A2 | 11/2004 |
| WO | WO 2007/047796 A2 | 4/2007 |
| WO | WO 2007/047796 A3 | 4/2007 |
| WO | WO 2009/002931 A2 | 12/2008 |
| WO | WO 2011/084685 A2 | 7/2011 |
| WO | WO-2013/096868 | 6/2013 |
| WO | WO-2014/151840 | 9/2014 |

OTHER PUBLICATIONS

O'Brien FASEBJ. 5: 301-308; 1991 (Year: 1991).*
PCT/US2010/061007, Aug. 30, 2011, International Search Report and Written Opinion.
PCT/US2010/061007, Jun. 28, 2012, International Preliminary Report on Patentability.
Examination Report for AU 2016222333 dated Apr. 3, 2017.
Examination report for AU 2016222333 dated Jan. 23, 2018.
Extended European Search Report for EP Application No. 15769874. 7, dated Aug. 28, 2017, 9 pages.
International Search Report and Written Opinion for International Application PCT/US2008/067899, dated Dec. 28, 2010, 25 pages.
International Search Report and Written Opinion for International Application PCT/US2010/061007, dated Aug. 30, 2011, 10 pages.
International Search Report and Written Opinion for International Application PCT/US2015/022745, dated Aug. 12, 2015, 9 pages.
GENBANK Submission; NIH/NCBI, Accession No. EAW54436. Venter et al., Dec. 18, 2006. 3 pages.

(Continued)

Primary Examiner — Satyanarayana R Gudibande
(74) Attorney, Agent, or Firm — Foley & Lardner LLP

(57) ABSTRACT

The invention relates to isolated peptides and chimeric polypeptides derived from Saposin A that have anti-angiogenic activity. These peptides are small, consisting essentially of at least 10 consecutive amino acid residues from the 31st-50th amino acid residue of Saposin A. The invention also relates to the use of these isolated peptides and chimeric polypeptides in compositions for the treatment, prevention, and inhibition of angiogenesis-related diseases and disorders such as cancer and cancer metastasis.

19 Claims, 27 Drawing Sheets
Specification includes a Sequence Listing.

(56) References Cited

OTHER PUBLICATIONS

[No Author Listed] Myc and Human cancer database. John Hopkins University School of medicine & john hopkins health system. Last updated Apr. 14, 2013. Last accessed at http://www.myccancergene.org/site/cancerDB.asp?PageID=1 on Jul. 15, 2013.
Vogelstein et al., p53: The most frequently altered gene in human cancers. Nature education. 2010;3(9):6. Last accessed at http://www.nature.com/scitable/topicpage/p53-the-most-frequently-altered-gene-in-14192717 on Jul. 15, 2013.
Yabkowitz et al., Motility of human carcinoma cells in response to thrombospondin: relationship to metastatic potential and thrombospondin structural domains. Cancer Res. Jan. 15, 1993;53(2):378-87.
Morimoto et al., Saposin A: second cerebrosidase activator protein. Proc Natl Acad Sci U S A. May 1989;86(9):3389-93.
O'Brien et al., Coding of two sphingolipid activator proteins (SAP-1 and SAP-2) by same genetic locus. Science. Aug. 26, 1988;241(4869):1098-101.
O'Brien et al., Saposin proteins: structure, function, and role in human lysosomal storage disorders. FASEB J. Mar. 1, 1991;5(3):301-8.
Examination Report on AU 2010339794 dated Aug. 30, 2016.
Extended European Search Report for EP 16161100.9 dated Dec. 6, 2016.
Office Action for CA 2,682,171 dated Feb. 11, 2016.
Office Action on EP 10842644.6 dated Sep. 29, 2016.
Campana et al., Secretion of prosaposin, a multifunctional protein, by breast cancer cells. Biochim Biophys Acta, May 24, 1999;1427(3):392-400.
De Fraipont et al., Expression of the angiogenesis markers vascular endothelial growth factor-A, thrombospondin-1, and platelet-derived endothelial cell growth factor in human sporadic adrenocortical tumors: correlation with genotypic alterations. J Clin Endocrinol Metab. Dec. 2000;85(12):4734-41.
Doll et al., Thrombospondin-1, vascular endothelial growth factor and fibroblast growth factor-2 are key functional regulators of angiogenesis in the prostate. Prostate. Dec. 1, 2001;49(4):293-305.
Gopalakrishnan et al., Purified recombinant human prosaposin forms oligomers that bind procathepsin D and affect its autoactivation. Biochem J. Nov. 1, 2004;383(Pt. 3):507-15.
Hu et al., Prosaposin down-modulation decreases metastatic prostate cancer cell adhesion, migration, and invasion. Mol Cancer. Feb. 4, 2010;9:30.
Kalas et al., Oncogenes and Angiogenesis: down-regulation of thrombospondin-1 in normal fibroblasts exposed to factors from cancer cells harboring mutant ras. Cancer Res. Oct. 1, 2005;65(19):8878-86.
Kang et al., Prosaposin inhibits tumor metastasis via paracrine and endocrine stimulation of stromal p53 and Tsp-1. Proc Natl Acad Sci U S A. Jul. 21, 2009;106(29):12115-20. Epub Jul. 6, 2009. Erratum in: Proc Natl Acad Sci U S A. Sep. 8, 2009;106(36):15513.
Koochekpour et al., Prosaposin is an AR-target gene and its neurotrophic domain upregulates AR expression and activity in prostate stromal cells. J Cell Biochem. Aug. 15, 2008;104(6):2272-85.
Koochekpour et al., Amplification and overexpression of prosaposin in prostate cancer. Genes Chromosomes Cancer. Dec. 2005;44(4):351-64.
Koochekpour et al., Prosaposin is a novel androgen-regulated gene in prostate cancer cell line LNCaP. J Cell Biochem. Jun. 1, 2007;101(3):631-41.
Koochekpour, PSAP (prosaposin (variant Gaucher disease and variant metachromatic leukodystrophy)). Atlas Genet Cytogenet Oncol Haematol. 2007;10:370-384.
Lee et al., Saposin C promotes survival and prevents apoptosis via PI3K/Akt-dependent pathway in prostate cancer cells. Mol Cancer. Nov. 17, 2004;3:31.
Panigone et al., Up-regulation of prosaposin by the retinoid HPR and the effect on ceramide production and integrin receptors. FASEB J. Jun. 2001;15(8):1475-7.
Qi et al., Functional human saposins expressed in *Escherichia coli*. Evidence for binding and activation properties of saposins C with acid beta-glucosidase. J Biol Chem. Jun. 17, 1994;269(24):16746-53.
EP 10842644.6, Jun. 26, 2013, Extended European Search Report.
PCT/US2012/07424, May 28, 2013, International Search Report and Written Opinion.
International Preliminary Report on Patentability for PCT/US2012/071424 dated May 21, 2015.
GenBank entry KHN41504, entered Dec. 17, 2014.
The instructions from STN/CAS for searching polypeptide sequences, pamphlet CAS2537-1108 (2008).
The pharmaceutical technology editors, "Peptide pegylation: the next generation," Pharm. Tech. (2011) S3.
U.S. Office Action on U.S. Appl. No. 15/128,617, dated May 4, 2018.
Lopez-Dee et al., "Thrombospondin-1 type 1 repeats in a model of inflammatory bowel disease: transcript profile and therapeutic effects," PLo5 One, vol. 7, Issue 4, 13 pages (Apr. 3, 2012).

\* cited by examiner

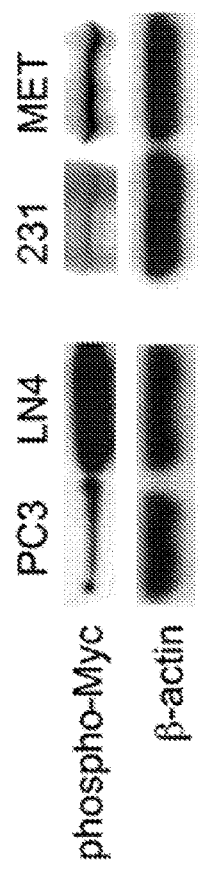
*FIG. 1A*
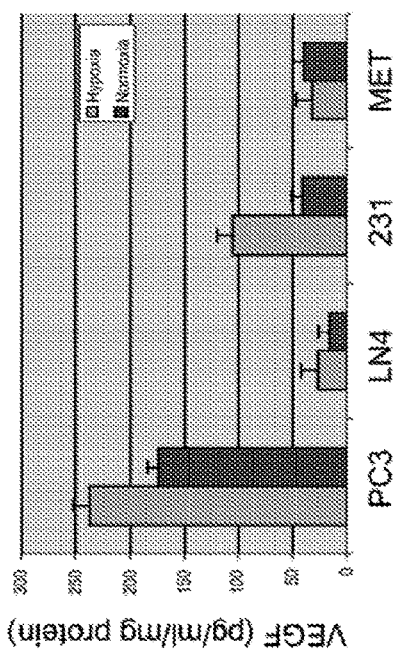
*FIG. 1B*
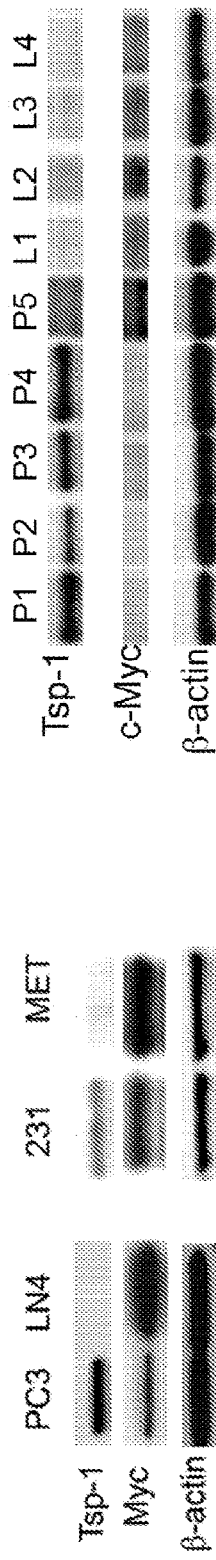
*FIG. 1C*
*FIG. 1D*

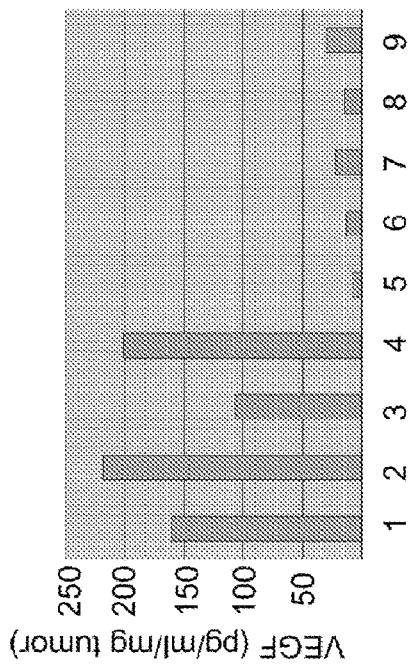

*FIG. 1E*

Table 1

Relationship between Tsp-1 expression in primary tumor and incidence of metastases

| Cell line/<br>Tsp-1<br>Expression | % of Total<br>Tumors<br>Formed | % lung<br>metastases<br>total | % lung<br>metastases in<br>group | % lymph node<br>metastases<br>total | % lymph node<br>metastases in<br>group |
|---|---|---|---|---|---|
| PC3 | | | | | |
| High Tsp-1 | 14/17 (82.4%) | 0/17 (0.0%) | 0/14 (0.0%) | 0/17 (0.0%) | 0/17 (0.0%) |
| Low Tsp-1 | 3/17 (17.6%) | 2/17 (11.8%) | 2/3 (66.7%) | 2/17 (11.8%) | 2/3 (66.7%) |
| PC3M-LN4 | | | | | |
| High Tsp-1 | 1/16 (6.2%) | 0/16 (0.0%) | 0/1 (0.0%) | 0/16 (0.0%) | 0/1 (0.0%) |
| Low Tsp-1 | 15/16 (93.8) | 10/16 (62.5%) | 10/15 (66.7%) | 12/16 (75%) | 12/15 (80.0%) |

*FIG. 1F*

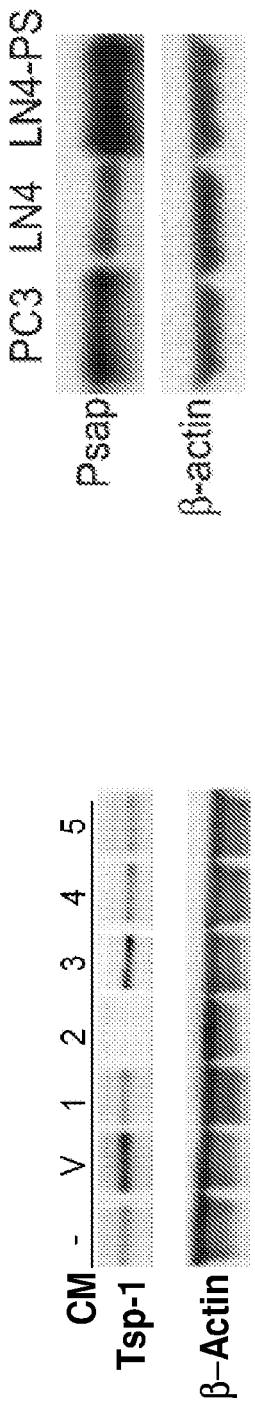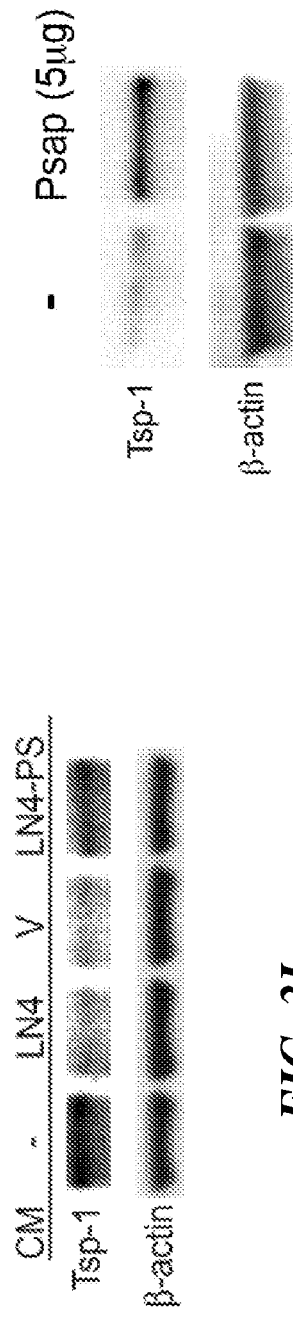
FIG. 3H
FIG. 3J
FIG. 3G
FIG. 3I

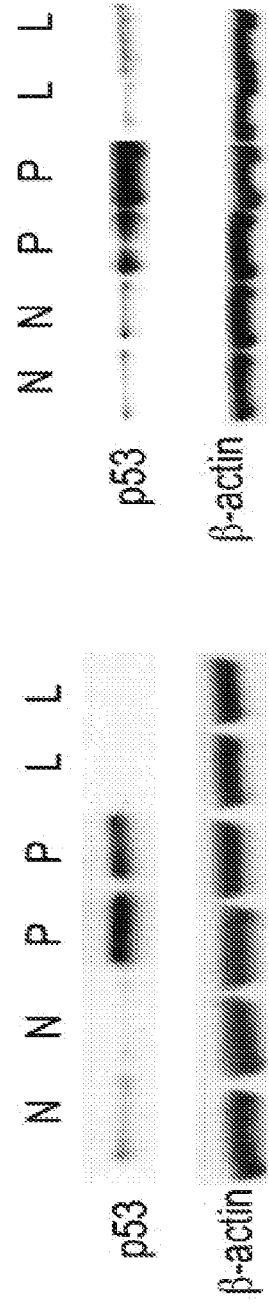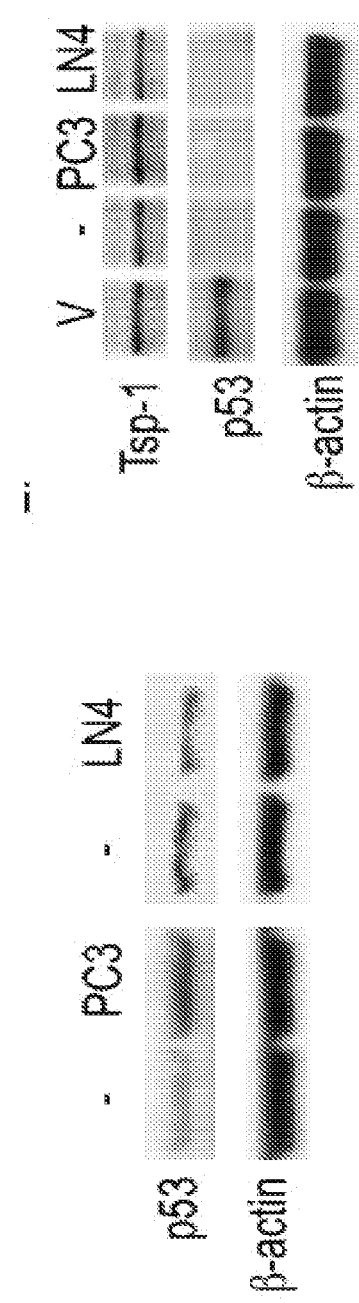
FIG. 4A  FIG. 4B  FIG. 4C  FIG. 4D

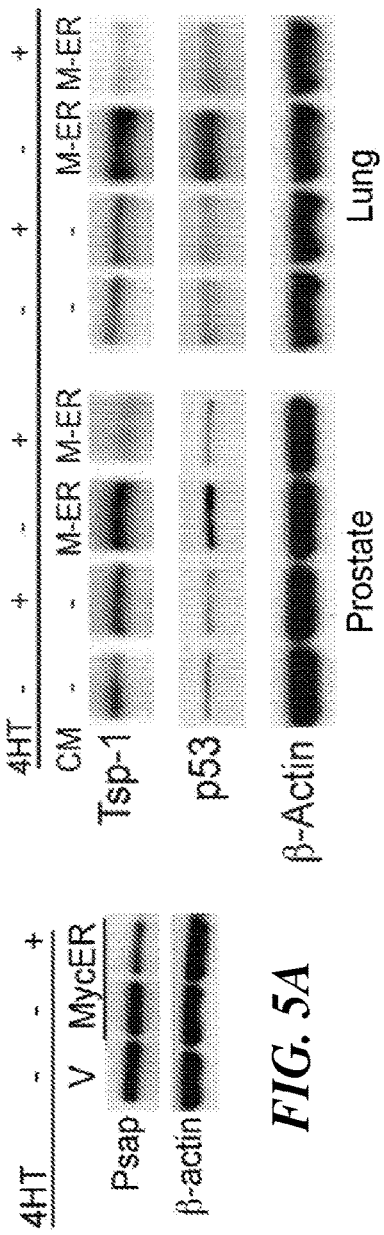
FIG. 5A
FIG. 5B
FIG. 5C
FIG. 5D
FIG. 5E

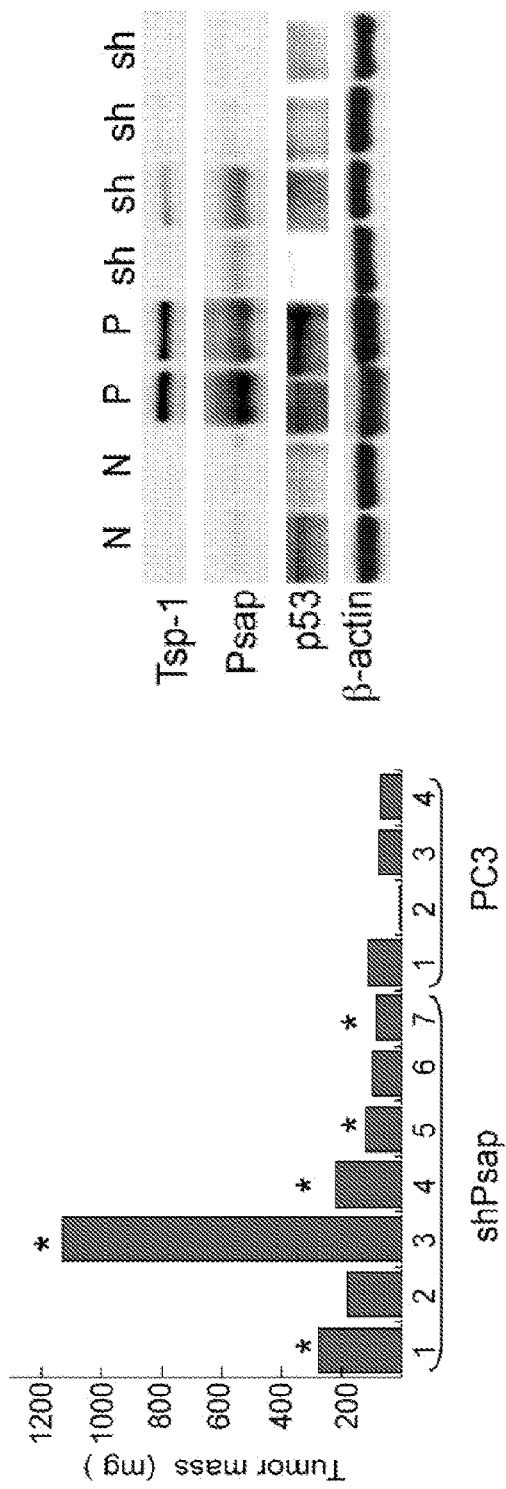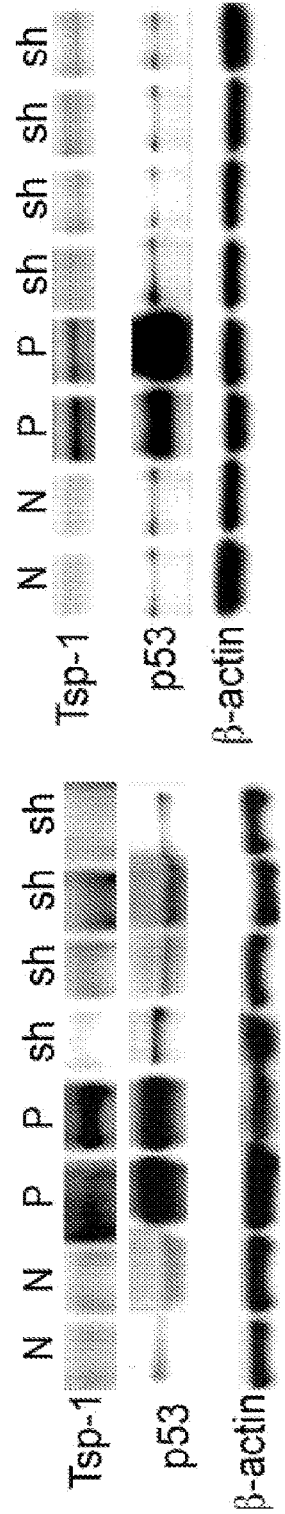
FIG. 6A  FIG. 6B  FIG. 6C  FIG. 6D

US 10,267,799 B2

SAPOSIN-A DERIVED PEPTIDES AND USES THEREOF

CROSS REFERENCE TO RELATED APPLICATIONS

This application is a national stage filing under 35 U.S.C. 371 of International Application PCT/US 2010/061007, filed Dec. 17, 2010, which claims the benefit under 35 U.S.C. § 120 as a continuation of U.S. application Ser. No. 12/640,788, filed Dec. 17, 2009, which is a continuation-in-part of International Application PCT/US2008/067899, filed Jun. 23, 2008, which claims benefit under 35 U.S.C. § 119(e) and priority to U.S. provisional application No. 60/936,792, filed Jun. 22, 2007. The teachings of International Application PCT/US2010/061007 and U.S. application Ser. No. 12/640,788 are incorporated by reference in their entirety. International Application PCT/US2010/061007 was published under PCT Article 21(2) in English.

FIELD OF THE INVENTION

The present invention relates to methods for treating of tumor metastasis, as well as methods for preventing, inhibiting, and predicting tumor metastasis. The invention further relates to treating angiogenesis-dependent diseases and disorders, screening methods for tumor cell derived anti-angiogenic factors and methods for cancer prognosis evaluation.

BACKGROUND OF THE INVENTION

The spread of cancer cells from a primary tumor site to distant organs is known as metastasis. The progression of human cancer to metastatic disease is the major contributing factor to its lethality. Metastasis has been considered one of the most intriguing aspects of the pathogenesis of cancer. Cancer tumor metastasis, or otherwise known as metastatic disease, is responsible for most therapeutic failures in treating the disease, as patients succumb to the multiple tumor growth, accounting for more than 90% of human cancer related deaths. See, for example, Cancer, A Comprehensive Treatise, F. F. Becker (editor), Volume 4, Chapter 3, Plenum Press, New York, 1975.

In order for a tumor to form lethal metastases it must acquire the ability to carry out a complex series of steps. These steps include: gaining access to the vasculature or lymphatic system (intravasation), surviving during transit, exiting the vascular or lymphatic channels (extravasation), and proliferating at the metastatic site. One of the rate limiting steps in the proliferation of tumors, both at the primary and metastatic sites, is the acquisition of the angiogenic phenotype (Folkman, 1971). The induction of angiogenesis not only allows tumors to grow beyond the size limitation imposed by the diffusion limit of oxygen, but also provides a conduit through which the tumor cells can travel and colonize distant organs (Brown et al., 1999; MacDougall and Matrisian, 1995). Once the tumor cells arrive at the metastatic site they must also induce neovascularization in order to grow beyond a microscopic size. It has been documented, however, that metastatic colonies can remain in a microscopic or dormant state and not progress beyond this size for months or years following the initial colonization (Fidler, 2003).

The presence of dormant or micro-metastases indicates that tumor growth and proliferation is not governed solely by cell-autonomous processes and that the conditions present in the microenvironment that permitted proliferation at the primary site can not exist at the metastatic site. Thus, the ability of a tumor to communicate with the surrounding stroma, composed of fibroblasts, immune cells and endothelium must be reestablished upon arrival at the metastatic site. One way in which heterotypic tumor-stromal signaling could affect tumor growth is through the regulation of the production and secretion of pro- and anti-angiogenic proteins by the surrounding stromal fibroblasts and endothelial cells.

The molecular and genetic events that facilitate escape from the primary site and homing to the metastatic site have been well studied. It has been demonstrated in a murine model of breast cancer metastasis that escape from the primary site was largely dependent on the activity of the transcription factor Twist (Yang et al., 2004). Furthermore, microarray analyses of metastatic human breast cancer cells, derived by serial injection into immuno-compromised mice, revealed sets of genes whose expression correlated with their preferred metastatic destination of bone or lung (Kang et al., 2003; Minn et al., 2005). These studies, though yielding key insights into two critical steps of tumor metastasis, namely intravasation and homing, did not address the requirements for tumor establishment and growth at the metastatic site.

It has been previously demonstrated that tumor cells can stimulate the expression of the pro-angiogenic protein VEGF in the surrounding stroma (Dong et al., 2004; Fukumura et al., 1998). However, the regulation of Thrombospondin (Tsp-1), one of the most potent endogenous anti-angiogenic proteins, in the tumor-associated stroma have not been as well studied (Kalas et al., 2005).

New research into the cell-to-cell signaling events between metastatic tumors and their surrounding stroma can yield novel strategies for treating metastatic disease. There is still a need for methods of treating metastatic disease that have less systemic toxicity than the current standard treatments comprising chemotherapy and/or radiation therapy.

SUMMARY OF THE INVENTION

In cancer patients, tumor and micrometastases can remain for prolonged periods of time in a dormant asymptomatic state before diagnosis and development of disease. Embodiments of the present invention are based in part on the discovery that a peptide fragment from the protein Saposin A stimulates the expression of thrombospondin (Tsp-1) in the surrounding environment of the tumor cells, namely the stroma comprised of fibroblasts and endothelial cells. Tsp-1 is also activated in distant environments such as the lymph nodes. Saposin A is made as a precursor polypeptide prosaposin (Psap). Tsp-1 is a potent endogenous anti-angiogenic factor, and its activation by the tumor-derived protein is via the activation of the tumor suppressor p53. P53 is a transcriptional activator of Tsp-1. The present discovery is contrary to current scientific literature wherein prosaposin and its metabolite derivative saposin C is a potent growth factor for promoting prostate cancer.

The inventors have discovered that two smaller fragments derived from saposin A can potently stimulate and induce Tsp-1 expression (see Example 15, FIGS. 21A and 22) and reduced angiogenesis. These include a 20-mer LEKTCD-WLPKPNMSASCKEI (SEQ. ID. No. 29) and a 13-mer CDWLPKPNMSASC (SEQ. ID. No. 37).

Accordingly, embodiments of the invention provide for an isolated peptide consisting essentially of at least ten consecutive amino acid residues from the sequence LEKTCD- WLPKPNMSASCKEI (SEQ. ID. No. 29) or a conservative substitution variant thereof. In some embodiments, the isolated peptide consists essentially of at least 11, at least 12, at least 13, at least 14, at least 15, at least 16, at least 17, at least 18, or at least 19 consecutive amino acid residues from SEQ. ID. No. 29 or a conservative substitution variant thereof. In some embodiments, the isolated peptide is flanked by 0, 1, 2, 3, or 4 amino acid residues on either terminus or both termini.

In one embodiment, the invention provide for an isolated peptide consisting essentially of the sequence CDWLPKPNMSASC (SEQ. ID. No. 37), LEKTCDWLPKPNMSASCKEI (SEQ. ID. No. 29) or a conservative substitution variant thereof, wherein the peptide is flanked by 0, 1, 2, 3, or 4 amino acid residues on either terminus or both termini.

In one embodiment, the isolated peptide described herein is capable of activating p53 and inducing Tsp-1 expression.

In one embodiment, the isolated peptide described herein is fused or conjugated to a therapeutic molecule.

In one embodiment, the isolated peptide having conservative substitutions described herein have at least 1, 2, 3, 4, or 5 conservative amino acid substitutions. In another embodiment, the isolated peptides having conservative substitutions described herein have no more than 1, 2, 3, 4, or 5 conservative amino acid substitutions. In another embodiment, the isolated peptides described herein have no conservative amino acid substitutions.

In one embodiment, provided herein is an isolated chimeric polypeptide comprising a first portion and a second portion, wherein the first portion is a peptide consisting essentially of the sequence CDWLPKPNMSASC (SEQ. ID. No. 37), LEKTCDWLPKPNMSASCKEI (SEQ. ID. No. 29) or a conservative substitution variant thereof, or a peptide consisting essentially of at least ten consecutive amino acid residues from the sequence LEKTCDWLPKPNMSASCKEI (SEQ. ID. No. 29) or a conservative substitution variant thereof, wherein the peptide is flanked by 0, 1, 2, 3, or 4 amino acid residues on either terminus or both termini, and wherein the second portion of the chimeric polypeptide is not a Psap protein. In some embodiments, the peptide making up first portion of the chimeric polypeptide consists essentially of at least 11, at least 12, at least 13, at least 14, at least 15, at least 16, at least 17, at least 18, or at least 19 consecutive amino acid residues from SEQ. ID. No. 29 or a conservative substitution variant thereof.

In one embodiment of the isolated chimeric polypeptide, the second portion comprises an amino acid sequence or a polymer that enhances the serum half life of the first portion of the chimeric polypeptide, e.g., but not limited to, albumin, transthyretin, Fc of IgGs.

In one embodiment of isolated chimeric polypeptide, the second portion is a therapeutic molecule, such as an anti-angiogenesis factor, an anti-VEGF agent or an anti-cancer drug.

In one embodiment, provided herein is a composition comprising a peptide or a chimeric polypeptide, and a pharmaceutically acceptable carrier, wherein the peptide consists of the sequence CDWLPKPNMSASC (SEQ. ID. No. 37) LEKTCDWLPKPNMSASCKEI (SEQ. ID. No. 29) or a conservative substitution variant thereof, or the peptide consists essentially of at least ten consecutive amino acid residues of the sequence LEKTCDWLPKPNMSASCKEI (SEQ. ID. No. 29) or a conservative substitution variant thereof, wherein the peptide is flanked by 0, 1, 2, 3, or 4 amino acid residues on either terminus or both termini, wherein the chimeric polypeptide comprises a first portion and a second portion, wherein the first portion is a peptide consisting essentially of the sequence CDWLPKPNMSASC (SEQ. ID. No. 37), LEKTCDWLPKPNMSASCKEI (SEQ. ID. No. 29) or a conservative substitution variant thereof, or is a peptide consisting essentially of at least ten consecutive amino acid residues of the sequence LEKTCDWLPKPNMSASCKEI (SEQ. ID. No. 29) or a conservative substitution variant thereof, wherein the peptide is flanked by 0, 1, 2, 3, or 4 amino acid residues on either terminus or both termini, and wherein the second portion of the chimeric polypeptide is not a Psap protein or fragment. In some embodiments, the peptide consists essentially of at least 11, at least 12, at least 13, at least 14, at least 15, at least 16, at least 17, at least 18, or at least 19 consecutive amino acid residues from SEQ. ID. No. 29 or a conservative substitution variant thereof.

In one embodiment, described herein is a method of treating an angiogenesis-dependent disease or disorder, comprising administering to a subject in need thereof, a therapeutically effective amount of a composition comprising of a peptide or a chimeric polypeptide, and a pharmaceutically acceptable carrier, wherein the peptide consists essentially of the sequence CDWLPKPNMSASC (SEQ. ID. No. 37) LEKTCDWLPKPNMSASCKEI (SEQ. ID. No. 29) or a conservative substitution variant thereof, or the peptide consists essentially of at least ten consecutive amino acid residues of the sequence LEKTCDWLPKPNMSASCKEI (SEQ. ID. No. 29) or a conservative substitution variant thereof, wherein the peptide is flanked by 0, 1, 2, 3, or 4 amino acid residues on either terminus or both termini, wherein the chimeric polypeptide comprises a first portion and a second portion, wherein the first portion is a peptide consisting essentially of the sequence CDWLPKPNMSASC (SEQ. ID. No. 37), LEKTCDWLPKPNMSASCKEI (SEQ. ID. No. 29) or a conservative substitution variant thereof, or is a peptide consisting essentially of at least ten consecutive amino acid residues of the sequence LEKTCDWLPKPNMSASCKEI (SEQ. ID. No. 29) or a conservative substitution variant thereof, wherein the peptide is flanked by 0, 1, 2, 3, or 4 amino acid residues on either terminus or both termini, and wherein the second portion of the chimeric polypeptide is not a Psap protein or fragment.

In one embodiment, described herein is a method of inhibiting the recurrence of an angiogenesis-dependent disease or disorder, the method comprising administering to a subject in need thereof, a therapeutically effective amount of a composition comprising of a peptide or a chimeric polypeptide, and a pharmaceutically acceptable carrier, wherein the peptide consists essentially of the sequence CDWLPKPNMSASC (SEQ. ID. No. 37) LEKTCDWLPKPNMSASCKEI (SEQ. ID. No. 29) or a conservative substitution variant thereof, or the peptide consists essentially of at least ten consecutive amino acid residues of the sequence LEKTCDWLPKPNMSASCKEI (SEQ. ID. No. 29) or a conservative substitution variant thereof, wherein the peptide is flanked by 0, 1, 2, 3, or 4 amino acid residues on either terminus or both termini, wherein the chimeric polypeptide comprises a first portion and a second portion, wherein the first portion is a peptide consisting essentially of the sequence CDWLPKPNMSASC (SEQ. ID. No. 37), LEKTCDWLPKPNMSASCKEI (SEQ. ID. No. 29) or a conservative substitution variant thereof, or is a peptide consisting essentially of at least ten consecutive amino acid residues of the sequence LEKTCDWLPKPNMSASCKEI (SEQ. ID. No. 29) or a conservative substitution variant thereof, wherein the peptide is flanked by 0, 1, 2, 3, or 4 amino acid residues on either terminus or both termini, and wherein the second portion of the chimeric polypeptide is not a Psap protein or fragment.

In one embodiment, the invention provides for a method of inhibiting metastasis of cancer in a subject diagnosed with cancer, the method comprising administering to a subject in need thereof, a therapeutically effective amount of a composition comprising of a peptide or a chimeric polypeptide, and a pharmaceutically acceptable carrier, wherein the peptide consists essentially of the sequence CDWLPKPNM-SASC (SEQ. ID. No. 37) LEKTCDWLPKPNMSASCKEI (SEQ. ID. No. 29) or a conservative substitution variant thereof, or the peptide consists essentially of at least ten consecutive amino acid residues of the sequence LEKTCD-WLPKPNMSASCKEI (SEQ. ID. No. 29) or a conservative substitution variant thereof, wherein the peptide is flanked by 0, 1, 2, 3, or 4 amino acid residues on either terminus or both termini, wherein the chimeric polypeptide comprises a first portion and a second portion, wherein the first portion is a peptide consisting essentially of the sequence CDWLP-KPNMSASC (SEQ. ID. No. 37), LEKTCDWLPKPNM-SASCKEI (SEQ. ID. No. 29) or a conservative substitution variant thereof, or is a peptide consisting essentially of at least ten consecutive amino acid residues of the sequence LEKTCDWLPKPNMSASCKEI (SEQ. ID. No. 29) or a conservative substitution variant thereof, wherein the peptide is flanked by 0, 1, 2, 3, or 4 amino acid residues on either terminus or both termini, and wherein the second portion of the chimeric polypeptide is not a Psap protein or fragment.

In one embodiment, described herein is a method of treating an individual diagnosed with cancer comprising: (a) determining a level of Psap in a tumor sample from said individual; (b) comparing the Psap level determined in (a) with a reference Psap level; and wherein when the Psap level determined in (a) is lower than 95% of said reference Psap level, administering a therapeutically effective amount of a composition comprising of a peptide or a chimeric polypeptide, and a pharmaceutically acceptable carrier, wherein the peptide consists essentially of the sequence CDWLPKPNM-SASC (SEQ. ID. No. 37) LEKTCDWLPKPNMSASCKEI (SEQ. ID. No. 29) or a conservative substitution variant thereof, or the peptide consists essentially of at least ten consecutive amino acid residues of the sequence LEKTCD-WLPKPNMSASCKEI (SEQ. ID. No. 29) or a conservative substitution variant thereof, wherein the peptide is flanked by 0, 1, 2, 3, or 4 amino acid residues on either terminus or both termini, wherein the chimeric polypeptide comprises a first portion and a second portion, wherein the first portion is a peptide consisting essentially of the sequence CDWLP-KPNMSASC (SEQ. ID. No. 37), LEKTCDWLPKPNM-SASCKEI (SEQ. ID. No. 29) or a conservative substitution variant thereof, or is a peptide consisting essentially of at least ten consecutive amino acid residues of the sequence LEKTCDWLPKPNMSASCKEI (SEQ. ID. No. 29) or a conservative substitution variant thereof, wherein the peptide is flanked by 0, 1, 2, 3, or 4 amino acid residues on either terminus or both termini, and wherein the second portion of the chimeric polypeptide is not a Psap protein or fragment.

In some embodiments of the methods described herein, the peptide making up the composition or the first portion of the chimeric polypeptide making up the composition consists essentially of at least 11, at least 12, at least 13, at least 14, at least 15, at least 16, at least 17, at least 18, or at least 19 consecutive amino acid residues from SEQ. ID. No. 29 or a conservative substitution variant thereof.

In one embodiment, the angiogenesis-dependent disease or disorder is selected from a group consisting of cancer, psoriasis, age-related macular degeneration, thyroid hyperplasia, preeclampsia, rheumatoid arthritis and osteoarthritis, Alzheimer's disease, obesity, pleural effusion, atherosclerosis, endometriosis, diabetic/other retinopathies, neovascular glaucoma, age-related macular degeneration, hemangiomas, and corneal neovascularization.

In one embodiment, the subject is diagnosed with a benign or malignant tumor.

In one embodiment, the treatment is administered in conjunction with chemotherapy, radiation therapy, a cytostatic agent, an anti-VEGF agent, an anti-angiogenesis factor, and/or a p53 reactivation agent.

BRIEF DESCRIPTION OF THE DRAWINGS

FIG. 1A. ELISA of VEGF secretion by PC3 and PC3M-LN4 (LN4) prostate cancer cells and MDA-MB-231 (231) and MDA-MET (MET) breast cancer cells cultured under 20% oxygen (normoxia) or 1% oxygen (hypoxia) Error bars represent SEM (Standard Error of Mean) of 3 independent experiments performed in triplicate).

FIG. 1B. Western blot analysis of Tsp-1, c-Myc, and β-Actin expression by PC3, PC3M-LN4 (LN4), MDA-MB-231 (231) and MDA-MET (MET) cells.

FIG. 1C. Western blot analysis of phosphorylated c-Myc (phospho-Myc) and β-Actin expression by PC3, PC3M-LN4 (LN4), MDA-MB-231 (231) and MDA-MET (MET) cells.

FIG. 1D. Western blot analysis of Tsp-1, c-Myc, and β-Actin expression in prostate tumors formed by PC3 (P1-P5) and PC3M-LN4 (L1-L4).

FIG. 1E. ELISA of VEGF secretion from murine stromal cells present in PC3 (P1-P5) and PC3M-LN4 (L1-L5) prostate tumors.

FIG. 1F. Tabular depiction of Tsp-1 expression in primary tumors formed by PC3 and PC3M-LN4 and the incidence of metastases in mice bearing these tumors.

FIG. 3G. Western blot analyses of Tsp-1 and β-actin expression in WI 38 lung fibroblasts treated with conditioned media (CM) from pLKO vector transduced PC3, and PC3 cells transduced with 5 shRNA sequences specific for Psap.

FIG. 3H. Western blot analyses of Psap and β-actin expression in PC3M-LN4 cells that were uninfected (LN4), infected with control pLNCX vector (V) or pLNCX-Psap (Psap).

FIG. 3I. Western blot analyses of Tsp-1 and β-actin expression in untreated prostate fibroblasts (−), or treated with conditioned media from PC3M-LN4 (LN4), PC3M-LN4-pLNCX (V) or PC3M-LN4-Psap (Psap) cells.

FIG. 3J. Western blot analyses of Tsp-1 and β-actin expression in untreated prostate fibroblasts (−) or treated with 5 μg of purified recombinant human Psap.

FIG. 4A. Western blot analyses of p53 and β-Actin expression in prostate tissue from non-tumor bearing mice (N), PC3 prostate tumor tissue (P) and PC3M-LN4 tumor tissue (L).

FIG. 4B. Western blot analyses of p53 and β-Actin expression in normal lymph node tissue (N), lymph node tissue from PC3 tumor bearing mice (P) and lymph node metastases from PC3M-LN4 tumor bearing mice (L).

FIG. 4C. Western blot analyses of p53 and β-Actin expression in prostate fibroblasts (PrF) that were untreated (−) or treated with the conditioned media from PC3 or PC3M-LN4 (LN4) cells;

FIG. 4D. Western blot analyses of Tsp-1, p53 and β-Actin expression in prostate fibroblasts containing empty pLKO vector, (V) or p53 shRNA that were untreated (−) or treated with the conditioned media from PC3 or PC3M-LN4 (LN4) cells.

FIG. 5A. Western blot analyses of Psap and β-actin expression in pBabepuro vector transduced PC3 or PC3-MycER cells that were untreated (−) or treated with 4-HT (+).

FIG. 5B. Western blot analyses of Tsp-1, p53 and β-actin expression in prostate fibroblasts and WI 38 lung fibroblasts that were untreated (−), treated with 4-HT alone (−/+) or treated with the conditioned media from 4-HT treated PC3-MycER cells (MycER/+).

FIG. 5C. Western blot analyses of Myc and β-actin expression in wild-type PC3M-LN4 cells (−), as well as PC3M-LN4 cells transduced with empty pLKO vector (V) or transduced with pLKO lentivirus specifying two different shRNA sequences for Myc (sh1, sh2).

FIG. 5D. Western blot analyses of Psap and β-actin expression in PC3M-LN4 cells containing empty pLKO vector (V) or expressing two different shRNA sequences for Myc (sh1, sh2).

FIG. 5E. Western blot analyses of Tsp-1, p53 and β-actin expression in prostate fibroblasts and WI 38 lung fibroblasts that were untreated (−) or treated with the conditioned media from PC3M-LN4-shMyc cells (sh1).

FIG. 6A. Plot of tumor mass of PC3shPsap tumors and PC3pLKO tumors from SCID mice.

FIG. 6B. Western blot analyses of Tsp-1, p53, Psap and β-actin expression in normal prostate (N) and prostate tumor formed by PC3pLKO (P) and PC3shPsap (sh) tumor bearing mice.

FIG. 6C. Western blot analyses of Tsp-1, p53 and β-actin expression in normal lymph node (N) and lymph node from PC3pLKO (P) or PC3shPsap (sh) tumor bearing mice.

FIG. 6D. Western blot analyses of Tsp-1, p53 and β-actin expression in normal lung tissue (N) and lung tissue from PC3pLKO (P) or PC3shPsap (sh) tumor bearing mice.

DETAILED DESCRIPTION OF THE INVENTION

Figure 2A:
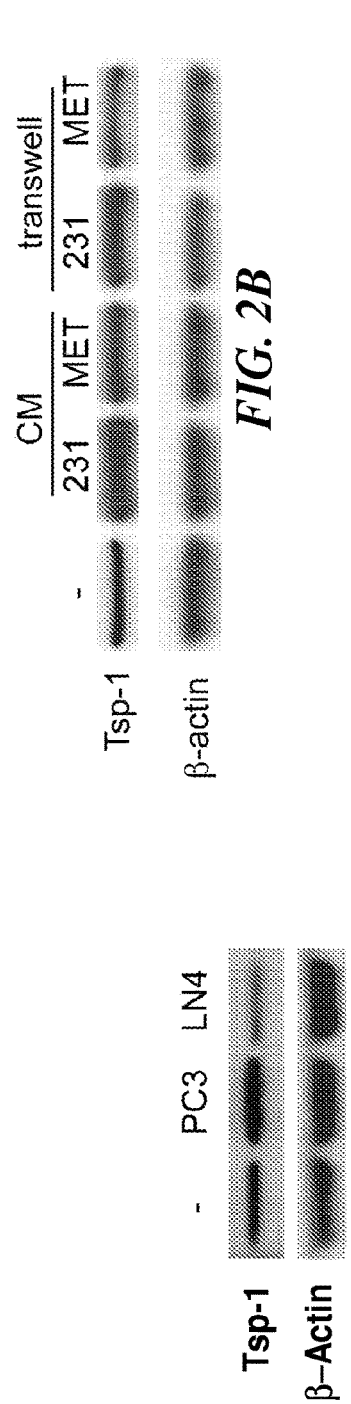
FIG. 2A. Western blot analyses of Tsp-1, c-Myc, and β-Actin expression in prostate fibroblasts that were untreated (−) or treated with the conditioned media from PC3, or PC3M-LN4 (LN4) cells.

Embodiments of the present invention are based on the discovery that non- or weakly metastatic tumor cells secrete a protein that stimulates the expression of thrombospondin (Tsp-1) in the surrounding environment of the tumor cells, namely the stroma comprised of fibroblasts and endothelial cells. While not wishing to be bound by theory, the increase in expression of Tsp-1 in the stroma keeps the tumor cells from metastasizing Tsp-1 is a potent endogenous anti-angiogenic factor, and the stimulation of Tsp-1 expression by the tumor-derived protein is via the activation of the tumor suppressor p53. The tumor suppressor p53 is a transcription activator of Tsp-1 expression. This tumor-associated protein secreted by non- or weakly metastatic tumor cells is prosaposin (Psap). In addition, the inventors have found that two peptide fragments from Saposin A, Saposin A being a cleavage product of Psap. These two peptide fragments CDWLPKPNMSASC (SEQ. ID. No. 37) and LEKTCDWLPKPNMSASCKEI (SEQ. ID. No. 29) were also capable of stimulating Tsp-1 expression in vitro and in vivo.

It was found that non- or weakly metastatic tumor cells express a high amount of Psap and Tsp-1, in addition to stimulating p53 and Tsp-1 expression in the surrounding tumor stroma. In contrast, metastatic tumor cells express low amounts of Psap and Tsp-1, and metastatic tumor cells also repress the expression of p53 and Tsp-1 in the tumor stroma. There is a strong correlation between metastasis, Psap and Tsp-1 expression in the tumor cells, and Psap and Tsp-1 expression in the tumor stroma. In addition, there is also a strong correlation between metastasis and the Psap level in the plasma and/or platelets of patients with metastatic cancers. Both the plasma and platelets of patients with non-metastatic cancers contained elevated levels of Psap compared to normal individuals not diagnosed with cancers. In contrast, the plasma and platelets of patients with metastatic cancers contain Psap levels that are comparable to normal individuals with no diagnosed cancers. While not wishing to be bound by theory, the shift from elevated levels of Psap levels to normal or lower than normal Psap levels indicates the transition from non-metastatic to metastatic cancer.

While not wishing to be bound by theory, high expression of Psap from a dormant primary tumor prevents the tumor from metastasis and also prevents the establishment secondary tumors at sites away from the primary tumor site. Conversely, low or no expression Psap in a primary tumor allows the tumor to metastasize and establish secondary tumors at sites far away from the primary tumor site. The Psap secreted by a tumor affects its local and distant environment via paracrine and endocrine signaling mechanisms, affecting whether a tumor cell can grow bigger and/or implant and grow at a different and distant location from the primary tumor site. Psap functions as a repressor of both lymphatic and vascular metastasis by inducing p53 and consequently Tsp-1 expression in stromal fibroblasts via both paracrine and endocrine signaling mechanisms.

These new discoveries are contrary to existing reports that Psap and/or its known active molecular derivatives (e.g., saposin C) function as a pluripotent growth factor with diverse biological activities that favor malignant phenotypes in prostate cancer (Koochekpour S, et al., J Cell Biochem. 2007, 101:631-41; J Cell Biochem. 2008, 104(6):2272-85).

In cancer patients, tumor and micrometastasis can remain for prolonged periods of time in a dormant asymptotic state before diagnosis and development of disease. It is unknown how this dormant state is maintained or how and why the dormant tumor changes to a metastatic form. This discovery of Psap expression by dormant tumors explains how the dormant non-metastatic tumor state can be maintained. Moreover, changes in Psap expression can account for how and why the dormant tumor changes to a metastatic form. Therefore, measurements of Psap in organism can provide valuable information regarding the status of a tumor or cancerous growth, such as dormant non-metastatic tumor state versus progressively metastatic or likelihood of metastasis.

Prosaposin (Psap) is the saposin precursor protein made up of approximately 524-527 amino acids which includes a 16 amino acids signal peptide. The full-length precursor 53-kDa polypeptide undergoes co-translational glycosylation and modification in the endoplasmic reticulum and Golgi system to yield a 70-72 kDa precursor protein. After transport to the lysosome, cathepsin D participates in its proteolytic processing to yield intermediate molecular forms of 35 to 53 kDa and then to a 13-kDa glycoprotein and finally to the mature 8-11 kDa partially glycosylated forms of individual saposin molecules (O'Brien J. S., and Kishimoto Y, The FASEB J., 5: 301-8, 1991; Kishimoto Y. et al., J. Lipid Res. 33:1255-67, 1992). There are currently three known splice variants of the precursor protein; isoforms a, b and c.

Psap and the individual saposin proteins are expressed by a wide variety of cells types originating from ectodermal, mesodermal, and endodermal germ layers including but not limited to lung, skin, fibroblast, stromal cells, bone, smooth muscle, skeletal muscle, cardiac muscle, placenta, red and white blood cells, pancreas, placenta, lymphoreticular system (spleen, thymus, liver), micro and macrovascular system, genitourinary system (e.g., prostate, testes, seminal vesicle), central and peripheral nervous system. Prosaposin and saposins are also present as soluble proteins in extracellular space/fluid including pleural fluid, cerebrospinal fluid, seminal fluid, milk, and serum (Campana W M., et al., 1999; Kishimoto Y. et al., 1992).

Psap is overexpressed in breast adenocarcinoma cell lines, non small-cell lung adenocarcinoma, neuroblastoma, and schwannoma cell lines, glioma cell lines, adult and pediatric brain tumors (e.g., medulloblastoma-, astrocytoma-, glioblastoma multiforme-cell lines), fibrosarcoma, osteosarcoma, and prostate cancer cell lines, different types of tumors (brain, colon, lung, pancreas, rectum, ovary, parotid, skin, bladder, small intestine, thymus, and uterus), including human prostate cancer cell lines. However the overall the expression and biofunctional significances of prosaposin and saposins in cancer are largely unknown (Koochekpour S. March 2006; Koochekpour S. September 2006).

In the cell, prosaposin is a dual function molecule; as the precursor of intracellular lysosomal saposin proteins involved in sphingolipid hydrolysis activity and as a secreted soluble protein with neurotrophic activities, including growth, development, and maintenance of the peripheral and central nervous system, nerve regeneration and plasticity, stimulation of neurite outgrowth, stimulation of neuroblastoma cells proliferation, protection from cell-death or apoptosis, and activation of MAPK- and PI3K/Akt-signaling pathways (Morales and Badran, 2003; Misasi R, et al., 2001; Campana W M, et al., 1998; Hiraiwa M, et al., 1997; Hiraiwa M, et al., 1997; Kotani Y., et al., 1996; Campana W M., et al., 1996; O'Brien J S., et al., 1995; O'Brien J S., et al., 1994). The use of prosaposin and its cytokine-derived peptide in neurite growth and cell myelination is described in U.S. Pat. No. 5,700,909.

Definitions

As used herein, the term "stroma" or "tumor stroma" refers to the connective tissue framework and non-tumor cells of a tumor. Examples of some non-tumor cells found in a tumor stroma are fibroblasts and endothelial cells.

As used herein, the term "tumor" means a mass of transformed cells that are characterized, at least in part, by containing angiogenic vasculature. The transformed cells are characterized by neoplastic uncontrolled cell multiplication which is rapid and continues even after the stimuli that initiated the new growth has ceased. The term "tumor" is used broadly to include the tumor parenchymal cells as well as the supporting stroma, including the angiogenic blood vessels that infiltrate the tumor parenchymal cell mass. Although a tumor generally is a malignant tumor, i.e., a cancer having the ability to metastasize (i.e., a metastatic tumor), a tumor also can be nonmalignant (i.e., non-metastatic tumor). Tumors are hallmarks of cancer, a neoplastic disease the natural course of which is fatal. Cancer cells exhibit the properties of invasion and metastasis and are highly anaplastic.

As used herein, the term "metastases" or "metastatic tumor refers to a secondary tumor that grows separately elsewhere in the body from the primary tumor and has arisen from detached, transported cells, wherein the primary tumor is a solid tumor. The primary tumor, as used herein, refers to a tumor that originated in the location or organ in which it is present and did not metastasize to that location from another location.

As used herein, a "malignant tumor" is one having the properties of invasion and metastasis and showing a high degree of anaplasia. Anaplasia is the reversion of cells to an immature or a less differentiated form, and it occurs in most malignant tumors.

As used herein, the term "recurrence" of an angiogenic disease or disorder refers to the re-manifestation/re-development of known symptoms associated with the angiogenic disease or disorder after previous successful treatment of the angiogenic disease or disorder. For example, a "recurrence" of a tumor refers to the enlargement of an existing tumor whose growth had stopped or reduced during an anti-cancer therapy, or the emergence of a tumor at the original (primary) site of tumor discovery after the original tumor had been excised or reduced in size. The recurrence of a tumor can also mean new tumor growth(s) of the same tumor type as the original tumor at a site different from the original site of tumor discovery. This can be an indication that the original primary tumor has spread to other locations, or the primary tumor has emerged as an anti-angiogenic resistant form. For example, a recurrence of rheumatoid arthritis can include localized swelling/pain/joint stiffness, and elevated leukocyte ingression after a period of disease remission and symptom free.

As used herein, the term "inhibit" or "inhibition" means the reduction or prevention of tumor growth and/or tumor metastasis in cancers. Inhibition includes slowing the rate of tumor growth and metastasis. The tumor growth rate can be reduced by about 20%, about 30%, about 40%, about 50%, about 60%, about 70%, about 80%, about 90%, about 100%, about 125%, about 150% or more compared to a control, untreated tumor of the same type. Inhibition also means a reduction in the size of the tumor of at least 10%, at least 20%, at least 30%, at least 40%, at least 50%, at least 60%, at least 70%, at least 80%, at least 90%, at least 100% or more compared to a control, untreated tumor of the same type. The prevention of tumor growth and/or metastasis means no further increase in the size of the tumors from the time of start of treatment administration. Prevention also means status quo of no new metastatic tumors detected (i.e., no further spread of cancer) and/or an increase amount of tumor markers detected by methods known in the art.

As used herein, the term "therapeutically effective amount" refers to the amount that is safe and sufficient to prevent or delay the development and further spread of metastases in cancer patients. The amount can also cure or cause the cancer to go into remission, slow the course of cancer progression, slow or inhibit tumor growth, slow or inhibit tumor metastasis, slow or inhibit the establishment of secondary tumors at metastatic sites, or inhibit the formation of new tumor metastasis.

The term "treat" or "treatment" refer to both therapeutic treatment and prophylactic or preventative measures, wherein the object is to prevent, slow down, and/or halt the development or spread of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already diagnosed with cancer as well as those likely to develop secondary tumors due to metastasis.

The term "angiogenesis", as used herein refers to the sprouting of new blood vessels from pre-existing blood vessels, characterized by endothelial cell proliferation and migration triggered by certain pathological conditions, such as the growth of solid tumors and metastasis.

As used herein, the term "angiogenesis-dependent disease or disorder" refers to diseases or disorders that are dependent on a rich blood supply and blood vessel proliferation for the disease pathological progression (e.g., metastatic tumors) or diseases or disorders that are the direct result of aberrant blood vessel proliferation (e.g., diabetic retinopathy and hemangiomas). Examples include abnormal vascular proliferation, ascites formation, psoriasis, age-related macular degeneration, thyroid hyperplasia, preeclampsia, rheumatoid arthritis and osteoarthritis, Alzheimer's disease, obesity, pleural effusion, atherosclerosis, endometriosis, diabetic/other retinopathies, ocular neovascularizations such as neovascular glaucoma and corneal neovascularization.

As used herein, the term "nucleic acid" refers to DNA or RNA. The term encompasses sequences that include any of the known base analogs of DNA and RNA.

The term "vector", as used herein, refers to a nucleic acid construct comprising the complete or partial cDNA of Psap (SEQ. ID. No. 2, 4, or 6) (Genbank Accession No. NM_002778, NM_001042466, or NM_001042465), wherein the nucleic acid construct is designed for delivery to a host cell, transfer between different host cells, or for the expression of Psap or functional fragments or variants thereof, in cells. As used herein, a vector can be viral or non-viral.

As used herein, the term "viral vector," refers to a nucleic acid vector construct that includes at least one element of viral origin and includes elements sufficient for or permissive of packaging into a viral vector particle. A viral vector can contain the coding sequence for a Psap protein in place of non-essential viral genes. The vector and/or particle can be utilized for the purpose of transferring DNA, RNA or other nucleic acids into cells either in vitro or in vivo. Numerous forms of viral vectors are known in the art.

As used herein, the term "prognosis" encompasses predictions and likelihood analysis of disease progression, particularly tumor recurrence, metastatic spread, and disease relapses. The prognosis method described herein is intended for clinical use in making decision concerning treatment modalities, including therapeutic interventions, diagnostic criteria such as disease staging, and disease monitoring and surveillance for metastasis or recurrence of neoplastic disease.

As used herein, a "tissue sample" refers to a portion, piece, part, segment, or fraction of a tissue which is obtained or removed from an intact tissue or organ of a subject, preferably a human subject.

As used herein, a "subject" refers to a mammal, preferably a human. The term "individual", "subject", and "patient" are used interchangeably.

As used herein, a "tumor sample" refers to a portion, piece, part, segment, or fraction of a tumor, for example, a tumor which is obtained or removed from a subject (e.g., removed or extracted from a tissue of a subject), preferably a human subject.

As used herein, the term "functional" refers to the fragments and variants of Psap protein having cellular functions substantially similar to that of the parent full-length Psap. At the minimum, "functional" refers to the capability of stimulating Tsp-1 and/or p53 expressions. In other embodiments, other cellular functions including capability of being glycosylated, of being proteolytically processed to give the smaller saposins which are required for the hydrolysis of glycosphingolipids by lysosomal lysozmes, ability to bind to membrane lipids, and have neurotrophic activities.

As used herein, the term "substantially similar" refers to no change to the course of direction of biological effects resulting from the actions of the fragments and variants of Psap in the cell. For example, the fragment and variant forms of Psap are still capable of stimulating Tsp-1 and p53 expression and activation, and they can still be processed proteolytically to give saposins, and these saposins can be used by the cell in the hydrolysis of glycosphingolipids. A "substantially similar" functional fragment of saposin A has an amino acid sequence differing from SEQ. ID. No. 13 by having one or more conservative amino acid substitution and/or modification but is still capable of stimulating Tsp-1 and p53 expressions and activation, the methods of assaying are described herein and are well known in the art.

As used herein, the term "variant" refers the splice variant of Psap protein (also known as isoforms) encoded by the nucleic acids of Psap (Genbank Accession No. NM_002778, SEQ. ID. No. 2), NM_001042465 (SEQ. ID. No. 4), or NM_001042466 (SEQ. ID. No. 6)). In one embodiment, "variant" also refers to Psap protein or molecule modified at one or more base pairs, codons, introns, exons, or amino acids, respectively, yet still retain the biological activity and cellular functions of a Psap protein, e.g., a conservative substitution variant where one or more of the amino acids have been substituted with their respective conservative amino acid but the variant still retain the ability to stimulate Tsp-1 expression. Thus the polypeptide sequence of the variant Psap protein is slightly different from that prescribed by the Psap coding nucleic acid (SEQ. ID. No. 2, 4, and 6). There are one or more amino acid mutations in the Psap protein. Conservative amino acid substitution can produced variant Psap proteins. For example, the amino acid serine can be substituted for threonine and the amino acid aspartate can be substituted for glutamate. The variant Psap proteins have comparable or greater Tsp-1 and p53 expression stimulation activity than the parent Psap protein. The variant Psap protein can have at least 80%, at least 90%, at least 100%, at least 110%, at least 120%, at least 130%, at least 140%, or at least 150% of the Tsp-1 and p53 expression stimulation activity of the parent Psap protein. Variants can be produced by a number of means including methods such as, for example, error-prone PCR, shuffling, oligonucleotide-directed mutagenesis, recursive ensemble mutagenesis, exponential ensemble mutagenesis, site-specific mutagenesis, gene reassembly, GSSM and any combination thereof.

As used herein, the term "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

As used herein, the term "fragment" refers to an amino acid sequence which is shorter than the original polypeptide encoded by the cDNA of Psap (Genbank Accession No. NM_002778, SEQ. ID. No. 2), NM_001042465.1 (SEQ. ID. No. 4) or NM_001042466.1 (SEQ. ID. No. 6) thus presenting an incomplete Psap protein. The Psap protein is shortened or truncated. The term "functional fragment" as used herein refers to the truncated Psap protein that has cellular functions including the stimulation of Tsp-1 and p53 expression. Fragments are at least 10 amino acids but are not the full-length Psap protein. In other words, fragments are 10 amino acids or more but are not the full-length Psap protein. Examples of fragments include fragments consisting of amino acids 1-300, amino acids 1-150, and amino acids 1-490 of the original full length Psap protein. These fragments contain the Saposin A- and Saposin B-domains and can be cleaved to give the smaller saposins or smaller fragments thereof. For example:

```
Saposin A: (protein)
                                               (SEQ. ID. No. 13)
SLPCDICKDVVTAAGDMLKDNATEEEILVYLEKTCDWLPKPNMSASCKEIVDSYLPVILDIIKGE

MSRPGEVCSALNLCES;

Saposin B: (Protein)
                                               (SEQ. ID. No. 14)
GDVCQDCIQMVTDIQTAVRTNSTFVQALVEHVKEECDRLGPGMADICKNYISQYSEIAIQMMM

HMQPKEICALVGFCDE;

Saposin C (Protein)
                                               (SEQ. ID. No. 15)
SDVYCEVCEFLVKEVTKLIDNNKTEKEILDAFDKMCSKLPKSLSEECQEVVDTYGSSILSILLEEV

SPELVCSMLHLCSG;

Saposin D (Protein)
                                               (SEQ. ID. No. 16)
DGGFCEVCKKLVGYLDRNLEKNSTKQEILAALEKGCSFLPDPYQKQCDQFVAEYEPVLIEILVEV

MDPSFVCLKIGACPS;

(SEQ. ID. No. 18)
SLPCDICKDVVTAAG;

(SEQ. ID. No. 19)
VTAAGDMLKDNATEE;

(SEQ. ID. No. 20)
NATEEEILVYLEKTC;
```

```
LEKTCDWLPKPNMSA;                              (SEQ. ID. No. 21)

PNMSASCKEIVDSYL;                              (SEQ. ID. No. 22)

VDSYLPVILDIIKGE;                              (SEQ. ID. No. 23)

IIKGEMSRPGEVCSA;                              (SEQ. ID. No. 24)

SRPGEVCSALNLCES;                              (SEQ. ID. No. 25)

SLPCDICKDVVTAAGDMLKD;                         (SEQ. ID. No. 26)

VTAAGDMLKDNATEEEILVY;                         (SEQ. ID. No. 27)

NATEEEILVYLEKTCDWLPK;                         (SEQ. ID. No. 28)

LEKTCDWLPKPNMSASCKEI;                         (SEQ. ID. No. 29)

PNMSASCKEIVDSYLPVILD;                         (SEQ. ID. No. 30)

VDSYLPVILDIIKGEMSRPG;                         (SEQ. ID. No. 31)
and

IIKGEMSRPGEVCSALNLCES.                        (SEQ. ID. No. 32)
```

The terms "polypeptide" and "peptide" are used interchangeably herein to refer to a polymer of amino acids. These terms do not connote a specific length of a polymer of amino acids. Thus, for example, the term includes oligomeric peptides, made up of two or more physically linked peptides, whether produced using recombinant techniques, chemical or enzymatic synthesis, or naturally occurring. This term also includes polypeptides that have been modified or derivatized, such as by glycosylation, acetylation, phosphorylation, and the like.

As used herein, the term "Psap protein" refers to the splice variant full-length human prosaposin isoform A preproprotein (Genbank Accession Nos.: NM_002778 (SEQ. ID. No. 2), NP_002769.1 (SEQ. ID. No. 1)); UniProtKB/Swiss-Prot P07602, UniProtKB/TrEMBL Q53Y86), the splice variant full-length human prosaposin isoform B preproprotein (Genbank Accession Nos.: NM_001042465.1 (SEQ. ID. No. 4), NP_001035930.1 (SEQ. ID. No. 3)); UniProtKB/Swiss-Prot entry P07602), the splice variant full-length human prosaposin isoform C preproprotein (Genbank Accession Nos.: NM_001042466.1 (SEQ. ID. No. 6), NP_001035931.1 SEQ. ID. No. 5)); GenPept/UniProtKB/TrEMBL: O75905, P07602.2, Q53FJ5, Q59EN5, Q5BJH1, Q5JQ36, and Q5JQ37; the secreted forms of these splice variants, functional fragments and conservative substitution variants thereof that are greater or equal to 10 amino acid residues, the functional fragments and variants of the isoforms that are greater or equal to 10 amino acid residues, differentially glycosylated forms of the full-length splice variant Psap protein, secreted differentially glycosylated forms of the Psap protein, differentially glycosylated functional fragments with less than 524 amino acids and that are greater or equal to 10 amino acid residues, and/or differentially glycosylated functional variants thereof. Psap protein includes substantially similar Psap proteins, saposin A and functional fragments thereof that are greater or equal to 10 amino acid residues.

As used herein, the term "differentially glycosylated" refers to differences in glycosylation at the available glycosylation sites of full-length Psap. There are five glycosylation sites on the full-length protein. Accordingly, a full-length Psap can have anywhere from zero and up to five glycosylated groups. In addition, the term also refers to the presence of different sugar groups on the polypeptide.

As used herein, the term "cancer" refers to any of various malignant neoplasms characterized by the proliferation of anaplastic cells that tend to invade surrounding tissue and metastasize to new body sites as well as to the pathological conditions characterized by such malignant neoplastic growths. The term "cancer" also refers to cells and tissue with neoplasms characteristics of anaplastic proliferation that are not invasive of surrounding tissue, i.e., anaplastic cells that are benign.

As used herein, the term "promptness" refers to any time within one month of positive laboratory test results confirming presence of cancer cells.

As used herein, the phrase "development of cancer" or "cancer development" refers to the development of primary or initial cancer, the development of metastasis from benign and/or malignant tumors, and/or the development of malignancy from benign tumors.

As used herein, the term "fusion protein" or "fusion polypeptide" refers to a protein created by joining two heterologous genes or two heterologous proteins/peptides or portions thereof together. By "heterologous" in reference to genes and proteins means the genes or proteins are two different and not similar entities. For example, two heterologous genes encode for two different and not similar proteins respectively. Thus, a "fusion protein" or "fusion polypeptide" is a chimeric protein, made of at least two different types of proteins or portions thereof. In the laboratory, "fusion protein" or "fusion polypeptide" is achieved through the creation of a fusion gene which is done through the removal of the stop codon from a DNA sequence of the first protein and then attaching the DNA sequence of the second protein in frame. The resulting DNA sequence can then be expressed by a cell as a single protein. Alternatively, in a fusion protein, the two heterologous proteins can be joined together with a linker or spacer peptide added between the two proteins. This linker or spacer peptide often contains protease cleavage site(s) to facilitate the separation of the two different proteins after expression and purification. The making of fusion protein as a technique is commonly used for the identification and purification of proteins through the fusion of a GST protein, FLAG peptide or a hexa-His peptide.

As used herein, a peptide linker is a short sequence of amino acids that is not part of the sequence of either of the two peptides being joined to form a fusion protein or fusion polypeptide. A peptide linker is attached on its amino-terminal end to one polypeptide or polypeptide domain and on its carboxyl-terminal end to another polypeptide or polypeptide domain. Examples of useful linker peptides include, but are not limited to, glycine polymers ((G)n) including glycine-serine and glycine-alanine polymers (e.g., a (Gly4Ser)n repeat where n=1-8, preferably, n=3, 4, 5, or 6). The peptide linker can be a flexible linker, in that the peptide sequence does not adopt any secondary structures known in proteins, e.g., alpha helices. Such flexible linkers are predominantly made of non-charged, apolar amino acid residues and are hydrophobic. Secondary protein structures can be determined by methods known in the art, for example, circular dichroism. An example of a flexible peptide linker is LGGGGSGGGGSA (SEQ. ID. No. 41). Alternately, the peptide linker can take the form a monomeric hydrophilic α-helix, for example, AEAAAKEAAAKEA (SEQ. ID. No. 42).

By "PEGylated" is meant the covalent attachment of at least one molecule of polyethylene glycol to a biologically active molecule. The average molecular weight of the reactant PEG is preferably between about 3,000 and about 50,000 daltons, more preferably between about 10,000 and about 40,000 daltons, and most preferably between about 15,000 and about 30,000 daltons. Particularly preferred are PEGs having nominal average sizes of about 20,000 and about 25,000 daltons. The method of attachment is not critical, but preferably does not alter, or only minimally alters, the activity of the biologically active molecule. Preferably the increase in half-life is greater than any decrease in biological activity. A preferred method of attachment is via N-terminal linkage to a polypeptide or peptide.

In one respect, the term "comprising" in reference to the herein described compositions and methods, refers to respective component(s) thereof, as essential to the invention, yet open to the inclusion of unspecified elements, essential or not.

In some embodiments, other elements that can be included in the description of the composition, method or respective component thereof are limited to those that do not materially affect the basic and novel characteristic(s) of the invention. This is referred to using the term "consisting essentially of". This applies equally to steps within a described method as well as compositions, peptides and components therein. In other embodiments, the inventions, peptides, compositions, methods, and respective components thereof, described herein are intended to be exclusive of any element not recited with respect to that composition, element, component or method. This is referred to using the term "consisting of".

In some embodiments, the term "essential" in reference to compositions and methods refers to the "essential" component in the composition or method being the peptide or protein sequence that, at the minimum, has the ability to stimulate Tsp-1 expression in the assays described herein, preferably also stimulate p53 expression. Non essential component in the composition or method would be heterologous protein that is not Psap, fusion portion of the fusion protein that is not Psap, PEG, polymer, immunoglobulin Fc region or conjugates etc.

The term "reducing the likelihood" in reference to the development of certain conditions refers to a reduction by at least 20% compared to when no treatment or administration of a therapeutically effective amount of a Psap protein or a vector described herein. The reduction can also be at least 30%, at least 40%, at least 50%, at least 60%, at least 70%, at least 80%, at least 90%, at least 100%, including all the percent between 20% and 100%.

In one embodiment, the invention provides a method of treating an angiogenesis-dependent disease or disorder, the method comprising administering to a subject in need thereof a therapeutically effective amount of a Psap protein or a vector comprising the nucleic acid encoding a Psap protein, and a pharmaceutically acceptable carrier.

In one embodiment, the invention provides a method of inhibiting the recurrence of an angiogenesis-dependent disease or disorder, the method comprising administering to a subject in need thereof, a therapeutically effective amount of a Psap protein or a vector comprising the nucleic acid encoding a Psap protein, and a pharmaceutically acceptable carrier.

The angiogenesis-dependent disease or disorder is selected from, but is not limited to, a group consisting of cancer, ascites formation, psoriasis, age-related macular degeneration, thyroid hyperplasia, preeclampsia, rheumatoid arthritis and osteoarthritis, Alzheimer's disease, obesity, pleural effusion, atherosclerosis, endometriosis, diabetic/other retinopathies, neovascular glaucoma, age-related macular degeneration (ARMD), hemangiomas, and corneal neovascularization.

In one embodiment, the angiogenesis-dependent disease or disorder is cancer, where the rapidly dividing neoplastic cancer cells require an efficient blood supply to sustain their continual growth of the tumor. As used herein, cancer refers to any of various malignant neoplasms characterized by the proliferation of anaplastic cells that tend to invade surrounding tissue and metastasize to new body sites and also refers to the pathological condition characterized by such malignant neoplastic growths. The blood vessels provide conduits to metastasize and spread elsewhere in the body. Upon arrival at the metastatic site, the cancer cells then work on establishing a new blood supply network. Administration of Psap proteins and/or the overexpression of Psap proteins lead to the activation of the potent angiogenesis inhibitor Tsp-1 in the tumor stroma. By inhibiting angiogenesis at the primary tumor site and secondary tumor site, embodiments of the invention serve to halt, prevent and limit the progression of the disease. Any solid tumor that requires an efficient blood supply to keep growing is a candidate target. For example, candidates for the treatment described herein include carcinomas and sarcomas found in the anus, bladder, bile duct, bone, brain, breast, cervix, colon/rectum, endometrium, esophagus, eye, gallbladder, head and neck, liver, kidney, larynx, lung, mediastinum (chest), mouth, ovaries, pancreas, penis, prostate, skin, small intestine, stomach, spinal marrow, tailbone, testicles, thyroid and uterus. The types of carcinomas include papilloma/carcinoma, choriocarcinoma, endodermal sinus tumor, teratoma, adenoma/adenocarcinoma, melanoma, fibroma, lipoma, leiomyoma, rhabdomyoma, mesothelioma, angioma, osteoma, chondroma, glioma, lymphoma/leukemia, squamous cell carcinoma, small cell carcinoma, large cell undifferentiated carcinomas, basal cell carcinoma and sinonasal undifferentiated carcinoma. The types of sarcomas include soft tissue sarcoma such as alveolar soft part sarcoma, angiosarcoma, dermatofibrosarcoma, desmoid tumor, desmoplastic small round cell tumor, extraskeletal chondrosarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, synovial sarcoma, and Askin's tumor, Ewing's sarcoma (primitive neuroectodermal tumor), malignant hemangioendothelioma, malignant schwannoma, osteosarcoma, and chondrosarcoma. Abnormal build up and growth of blood vessels in the skin or internal organs in the form of hemangiomas can also be treated according to the methods described herein.

In one embodiment, the angiogenesis-dependent disease or disorder is age-related macular degeneration. It is known that VEGF contributes to abnormal blood vessel growth from the choroid layer of the eye into the retina, similar to what occurs during the wet or neovascular form of age-related macular degeneration. Macular degeneration, often called AMD or ARMD (age-related macular degeneration), is the leading cause of vision loss and blindness in Americans aged 65 and older. New blood vessels grow (neovascularization) beneath the retina and leak blood and fluid. This leakage causes permanent damage to light-sensitive retinal cells, which die off and create blind spots in central vision or the macula.

In one embodiment, the angiogenic disease or disorder is diabetic retinopathy-abnormal blood vessel growth associated with diabetic eye diseases. The activation of Tsp-1 via prosaposin serves to antagonize VEGF, a substance naturally produced in the body that promotes blood vessel formation. Released by the retina (light-sensitive tissue in back of the eye) when normal blood vessels are damaged by tiny blood clots due to diabetes, VEGF turns on its receptor, igniting a chain reaction that culminates in new blood vessel growth. However, the backup blood vessels are faulty; they leak, bleed and encourage scar tissue that detaches the retina, resulting in severe loss of vision. Such growth is the hallmark of diabetic retinopathy, the leading cause of blindness among young people in developed countries. In one embodiment, the subject in need of treatment can be a mammal, such as a dog or a cat, preferably a human.

In one embodiment, the angiogenesis-dependent disease or disorder is rheumatoid arthritis. Rheumatoid arthritis (RA) is characterized by synovial tissue swelling, leucocyte ingress and angiogenesis, or new blood vessel growth. The disease is thought to occur as an immunological response to an as yet unidentified antigen. The expansion of the synovial lining of joints in rheumatoid arthritis (RA) and the subsequent invasion by the pannus of underlying cartilage and bone necessitate an increase in the vascular supply to the synovium, to cope with the increased requirement for oxygen and nutrients. Angiogenesis is now recognised as a key event in the formation and maintenance of the pannus in RA (Paleolog, E. M., 2002). Even in early RA, some of the earliest histological observations are blood vessels. A mononuclear infiltrate characterizes the synovial tissue along with a luxuriant vasculature. Angiogenesis is integral to formation of the inflammatory pannus and without angiogenesis; leukocyte ingress could not occur (Koch, A. E., 2000). Disruption of the formation of new blood vessels would not only prevent delivery of nutrients to the inflammatory site, it could also reduce joint swelling due to the additional activity of VEGF, a potent pro-angiogenic factor in RA, as a vascular permeability factor.

In one embodiment, the angiogenesis-dependent disease or disorder is Alzheimer's disease. Alzheimer's disease (AD) is the most common cause of dementia worldwide. AD is characterized by an excessive cerebral amyloid deposition leading to degeneration of neurons and eventually to dementia. The exact cause of AD is still unknown. It has been shown by epidemiological studies that long-term use of non-steroidal anti-inflammatory drugs, statins, histamine H2-receptor blockers, or calcium-channel blockers, all of which are cardiovascular drugs with anti-angiogenic effects, seem to prevent Alzheimer's disease and/or influence the outcome of AD patients. Therefore, it has been speculated that in AD angiogenesis in the brain vasculature may play an important role in AD. In Alzheimer's disease, the brain endothelium secretes the precursor substrate for the beta-amyloid plaque and a neurotoxic peptide that selectively kills cortical neurons. Moreover amyloid deposition in the vasculature leads to endothelial cell apoptosis and endothelial cell activation which leads to neovascularization. Vessel formation could be blocked by the VEGF antagonist SU 4312 as well as by statins, indicating that anti-angiogenesis strategies can interfere with endothelial cell activation in AD (Schultheiss C., el. al., 2006; Grammas P., et al., 1999) and can be used for preventing and/or treating AD.

In one embodiment, the angiogenesis-dependent disease or disorder is obesity. It has been shown that the angiogenesis inhibitor, TNP-470 was able to prevent diet-induced and genetic obesity in mice (Ebba Bråkenhielm et al., Circulation Research, 2004, 94:1579). TNP-470 reduced vascularity in the adipose tissue, thereby inhibiting the rate of growth of the adipose tissue and obesity development.

In one embodiment, the angiogenesis-dependent disease or disorder is endometriosis. Excessive endometrial angiogenesis is proposed as an important mechanism in the pathogenesis of endometriosis (Healy, D L., et al., 1998). The endometrium of patients with endometriosis shows enhanced endothelial cell proliferation. Moreover there is an elevated expression of the cell adhesion molecule integrin vβ3 in more blood vessels in the endometrium of women with endometriosis when compared with normal women. Strategies that inhibit angiogenesis can be used to treat endometriosis.

In one embodiment, the method of treating cancer is applicable to all carcinomas and sarcomas. Preferably, the method is applicable to cancers selected from the group consisting of papilloma/carcinoma, choriocarcinoma, endodermal sinus tumor, teratoma, adenoma/adenocarcinoma, melanoma, fibroma, lipoma, leiomyoma, rhabdomyoma, mesothelioma, angioma, osteoma, chondroma, glioma, lymphoma/leukemia, squamous cell carcinoma, small cell carcinoma, large cell undifferentiated carcinomas, basal cell carcinoma, sinonasal undifferentiated carcinoma, soft tissue sarcoma such as alveolar soft part sarcoma, angiosarcoma, dermatofibrosarcoma, desmoid tumor, desmoplastic small round cell tumor, extraskeletal chondrosarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, synovial sarcoma, and Askin's tumor, Ewing's sarcoma (primitive neuroectodermal tumor), malignant hemangioendothelioma, malignant schwannoma, osteosarcoma, and chondrosarcoma, that are found in the anus, bladder, bile duct, bone, brain, breast, cervix, colon/rectum, endometrium, esophagus, eye, gallbladder, head and neck, liver, kidney, larynx, lung, mediastinum (chest), mouth, ovaries, pancreas, penis, prostate, skin, small intestine, stomach, spinal marrow, tailbone, testicles, thyroid and uterus.

In one embodiment, the method of treating cancer is administered promptly after the detection of cancer. As used herein, promptness refers to any time within one month of positive laboratory test results confirming presence of cancer cells. Diagnosis and detection of cancer cells are well known to one skilled in the art. Laboratory tests can be in the form of histology and/or biomarkers that are known in the art but are not limited to these examples. Some laboratory tests include testing for cancer biomarkers such as cancer antigen (CA) 15-3, carcinoembryonic antigen (CEA) and HER-2 for breast cancer, human papillomavirus (HPV) E6 and E7 oncoproteins for cervical cancer, alpha-fetoprotein (AFP), AFP fractions L3, P4/5, and the +II band, and ultrasonography for hepatocellular carcinoma (HCC), prostate-specific antigen (PSA) for prostate cancer, and scrum CA-125 for ovarian and HCC. Tissue biopsy and histology are usually performed for confirmation and tissue typing of the original of cancer cell type.

In one embodiment, the invention provides a method of inhibiting metastasis of cancer in a subject diagnosed with cancer, the method comprising administering to a subject in need thereof, a therapeutically effective amount of a Psap protein or a vector comprising the nucleic acid encoding a Psap protein, and a pharmaceutically acceptable carrier. The subject can be diagnosed with a benign or malignant cancer. Psap protein can be administered to inhibit the establishment of secondary tumor from the initially discovered benign or malignant tumor.

In one embodiment, the subject is a mammal, such as a dog or a cat, preferably a human, who has previously been diagnosed with cancer. The cancer can be benign or malignant, and it may or may not have metastasized. As used herein, individual and subject are used interchangeably. In one embodiment, the method of treatment is administered promptly after the diagnosis of cancer.

In one embodiment, the invention provides a method of inhibiting recurrence of cancer in a subject diagnosed with cancer, the method comprises administering to a subject in need thereof, a therapeutically effective amount of a Psap protein or a vector comprising the nucleic acid encoding a Psap protein, and a pharmaceutically acceptable carrier. The subject can be diagnosed with a benign or malignant cancer. Psap protein can be administered to inhibit the re-growth of the primary tumor, development of tumors not related to the primary tumor, and/or establishment of secondary tumors from the initially discovered benign or malignant tumor.

In one embodiment, the invention provides a method for reducing the likelihood of cancer development in a subject, the method comprising administering to a subject in need thereof, a therapeutically effective amount of a Psap protein or a vector comprising the nucleic acid encoding a Psap protein, and a pharmaceutically acceptable carrier. In one embodiment, Psap protein can be administered to prevent the development of cancer, the development of metastasis, and/or the development of malignancy. For example, for a subject who is predisposed to, or at risk of developing cancer (e.g., family history of early onset colon-rectal cancer, previous exposure to hepatitis B or C, or the subject carries some gene mutations that are associated with certain cancer types, e.g., BRCA1 and BRCA2), Psap can be administered to the subject for preventing cancer development in this subject. For a subject who has been diagnosed with a benign tumor, the benign tumor can be removed by surgery. Psap can be administered to the subject for preventing any remaining existing benign tumor cells from developing into a malignant cancer as well as to prevent the development of metastasis. For a subject who has been diagnosed with a malignant tumor, Psap can be administered to the subject for preventing the malignant tumor from further metastasis.

Accordingly, in one embodiment, the invention provides a method for reducing the likelihood of the cancer development in a subject at risk of development of cancer, the method comprises administering to a subject in need thereof, a therapeutically effective amount of a Psap protein or a vector comprising the nucleic acid encoding a Psap protein, and a pharmaceutically acceptable carrier.

In another embodiment, the invention provides a method for reducing the likelihood of the development of cancer malignancy in a subject previously diagnosed with cancer, the method comprises administering to a subject in need thereof, a therapeutically effective amount of a Psap protein or a vector comprising the nucleic acid encoding a Psap protein, and a pharmaceutically acceptable carrier.

In another embodiment, the invention provides a method for reducing the likelihood of cancer metastasis in a subject previously diagnosed with cancer, the method comprises administering to a subject in need thereof, a therapeutically effective amount of a Psap protein or a vector comprising the nucleic acid encoding a Psap protein, and a pharmaceutically acceptable carrier.

In one embodiment, the administration is in conjunction with a p53 reactivation agent.

In one embodiment, the administration is in conjunction with chemotherapy, radiation therapy, and/or a cytostatic agent.

In one embodiment, the administration is in conjunction with an anti-VEGF agent or an anti-angiogenesis factor.

In one embodiment, in the methods described herein, the Psap protein can be the full-length human prosaposin isoform A preproprotein, isoform B preproprotein, isoform C preproprotein, the secreted forms of these splice variants, functional fragments and variants thereof that are greater than or equal to 10 amino acid residues, the functional fragments and variants that are greater than or equal to 10 amino acid residues of the isoforms, differentially glycosylated forms of the full-length splice variant Psap protein, secreted differentially glycosylated forms of the Psap protein, differentially glycosylated functional fragments with less than 524 amino acids and are greater than or equal to 10 amino acid residues, and/or differentially glycosylated functional variants thereof are greater than or equal to 10 amino acid residues. Examples of functional fragments of Psap include Saposin A: SLPCDICKDVVTAAGDMLKDNA-TEEEILVYLEKTCDWLPKPNMSASCKEIVDSYLPVIL-DIIKGE MSRPGEVCSALNLCES (SEQ. ID. No. 13); Saposin B: GDVCQDCIQMVTDIQTAVRTNST-FVQALVEHVKEECDRLGPGMADICKNYISQYSEIAI-QMMM HMQPKEICALVGFCDE (SEQ. ID. No. 14); Saposin C SDVYCEVCEFLVKEVTKLIDNNK-TEKEILDAFDKMCSKLPKSLSEECQEVVDTYGSSIL-SILLEEV SPELVCSMLHLCSG (SEQ. ID. No. 15); Saposin D DGGFCEVCKKLVGYLDRNLEKNSTKQEI- LAALEKGCSFLPDPYQKQCDQFVAEYEPVLIEILVEV MDPSFVCLKIGACPS (SEQ. ID. No. 16); SLPCDTCK-DVVTAAG (SEQ. ID. No. 18); VTAAGDMLKDNATEE (SEQ. ID. No. 19); NATEEEILVYLEKTC (SEQ. ID. No. 20); LEKTCDWLPKPNMSA (SEQ. ID. No. 21); PNM-SASCKEIVDSYL (SEQ. ID. No. 22); VDSYLPVIL-DIIKGE (SEQ. ID. No. 23); IIKGEMSRPGEVCSA (SEQ. ID. No. 24); SRPGEVCSALNLCES (SEQ. ID. No. 25); SLPCDICKDVVTAAGDMLKD (SEQ. ID. No. 26); VTAAGDMLKDNATEEETLVY (SEQ. ID. No. 27); NATEEETLVYLEKTCDWLPK (SEQ. ID. No. 28); LEK-TCDWLPKPNMSASCKEI (SEQ. ID. No. 29); PNM-SASCKEIVDSYLPVILD (SEQ. ID. No. 30); VDSYLPVILDIIKGEMSRPG (SEQ. ID. No. 31); and IIK-GEMSRPGEVCSALNLCES (SEQ. ID. No. 32). The functional fragments of saposin A, saposin B, saposin C, or saposin D, and the substantially similar functional fragments thereof described herein are capable of activating p53 and inducing Tsp-1 expression. Short peptides of at least 10 amino acid residues of saposin A, B, C, or D, and their peptidomimetics are also encompassed herein. Such a peptide mimetic can have different amino acids from the peptide that it mimics but retains the p53 and Tsp-1 activation and induction activity of the peptide that it mimics. Conservative amino acid substitution of these Psap proteins is also specifically contemplated. The methods for determining p53 activating activity and Tsp-1 expression induction activity are described herein and are also well known to one skilled in the art.

In one embodiment, in the methods described herein, the Psap protein is saposin A: SLPCDICKDVVTAAGDM-LKDNATEEEILVYLEKTCDWLPKPNMSASCK-EIVDSYLPVILDIIKGE MSRPGEVCSALNLCES (SEQ. ID. No. 13). In another embodiment, the Psap protein is a functional fragment of saposin A that is less than 81 amino acid residues. In one embodiment, the functional fragment of saposin A is any of SEQ. ID. No. 18-31. Conservative amino acid substitution of saposin A and of functional fragments thereof is also specifically contemplated. The functional fragments of saposin A and substantially similar fragments of saposin A induce p53 activation and/or Tsp-1 expression. In yet another embodiment, the Psap protein is a functional fragment of saposin A that comprises at least 10 amino acid residues. In another embodiment, the Psap protein is a peptidomimetic of a functional fragment of saposin A.

The inventors have found that two fragments of saposin A, a 20-mer LEKTCDWLPKPNMSASCKEI (SEQ. ID. No. 29) and a 13-mer CDWLPKPNMSASC (SEQ. ID. No. 37) were able to stimulate and induce Tsp-1 expression (see Example 15, FIGS. 21A and 22). It is specifically contemplated that smaller fragments of this 20-mer that contain sequence of the 13-mer (SEQ. ID. No. 37) will also function in this regard. It is also specifically contemplated that conservative substitution variant of these smaller fragments will also function in this regard. Compositions comprising the peptide consisting essentially of either SEQ. ID. No. 37, 29, or a conservative substitution variant thereof and mixtures of the two peptides (SEQ. ID. Nos. 37 and 29) or their respective conservative substitution variant thereof are also contemplated.

Accordingly, in one embodiment, provided herein is an isolated peptide consisting essentially of at least ten consecutive amino acid residues of the sequence LEKTCD-WLPKPNMSASCKEI (SEQ. ID. No. 29) or a conservative substitution variant thereof, wherein the peptide is flanked by 0, 1, 2, 3, or 4 amino acid residues on either terminus or both termini. In one embodiment, this at least ten consecutive amino acid residues should be derived from between the $31^{st}$ to the $50^{th}$ amino acid residues of saposin A (SEQ. ID. No. 13). In some embodiments, the isolated peptide consists essentially of at least 11, at least 12, at least 13, at least 14, at least 15, at least 16, at least 17, at least 18, or at least 19 consecutive amino acid residues from SEQ. ID. No. 29 or a conservative substitution variant thereof.

In another embodiment, described herein is an isolated peptide consisting of at least ten consecutive amino acid residues of the sequence LEKTCDWLPKPNMSASCKEI (SEQ. ID. No. 29) or a conservative substitution variant thereof, wherein the peptide is flanked by 0-4 amino acid residues on either terminus or both termini. In some embodiments, the isolated peptide consists of at least 11, at least 12, at least 13, at least 14, at least 15, at least 16, at least 17, at least 18, or at least 19 consecutive amino acid residues from SEQ. ID. No. 29 or a conservative substitution variant thereof.

Examples of isolated peptides consisting of at least ten consecutive amino acid residues of SEQ. ID. No. 13 include but are not limited to LEKTCDWLPK (SEQ. ID. No. 44), LEKTCDWLPKP (SEQ. ID. No. 45), LEKTCDWLPKPN (SEQ. ID. No. 46), LEKTCDWLPKPNM (SEQ. ID. No. 47), LEKTCDWLPKPNMS (SEQ. ID. No. 48), LEKTCD-WLPKPNMSA (SEQ. ID. No. 21), LEKTCDWLPKPNM-SAS (SEQ. ID. No. 49), LEKTCDWLPKPNMSASC (SEQ. ID. No. 43), LEKTCDWLPKPNMSASCK (SEQ. ID. No. 50), LEKTCDWLPKPNMSASCKE (SEQ. ID. No. 51), EKTCDWLPKPNMSASCKEI (SEQ. ID. No. 52), KTCD-WLPKPNMSASCKEI (SEQ. ID. No. 53), TCDWLPKP-NMSASCKET (SEQ. ID. No. 54), CDWLPKPNM-SASCKEI (SEQ. ID. No. 55), DWLPKPNMSASCKEI (SEQ. ID. No. 56), WLPKPNMSASCKEI (SEQ. ID. No. 57), LPKPNMSASCKEI (SEQ. ID. No. 58), PKPNM-SASCKEI (SEQ. ID. No. 59), KPNMSASCKEI (SEQ. ID. No. 60), PNMSASCKEI (SEQ. ID. No. 61), KTCDWLP-KPNMSASC (SEQ. ID. No. 62), TCDWLPKPNMSA (SEQ. ID. No. 63), and CDWLPKPNMSASCK (SEQ. ID. No. 64).

In one embodiment, provided herein is an isolated peptide consisting essentially of the sequence CDWLPKPNMSASC (SEQ. ID. No. 37) or a conservative substitution variant thereof, wherein the peptide is flanked by 0, 1, 2, 3, or 4 amino acid residues on either terminus or both termini.

In one embodiment, provided herein is an isolated peptide consisting of the sequence CDWLPKPNMSASC (SEQ. ID. No. 37) or a conservative substitution variant thereof, wherein the peptide is flanked by 0-4 amino acid residues on either terminus or both termini.

In another embodiment, provided herein is an isolated peptide consisting essentially of the sequence LEKTCD-WLPKPNMSASCKEI (SEQ. ID. No. 29) or a conservative substitution variant thereof, wherein the peptide is flanked by 0, 1, 2, 3, or 4 amino acid residues on either terminus or both termini.

In another embodiment, provided herein is an isolated peptide consisting of the sequence LEKTCDWLPKPNM-SASCKEI (SEQ. ID. No. 29) or a conservative substitution variant thereof, wherein the peptide is flanked by 0, 1, 2, 3, or 4 amino acid residues on either terminus or both termini.

In some embodiments, any of the known 20 amino acid residues can flank the peptides SEQ. ID. No. 37 and 29. Examples of some conservative substitution variants include but are not limited to LDKTCDWLPKPNMSASCKDI (SEQ. ID. No. 65), LEKTCDWIPKPNMSASCKDI (SEQ. ID. No. 66), LEKTCDWLPKPNMSASCREI (SEQ. ID. No.

67), LERTCDWIPKPNMSASCKDI (SEQ. ID. No. 68), CDWIPRPNMSASC (SEQ. ID. No. 69), CEWLPRPNM-SASC (SEQ. ID. No. 70),CDWIPKPNMSASC (SEQ. ID. No. 71), CEWLPKPNMSGSC (SEQ. ID. No. 72), CEWLPHPNMSASC (SEQ. ID. No. 73), PHP-NMSGSCKEL (SEQ. ID. No. 74), RPNMSASCREI (SEQ. ID. No. 75), PNMSASCREI (SEQ. ID. No. 76), KTCE-WLPHPNMSGSC (SEQ. ID. No. 77), TCDWIPKPNMSA (SEQ. ID. No. 78), CDWIPKPNMSASCR (SEQ. ID. No. 79), CDWIPKPNMSASCKDT (SEQ. ID. No. 80), and LDKTCDWLPRPNMS (SEQ. ID. No. 81) wherein the conservative substitutions are shown in bold.

In some embodiments, the isolated peptides are capable of activating p53 and inducing Tsp-1 expression.

In one embodiment, the isolated peptide is fused or conjugated to a therapeutic molecule described herein.

In some embodiments, any of the amino acid residues in the peptides SEQ. ID. No. 37 and 29 can be conservatively substituted.

In some embodiments, the isolated conservative substitution variant peptide has at least 1, 2, 3, 4, or 5 conservative amino acid substitutions. In other embodiments, the isolated conservative substitution variant peptide has no more than 1, 2, 3, 4, or 5 conservative amino acid substitutions. In another embodiment, the isolated conservative substitution variant peptide does not have any conservative amino acid substitution.

In one embodiment, provided herein is an isolated chimeric polypeptide comprising a first portion and a second portion, wherein the first portion is a peptide consisting essentially of the sequence CDWLPKPNMSASC (SEQ. ID. No. 37), LEKTCDWLPKPNMSASCKEI (SEQ. ID. No. 29) or a conservative substitution variant thereof, or a peptide consisting essentially of at least ten consecutive amino acid residues of the sequence LEKTCDWLPKPNMSASCKEI (SEQ. ID. No. 29) or a conservative substitution variant thereof, wherein the peptide is flanked by 0, 1, 2, 3, or 4 amino acid residues on either terminus or both termini, and wherein the second portion is not a Psap protein or fragment. In some embodiments, the peptide consists essentially of at least 11, at least 12, at least 13, at least 14, at least 15, at least 16, at least 17, at least 18, or at least 19 consecutive amino acid residues from SEQ. ID. No. 29 or a conservative substitution variant thereof.

In another embodiment, provided herein is an isolated chimeric polypeptide comprising a first portion and a second portion, wherein the first portion is an isolated peptide consisting of the sequence CDWLPKPNMSASC (SEQ. ID. No. 37), LEKTCDWLPKPNMSASCKEI (SEQ. ID. No. 29) or a conservative substitution variant thereof, or a peptide consisting of at least ten consecutive amino acid residues of the sequence LEKTCDWLPKPNMSASCKEI (SEQ. ID. No. 29) or a conservative substitution variant thereof, wherein the peptide is flanked by 0, 1, 2, 3, or 4 amino acid residues on either terminus or both termini, and wherein the second portion is not a Psap protein. In some embodiments, the peptide consists of at least 11, at least 12, at least 13, at least 14, at least 15, at least 16, at least 17, at least 18, or at least 19 consecutive amino acid residues from SEQ. ID. No. 29 or a conservative substitution variant thereof.

In one embodiment of the isolated chimeric polypeptide, the second portion comprises an amino acid sequence or a polymer that enhances the serum half life of the first portion.

In one embodiment of the isolated chimeric polypeptide, the second portion is a therapeutic molecule.

In one embodiment, described herein is a composition comprising a peptide consisting of the sequence CDWLP-KPNMSASC (SEQ. ID. No. 37) or a conservative substitution variant thereof, and a pharmaceutically acceptable carrier. In another embodiment, the invention also provides a composition comprising a peptide consisting essentially of the sequence CDWLPKPNMSASC (SEQ. ID. No. 37) or a conservative substitution variant thereof and a pharmaceutically acceptable carrier. The peptide is derived from saposin A. In one embodiment, the essential sequence sufficient to stimulate Tsp-1 expression is SEQ. ID. No. 37.

In one embodiment, provided herein a composition comprising a peptide consisting of the sequence LEKTCDWLP-KPNMSASCKEI (SEQ. ID. No. 29) or a conservative substitution variant thereof, and a pharmaceutically acceptable carrier. In another embodiment, the invention also provides a composition comprising a peptide consisting essentially of the sequence LEKTCDWLPKPNMSASCKEI (SEQ. ID. No. 29) or a conservative substitution variant thereof and a pharmaceutically acceptable carrier. The peptide can be derived from saposin A.

In some aspects, the peptide consists of at least 10 amino acid residues derived form SEQ. ID. Nos. 37 and 29, e.g., DWLPKPNMSA (SEQ. ID. No. 38), CDWLPKPNMS (SEQ. ID. No. 39) or WLPKPNMSAS (SEQ. ID. No. 40) but is not saposin A (SEQ. ID. No. 13).

In some embodiments, the peptides described herein have conservative amino acid substitution for one, two, three, four or up to five amino acid residues.

In one embodiment, provided herein is a composition comprising a peptide consisting of the sequence CDWLP-KPNMSASC (SEQ. ID. No. 37), LEKTCDWLPKPNM-SASCKEI (SEQ. ID. No. 29) or a conservative substitution variant thereof, and a pharmaceutically acceptable carrier, wherein the peptide is flanked by 0, 1, 2, 3, or 4 amino acid residues on either terminus or both termini.

In one embodiment, described herein is a composition comprising a peptide and a pharmaceutically acceptable carrier, wherein the peptide consists essentially of the sequence CDWLPKPNMSASC (SEQ. ID. No. 37), LEK-TCDWLPKPNMSASCKEI (SEQ. ID. No. 29) or a conservative substitution variant thereof, or the peptide consists essentially of at least ten consecutive amino acid residues of the sequence LEKTCDWLPKPNMSASCKEI (SEQ. ID. No. 29) or a conservative substitution variant thereof, wherein the peptide is flanked by 0, 1, 2, 3, or 4 amino acid residues on either terminus or both termini.

In one embodiment, described herein is a composition comprising a peptide and a pharmaceutically acceptable carrier, wherein the peptide consists of the sequence CDWLPKPNMSASC (SEQ. ID. No. 37), LEKTCDWLP-KPNMSASCKEI (SEQ. ID. No. 29) or a conservative substitution variant thereof, or the peptide consists of at least ten consecutive amino acid residues of the sequence LEK-TCDWLPKPNMSASCKEI (SEQ. ID. No. 29) or a conservative substitution variant thereof, wherein the peptide is flanked by 0, 1, 2, 3, or 4 amino acid residues on either terminus or both termini.

In another embodiment, described herein is a composition comprising a chimeric polypeptide, and a pharmaceutically acceptable carrier, wherein the chimeric polypeptide comprises a first portion and a second portion, wherein the first portion comprises a peptide consisting essentially of the sequence CDWLPKPNMSASC (SEQ. ID. No. 37), LEK-TCDWLPKPNMSASCKEI (SEQ. ID. No. 29) or a conservative substitution variant thereof, or the first portion of the chimeric polypeptide consists essentially of at least ten consecutive amino acid residues of the sequence LEKTCD-WLPKPNMSASCKEI (SEQ. ID. No. 29) or a conservative substitution variant thereof, wherein the peptide is flanked by 0, 1, 2, 3, or 4 amino acid residues on either terminus or both termini, and wherein the second portion of the chimeric polypeptide is not a Psap protein.

In another embodiment, provided herein is a composition comprising a chimeric polypeptide and a pharmaceutically acceptable carrier, wherein the chimeric polypeptide comprises a first portion and a second portion, wherein the first portion of the chimeric polypeptide is a peptide consisting of the sequence CDWLPKPNMSASC (SEQ. ID. No. 37), LEKTCDWLPKPNMSASCKEI (SEQ. ID. No. 29) or a conservative substitution variant thereof, or the first portion of the chimeric polypeptide consists of at least ten consecutive amino acid residues of the sequence LEKTCDWLPKPNMSASCKEI (SEQ. ID. No. 29) or a conservative substitution variant thereof, wherein the peptide is flanked by 0, 1, 2, 3, or 4 amino acid residues on either terminus or both termini, and wherein the second portion of the chimeric polypeptide is not a Psap protein.

In some embodiments of the compositions described herein, the peptide consists essentially of at least 11, at least 12, at least 13, at least 14, at least 15, at least 16, at least 17, at least 18, or at least 19 consecutive amino acid residues from SEQ. ID. No. 29 or a conservative substitution variant thereof.

In other embodiments of the compositions described herein, the peptide consists of at least 11, at least 12, at least 13, at least 14, at least 15, at least 16, at least 17, at least 18, or at least 19 consecutive amino acid residues from SEQ. ID. No. 29 or a conservative substitution variant thereof.

In some embodiments, the compositions comprise a plurality of peptides or fragments, wherein the peptides are not identical. In one embodiment, the plurality of peptides is derived from saposin A and the peptides are greater that or equal to 10 amino acid residues long but is not saposin A (SEQ. ID. No. 13). For example, a composition can comprise of CDWLPKPNMSASC (SEQ. ID. No. 37) and WLPKPNMSAS (SEQ. ID. No. 40); CDWLPKPNMSASC (SEQ. ID. No. 37) and LEKTCDWLPKPNMSA (SEQ. ID. No. 21).

In some embodiments, the compositions comprise a multimer of peptides or fragments, wherein the peptides are identical and wherein the plurality of peptides is derived from saposin A. For example, a plurality of CDWLPKPNMSASC (SEQ. ID. No. 37) only or LEKTCDWLPKPNMSASCKEI (SEQ. ID. No. 29) only.

In some embodiments, the multimer of peptides are concatamerically linked. The physical joining of a plurality of peptides by a molecular linker results in an oligomer of peptides. The composition can comprise an oligomeric peptide that is a dimer of two peptides, a trimer of three peptides, a tetramer of four peptides, or a pentamer of five peptides. In a preferred embodiment, the oligomeric peptide is a dimer of two peptides and/or a trimer of three peptides. In one embodiment, the oligomeric peptide is a homo-oligomeric peptide, comprising identical peptides according to the invention disclosed herein. Hetero-oligomeric peptides comprising different peptides, fragments, and/or variants thereof that are greater than or equal to 10 amino acid residues are also contemplated.

In one embodiment, the molecular linker that joins the peptides to form an oligomeric peptide can be a peptide linker molecule or a chemical linker. The peptide linker molecule can comprise e.g., at least 2, 3, 4, 5, 6, 7, 8, 9, 10 or more amino acids residues and preferably less that 50 amino acids residues.

In one embodiment, the composition can also include the monomeric peptide along with oligomeric peptide. It is contemplated that all possible combinations of monomeric, dimeric, trimeric, tetrameric, and pentameric peptides, and homo-oligomeric peptides as well as hetero-oligomeric peptides can be included in the compositions described herein.

In one embodiment, the molecular linker used for forming the oligomeric polypeptides is a peptide linker molecule. In one embodiment, the peptide linking molecule comprises at least one amino acid residue which links at least two peptides according to the invention. The peptide linker comprises, e.g., at least 2, 3, 4, 5, 6, 7, 8, 9, 10 or more amino acids residues and preferably less that 50 amino acids residues. The peptide linking molecule can couple polypeptides or proteins covalently or non-covalently. Typical amino acid residues used for linking are glycine, tyrosine, cysteine, lysine, glutamic and aspartic acid, or the like. A peptide linker is attached on its amino-terminal end to one peptide, polypeptide or polypeptide domain (e.g., a C-peptide) and on its carboxyl-terminal end to another peptide, polypeptide or polypeptide domain (again, e.g., a C-peptide). Examples of useful linker peptides include, but are not limited to, glycine polymers ((G)n) including glycine-serine and glycine-alanine polymers (e.g., a (Gly4Ser)n repeat where n=1-8, preferably, n=3, 4, 5, or 6). Other examples of peptide linker molecules are described in U.S. Pat. No. 5,856,456 and are hereby incorporated by reference.

In another embodiment, the molecular linker is a chemical linker such as linkages by disulfide bonds between cysteine amino acid residues or by chemical bridges formed by amine crosslinkers, for example, glutaraldehyde, bis(imido ester), bis(succinimidyl esters), diisocyanates and diacid chlorides. Extensive data on chemical cross-linking agents can be found at INVITROGEN's Molecular Probe under section 5.2.

In one embodiment, the oligomeric peptide can be made by linking individual isolated peptides. The individual peptides can be made by chemical methods known in the art or by recombinant methods also known in the art. For recombinant methods, the DNA coding sequence of a peptide can be made by amplification using the polymerase chain reaction (PCR). Specially designed PCR primers that incorporate restriction enzyme digestion sites and/or extra spacer or tag amino acid residues can be used to facilitate DNA ligation, recombinant protein expression, and protein purification. In order to facilitate linking of the peptides together, additional amino acid residues can be added, by way of the DNA coding sequence, to the peptides. For example, the thiol-group containing amino acid cysteine and the amine-group containing amino acid lysine can be added. The thiol-group and the amine group provide reactive groups useful for cross-kinking reactions. In one embodiment, the additional amino acids are added at the ends of the peptides. The extra amino acids can be engineered into the coding sequence using standard recombinant molecular biology methods that are known in the art. In addition, extra amino acids that constitute a tag can be added to facilitate peptide expression and purifications. Examples of such tags include the thioredoxin first 105 amino acids, the tandem six histidine-tag, HA-tag, and the flag-tag. An example of such a peptide with terminally added cysteine groups and histidine (6x) purification tag.

The DNA coding sequences of the different individual peptides can be ligated into expression vectors which are then transfected into appropriate expression host cells and induced to express the recombinant peptide. Subsequently, the expressed recombinant peptide can be purified and then used in cross-linking to form the dimeric, trimer, tetrameric, or pentameric oligomeric peptide compositions described herein by methods known in the art.

In the instance where the peptide contains no available reactive thiol-group for chemical cross-linking, several methods are available for introducing thiol-groups into proteins and peptides, including but not limited to the reduction of intrinsic disulfides, as well as the conversion of amine or carboxylic acid groups to thiol group. Such methods are known to one skilled in the art and there are many commercial kits for that purpose, such as from Molecular Probes division of Invitrogen Inc. and Pierce Biotechnology.

In another embodiment, the oligomeric peptide can be made by recombinant methods without the need for linking individual isolated peptides by chemical cross linking. Recombinant methods can be use to synthesize a single coding DNA sequence that comprises the several coding sequences of a peptide. For example, two and up to five peptide coding sequences are ligated in tandem. Additional amino acid coding sequences, coding for, e.g., 2-10 amino acids, can be added between each pair of adjoining peptides as spacer sequences. When the single coding DNA is transcribed and translated, the expressed polypeptide can contain tandem repeats of peptides, each separated by, e.g., 2-10 extra amino acids. Typical amino acid residues used for spacing sequences are glycine, tyrosine, cysteine, lysine, proline, glutamic and aspartic acid, or the like. In a preferred embodiment, the oligomeric peptide is expressed in an amino-carboxyl-amino-carboxyl tandem configuration. Similarly, the oligomeric peptide synthesized can include a tag amino acid sequence for facilitating oligomeric peptide expression, identification and purifications. Such recombinant methods are well known to one skilled in the art.

In some embodiments, the complex of oligomeric peptides or monomeric peptides are modified by $NH_2$-terminal acylation, e.g., acetylation, or thioglycolic acid amidation, by terminal-carboxylamidation, e.g., with ammonia, methylamine, and the like terminal modifications that are known in the art. Terminal modifications are useful to reduce susceptibility by proteinase digestion, and therefore serve to prolong half life of the peptides in solutions, particularly biological fluids where proteases may be present.

In one embodiment, the peptide described herein, e.g., LEKTCDWLPKPNMSASCKEI (SEQ. ID. No. 29), CDWLPKPNMSASC (SEQ. ID. No. 37) or a conservative substitution variant thereof, is linked or fused to an amino acid sequence or a polymer that enhances the serum half life.

In one embodiment, the peptide described herein, e.g., LEKTCDWLPKPNMSASCKEI (SEQ. ID. No. 29), CDWLPKPNMSASC (SEQ. ID. No. 37) or a conservative substitution variant thereof, is linked or fused to an amino acid sequence that facilitates protein expression and/or purification of the first portion.

In one embodiment, the peptide described herein, e.g., LEKTCDWLPKPNMSASCKEI (SEQ. ID. No. 29), CDWLPKPNMSASC (SEQ. ID. No. 37) or a conservative substitution variant thereof, is linked or fused to a therapeutic molecule.

Methods of linking a peptide to an amino acid sequence or a polymer can be by chemical cross-linking or by recombinant methods which are well known in the art and are described herein.

In one embodiment, the peptide described herein, e.g., LEKTCDWLPKPNMSASCKEI (SEQ. ID. No. 29), CDWLPKPNMSASC (SEQ. ID. No. 37) or a conservative substitution variant thereof, is a cyclic peptide. Cyclic peptides (or cyclic proteins) are polypeptide chains whose amino and carboxyl termini are they linked together with a peptide bond or other covalent bond, forming a circular chain. In one embodiment, the peptide contains amino and carboxyl terminal cysteine amino acid residues. Cysteines facilitate S—S disulphide bond formation. In one embodiment, the peptide contains additional cysteine amino acid residues, wherein the cysteine amino acid residues are near the termini but not necessarily at the very end. In some embodiments, the cysteine amino acid residues are within the five amino acid residues at the termini of the peptide. e.g., LEKTCDWLPKPNMSACA (SEQ. ID. No. 43) or a conservative substitution variant thereof. Methods of design and synthesis of cyclic peptides are well known in the art, e.g., as described in U.S. Pat. Nos. 5,596,078; 5,990,273; 7,589,170 and U.S. Patent Application No. 20080287649. A skilled artisan would be readily able to modify and apply the methods and techniques for the synthesis of a cyclic saposin A peptide described herein.

In one embodiment, the peptide described herein, whether monomeric, oligomeric or cyclic, is PEGylated. PEGylation is the process of covalent attachment of Polyethylene glycol polymer chains to another molecule, normally a drug or therapeutic protein. PEGylation is routinely achieved by incubation of a reactive derivative of PEG with the target macromolecule. The covalent attachment of PEG to a drug or therapeutic protein can "mask" the agent from the host's immune system (reduced immunogenicity and antigenicity), and increase the hydrodynamic size (size in solution) of the agent which prolongs its circulatory time by reducing renal clearance. PEGylation can also provide water solubility to hydrophobic drugs and proteins. PEGylation, by increasing the molecular weight of a molecule, can impart several significant pharmacological advantages over the unmodified form, such as: improved drug solubility, reduced dosage frequency, without diminished efficacy with potentially reduced toxicity, extended circulating life, increased drug stability, and enhanced protection from proteolytic degradation. In addition, PEGylated drugs are have wider opportunities for new delivery formats and dosing regimens. Methods of PEGylating molecules, proteins and peptides are well known in the art, e.g., as described in U.S. Pat. Nos. 5,766,897; 7,610,156; 7,256,258 and the International Application No. WO/1998/032466.

In some aspects, the composition comprising the various peptides described herein are useful for the following: (1) the treatment of an angiogenesis-dependent disease or disorder; (2) the treatment of cancer; (3) the inhibition of the recurrence of an angiogenesis-dependent disease or disorder; (4) the inhibition of the recurrence of cancer; (5) the inhibition of metastasis of cancer in a subject diagnosed with cancer; (6) the inhibition of recurrence of cancer in a subject diagnosed with cancer; (7) the prevention of cancer development in a subject at risk of development of cancer; (8) the prevention of cancer metastasis in a subject previously diagnosed with cancer; and (9) the prevention of the development of cancer malignancy in a subject previously diagnosed with cancer.

Accordingly, provided herein is a method of treating an angiogenesis-dependent disease or disorder comprising administering to a subject in need thereof a therapeutically effective amount of a composition comprising a peptide consisting essentially of the sequence CDWLPKPNMSASC (SEQ. ID. No. 37) or a conservative substitution variant thereof and a pharmaceutically acceptable carrier.

In another embodiment, provided herein is a method of treating an angiogenesis-dependent disease or disorder comprising administering to a subject in need thereof a therapeutically effective amount of a composition comprising a peptide consisting of the sequence CDWLPKPNMSASC (SEQ. ID. No. 37) or a conservative substitution variant thereof and a pharmaceutically acceptable carrier.

In another embodiment, provided herein is a method of treating an angiogenesis-dependent disease or disorder comprising administering to a subject in need thereof a therapeutically effective amount of a composition comprising a peptide or a chimeric polypeptide, and a pharmaceutically acceptable carrier, wherein the peptide consists essentially of the sequence CDWLPKPNMSASC (SEQ. ID. No. 37), LEKTCDWLPKPNMSASCKEI (SEQ. ID. No. 29) or a conservative substitution variant thereof, or the peptide consists essentially of at least ten consecutive amino acid residues of the sequence LEKTCDWLPKPNMSASCKEI (SEQ. ID. No. 29) or conservative substitution variant thereof, wherein the peptide is flanked by 0, 1, 2, 3, or 4 amino acid residues on either terminus or both termini, wherein the chimeric polypeptide comprises a first portion and a second portion, wherein the first portion of the chimeric polypeptide is a peptide consisting essentially of the sequence CDWLPKPNMSASC (SEQ. ID. No. 37), LEKTCDWLPKPNMSASCKEI (SEQ. ID. No. 29) or a conservative substitution variant thereof, or the peptide consisting essentially of at least ten consecutive amino acid residues of the sequence LEKTCDWLPKPNMSASCKEI (SEQ. ID. No. 29) or a conservative substitution variant thereof, wherein the peptide is flanked by 0, 1, 2, 3, or 4 amino acid residues on either terminus or both termini, and wherein the second portion of the chimeric polypeptide is not a Psap protein.

In one embodiment, provided herein is a method of treating psoriasis, the method comprises administering to a subject in need thereof a therapeutically effective amount of a composition comprising a peptide consisting essentially of the sequence CDWLPKPNMSASC (SEQ. ID. No. 37) or a conservative substitution variant thereof, and a pharmaceutically acceptable carrier.

In another embodiment, provided herein is a method of treating psoriasis, the method comprises administering to a subject in need thereof a therapeutically effective amount of a composition comprising a peptide consisting of the sequence CDWLPKPNMSASC (SEQ. ID. No. 37) or a conservative substitution variant thereof, and a pharmaceutically acceptable carrier.

In another embodiment, provided herein is a method of treating psoriasis, the method comprises administering to a subject in need thereof a therapeutically effective amount of a composition comprising a peptide or a chimeric polypeptide, and a pharmaceutically acceptable carrier, wherein the peptide consists essentially of the sequence CDWLPKPNMSASC (SEQ. ID. No. 37), LEKTCDWLPKPNMSASCKEI (SEQ. ID. No. 29) or a conservative substitution variant thereof, wherein the peptide is flanked by 0, 1, 2, 3, or 4 amino acid residues on either terminus or both termini, wherein the chimeric polypeptide comprises a first portion and a second portion, wherein the first portion of the chimeric polypeptide is a peptide consisting essentially of the sequence CDWLPKPNMSASC (SEQ. ID. No. 37) LEKTCDWLPKPNMSASCKEI (SEQ. ID. No. 29) or a conservative substitution variant thereof, wherein the peptide is flanked by 0, 1, 2, 3, or 4 amino acid residues on either terminus or both termini, and wherein the second portion of the chimeric polypeptide is not a Psap protein.

In one embodiment, provided herein is a method of inhibiting the recurrence of an angiogenesis-dependent disease or disorder, the method comprising administering to a subject in need thereof a therapeutically effective amount of a composition comprising a peptide consisting essentially of the sequence CDWLPKPNMSASC (SEQ. ID. No. 37) or a conservative substitution variant thereof, and a pharmaceutically acceptable carrier.

In another embodiment, provided herein is a method of inhibiting the recurrence of an angiogenesis-dependent disease or disorder, the method comprising administering to a subject in need thereof a therapeutically effective amount of a composition comprising a peptide consisting of the sequence CDWLPKPNMSASC (SEQ. ID. No. 37) or a conservative substitution variant thereof, and a pharmaceutically acceptable carrier.

In another embodiment, provided herein is a method of inhibiting the recurrence of an angiogenesis-dependent disease or disorder, the method comprising administering to a subject in need thereof a therapeutically effective amount of a composition comprising a peptide or a chimeric polypeptide, and a pharmaceutically acceptable carrier, wherein the peptide consists essentially of the sequence CDWLPKPNMSASC (SEQ. ID. No. 37), LEKTCDWLPKPNMSASCKEI (SEQ. ID. No. 29) or a conservative substitution variant thereof, wherein the peptide is flanked by 0, 1, 2, 3, or 4 amino acid residues on either terminus or both termini, wherein the chimeric polypeptide comprises a first portion and a second portion, wherein the first portion of the chimeric polypeptide is a peptide consisting essentially of the sequence CDWLPKPNMSASC (SEQ. ID. No. 37), LEKTCDWLPKPNMSASCKEI (SEQ. ID. No. 29) or a conservative substitution variant thereof, wherein the peptide is flanked by 0, 1, 2, 3, or 4 amino acid residues on either terminus or both termini, and wherein the second portion of the chimeric polypeptide is not a Psap protein.

In one embodiment, provided herein is a method of inhibiting metastasis of cancer in a subject diagnosed with cancer, the method comprising administering to the subject in need thereof a therapeutically effective amount of a composition comprising a peptide consisting essentially of the sequence CDWLPKPNMSASC (SEQ. ID. No. 37) or a conservative substitution variant thereof, and a pharmaceutically acceptable carrier.

In another embodiment, provided herein is a method of inhibiting metastasis of cancer in a subject diagnosed with cancer, the method comprising administering to the subject in need thereof a therapeutically effective amount of a composition comprising a peptide consisting of the sequence CDWLPKPNMSASC (SEQ. ID. No. 37) and a pharmaceutically acceptable carrier.

In another embodiment, provided herein is a method of inhibiting metastasis of cancer in a subject diagnosed with cancer, the method comprising administering to the subject in need thereof a therapeutically effective amount of a composition comprising a peptide or a chimeric polypeptide, and a pharmaceutically acceptable carrier, wherein the peptide consists essentially of the sequence CDWLPKPNMSASC (SEQ. ID. No. 37), LEKTCDWLPKPNMSASCKEI (SEQ. ID. No. 29) or a conservative substitution variant thereof, wherein the peptide is flanked by 0-4 amino acid residues on either terminus or both termini, wherein the chimeric polypeptide comprises a first portion and a second portion, the first portion of the chimeric polypeptide is a peptide consisting essentially of the sequence CDWLPKPNMSASC (SEQ. ID. No. 37), LEKTCDWLPKPNMSASCKEI (SEQ. ID. No. 29) or a conservative substitution variant thereof, wherein the peptide is flanked by 0-4 amino acid residues on either terminus or both termini, and wherein the second portion of the chimeric polypeptide is not a Psap protein.

In one embodiment, provided herein is a method of inhibiting recurrence of cancer in a subject diagnosed with cancer, the method comprises administering to the subject in need thereof a therapeutically effective amount of a composition comprising a peptide consisting essentially of the sequence CDWLPKPNMSASC (SEQ. ID. No. 37) or a conservative substitution variant thereof, and a pharmaceutically acceptable carrier.

In another embodiment, provided herein is a method of inhibiting recurrence of cancer in a subject diagnosed with cancer, the method comprises administering to the subject in need thereof a therapeutically effective amount of a composition comprising a peptide consisting of the sequence CDWLPKPNMSASC (SEQ. ID. No. 37) or a conservative substitution variant thereof, and a pharmaceutically acceptable carrier.

In another embodiment, provided herein is a method of inhibiting recurrence of cancer in a subject diagnosed with cancer, the method comprises administering to a subject in need thereof a therapeutically effective amount of a composition comprising a peptide or a chimeric polypeptide, and a pharmaceutically acceptable carrier, wherein the peptide consists essentially of the sequence CDWLPKPNMSASC (SEQ. ID. No. 37), LEKTCDWLPKPNMSASCKEI (SEQ. ID. No. 29) or a conservative substitution variant thereof, wherein the peptide is flanked by 0, 1, 2, 3, or 4 amino acid residues on either terminus or both termini, wherein the chimeric polypeptide comprises a first portion and a second portion, wherein the first portion of the chimeric polypeptide is a peptide consisting essentially of the sequence CDWLPKPNMSASC (SEQ. ID. No. 37), LEKTCDWLPKPNMSASCKEI (SEQ. ID. No. 29) or a conservative substitution variant thereof, wherein the peptide is flanked by 0, 1, 2, 3, or 4 amino acid residues on either terminus or both termini, and wherein the second portion of the chimeric polypeptide is not a Psap protein.

In one embodiment, provided herein is a method for reducing the likelihood of cancer development in a subject at risk of development of cancer, the method comprising administering to a subject in need thereof a therapeutically effective amount of a composition comprising a peptide consisting essentially of the sequence CDWLPKPNMSASC (SEQ. ID. No. 37) or a conservative substitution variant thereof, and a pharmaceutically acceptable carrier.

In another embodiment, provided herein is a method for reducing the likelihood of cancer development in a subject at risk of development of cancer, the method comprising administering to a subject in need thereof a therapeutically effective amount of a composition comprising a peptide consisting of the sequence CDWLPKPNMSASC (SEQ. ID. No. 37) or a conservative substitution variant thereof, and a pharmaceutically acceptable carrier.

In another embodiment, provided herein is a method for reducing the likelihood of cancer development in a subject at risk of development of cancer, the method comprising administering to a subject in need thereof a therapeutically effective amount of a composition comprising a peptide or a chimeric polypeptide, and a pharmaceutically acceptable carrier, wherein the peptide consists essentially of the sequence CDWLPKPNMSASC (SEQ. ID. No. 37), LEKTCDWLPKPNMSASCKEI (SEQ. ID. No. 29) or a conservative substitution variant thereof, wherein the peptide is flanked by 0, 1, 2, 3, or 4 amino acid residues on either terminus or both termini, wherein the chimeric polypeptide comprises a first portion and a second portion, wherein the first portion of the chimeric polypeptide is a peptide consisting essentially of the sequence CDWLPKPNMSASC (SEQ. ID. No. 37), LEKTCDWLPKPNMSASCKEI (SEQ. ID. No. 29) or a conservative substitution variant thereof, wherein the peptide is flanked by 0, 1, 2, 3, or 4 amino acid residues on either terminus or both termini, and wherein the second portion of the chimeric polypeptide is not a Psap protein.

In one embodiment, provided herein is a method for reducing the likelihood of cancer metastasis in a subject previously diagnosed with cancer, the method comprising administering to a subject in need thereof a therapeutically effective amount of a composition comprising a peptide consisting essentially of the sequence CDWLPKPNMSASC (SEQ. ID. No. 37) or a conservative substitution variant thereof, and a pharmaceutically acceptable carrier.

In another embodiment, provided herein is a method for reducing the likelihood of cancer metastasis in a subject previously diagnosed with cancer, the method comprising administering to a subject in need thereof a therapeutically effective amount of a composition comprising a peptide consisting of the sequence CDWLPKPNMSASC (SEQ. ID. No. 37) or a conservative substitution variant thereof, and a pharmaceutically acceptable carrier.

In another embodiment, provided herein is a method for reducing the likelihood of cancer metastasis in a subject previously diagnosed with cancer, the method comprising administering to a subject in need thereof a therapeutically effective amount of a composition comprising a peptide or a chimeric polypeptide, and a pharmaceutically acceptable carrier, wherein the peptide consists essentially of the sequence CDWLPKPNMSASC (SEQ. ID. No. 37), LEKTCDWLPKPNMSASCKEI (SEQ. ID. No. 29) or a conservative substitution variant thereof, wherein the peptide is flanked by 0, 1, 2, 3, or 4 amino acid residues on either terminus or both termini, wherein the chimeric polypeptide comprises a first portion and a second portion, wherein the first portion of the chimeric polypeptide is a peptide consisting essentially of the sequence CDWLPKPNMSASC (SEQ. ID. No. 37), LEKTCDWLPKPNMSASCKEI (SEQ. ID. No. 29) or a conservative substitution variant thereof, wherein the peptide is flanked by 0, 1, 2, 3, or 4 amino acid residues on either terminus or both termini, and wherein the second portion of the chimeric polypeptide is not a Psap protein.

In one embodiment, provided herein is a method for reducing the likelihood of the development of cancer malignancy in a subject previously diagnosed with cancer, the method comprising administering to a subject in need thereof a therapeutically effective amount of a composition comprising a peptide consisting essentially of the sequence CDWLPKPNMSASC (SEQ. ID. No. 37) or a conservative substitution variant thereof, and a pharmaceutically acceptable carrier.

In another embodiment, provided herein is a method for reducing the likelihood of the development of cancer malignancy in a subject previously diagnosed with cancer, the method comprising administering to a subject in need thereof a therapeutically effective amount of a composition comprising a peptide consisting of the sequence CDWLPKPNMSASC (SEQ. ID. No. 37) or a conservative substitution variant thereof, and a pharmaceutically acceptable carrier.

In another embodiment, provided herein is a method for reducing the likelihood of the development of cancer malignancy in a subject previously diagnosed with cancer, the method comprising administering to a subject in need thereof a therapeutically effective amount of a composition comprising a peptide or a chimeric polypeptide, and a pharmaceutically acceptable carrier, wherein the peptide consists essentially of the sequence CDWLPKPNMSASC (SEQ. ID. No. 37), LEKTCDWLPKPNMSASCKEI (SEQ. ID. No. 29) or a conservative substitution variant thereof, wherein the peptide is flanked by 0, 1, 2, 3, or 4 amino acid residues on either terminus or both termini, wherein the chimeric polypeptide comprises a first portion and a second portion, wherein the first portion of the chimeric polypeptide is a peptide consisting essentially of the sequence CDWLP-KPNMSASC (SEQ. ID. No. 37), LEKTCDWLPKPNM-SASCKEI (SEQ. ID. No. 29) or a conservative substitution variant thereof, wherein the peptide is flanked by 0, 1, 2, 3, or 4 amino acid residues on either terminus or both termini, and wherein the second portion of the chimeric polypeptide is not a Psap protein.

In other embodiments, in the methods described herein, the composition comprises of a peptide or a chimeric polypeptide, and a pharmaceutically acceptable carrier, wherein the peptide consists of the sequence CDWLPKP-NMSASC (SEQ. ID. No. 37), LEKTCDWLPKPNM-SASCKEI (SEQ. ID. No. 29) or a conservative substitution variant thereof, wherein the peptide is flanked by 0, 1, 2, 3, or 4 amino acid residues on either terminus or both termini, wherein the chimeric polypeptide comprises a first portion and a second portion, wherein the first portion of the chimeric polypeptide is a peptide consisting of the sequence CDWLPKPNMSASC (SEQ. ID. No. 37), LEKTCDWLP-KPNMSASCKEI (SEQ. ID. No. 29) or a conservative substitution variant thereof, wherein the peptide is flanked by 0, 1, 2, 3, or 4 amino acid residues on either terminus or both termini, and wherein the second portion of the chimeric polypeptide is not a Psap protein.

The peptide LEKTCDWLPKPNMSASCKEI (SEQ. ID. No. 29) or a conservative substitution variant thereof, is also specifically contemplated for the therapeutic methods described herein.

In other embodiments, in the methods described herein, the composition comprises of a peptide consisting of the sequence LEKTCDWLPKPNMSASCKEI (SEQ. ID. No. 29) or a conservative substitution variant thereof, and a pharmaceutically acceptable carrier.

In other embodiments, in the methods described herein, the composition comprises of a peptide consisting essentially of the sequence LEKTCDWLPKPNMSASCKEI (SEQ. ID. No. 29) or a conservative substitution variant thereof, and a pharmaceutically acceptable carrier.

In some embodiments of the methods described herein, the peptide making up the composition or the first portion of the chimeric polypeptide making up the composition consists essentially of at least 11, at least 12, at least 13, at least 14, at least 15, at least 16, at least 17, at least 18, or at least 19 consecutive amino acid residues from SEQ. ID. No. 29 or a conservative substitution variant thereof.

In some embodiments of the methods described herein, the peptide making up the composition or the first portion of the chimeric polypeptide making up the composition consists of at least 11, at least 12, at least 13, at least 14, at least 15, at least 16, at least 17, at least 18, or at least 19 consecutive amino acid residues from SEQ. ID. No. 29 or a conservative substitution variant thereof.

In other embodiments, in the methods described herein, the composition comprises of a plurality of peptides or fragments, wherein the peptides are not identical and wherein the peptides are derived from saposin A, are greater than or equal to 10 amino acids long and are not saposin A (SEQ. ID. No. 13).

In some embodiments, in the methods described herein, the composition comprises a multimer of peptides or fragments, wherein the peptides are identical and wherein the peptides are derived from saposin A.

In some aspects, in the methods described herein, the composition comprises of a plurality of peptides that are concatamerically linked.

In some embodiments, in the methods described herein, the composition comprises of a peptide that linked or fused to an amino acid sequence or a polymer that enhances the serum half life.

In some embodiments, in the methods described herein, the composition comprises of a peptide that linked or fused to an amino acid sequence that facilitates protein expression and/or purification In some embodiments, in the methods described herein, the composition comprises of a peptide that is linked or fused to a therapeutic molecule.

In some embodiments, in the methods described herein, the composition comprises of a peptide that is PEGylated.

In some embodiments, in the methods described herein, the administration is in conjunction with a p53 reactivation agent.

In some embodiments, in the methods described herein, the administration is in conjunction with chemotherapy, radiation therapy, and/or a cytostatic agent.

In some embodiments, in the methods described herein, the administration is in conjunction with an anti-VEGF agent or an anti-angiogenesis factor.

In one embodiment, the invention provides an isolated chimeric polypeptide comprising a first portion and a second portion, wherein the first portion is saposin A (SEQ. ID. No. 13) or a functional fragment thereof, and the second portion comprises an amino acid sequence or a polymer that enhances the serum half life of the first portion. The second portion is not a Psap protein, and the first portion, at the minimum, is capable of activating p53 and inducing Tsp-1 expression. In other embodiments, the first portion is a conservative amino acid substitution variant of saposin A, a functional fragment of saposin A, or a functional peptide mimetic of a functional fragment of saposin A. Examples of the second portion are serum transferrin or portions thereof, albumin, transthyretin, Fc of IgG (See G. M. Subramanian, (2007), Nature Biotechnology 25, 1411-141), and polymers such as polyethylene glycol for the purpose of enhancing the serum half life. The suitable polymers include, for example, polyethylene glycol (PEG), polyvinyl pyrrolidone, polyvinyl alcohol, polyamino acids, divinylether maleic anhydride, N-(2-Hydroxypropyl)-methacryl amide, dextran, dextran derivatives including dextran sulfate, polypropylene glycol, polyoxyethylated polyol, heparin, heparin fragments, polysaccharides, cellulose and cellulose derivatives, including methylcellulose and carboxymethyl cellulose, starch and starch derivatives, polyalkylene glycol and derivatives thereof, copolymers of polyalkylene glycols and derivatives thereof, polyvinyl ethyl ethers, and α,β-Poly[(2-hydroxyethyl)-DL-aspartamide, and the like, or mixtures thereof. A polymer may or may not have its own biological activity. The polymers can be covalently or non-covalently conjugated to the first portion. Methods of conjugation for increasing serum half life and for radiotherapy are known in the art, for example, in U.S. Pat. Nos. 5,180,816, 6,423,685, 6,884,780, and 7,022,673, which are hereby incorporated by reference in their entirety.

In one embodiment, the invention provides an isolated chimeric polypeptide comprising a first portion and a second portion, wherein the first portion is saposin A (SEQ. ID. No. 13) or a functional fragment thereof, and the second portion comprises an amino acid sequence that facilitates protein expression and/or purification of the first portion. The second portion is not a Psap protein, and the first portion is capable of activating p53 and inducing Tsp-1 expression. For example, a short peptide of saposin A, a peptidomimetic thereof or conservative amino acid substitution variant thereof, can be fused with other proteins or short amino acid residues for the purposes of facilitating protein expression and purification, e.g., thioredoxin and six histidine tags.

In one embodiment, the conservative substitution variant of the peptides described herein are functional peptide variants, that is these peptides at the minimum stimulate the expression of Tsp-1 in fibroblasts an in vitro assay as described herein.

In one embodiment, provided herein is an isolated chimeric polypeptide comprising a first portion and a second portion, wherein the first portion is saposin A (SEQ. ID. No. 13), CDWLPKPNMSASC (SEQ. ID. No. 37) or LEKTCDWLPKPNMSASCKEI (SEQ. ID. No. 29) or a conservative substitution variant and the second portion is a therapeutic molecule.

In one embodiment, provided herein is an isolated chimeric polypeptide comprising a first portion and a second portion, wherein the first portion is a peptide consisting essentially of at least ten consecutive amino acid residues of the sequence LEKTCDWLPKPNMSASCKEI (SEQ. ID. No. 29) or conservative substitution variant thereof, wherein the peptide is flanked by 0, 1, 2, 3, or 4 amino acid residues on either terminus or both termini, and the second portion is a therapeutic molecule.

In some embodiments, the second portion is not a Psap protein, and the first portion is capable of activating p53 and inducing Tsp-1 expression. In one embodiment, the first portion is conjugated to a therapeutic molecule. In one embodiment, the therapeutic molecule is an anti-angiogenic therapeutic molecule, e.g., angiostatin and endostatin. Numerous anti-angiogenic therapeutic molecules are known in the art, including but not limited to bevacizumab sunitinib, thalidomide, lenalidomide and sorafenib. In one embodiment, the therapeutic molecule is an anti-VEGF agent. In another embodiment, the therapeutic molecule can be a toxin, a radiotherapy molecule or anti-cancer drug such as thalidomide and lenalidomide. Again, numerous anti-angiogenic therapeutic molecules are known in the art. Functional fragments of Psap, for example, a short peptide of saposin A, a peptidomimetic thereof, or conservative amino acid substitution variant thereof can be fused with other anti-angiogenic factors and/or anti-VEGF agent, e.g., angiostatin or endostatin to enhance anti-angiogenic potency. Fusions or conjugates of such Psap peptides have dual functions: activate p53 and induce Tsp-1 expression as well as anti-angiogenic activity. Methods of determining p53 activating activity and Tsp-1 expression inducing activity are described herein. Determining anti-angiogenic activities are well known to one skilled in the art, for example by, a chick chorioallantoic membrane assay.

In one embodiment, the Psap proteins, peptides, chimeric polypeptides, fusion protein of saposin A or conservative amino acid substitution variant thereof include modification within the sequence, such as, modification by terminal-$NH_2$ acylation, e.g., acetylation, or thioglycolic acid amidation, by terminal-carboxylamidation, e.g., with ammonia, methylamine, and the like terminal modifications. Terminal modifications are useful, and are well known, to reduce susceptibility to proteinase digestion, and therefore serve to prolong half life of the polypeptides in solutions, particularly biological fluids where proteases may be present.

In another embodiment, the methods described herein can be used in combination with other treatment options available for the angiogenesis-dependent disease or disorder. For example, the treatment methods described herein can be administered in conjunction with chemotherapy, radiation therapy, and/or a cytostatic agent. The treatment methods described herein are administered in conjunction with anti-VEGF or anti-angiogenic factor, and/or p53 reactivation agent. Examples of cancer chemotherapeutic agents include, but are not limited to, irinotecan (CPT-11); erlotinib; oxalipatin; anthracyclins-idarubicin and daunorubicin; doxorubicin; alkylating agents such as melphalan and chlorambucil; cis-platinum, methotrexate, and alkaloids such as vindesine and vinblastine. A cytostatic agent is any agent capable of inhibiting or suppressing cellular growth and multiplication. Examples of cytostatic agents used in the treatment of cancer are paclitaxel, 5-fluorouracil, 5-fluorouridine, mitomycin-C, doxorubicin, and zotarolimus. Other cancer therapeutics includes inhibitors of matrix metalloproteinases such as marimastat, growth factor antagonists, signal transduction inhibitors and protein kinase C inhibitors.

In another embodiment, the methods described herein are administered in conjunction with an anti-VEGF agent. Some examples of anti-VEGF agents include bevacizumab (Avastin™), VEGF Trap, CP-547,632, AG13736, AG28262, SU5416, SU11248, SU6668, ZD-6474, ZD4190, CEP-7055, PKC 412, AEE788, AZD-2171, sorafenib, vatalanib, pegaptanib octasodium, IM862, DC101, angiozyme, Sirna-027, caplostatin, neovastat, ranibizumab, thalidomide, and AGA-1470, a synthetic analog of fumagillin (alternate names: Amebacilin, Fugillin, Fumadil B, Fumadil) (A. G. Scientific, catalog #F1028), an angio-inhibitory compound secreted by *Aspergillus fumigates*.

As used herein the term "anti-VEGF agent" refers to any compound or agent that produces a direct effect on the signaling pathways that promote growth, proliferation and survival of a cell by inhibiting the function of the VEGF protein, including inhibiting the function of VEGF receptor proteins. The term "agent" or "compound" as used herein means any organic or inorganic molecule, including modified and unmodified nucleic acids such as antisense nucleic acids, RNAi agents such as siRNA or shRNA, peptides, peptidomimetics, receptors, ligands, and antibodies. Preferred VEGF inhibitors, include for example, AVASTIN® (bevacizumab), an anti-VEGF monoclonal antibody of Genentech, Inc. of South San Francisco, Calif., VEGF Trap (Regeneron/Aventis). Additional VEGF inhibitors include CP-547,632 (3-(4-Bromo-2,6-difluoro-benzyloxy)-5-[3-(4-pyrrolidin 1-yl-butyl)-ureido]-isothiazole-4-carboxylic acid amide hydrochloride; Pfizer Inc., NY), AG13736, AG28262 (Pfizer Inc.), SU5416, SU11248, & SU6668 (formerly Sugen Inc., now Pfizer, New York, N.Y.), ZD-6474 (AstraZeneca), ZD4190 which inhibits VEGF-R2 and -R1 (AstraZeneca), CEP-7055 (Cephalon Inc., Frazer, Pa.), PKC 412 (Novartis), AEE788 (Novartis), AZD-2171, NEXAVAR® (BAY 43-9006, sorafenib; Bayer Pharmaceuticals and Onyx Pharmaceuticals), vatalanib (also known as PTK-787, ZK-222584: Novartis & Schering: AG), MACUGEN® (pegaptanib octasodium, NX-1838, EYE-001, Pfizer Inc./Gilead/Eyetech), IM862 (glufanide disodium, Cytran Inc. of Kirkland, Wash., USA), VEGFR2-selective monoclonal antibody DC101 (ImClone Systems, Inc.), angiozyme, a synthetic ribozyme from Ribozyme (Boulder, Colo.) and Chiron (Emeryville, Calif.), Sirna-027 (an siRNA-based VEGFR1 inhibitor, Sirna Therapeutics, San Francisco, Calif.) Caplostatin, soluble ectodomains of the VEGF receptors, Neovastat (Æterna Zentaris Inc; Quebec City, Calif.) and combinations thereof.

Anti-angiogenesis factors or therapeutics include any agent that directly or indirectly inhibits, prevents, and stops angiogenesis and/or neovascularization. Anti-angiogenesis factors include anti-VEGF agent. Other anti-angiogenesis factors include, but are not limited to angiostatin, endostatin and cleaved antithrombin III, alpha-2 antiplasmin (fragment), angiostatin (plasminogen fragment), antiangiogenic antithrombin III, cartilage-derived inhibitor (CDI), CD59 complement fragment, endostatin (collagen XVIII fragment), fibronectin fragment, gro-beta (a C-X-C chemokine), heparinases heparin hexasaccharide fragment, human chorionic gonadotropin (hCG), interferon alpha/beta/gamma, interferon inducible protein (IP-10), interleukin-12, kringle 5 (plasminogen fragment), beta-thromboglobulin, EGF (fragment), VEGF inhibitor, endostatin, fibronection (45 kD fragment), high molecular weight kininogen (domain 5), NK1, NK2, NK3 fragments of HGF, PF-4, serpin proteinase inhibitor 8, TGF-beta-1, p53, angioarrestin, metalloproteinase inhibitors (TIMPs), 2-Methoxyestradiol, placental ribonuclease inhibitor, plasminogen activator inhibitor, prolactin 16 kD fragment, proliferin-related protein (PRP), retinoids, tetrahydrocortisol-S transforming growth factor-beta (TGF-β), vasculostatin, and vasostatin (calreticulin fragment), pamidronate thalidomide, TNP470, the bisphosphonate family such as amino-bisphosphonate zoledronic acid. bombesin/gastrin-releasing peptide (GRP) antagonists such as RC-3095 and RC-3940-II (Bajol A M, et al., British Journal of Cancer (2004) 90, 245-252), monoclonal antibody therapies directed against specific pro-angiogenic growth factors and/or their receptors: example: bevacizumab (AVASTIN®), cetuximab (ERBITUX®), panitumumab (VECTIBIX™), and trastuzumab (HERCEPTIN®); small molecule tyrosine kinase inhibitors (TKIs) of multiple pro-angiogenic growth factor receptors. The three TKIs that are currently approved as anti-cancer therapies are erlotinib (TARCEVA®), sorafenib (NEXAVAR®), and sunitinib (SUTENT®); and inhibitors of mTOR (mammalian target of rapamycin) such as temsirolimus (TORICEL™) bortezomib (VELCADE®), thalidomide (THALOMID®), and doxycyclin.

Methods of determining anti-VEGF activity and/or anti-angiogenesis activity are well known to one skilled in the art. For example, the human umbilical vein endothelial cell phosphorylation assay and the VEGF-induced proliferation assay as described by Holash et al., 2002, in Proc. Natl. Acad. Sci. USA, 99:11393-98, can be used to determine the anti-VEGF inhibitory activity of an anti-VEGF agent and are hereby explicitly incorporated by reference. The human $VEGF_{165}$ can be used as the positive control in the cell phosphorylation and proliferation assays. The cell phosphorylation assay detects tyrosine phosphorylation which is an indicator of the activation of the VEGF signaling pathway. The proliferation assay detects cell proliferation induced by the activation of the VEGF signaling pathway. An anti-VEGF agent that blocks the activation of the VEGF signaling pathway will give reduced tyrosine phosphorylation and reduced cell proliferation in these assays compared to the results when the human $VEGF_{165}$ is used as a positive control.

In yet another embodiment, the methods described herein are administered in conjunction with a p53 reactivation agent. Around half of all human tumors carry p53 mutations, mostly point mutations that abrogate p53's specific DNA binding and transactivation activity. p53 mutation is associated with poor therapeutic response and prognosis. Tumors that carry wild type p53 often have other alterations in the p53 pathway that ablate the p53 tumor suppression response. Several strategies have been designed to restore p53 function in human tumors, including p53 gene therapy, reactivation of mutant p53, and activation of wild type p53 by inhibition of the p53 antagonist MDM2. In all cases, the aim is to eliminate the tumor through induction of massive apoptosis (Bykov V J and Wiman K G. 2003).

A p53 reactivation agent is any organic or inorganic chemical, compound, including protein and nucleic acid molecule that can restore the p53 response of a tumor cell. The p53 reactivation agent can be a gene therapy agent, such as a vector, carrying a wild-type p53 gene for reconstitution into tumor cells with deletions in the p53 gene, that is, introduction of an intact cDNA copy of the p53 gene using a suitable viral vector, typically one based on adenovirus (Adp53) (Wiman, 2006) or ADVEXIN (Introgen Inc.). The end result is to have functional p53 protein expression in the tumor cells. Functional p53 will perform the tumor suppression activities that are well known in the art.

Some cancer cells carry the wild-type p53 gene and should express theoretically functional p53 protein yet tumor growth is not regulated by the expressed p53 (Gurova, et al., 2004). It is speculated that p53 is somehow deactivated. A frequent observation in wild-type p53 gene carrying tumors is the overexpression of MDM2. The deactivation of p53 has been shown to be the result of MDM2-mediated p53 ubiquitination and the deregulation of HDM-2, which binds to p53 and targets it for proteasomal degradation. The deactivation of p53 has been shown to be also mediated by suppression of NF-κB activity as it was shown that p53 tumor suppressor activity was restored by ectopic expression of a super-repressor of IκB such as 9-aminoacridine (9ΛΛ), its derivatives, and the anti-malaria drug quinacrine (Gurova, et al., 2004). P53 reactivation agents that activate p53 by blocking the p53/MDM2 and the p53/HDM-2 protein-protein interactions to prevent p53 degradation are MDM-2 inhibitors and HDM-2 inhibitors. Some examples include a group of imidazoline compounds dubbed Nutlins (Vassilev L T et al., 2004) which fit neatly into the small pocket where MDM-2 contacts p53 and prevent the interaction between the two proteins.

Mutant p53 proteins have point mutations that abrogate p53's specific DNA binding and transactivation activity. These mutant p53 often fold abnormally and thus lose the ability to regulate their target genes. New small molecules that help these mutant p53 proteins fold more normally have been successful in reactivating the mutant p53 protein. Examples are the novel compounds RITA (Issaeva N., et al., 2004; Espinoza-Fonseca L M. 2005), the related PRIMA-1 and MIRA-1 (Rehman, Λ. 2005), and CP-31398 (Tanner S and Barberis A., 2004; Ho C K and Li G., 2005). For tumors with mutations in p53 that abolish the DNA binding activity in p53, a p53 reactivation agent can be one that facilitates DNA binding of the mutant p53 thus enabling the mutant p53 to function again as an activator of transcription. An example of such a p53 reactivation agent is described in Roth, J. et al., 2003, where a chimeric adaptor protein made of the DNA-binding and tetramerizing portions of the p53-homologue p73 (i.e., having tumor suppressive effects) fused to the oligomerization domain of p53 enables the mutant p53 to bind to its respective p53 response elements and initiate apoptosis. In addition, drugs that mimic p53's effects in activating gene transcription are also contemplated. Furthermore, agents that increase the production, expression, and/or stability of p73, the p53 homologue, can also be used in combination with the methods described herein. The increase of p73 production, expression, and/or stability in tumor cells serves to promote apoptosis.

In yet another embodiment, the methods described herein are administered in conjunction with therapeutics, physiotherapy and/or behavioral psychotherapy used in the treatment of rheumatoid arthritis, obesity, endometriosis, and Alzheimer's disease.

For examples of treatments of rheumatoid arthritis, there are therapeutic drugs that decrease pain and local inflammation including aspirin and non-steroidal anti-inflammatory drugs or NSAIDS (such as ibuprofen or naproxen) and other immunosuppressive drugs that decrease pain and inflammation while decreasing the growth of abnormal synovial tissue (the tissue that lines the inside of the joint). These drugs include methotrexate and low doses of corticosteroids (such as prednisone or cortisone). Other medications used to treat rheumatoid arthritis include: anti-malarial medications (such as hydroxychloroquine), gold, sulfasalazine, penicillamine, cyclophosphamide, cyclosporine, minocycline, and interleukin receptor antagonist and anti-I12 antibodies.

Treatment for Alzhemier's disease include, but are not be limited to, nonsteroidal anti-inflammatory drugs (NSAIDs), estrogen, steroids such as prednisone, vitamin E, menantine, donepezil, rivastigmine, tacrine, and galantamine. Holistic medicine include example such as gingko nuts extracts.

Treatment of endometrosis include, but should not be construed as limited to, a combination oral contraceptives (estrogen plus a progestin), progestins (such as medroxyprogesterone, danazol (a synthetic hormone related to testosterone, gonadotropin-releasing hormone agonists (GnRH agonists—such as buserelin, goserelin, leuprolide and nafarelin), and nonsteroidal anti-inflammatory drugs (NSAIDs) for pain control.

Examples of treatment options for obesity include dieting and nutritional counseling, exercise regime, gastric-bypass surgery, and drugs such as a combination of fenfluramine and phentermine (often called fen-phen), orlistat, sibutramine, phentermine, benzphetamine, diethylpropion, mazindol, and phendimetrazine.

Functional Peptides

Functional peptides of saposin A can be chemically synthesized and purified by biochemical methods that are well known in the art such as solid phase peptide synthesis using t-Boc (tert-butyloxycarbonyl) or FMOC (9-flourenylmethloxycarbonyl) protection group described in "Peptide synthesis and applications" in Methods in molecular biology Vol. 298, Ed. by John Howl and "Chemistry of Peptide Synthesis" by N. Leo Benoiton, 2005, CRC Press, (ISBN-13: 978-1574444544) and "Chemical Approaches to the Synthesis of Peptides and Proteins" by P. Lloyd-Williams, et al., 1997, CRC-Press, (ISBN-13: 978-0849391422). Solid phase peptide synthesis, developed by R. B. Merrifield, 1963, J. Am. Chem. Soc. 85 (14): 2149-2154, was a major breakthrough allowing for the chemical synthesis of peptides and small proteins. An insoluble polymer support (resin) is used to anchor the peptide chain as each additional alpha-amino acid is attached. This polymer support is constructed of 20-50 μm diameter particles which are chemically inert to the reagents and solvents used in solid phase peptide synthesis. These particles swell extensively in solvents, which makes the linker arms more accessible.

Organic linkers attached to the polymer support activate the resin sites and strengthen the bond between the (-amino acid and the polymer support. Chloromethyl linkers, which were developed first, have been found to be unsatisfactory for longer peptides due to a decrease in step yields. The PAM (phenylacetamidomethyl) resin, because of the electron withdrawing power of the acid amide group on the phenylene ring, provides a much more stable bond than the classical resin. Another alternative resin for peptides under typical peptide synthesis conditions is the Wang resin. This resin is generally used with the FMOC labile protecting group.

A labile group protects the alpha-amino group of the amino acid. This group should be easily removed after each coupling reaction so that the next alpha-amino protected amino acid may be added. Typical labile protecting groups include t-Boc and FMOC t-Boc is a very satisfactory labile group which is stable at room temperature and easily removed with dilute solutions of trifluoroacetic acid (TFA) and dichloromethane. FMOC is a base labile protecting group which is easily removed by concentrated solutions of amines (usually 20-55% piperidine in N-methylpyrrolidone). When using FMOC alpha-amino acids, an acid labile (or base stable) resin, such as an ether resin, is desired.

The stable blocking group protects the reactive functional group of an amino acid and prevents formation of complicated secondary chains. This blocking group must remain attached throughout the synthesis and may be removed after completion of synthesis. When choosing a stable blocking group, the labile protecting group and the cleavage procedure to be used should be considered.

After generation of the resin bound synthetic peptide, the stable blocking groups are removed and the peptide is cleaved from the resin to produce a "free" peptide. In general, the stable blocking groups and organic linkers are labile to strong acids such as TFA. After the peptide is cleaved from the resin, the resin is washed away and the peptide is extracted with ether to remove unwanted materials such as the scavengers used in the cleavage reaction. The peptide is then frozen and lyophilized to produce the solid peptide. This is then characterized by HPLC and MALDI before being used. In addition, the peptide should be purified by HPLC to higher purity before use.

Commercial peptide synthesizing machines are available for solid phase peptide synthesis. For example, the Advanced Chemtech Model 396 Multiple Peptide Synthesizer and an Applied Biosystems Model 432A Peptide synthesizer. There are commercial companies that make custom synthetic peptide to order, e.g., Abbiotec, Abgent, AnaSpcc Global Peptide Services, LLC., INVITROGEN™ and rPeptide, LLC.

Synthesis of Psap Proteins

Functional fragments of Psap or saposin A, functional variants and functional peptide mimetics thereof and fusion proteins thereof can also be synthesized and purified by molecular methods that are well known in the art. Preferably molecular biology methods and recombinant heterologous protein expression systems can be used. For example, recombinant protein may be expressed in bacteria, mammal, insects, yeast, or plant cells.

The Psap proteins can be synthesized and purified by protein and molecular methods that are well known in the art. Preferably molecular biology methods and recombinant heterologous eukaryotic protein expression systems are used. An example of expression and purification of the human prosaposin is described in Gopalakrishnan, M. M., et al., 2004 and in U.S. Pat. No. 5,700,909. The purification of rat prosaposin is described in Morales, C R., 1998. These references are hereby incorporated by reference in their entirety. The approach can be applied to the purification of human Psap proteins by one skilled in the art.

Standard techniques known to those of skill in the art can be used to introduce mutations in the nucleotide sequence encoding prosaposin, including, for example, site-directed mutagenesis and PCR-mediated mutagenesis which result in amino acid substitutions. Preferably, the variants encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the prosaposin protein.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, error-prone PCR, shuffling, oligonucleotide-directed mutagenesis, recursive ensemble mutagenesis, exponential ensemble mutagenesis, site-specific mutagenesis, gene reassembly, GSSM and any combination thereof. The resultant mutants can be screened for Tsp-1 and p53 expression stimulating activity by the assays described herein to identify mutants that retain or have enhanced Tsp-1 and p53 expression stimulating activity.

Methods of assaying the effects of mutant, fragment or variant Psap on Tsp-1 and p53 expression are described herein. Briefly, full-length, mutant, fragment and variant Psap are applied to the cell cultures prostate fibroblast. The conditioned media from PC3M-LN4 (LN4) and PC3 cells are used as controls, with PC3 as positive/stimulating control and LN4 as negative/inhibiting controls. After a period of included (~16 h), the cells are harvested, rinsed, and lysed. The lysates are analyzed for the level of Tsp-1 and p53 expression by western blot analyses, with β-actin as the internal lysate protein loading control.

Functional fragments of Psap are incomplete proteins of Psap and will therefore have less than the 524 amino acids in the polypeptide. The full-length polypeptide can be truncated at the amino terminus or the carboxyl terminus or at both ends. The polypeptide can also have an internal deletion of the amino acids such as the deletion of the SapB or SapA coding regions. Preferably, the functional fragments has less than 50 amino acid deletion, less than 40 amino acid deletion, less than 30 amino acid deletion, less than 25 amino acid deletion, less than 20 amino acid deletion, less than 15 amino acid deletion, less than 10 amino acid deletion, less than 5 amino acid deletion, less than 4 amino acid deletion, less than 3 amino acid deletion, or less than 2 amino acid deletion, relative to the parent Psap protein.

As used herein, the Tsp-1 and p53 expression stimulating activity refers to Psap protein's ability to induce an increase in the expression levels of Tsp-1 and p53 in surrounding tumor stroma or fibroblast cells. The stimulating activity also includes the effects on tumor and non-tumor cells.

The introduced mutations can be silent or neutral missense mutations, i.e., have no, or little, effect on Psap protein's Tsp-1 and p53 expression stimulating activity. These types of mutations can be useful to optimize codon usage, or improve recombinant Psap protein expression and production. Alternatively, non-neutral missense mutations can alter Psap protein's ability to stimulate Tsp-1 and p53 expression. One of skill in the art would be able to design and test mutant molecules for desired properties such as no alteration of Psap protein's ability to stimulate Tsp-1 and p53 expression. Following mutagenesis, the encoded protein can routinely be expressed and the functional and/or biological activity of the encoded protein, (e.g., ability to stimulate Tsp-1 and p53 in tumor-derived fibroblasts) can be determined using techniques described herein or by routinely modifying techniques known in the art.

Embodied in the invention is a vector carrying a cDNA encoding prosaposin, or coding cDNA fragments of prosaposin. Conventional polymerase chain reaction (PCR) cloning techniques can be used to generate the complete cDNA sequence, using, e.g., the PCR primers: 5'-CGGGCTACG-TAATGTACGCCCTCTTCCTCCTGG (SEQ. ID. No. 7) and 3'-GGCGGGGTCGACCTAGTTCCACACATGGCG (SEQ. ID. No. 8).

In one embodiment, the amplified cDNA of Psap is: 5' ATGTACGCCCTCTTCCTCCTGGCCAGCCTC-CTGGGCGCGGCTCTAGCCGGCCCGGTCCTTG GACTGAAAGAATGCACCAGGGGCTCGGCAGTGTG-GTGCCAGAATGTGAAGACGGCGTCCGA CTGCGGGGCAGTGAAGCACTGCCTGCAGAC-CGTTTGGAACAAGCCAACAGTGAAATCCCTT CCCTGCGACATATGCAAAGACGTTGTCACCGCA-GCTGGTGATATGCTGAAGGACAATGCCA CTGAG-GAGGAGATCCTTGTTTACTTGGAGAAGACCTGT-GACTGGCTTCCGAAACCGAACAT GTCTGCTTCATGCAAGGAGATAGTGGACTCCTAC-CTCCCTGTCATCCTGGACATCATTAAAG GAGAAAT-GAGCCGTCCTGGGGAGGTGTGCTCTGCTCTCAAC-CTCTGCGAGTCTCTCCAGAAG CACCTAGCAGAGCTGAATCACCAGAAGCAGCTG-GAGTCCAATAAGATCCCAGAGCTGGACA TGACT-GAGGTGGTGGCCCCCTTCATGGCCAACATC-CCTCTCCTCCTCTACCCTCAGGACGGC CCCCGCAGCAAGCCCCAGCCAAAGGA-TAATGGGGACGTTTGCCAGGACTGCATTCAGATGG TGACTGACATCCAGACTGCTGTACGGACCAACTC-CACCTTTGTCCAGGCCTTGGTGGAACAT GTCAAGGAGGAGTGTGACCGCCTGGGCCCTG-GCATGGCCGACATATGCAAGAACTATATCA GCCAG-TATTCTGAAATTGCTATCCAGATGATGATGCACATG-CAACCCAAGGAGATCTGTGCG CTGGTTGGGTTCTGTGATGAGGTGAAAGAGATGC-CCATGCAGACTCTGGTCCCCGCCAAAGT GGCCTC-CAAGAATGTCATCCCTGCCCTGGAACTGGTG-GAGCCCATTAAGAAGCACGAGGTC CCAGCAAAGTCTGATGTTTACTGTGAGGTGTGT-GAATTCCTGGTGAAGGAGGTGACCAAGCT GATT-GACAACAACAAGACTGAGAAAGAAATACTC-GACGCTTTTGACAAAATGTGCTCGAAG CTGCCGAAGTCCCTGTCGGAAGAGTGCCAGGAG-GTGGTGGACACGTACGGCAGCTCCATCC TGTC-CATCCTGCTGGAGGAGGTCAGCCCTGAGCTGGT-GTGCAGCATGCTGCACCTCTGCTCT GGCACGCGGCTGCCTGCACTGACCGTTCACGT- GACTCAGCCAAAGGACGGTGGCTTCTGCG AAGT-GTGCAAGAAGCTGGTGGGTTATTTGGATCGCAAC-CTGGAGAAAAACAGCACCAAGCA
GGAGATCCTGGCTGCTCTTGAGAAAGGCTGCA-GCTTCCTGCCAGACCCTTACCAGAAGCAGT
GTGATCAGTTTGTGGCAGAGTACGAGCCCGTGCT-GATCGAGATCCTGGTGGAGGTGATGGA TCCTTCCT-TCGTGTGCTTGAAAATTGGAGCCTGCCCCTCGGC-CCATAAGCCCTTGTTGGGAA
CTGAGAAGTGTATATGGGGCCCAAGCTACTGGTGC-CAGAACACAGAGACAGCAGCCCAGTG CAATGCT-GTCGAGCATTGCAAACGCCATGTGTGGAACTAG-3' (SEQ. ID. No. 17). To generate various functional fragments of prosaposin, specific primers will be designed to correspond to the desired coding region of the protein's cDNA (SEQ. ID. No. 17). The cDNAs can be cloned into a general purpose cloning vector such as pUC19, pBR322, pBluescript vectors (Stratagene Inc.) or pCR TOPO® from Invitrogen Inc. In the example below, the cDNA is subcloned into the vector pDNR-dual. The resultant recombinant vector carrying cDNA sequence encoding prosaposin can then be used for further molecular biological manipulations such as site-directed mutagenesis to enhance Tsp-1 and/or p53 expression stimulating activity, or can be subcloned into protein expression vectors or viral vectors for protein synthesis in a variety of protein expression systems using host cells selected from the group consisting of mammalian cell lines, insect cell lines, yeast, and plant cells. In the example below, Cre recombinase to move the cDNA's into pCMV-neo for expression.

Examples of other expression vectors and host cells are the pET vectors (Novagen), pGEX vectors (Amersham Pharmacia), and pMAL vectors (New England labs. Inc.) for protein expression in *E. coli* host cell such as BL21, BL21 (DE3) and AD494(DE3)pLysS, Rosetta (DE3), and Origami (DE3) (Novagen); the strong CMV promoter-based pcDNA3.1 (Invitrogen) and pCIneo vectors (Promega) for expression in mammalian cell lines such as CHO, COS, HEK-293, Jurkat, and MCF-7; replication incompetent adenoviral vector vectors pAdeno X, pAd5F35, pLP-Adeno-X-CMV (Clontech), pAd/CMV/V5-DEST, pAd-DEST vector (Invitrogen) for adenovirus-mediated gene transfer and expression in mammalian cells; pLNCX2, pLXSN, and pLAPSN retrovirus vectors for use with the Retro-X™ system from Clontech for retroviral-mediated gene transfer and expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells; adenovirus-associated virus expression vectors such as pAAV-MCS, pAAV-IRES-hrGFP, and pAAV-RC vector (Stratagene) for adeno-associated virus-mediated gene transfer and expression in mammalian cells; BACpak6 baculovirus (Clontech) and pFastBac™ HT (Invitrogen) for the expression in *Spodopera frugiperda* 9 (Sf9) and Sf11 insect cell lines; pMT/BiP/V5-His (Invitrogen) for the expression in *Drosophila* Schneider S2 cells; *Pichia* expression vectors pPICZα, pPICZ, pFLDα and pFLD (Invitrogen) for expression in *Pichia pastoris* and vectors pMETα and pMET for expression in *P. methanolica*; pYES2/GS and pYD1 (Invitrogen) vectors for expression in yeast *Saccharomyces cerevisiae*. Recent advances in the large scale expression heterologous proteins in *Chlamydomonas reinhardtii* are described by Griesbeck C. et al., 2006 Mol. Biotechnol. 34:213-33 and Fuhrmann M. 2004, Methods Mol Med. 94:191-5. Foreign heterologous coding sequences are inserted into the genome of the nucleus, chloroplast and mitochondria by homologous recombination. The chloroplast expression vector p64 carrying the most versatile chloroplast selectable marker aminoglycoside adenyl transferase (aadA), which confer resistance to spectinomycin or streptomycin, can be used to express foreign protein in the chloroplast. Biolistic gene gun method is used to introduce the vector in the algae. Upon its entry into chloroplasts, the foreign DNA is released from the gene gun particles and integrates into the chloroplast genome through homologous recombination.

Specific site-directed mutagenesis of Psap cDNA sequence in a vector can be used to create specific amino acid mutations and substitutions. Site-directed mutagenesis can be carried out using the QUIKCHANGE® site-directed mutagenesis kit from Stratagene according to manufacture's instructions or any method known in the art.

In one embodiment, provided herein are expression vectors carrying the Psap cDNA that encodes prosaposin or fragments, derivatives, or variants thereof for the expression and purification of the recombinant Psap proteins produced from a eukaryotic protein expression system using host cells selected from the group consisting of mammal, insects, yeast, or plant cells.

Specifically contemplated in the methods described herein are fusion Psap proteins. For example, Psap protein can be fused to transferrin, IgG, or albumin, to name a few, to enhance serum half life and pharmacokinetics in the individual being treated. Psap protein can also be fused to a tag protein such as tandem histidine residues (6×His), GST, myc, thioredoxin first 105 amino acids or HA tag for the purification and/or enhance solubility of the expressed recombinant protein in heterologous system. Enzymatic digestion with serine proteases such as thrombin and enterokinase cleave and release the Psap protein from the histidine or myc tag, releasing the recombinant Psap protein from the affinity resin while the histidine-tags and myc-tags are left attached to the affinity resin. Other reasons for tagging the Psap protein include monitoring the distribution of the protein over time in the individual, since the tagged Psap is distinguishable from the native Psap protein.

In one embodiment, the recombinant vector that expresses prosaposin is a viral vector. The viral vector can be any viral vector known in the art including but not limited to those derived from adenovirus, adeno-associated virus (AAV), retrovirus, and lentivirus. Recombinant viruses provide a versatile system for gene expression studies and therapeutic applications.

A simplified system for generating recombinant adenoviruses is presented by He T C. et al., Proc. Natl. Acad. Sci. USA 95:2509-2514, 1998. The gene of interest is first cloned into a shuttle vector, e.g., pAdTrack-CMV. The resultant plasmid is linearized by digesting with restriction endonuclease Pme I, and subsequently co-transformed into *E. coli*. BJ5183 cells with an adenoviral backbone plasmid, e.g., pAdEasy-1 of Stratagene's AdEasy™ Adenoviral Vector System. Recombinant adenovirus vectors are selected for kanamycin resistance, and recombination confirmed by restriction endonuclease analyses. Finally, the linearized recombinant plasmid is transfected into adenovirus packaging cell lines, for example HEK 293 cells (E1-transformed human embryonic kidney cells) or 911 (E1-transformed human embryonic retinal cells) (Human Gene Therapy 7:215-222, 1996). Recombinant adenoviruses are generated within the HEK 293 cells.

In one embodiment, provided herein is a recombinant lentivirus for the delivery and expression of prosaposin protein in either dividing or non-dividing mammalian cells. The HIV-1 based lentivirus can effectively transduce a broader host range than the Moloney Leukemia Virus (MoMLV)-base retroviral systems. Preparation of the recombinant lentivirus can be achieved using the pLenti4/V5-DEST™, pLenti6/V5-DEST™ or pLenti vectors together with ViraPower™ Lentiviral Expression systems from Invitrogen.

In one embodiment, the invention provides a recombinant adeno-associated virus (rAAV) vector for the expression of a prosaposin protein. In one embodiment, the rAAV vector encoding a prosaposin protein is administered to slow, inhibit, or prevent the growth of cancer and tumors such as glioma. Using rAAV vectors, genes can be delivered into a wide range of host cells including many different human and non-human cell lines or tissues. Because AAV is non-pathogenic and does not elicit an immune response, a multitude of pre-clinical studies have reported excellent safety profiles. rAAVs are capable of transducing a broad range of cell types, and transduction is not dependent on active host cell division. High titers, >$10^8$ viral particles/ml, are easily obtained in the supernatant and $10^{11}$-$10^{12}$ viral particles/ml can be obtained with further concentration. The transgene is integrated into the host genome so expression is long term and stable.

The use of alternative AAV serotypes other than AAV-2 (Davidson et al (2000), PNAS 97(7)3428-32; Passini et al (2003), J. Virol 77(12):7034-40) has demonstrated different cell tropisms and increased transduction capabilities. With respect to brain cancers, the development of novel injection techniques into the brain, specifically convection enhanced delivery (CED; Bobo et al (1994), PNAS 91(6):2076-80; Nguyen et al (2001), Neuroreport 12(9):1961-4), has significantly enhanced the ability to transduce large areas of the brain with an AAV vector.

Large scale preparation of AAV vectors is made by a three-plasmid cotransfection of a packaging cell line: AAV vector carrying the Psap DNA coding sequence, AAV RC vector containing AAV rep and cap genes, and adenovirus helper plasmid pDF6, into 50×150 mm plates of subconfluent 293 cells. Cells are harvested three days after transfection, and viruses are released by three freeze-thaw cycles or by sonication.

AAV vectors are then purified by two different methods depending on the serotype of the vector. AAV2 vector is purified by the single-step gravity-flow column purification method based on its affinity for heparin (Auricchio, A., et al., 2001, Human Gene therapy 12:71-6; Summerford, C. and R. Samulski, 1998, J. Virol. 72:1438-45; Summerford, C. and R. Samulski, 1999, Nat. Med. 5: 587-88). AAV2/1 and AAV2/5 vectors are currently purified by three sequential CsCl gradients.

Therapeutic Compositions and Administration

In one embodiment, the invention provides for a pharmaceutical composition comprising prosaposin, functional fragments or variants thereof and a pharmaceutically acceptable carrier. In another embodiment, the invention also provides for a pharmaceutical composition comprising the expression vector carrying the cDNA that encodes prosaposin, functional fragments or variants thereof and a pharmaceutically acceptable carrier.

As used herein, the term "pharmaceutical composition" refers to the Psap proteins in combination with a pharmaceutically acceptable carrier. The pharmaceutical composition does not include tissue culture media, water, and serum.

When used in mammalian therapy, the therapeutic composition of the invention can be administered in any convenient vehicle that is physiologically acceptable. The compounds can be formulated for a variety of modes of administration, including systemic, topical or localized administration. Techniques and formulations generally can be found in Remington's Pharmaceutical Sciences, Mack Publishing Co., Easton, Pa., latest edition. In each case, a therapeutically effective amount of Psap, functional fragments or variants, or vector comprising the cDNA encoding Psap or fragments or variants thereof is administered in order to prevent or inhibit the progression of the angiogenesis-dependent disease or disorder. The Psap, functional fragments or variants, or vector comprising a cDNA encoding Psap or fragments or variants thereof are generally combined with a carrier such as a diluent or excipient which can include fillers, extenders, binding, wetting agents, disintegrants, surface-active agents, or lubricants, depending on the nature of the mode of administration and dosage forms. Typical dosage forms include tablets, powders, liquid preparations including suspensions, emulsions and solutions, granules, capsules and suppositories, as well as liquid preparations for injections.

For angiogenesis-dependent diseases or disorders that are accessible externally on the skin, such as dermal hemangiomas and skin cancer lesions (melanoma), gene therapy virus, expression vectors, or Psap, fragments or variants can be preferably applied topically to the hemangioma or cancer lesion site in a therapeutically effective amount in admixture with pharmaceutical carriers, in the form of topical pharmaceutical compositions. The gene therapy virus can be in the form of an adenovirus, adeno-associated virus or lentivirus. Such compositions include solutions, suspensions, lotions, gels, creams, ointments, emulsions, skin patches, etc. All of these dosage forms, along with methods for their preparation, are well known in the pharmaceutical and cosmetic art. HARRY'S COSMETICOLOGY (Chemical Publishing, 7th ed. 1982); REMINGTON'S PHARMACEUTICAL SCIENCES (Mack Publishing Co., 18th ed. 1990). Typically, such topical formulations contain the active ingredient in a concentration range of 0.1 to 100 mg/ml, in admixture with suitable vehicles. For gene therapy viruses, the dosage ranges from $10^6$ to $10^{14}$ particle per application. Other desirable ingredients for use in such preparations include preservatives, co-solvents, viscosity building agents, carriers, etc. The carrier itself or a component dissolved in the carrier can have palliative or therapeutic properties of its own, including moisturizing, cleansing, or anti-inflammatory/anti-itching properties. Penetration enhancers can, for example, be surface active agents; certain organic solvents, such as di-methylsulfoxide and other sulfoxides, dimethyl-acetamide and pyrrolidone; certain amides of heterocyclic amines, glycols (e.g., propylene glycol); propylene carbonate; oleic acid; alkyl amines and derivatives; various cationic, anionic, nonionic, and amphoteric surface active agents; and the like.

Topical administration of a pharmacologically effective amount can utilize transdermal delivery systems well known in the art. An example is a dermal patch. Alternatively the biolistic gene gun method of delivery can be used. The gene gun is a device for injecting cells with genetic information, originally designed for plant transformation. The payload is an elemental particle of a heavy metal coated with plasmid DNA. This technique is often simply referred to as biolistics. Another instrument that uses biolistics technology is the PDS-1000/Ile particle delivery system. The Psap, functional fragments, or variants, expression vector, and/or gene therapy virus can be coated on minute gold particles, and these coated particles are "shot" into biological tissues such as hemangiomas and melanoma under high pressure. An example of gene gun-based method is described for DNA based vaccination of cattle by Loehr B. I. et al., J. Virol. 2000, 74:6077-86.

In one embodiment, the compositions described herein can be administered directly by intratumoral injection. If the solid tumors and hemangiomas are accessible by injection, the Psap, functional fragments, or variants, expression vector, and/or viral vector can be administered by injection directly to the tumor mass as a pharmaceutical formulation. The preferred formulation is also sterile saline or Lactated Ringer's solution. Lactated Ringer's solution is a solution that is isotonic with blood and intended for intravenous administration.

In the treatment and prevention of diabetic retinopathy and wet macular degeneration, pharmaceutical formulation of the present invention can be applied to the eye by intra-vitral or intraocular injection. In one embodiment, the invention can be formulated as an eye drop solution for direct application on the eyes.

In addition to topical therapy, the compositions described herein can also be administered systemically as a pharmaceutical formulation. Systemic routes include but are not limited to oral, parenteral, nasal inhalation, intratracheal, intrathecal, intracranial, and intrarectal. The pharmaceutical formulation is a liquid, preferably in sterile saline, lactated Ringer's or Hank's solution. In addition, the pharmaceutical formulation can be in solid forms and re-dissolved or suspended immediately prior to use. Lyophilized forms are also included.

For therapeutic applications, the compositions described herein are administered to a mammal, preferably a human, in a pharmaceutically acceptable dosage form, including those that can be administered to a human intravenously as a bolus or by continuous infusion over a period of time, by intramuscular, intraperitoneal, intracerebrospinal, subcutaneous, intra-arterial, intrasynovial, intrathecal, oral, topical, or inhalation routes. The pharmaceutical formulation can be infused upstream from the site of the cells whose activity is to be modulated. Implantable drug pumps, as for example, INFUSAID® pumps (Infusaid, Inc.), are useful for delayed-release intraarterial administration. The preferred embodiment is the intramuscular injection of AAV viral vectors encoding the cDNA of Psap, functional fragments or variants thereof.

The compositions described herein are also suitably administered by intratumoral, peritumoral, intralesional or perilesional routes, to exert local as well as systemic effects. The intraperitoneal route is expected to be particularly useful, for example, in the treatment of ovarian tumors. For these uses, additional conventional pharmaceutical preparations such as tablets, granules, powders, capsules, and sprays can be preferentially required. In such formulations further conventional additives such as binding-agents, wetting agents, propellants, lubricants, and stabilizers can also be required.

In one embodiment, the composition described herein takes the form of a cationic liposome formulation such as those described for intratracheal gene therapy treatment of early lung cancer treatment (Zou Y. et al., Cancer Gene Ther. 2000, 7(5):683-96). The liposome formulations are especially suitable for aerosol use in lung cancer patients. The pharmaceutical formulation can be contained within a lipid particle or vesicle, such as a liposome or microcrystal, which is also suitable for parenteral administration. The particles can be of any suitable structure, such as unilamellar or plurilamellar, so long as Psap, fragments, variants thereof, or vector carrying the cDNA of Psap fragments, variants thereof are contained therein. Vector DNA and/or virus can be entrapped in 'stabilized plasmid-lipid particles' (SPLP) containing the fusogenic lipid dioleoylphosphatidylethanolamine (DOPE), low levels (5-10 mol %) of cationic lipid, and stabilized by a polyethyleneglycol (PEG) coating (Zhang Y. P. et al., Gene Ther. 1999, 6:1438-47). Positively charged lipids such as N-[1-(2,3-dioleoyloxi)propyl]-N,N, N-trimethyl-amoniummethylsulfate, or "DOTAP," are particularly preferred for such particles and vesicles. The preparation of such lipid particles is well known. See, e.g., U.S. Pat. Nos. 4,880,635; 4,906,477; 4,911,928; 4,917,951; 4,920,016; and 4,921,757. Other non-toxic lipid based vehicle components can likewise be utilized to facilitate uptake of the vector carrying the cDNA encoding Psap, fragments, or variant thereof by the cell. Other techniques in formulating expression vectors and virus as therapeutics are found in "DNA-Pharmaceuticals: Formulation and Delivery in Gene Therapy, DNA Vaccination and Immunotherapy" by Martin Schleef (Editor) December 2005, Wiley Publisher, and "Plasmids for Therapy and Vaccination" by Martin Schleef (Editor) Can 2001, are incorporated herein as reference. In one embodiment, the dosage for viral vectors is $10^6$ to $1 \times 10^{14}$ viral vector particles per application per patient.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, bile salts and fusidic acid derivatives for transmucosal administration. In addition, detergents can be used to facilitate permeation. Transmucosal administration can be through use of nasal sprays, for example, as well as formulations suitable for administration by inhalation, or suppositories. For oral administration, the Psap proteins or vector are formulated into conventional as well as delayed release oral administration forms such as capsules, tablets, and tonics.

The route of administration, dosage form, and the effective amount vary according to the potency of the Psap proteins, expression vectors and viral vectors, their physicochemical characteristics, and according to the treatment location. The selection of proper dosage is well within the skill of an ordinary skilled physician. Topical formulations can be administered up to four-times a day.

In one embodiment, dosage forms of the compositions described herein include pharmaceutically acceptable carriers that are inherently non-toxic and non-therapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. Carriers for topical or gel-based forms of Psap proteins include polysaccharides such as sodium carboxymethylcellulose or methylcellulose, polyvinylpyrrolidone, polyacrylates, polyoxyethylene-polyoxypropylene-block polymers, polyethylene glycol and wood wax alcohols. For all administrations, conventional depot forms are suitably used. Such forms include, for example, microcapsules, nano-capsules, liposomes, plasters, inhalation forms, nose sprays, sublingual tablets, and sustained release preparations. For examples of sustained release compositions, see U.S. Pat. Nos. 3,773,919 and 3,887,699, EP 58,481A and EP 158,277A, Canadian Patent No. 1176565, U. Sidman et al., Biopolymers 22:547 (1983) and R. Langer et al., Chem. Tech. 12:98 (1982). The Psap proteins will usually be formulated in such vehicles at a concentration of about 0.1 mg/ml to 100 mg/ml and the vector should be in the range of $10^6$ to $1 \times 10^{14}$ viral vector particles per application per patient.

In one embodiment, other ingredients can be added to the pharmaceutical formulations as described herein, such as anti-oxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

In one embodiment, the pharmaceutical formulation used for therapeutic administration must be sterile. Sterility is readily accomplished by filtration through sterile filtration membranes (e.g., 0.2 micron membranes). Alternatively, preservatives can be used to prevent the growth or action of microorganisms. Various preservatives are well known and include, for example, phenol and ascorbic acid. The Psap proteins ordinarily will be stored in lyophilized form or as an aqueous solution if it is highly stable to thermal and oxidative denaturation. The pH of the Psap proteins preparations typically will be about from 6 to 8, although higher or lower pH values can also be appropriate in certain instances.

The localized concentration or amount administered to a subject can be determined empirically and will depend upon the purpose of the administration, the area to be treated, the effectiveness of the composition, and the manner of administration. The localized concentration at the site of the targeted cells will desirably be in the range of about 0.05 to 50 µM, or more particularly 0.2 to 5 µM, although higher or lower dosages can be employed as appropriate. For administration to a subject such as a human, a dosage of from about 0.01, 0.1, or 1 mg/kg up to 50, 100, or 150 mg/kg or more can typically be employed.

Treatment Applications of the Peptides and Chimeric Polypeptides

In one embodiment, the methods described herein provide a method of treating an individual diagnosed with cancer comprising making a prognosis evaluation based on the levels of Psap in the tumor sample and tumor stroma, and administering a therapeutically effective amount of Psap protein or a vector comprising a nucleic acid encoding Psap protein and a pharmaceutically acceptable carrier if the Psap level is lower than 95% of a reference Psap level and the prognosis is poor.

In one embodiment, the methods described herein provide a method of treating an individual diagnosed with cancer, the method comprising making a prognosis evaluation based on the levels of Psap in the tumor sample and tumor stroma, and if the Psap level is lower than 95% of a reference Psap level and the prognosis is poor, administering a therapeutically effective amount of a composition comprising an isolated peptide and a pharmaceutically acceptable carrier, wherein the isolated peptide consists essentially of the sequence CDWLPKPNMSASC (SEQ. ID. No. 37) or LEKTCDWLPKPNMSASCKEI (SEQ. ID. No. 29), wherein the peptide is flanked by 0, 1, 2, 3, or 4 amino acid residues on either terminus or both termini.

In one embodiment, provided herein is a method of treating an individual diagnosed with cancer comprising: (a) determining a level of Psap in a tumor sample from the individual; (b) comparing the Psap level determined in (a) with a reference Psap level; and when the Psap level determined in (a) is lower than 95% of said reference Psap level, administering a therapeutically effective amount of a composition comprising an isolated peptide and a pharmaceutically acceptable carrier, wherein the isolated peptide consists essentially of the sequence CDWLPKPNMSASC (SEQ. ID. No. 37) LEKTCDWLPKPNMSASCKEI (SEQ. ID. No. 29) or a conservative substitution variant thereof, or a peptide consisting essentially of at least ten consecutive amino acid residues of the sequence LEKTCDWLPKPNMSASCKEI (SEQ. ID. No. 29) or conservative substitution variant thereof, wherein the peptide is flanked by 0, 1, 2, 3, or 4 amino acid residues on either terminus or both termini. In some embodiments, the isolated peptide consists essentially of at least 11, at least 12, at least 13, at least 14, at least 15, at least 16, at least 17, at least 18, or at least 19 consecutive amino acid residues from SEQ. ID. No. 29 or a conservative substitution variant thereof.

In another embodiment, the composition comprises a chimeric polypeptide comprising a first portion and a second portion, wherein the first portion of the chimeric polypeptide is a peptide consisting essentially of the sequence CDWLPKPNMSASC (SEQ. ID. No. 37), LEKTCDWLPKPNMSASCKEI (SEQ. ID. No. 29) or a conservative substitution variant thereof, or is a peptide consisting essentially of at least ten consecutive amino acid residues of the sequence LEKTCDWLPKPNMSASCKEI (SEQ. ID. No. 29) or conservative substitution variant thereof, wherein the peptide is flanked by 0, 1, 2, 3, or 4 amino acid residues on either terminus or both termini, and wherein the second portion is not a Psap protein. In some embodiments, the peptide consists essentially of at least 11, at least 12, at least 13, at least 14, at least 15, at least 16, at least 17, at least 18, or at least 19 consecutive amino acid residues from SEQ. ID. No. 29 or a conservative substitution variant thereof.

A reference level of Psap is, for example, that obtained from a control sample of non-tumor, healthy cells in the same tissue type or organ type from which a tumor sample was excised. The reference Psap level is normalized to 100%.

In one embodiment, the reference Psap level is the average of the Psap levels obtained from a population of healthy individuals and the reference Psap level is normalized to 100%.

In one embodiment, the average Psap level from a population of healthy individuals is for a specific tissue type or organ type, e.g., the liver or lungs. For example, the average Psap level is from obtained from the liver Psap levels of a population of healthy individuals. The reference Psap level is normalized to 100%.

As used herein, the term "prognosis" is intended to encompass predictions and likelihood analyses of disease progression, particularly tumor recurrence, metastatic spread and disease relapse. The prognostic methods of the invention are intended to be used clinically in making decisions concerning treatment modalities, including therapeutic intervention, diagnostic criteria such as disease staging, and disease monitoring and surveillance for metastasis or recurrence of neoplastic disease.

In one embodiment, the method for prognosis evaluation is carried out on tissue samples removed from a subject in a surgical procedure, for example, in a biopsy. Preferably, the method is carried out using human cancer patient tumor samples, or samples from human patients suspected of having cancer or having abnormal growth or lesions. Various methods of harvesting a tissue sample are known to those skilled in the art and include, for example, fine needle aspiration, image-guided needle core aspiration, liposuction, laser capture microdissection, and ultrasound guided needle core aspiration, to name a few. Preferably, the samples are preserved, for example, in paraffin, and prepared for histological and immunohistochemical analysis. Alternatively, the samples can be prepared for other methods of determining and quantifying protein expression levels that are well known in the art. Tissues samples are often dissolved in TRIZOL™ reagent to prevent the breakdown and to preserve the integrity of the nucleic acids and proteins. Nucleic acid molecules can then be extracted and isolated from the TRIZOL™ dissolved sample using any of a number of procedures, which are well-known in the art. For example, the most common approach is the alcohol salt precipitation of nucleic acids.

In one embodiment, the individual is diagnosed with a benign or malignant tumor. Methods of determining whether a tumor or cancer is metastatic or benign are well known to one skilled in the art, e.g., measurement of biomarkers such as metalloproteinase pump-1 (U.S. Pat. No. 5,726,015), CA125, or CEA.

In one embodiment, the sample from the individual need not be a tumor sample. In some embodiments, the sample from the individual is a biopsy tissue sample or a fluid sample such as a blood sample.

In one embodiment, the prognosis evaluation method described herein is not restricted to the analyses of Psap. Analysis of the levels of c-Myc and Tsp-1 are also contemplated. The levels of a variety of angiogenic growth factors and angiogenesis inhibitors are also contemplated as being relevant to prognosis, and methods for evaluating them are known to one skilled in the art.

In one embodiment, the angiogenesis-dependent disease or disorder is selected from a group consisting of cancer, psoriasis, age-related macular degeneration, thyroid hyperplasia, preeclampsia, rheumatoid arthritis and osteoarthritis, Alzheimer's disease, obesity, pleural effusion, atherosclerosis, endometriosis, diabetic/other retinopathies, neovascular glaucoma, age-related macular degeneration, hemangiomas, and corneal neovascularization.

In another embodiment, the treatment is administered in conjunction with chemotherapy, radiation therapy, a cytostatic agent, an anti-VEGF agent, an anti-angiogenesis factor, and/or a p53 reactivation agent.

In one embodiment, the method for diagnosing metastasis an individual diagnosed with cancer comprises determining the level of Psap expression in a sample from an individual diagnosed with cancer, wherein when the level of Psap in the sample is the same or lower than a reference Psap level, there is an increased likelihood of cancer metastasis and/or recurrence of neoplastic disease, and thus a poor prognosis. The sample can be blood, preferably platelet, scrum or plasma. Methods of collecting and isolating platelets, serum or plasma are well known in the art. The reference Psap level is the average Psap level in the corresponding platelets, serum or plasma of normal healthy individuals not diagnosed with any cancer. The reference Psap levels are normalized to 100%. The Psap levels in the platelets, serum or plasma of patients having non-metastatic cancer are higher than the reference Psap levels, e.g., at least 5% higher. On the other hand, the Psap levels in platelets, scrum or plasma of patients having metastatic cancer tend to be comparable, and can even be lower than the reference Psap levels. Hence, when a sample from an individual recently diagnosed with cancer has a slightly lower Psap level in the plasma compared to the reference Psap level, there is an increased likelihood that individual's cancer has already metastasized.

In one embodiment, the method for prognostic evaluation of an individual diagnosed with cancer comprises determining the level of Psap expression in a tumor sample from an individual diagnosed with cancer, wherein when the level of Psap in the tumor sample is lower than a reference Psap level, there is an increased likelihood of cancer metastasis and/or recurrence of neoplastic disease, and thus a poor prognosis.

In one embodiment, the method for prognostic evaluation in an individual diagnosed with cancer comprises: (a) determining the level of Psap expression in a sample from an individual diagnosed with cancer at a first time point; (b) determining the level of Psap expression in a sample from an individual diagnosed with cancer at a second time point, the first time point being before the second time point; and (c) comparing the levels of Psap from the time points with a reference Psap level; wherein when the level of Psap at the second time point becomes lower than the reference Psap level, the cancer has likely metastased.

In one embodiment, the sample is blood, platelets, serum or plasma.

The method described herein makes a prediction on the likelihood of cancer metastasis, recurrence, and relapse of neoplastic disease in a subject diagnosed with cancer by comparing the level of Psap in the tumor to a reference level of Psap. A reference level of Psap can be that obtained from a control sample of non-tumor, healthy cells in the same tissue type or organ type from which a tumor sample was excised. The reference Psap level is normalized to 100%. A lower level of Psap determined in a tumor sample compared to a reference Psap level is about 95% to 0% of the reference Psap level, including all percentages between 95% and 0%, i.e., about 95%, 80%, 70%, . . . , 20%, . . . , 10%, . . . 0.5%, . . . 0.2% . . . 0% of the reference Psap level. For example, if the prognosis is for breast cancer in a female subject, the reference Psap level is determined using healthy breast tissue from a female subject. This reference breast Psap level is compared with a level of Psap determined in a breast cancer tissue sample. If the breast cancer tissue sample has a Psap level of 65% of a reference Psap level found in a healthy breast tissue sample, the prognosis is an increased likelihood of cancer metastasis and/or recurrence of neoplastic disease, and thus a poor prognosis.

In one embodiment, the method for prognostic evaluation of an individual diagnosed with cancer further comprises: (a) determining the level of Psap expression in the tumor stroma; and (b) determining the level of Tsp-1 expression in the tumor stroma, wherein when the levels of Psap and Tsp-1 in the tumor stroma are lower than a reference Psap level and a reference Tsp-1 level respectively, there is an increased likelihood of cancer metastasis and/or recurrence of neoplastic disease, and thus a poor prognosis. The method described herein makes a prediction on the likelihood of cancer metastasis, recurrence, and relapse of neoplastic disease in a subject diagnosed with cancer by comparing the levels of Psap and Tsp-1 in the tumor stroma with reference levels of Psap and Tsp-1. Reference levels of Psap and Tsp-1 are those obtained from a control sample of non-tumor, healthy cells in the same tissue type or organ type from which a tumor sample was excised. The reference Psap and Tsp-1 levels are normalized to 100%. Lower levels of Psap and Tsp-1 in a tumor sample compared to the reference Psap and Tsp-1 levels are about 95% to 0% of the reference Psap level, including all percentages between 95% and 0%, i.e., about 95%, 80%, 70% . . . , 20%, . . . , 10%, . . . 5%, . . . 2% . . . 0% of the reference Psap or Tsp-1 levels. For example, if the prognosis is for lung cancer in a male subject, the reference Psap and Tsp-1 levels are determined using healthy lung tissue from a male subject. These reference lung Psap and Tsp-1 levels are then compared with levels of Psap and Tsp-1 determined in a lung cancer tissue sample. If the lung cancer tissue sample has a Psap level of 25% and a Tsp-1 level of 5% compared to the respective reference Psap and Tsp-1 levels found in healthy lung tissue, the prognosis is an increased likelihood of cancer metastasis and/or recurrence of neoplastic disease, and thus a poor prognosis. Since highly metastatic tumors have virtually no detectable Tsp-1 and Psap, extremely low levels (i.e., about 30%-0% of the reference levels) or undetectable amounts of Psap and Tsp-1 in the cancer tissue sample strongly indicate definite cancer metastasis and/or recurrence of neoplastic disease, and thus a poor prognosis, and would require an aggressive treatment plan. On the basis of the prognosis and the levels of Tsp-1 and Psap in a cancer tissue sample, a clinician skilled in the art can design a customized treatment plan for an afflicted individual. The treatment plan can include administering isolated peptide consisting essentially of the sequence CDWLPKPNMSASC (SEQ. ID. No. 37), LEKTCDWLPKPNMSASCKEI (SEQ. ID. No. 29) or a conservative substitution variant thereof, wherein the peptide is flanked by 0-4 amino acid residues on either terminus or both termini and/or chimeric polypeptides described herein, in conjunction with surgical removal of tumors or tissue with cancerous lesions, chemotherapy, radiation therapy, a cytostatic agent, an anti-VEGF agent, an anti-angiogenesis factor and/or a p53 reactivation agent. Administering a composition comprising isolated peptide consisting essentially of the sequence CDWLPKPNMSASC (SEQ. ID. No. 37), LEKTCDWLPKPNMSASCKEI (SEQ. ID. No. 29) or conservative substitution variant thereof, wherein the peptide is flanked by 0-4 amino acid residues on either terminus or both termini systemically raises the level of Psap and consequently the Tsp-1 and p53 in the cancer cells, surrounding tissue, and potential metastatic sites to which a metastatic cancer cell can target. This can prevent future metastasis and also establishment of secondary tumors. Compositions comprising of isolated peptide consisting essentially of the sequence CDWLPKPNMSASC (SEQ. ID. No. 37) or LEKTCDWLPKPNMSASCKEI (SEQ. ID. No. 29), wherein the peptide is flanked by 0-4 amino acid residues on either terminus or both termini and/or chimeric polypeptides described herein can also be injected intratumorly.

In another embodiment, the method for monitoring or surveillance for the development of metastasis in an individual diagnosed with cancer comprises determining the level of Psap expression in a sample from an individual at a first time point, determining the level of Psap expression in a sample from the individual at a second time point, the first time point being before the second time point; comparing the levels of Psap from the time points with a reference Psap level, wherein when the levels of Psap at the second lime point are lower than the reference Psap level, e.g., 95% or less, the cancer is deemed likely to have developed into a metastasic cancer and thus evidences a poor prognosis. The sample can be blood, preferably platelets, serum or plasma. The reference Psap level is the average Psap level in the corresponding platelets, serum or plasma of normal healthy individuals not diagnosed with any cancer. The reference Psap levels are normalized to 100%. The Psap levels in the platelets, serum or plasma of patients diagnosed having non-metastatic cancer is higher than the reference Psap levels, at least 5% higher. On the other hand, the Psap levels in platelet, serum or plasma of patients having metastatic cancer can be the same, and/or lower than the reference Psap levels. The Psap level in the sample can be used as a biomarker for the progression of the disease into the metastatic form. For example, in a patient who has been newly diagnosed with breast cancer. A single tumor mass was found and excised. There was no indication that the tumor had metastasized. A sample of her plasma is collected at this initial diagnosis and the Psap level in her plasma is determined and compared to the reference Psap level. Over the next few years, periodic sampling of her plasma Psap level can be performed, e.g., every three months initially for the first two years, then every six months for the next five years thereafter if she remains cancer free in the first two years. These samplings of plasma Psap level can be compared to the reference Psap level and charted over time. When there is a drop in her plasma Psap level compared to the reference Psap level, at least 5%, this is an indication that possibly the cancer has recurred and is of the metastatic form. Her physician can then perform a thorough screening for the cancer recurrence. The method described herein provides a method of prognosis evaluation in an individual diagnosed with cancer.

Plasma, Serum, and Platelet Sampling

The patient's blood can be drawn directly into anti-coagulants containing citrate, EDTA, PGE, and theophylline. The whole blood should be separated into the plasma portion, the cells, and platelets portion by refrigerated centrifugation at 3500 g, 2 minutes. Since platelets have a tendency to adhere to glass, it is preferred that the collection tube be siliconized. After centrifugation, the supernatant is the plasma. The plasma is filtered though a 0.2 µm filter to remove residual platelets and is kept at −20° C. before measurements are performed.

Alternately, the serum can be collected from the whole blood. Collect the blood in a hard plastic or glass tube; blood will not clot in soft plastic. Draw 15 mL of whole blood for 6 mL of serum. The whole blood is allowed to stand at room temperature for 30 minutes to 2 hours until a clot has formed. Carefully separate clot from the sides of the container using a glass rod or wooden applicator stick and leave overnight at 4° C. After which, decant serum, centrifuge, and/or using a Pasteur pipette, remove serum into a clean tube. Clarify the serum by centrifugation at 2000-3000 rpm for 10 minutes. The serum is stored at −20° or −80° C. measurement is performed. Detailed described of obtaining serum using collection tubes can be found in U.S. Pat. No. 3,837,376 and is incorporated by reference. Blood collection tubes can also be purchased from BD Diagnostic Systems, Greiner Bio-One, and Kendall Company.

Platelets can be separated from whole blood. When whole blood is centrifuged as described herein to separate the blood cells from the plasma, a pellet is formed at the end of the centrifugation, with the plasma above it. Centrifugation separates out the blood components (red blood cells, white blood cells, and platelets) by their various densities. The red blood cells (RBCs) are denser and will be the first to move to the bottom of the collection/centrifugation tube, followed by the smaller white blood cells, and finally the platelets. The plasma fraction is the least dense and is found on top of the pellet. The "buffy coat" which contains the majority of platelets will be sandwiched between the plasma and above the RBCs. Centrifugation of whole blood (with anti-coagulant, PGE and theophylline) can produce an isolated a platelet rich "buffy coat" that lies just above the buoy. The "buffy" coat contains the concentrated platelets and white blood cells.

Platelets can be separated from blood according to methods described in U.S. Pat. No. 4,656,035 using lectin to agglutinate the platelets in whole blood. Alternatively, the methods and apparatus described in U.S. Pat. No. 7,223,346 can be used involving a platelet collection device comprising a centrifugal spin-separator container with a cavity having a longitudinal inner surface in order to collect the "huffy coat" enriched with platelets after centrifugation. As another alternative, the methods and apparatus as described in WO/2001/066172 can be used. Each of these are incorporated by reference herein in their entirety.

Platelets can be isolated by the two methods described in A. L. Copley and R. B. Houlihan, Blood, 1947, 2:170-181, which is incorporated by reference herein in its entirety. Both methods are based on the principle that the platelet layer can be obtained by repeated fractional centrifugation.

The whole blood can be first separated into platelet-rich plasma and cells (white and red blood cells). Platelet rich plasma (PRP) can be isolated from the blood centrifugation of citrated whole blood at 200×G for 20 minutes. The platelet rich plasma is then transferred to a fresh polyethylene tube. This PRP is then centrifuged at 800×G to pellet the platelets and the supernatant (platelet poor plasma [PPP]) can be saved for analysis by ELIZA at a later stage. Platelets can be then gently re-suspended in a buffer such as Tyrodes buffer containing 1 U/ml PGE2 and pelleted by centrifugation again. The wash can be repeated twice in this manner before removing the membrane fraction of platelets by centrifugation with Triton X, and lysing the pellet of platelet for Psap analyses. Platelets can be lysed using 50 mM Tris HCL, 100-120 mM NaCl, 5 mM EDTA, 1% Igepal and Protease Inhibitor Tablet (complete TM mixture, Boehringer Manheim, Indianapolis, Ind.). For the analysis of Psap mRNA, the pellet of platelets can be dissolved in TRIZOL® immediately after separation from the plasma.

Determining Expression Level by Measuring mRNA

Real time PCR is an amplification technique that can be used to determine levels of mRNA expression. (See, e.g., Gibson et al., Genome Research 6:995-1001, 1996; Heid et al., Genome Research 6:986-994, 1996). Real-time PCR evaluates the level of PCR product accumulation during amplification. This technique permits quantitative evaluation of mRNA levels in multiple samples. For mRNA levels, mRNA is extracted from a biological sample, e.g., a tumor and normal tissue, and cDNA is prepared using standard techniques. Real-time PCR can be performed, for example, using a Perkin Elmer/Applied Biosystems (Foster City, Calif.) 7700 Prism instrument. Matching primers and fluorescent probes can be designed for genes of interest using, for example, the primer express program provided by Perkin Elmer/Applied Biosystems (Foster City, Calif.). Optimal concentrations of primers and probes can be initially determined by those of ordinary skill in the art, and control (for example, beta-actin) primers and probes can be obtained commercially from, for example, Perkin Elmer/Applied Biosystems (Foster City, Calif.). To quantitate the amount of the specific nucleic acid of interest in a sample, a standard curve is generated using a control. Standard curves can be generated using the Ct values determined in the real-time PCR, which are related to the initial concentration of the nucleic acid of interest used in the assay. Standard dilutions ranging from $10^1$-$10^6$ copies of the gene of interest are generally sufficient. In addition, a standard curve is generated for the control sequence. This permits standardization of initial content of the nucleic acid of interest in a tissue sample to the amount of control for comparison purposes.

Methods of real-time quantitative PCR using TaqMan probes are well known in the art. Detailed protocols for real-time quantitative PCR can be found in, e.g., for RNA in Gibson et al., 1996, Genome Res., 10:995-1001 and for DNA in Heid et al., 1996, Genome Res., 10:986-994.

The TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, for example, AmpliTaq, results in the cleavage of the TaqMan probe. This cleavage separates the 5' fluorescent dye and the 3' quenching agent, thereby resulting in an increase in fluorescence as a function of amplification (see, for example, www2.perkin-elmer.com).

In another embodiment, detection of RNA transcripts can be achieved by Northern blotting, wherein a preparation of RNA is run on a denaturing agarose gel, and transferred to a suitable support, such as activated cellulose, nitrocellulose or glass or nylon membranes. Labeled (e.g., radiolabeled) cDNA or RNA is then hybridized to the preparation, washed and analyzed by methods such as autoradiography.

Detection of RNA transcripts can further be accomplished using known amplification methods. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap lipase chain reaction (RT-AGLCR) as described by R. L. Marshall, et al., PCR Methods and Applications 4: 80-84 (1994). One suitable method for detecting enzyme mRNA transcripts is described in reference Pabic et al., Hepatology, 37(5): 1056-1066, 2003, which is herein incorporated by reference in its entirety.

Other known amplification methods which can be utilized herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; and target mediated amplification, as described by PCT Publication WO 9322461.

In situ hybridization visualization can also be employed, wherein a radioactively labeled antisense RNA probe is hybridized with a thin section of a biopsy sample, washed, cleaved with RNase and exposed to a sensitive emulsion for autoradiography. The samples can be stained with haematoxylin to demonstrate the histological composition of the sample, and dark field imaging with a suitable light filter shows the developed emulsion. Non-radioactive labels such as digoxigenin can also be used.

Alternatively, mRNA expression can be detected on a DNA array, chip or a microarray. Oligonucleotides corresponding to enzyme are immobilized on a chip which is then hybridized with labeled nucleic acids of a test sample obtained from a patient. Positive hybridization signal is obtained with the sample containing enzyme transcripts. Methods of preparing DNA arrays and their use are well known in the art. (See, for example U.S. Pat. Nos. 6,618, 6796; 6,379,897; 6,664,377; 6,451,536; 548,257; U.S. Patent Application No. 20030157485 and Schena et al., 1995

Science 20:467-470; Gerhold et al., 1999 Trends in Biochem. Sci. 24, 168-173; and Lennon et al. 2000 Drug discovery Today 5: 59-65, which are herein incorporated by reference in their entirety). Serial Analysis of Gene Expression (SAGE) can also be performed (See for example U.S. Patent Application 20030215858).

To monitor mRNA levels, for example, mRNA is extracted from the tissue sample to be tested, reverse transcribed, and fluorescent-labeled cDNA probes are generated. The microarrays capable of hybridizing to enzyme cDNA are then probed with the labeled cDNA probes, the slides scanned and fluorescence intensity measured. This intensity correlates with the hybridization intensity and expression levels.

Methods of "quantitative" amplification are well known to those of skill in the art. For example, quantitative PCR involves simultaneously co-amplifying a known quantity of a control sequence using the same primers. This provides an internal standard that can be used to calibrate the PCR reaction. Detailed protocols for quantitative PCR are provided, for example, in Innis et al., (1990) PCR Protocols, A Guide to Methods and Applications, Academic Press, Inc. N.Y.

Determining Expression Level by Measuring Protein

In one embodiment, the levels of Psap and Tsp-1 proteins are measured by contacting the tissue sample with an antibody-based binding moiety that specifically binds to Psap or Tsp-1, or to a fragment of Psap or Tsp-1. Formation of the antibody-protein complex is then detected by a variety of methods known in the art.

The term "antibody-based binding moiety" or "antibody" includes immunoglobulin molecules and immunologically active determinants of immunoglobulin molecules, e.g., molecules that contain an antigen binding site which specifically binds (immunoreacts with) to the Psap proteins. The term "antibody-based binding moiety" is intended to include whole antibodies, e.g., of any isotype (IgG, IgA, IgM, IgE, etc), and includes fragments thereof which are also specifically reactive with the Psap proteins. Antibodies can be fragmented using conventional techniques. Thus, the term includes segments of proteolytically-cleaved or recombinantly-prepared portions of an antibody molecule that are capable of selectively reacting with a certain protein. Non limiting examples of such proteolytic and/or recombinant fragments include Fab, F(ab')2, Fab', Fv, dAbs and single chain antibodies (scFv) containing a VL and VH domain joined by a peptide linker. The scFv's can be covalently or non-covalently linked to form antibodies having two or more binding sites. Thus, "antibody-base binding moiety" includes polyclonal, monoclonal, or other purified preparations of antibodies and recombinant antibodies. The term "antibody-base binding moiety" is further intended to include humanized antibodies, bispecific antibodies, and chimeric molecules having at least one antigen binding determinant derived from an antibody molecule. In a preferred embodiment, the antibody-based binding moiety detectably labeled.

"Labeled antibody", as used herein, includes antibodies that are labeled by a detectable means and include, but are not limited to, antibodies that are enzymatically, radioactively, fluorescently, and chemiluminescently labeled. Antibodies can also be labeled with a detectable tag, such as c-Myc, HA, VSV-G, HSV, FLAG, V5, or HIS. The detection and quantification of Psap or Tsp-1 present in the tissuel samples correlate to the intensity of the signal emitted from the detectably labeled antibody.

In one preferred embodiment, the antibody-based binding moiety is detectably labeled by linking the antibody to an enzyme. The enzyme, in turn, when exposed to its substrate, will react with the substrate in such a manner as to produce a chemical moiety which can be detected, for example, by spectrophotometric, fluorometric or by visual means. Enzymes which can be used to detectably label the antibodies of the present invention include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase.

Detection can also be accomplished using any of a variety of other immunoassays. For example, by radioactively labeling an antibody, it is possible to detect the antibody through the use of radioimmune assays. The radioactive isotope can be detected by such means as the use of a gamma counter or a scintillation counter or by audioradiography. Isotopes which are particularly useful for the purpose of the present invention are $^{3}H$, $^{131}I$, $^{35}S$, $^{14}C$, and preferably $^{125}I$.

It is also possible to label an antibody with a fluorescent compound. When the fluorescently labeled antibody is exposed to light of the proper wavelength, its presence can then be detected due to fluorescence. Among the most commonly used fluorescent labeling compounds are CYE dyes, fluorescein isothiocyanate, rhodamine, phycoerytherin, phycocyanin, allophycocyanin, o-phthaldehyde and fluorescamine.

An antibody can also be detectably labeled using fluorescence emitting metals such as 152Eu, or others of the lanthanide series. These metals can be attached to the antibody using such metal chelating groups as diethylenetriaminepentaacetic acid (DTPA) or ethylenediaminetetraacetic acid (EDTA).

An antibody also can be detectably labeled by coupling it to a chemiluminescent compound. The presence of the chemiluminescent-antibody is then determined by detecting the presence of luminescence that arises during the course of a chemical reaction. Examples of particularly useful chemiluminescent labeling compounds are luminol, luciferin, isoluminol, theromatic acridinium ester, imidazole, acridinium salt and oxalate ester.

As mentioned above, levels of enzyme protein can be detected by immunoassays, such as enzyme linked immunoabsorbant assay (ELISA), radioimmunoassay (RIA), Immunoradiometric assay (IRMA), Western blotting, immunocytochemistry or immunohistochemistry, each of which are described in more detail below. Immunoassays such as ELISA or RIA, which can be extremely rapid, are more generally preferred. Antibody arrays or protein chips can also be employed, see for example U.S. Patent Application Nos: 20030013208A1; 20020155493A1; 20030017515 and U.S. Pat. Nos. 6,329,209; 6,365,418, which are herein incorporated by reference in their entirety.

Immunoassays

The most common enzyme immunoassay is the "Enzyme-Linked Immunosorbent Assay (ELISA)." ELISA is a technique for detecting and measuring the concentration of an antigen using a labeled (e.g., enzyme linked) form of the antibody. There are different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. 1984, J. Clin. Chem. Clin. Biochem., 22:895-904.

In a "sandwich ELISA", an antibody (e.g., anti-enzyme) is linked to a solid phase (i.e., a microliter plate) and exposed to a biological sample containing antigen (e.g., enzyme). The solid phase is then washed to remove unbound antigen. A labeled antibody (e.g., enzyme linked) is then hound to the bound-antigen (if present) forming an antibody-antigen-antibody sandwich. Examples of enzymes that can be linked to the antibody are alkaline phosphatase, horseradish peroxidase, luciferase, urease, and B-galactosidase. The enzyme linked antibody reacts with a substrate to generate a colored reaction product that can be measured.

In a "competitive ELISA", antibody is incubated with a sample containing antigen (i.e., enzyme). The antigen-antibody mixture is then contacted with a solid phase (e.g., a microtiter plate) that is coated with antigen (i.e., enzyme). The more antigen present in the sample, the less free antibody that will be available to bind to the solid phase. A labeled (e.g., enzyme linked) secondary antibody is then added to the solid phase to determine the amount of primary antibody bound to the solid phase.

In an "immunohistochemistry assay" a section of tissue is tested for specific proteins by exposing the tissue to antibodies that are specific for the protein that is being assayed. The antibodies are then visualized by any of a number of methods to determine the presence and amount of the protein present. Examples of methods used to visualize antibodies are, for example, through enzymes linked to the antibodies (e.g., luciferase, alkaline phosphatase, horseradish peroxidase, or beta-galactosidase), or chemical methods (e.g., DAB/Substrate chromagen). The sample is then analysed microscopically, most preferably by light microscopy of a sample stained with a stain that is detected in the visible spectrum, using any of a variety of such staining methods and reagents known to those skilled in the art.

Alternatively, "Radioimmunoassays" can be employed. A radioimmunoassay is a technique for detecting and measuring the concentration of an antigen using a labeled (e.g., radioactively or fluorescently labeled) form of the antigen. Examples of radioactive labels for antigens include 3H, 14C, and 125I. The concentration of antigen enzyme in a biological sample is measured by having the antigen in the biological sample compete with the labeled (e.g., radioactively) antigen for binding to an antibody to the antigen. To ensure competitive binding between the labeled antigen and the unlabeled antigen, the labeled antigen is present in a concentration sufficient to saturate the binding sites of the antibody. The higher the concentration of antigen in the sample, the lower the concentration of labeled antigen that will bind to the antibody.

In a radioimmunoassay, to determine the concentration of labeled antigen hound to antibody, the antigen-antibody complex must be separated from the free antigen. One method for separating the antigen-antibody complex from the free antigen is by precipitating the antigen-antibody complex with an anti-isotype antiserum. Another method for separating the antigen-antibody complex from the free antigen is by precipitating the antigen-antibody complex with formalin-killed *S. aureus*. Yet another method for separating the antigen-antibody complex from the free antigen is by performing a "solid-phase radioimmunoassay" where the antibody is linked (e.g., covalently) to Sepharose beads, polystyrene wells, polyvinylchloride wells, or microtiter wells. By comparing the concentration of labeled antigen bound to antibody to a standard curve based on samples having a known concentration of antigen, the concentration of antigen in the biological sample can be determined.

An "Immunoradiometric assay" (IRMA) is an immunoassay in which the antibody reagent is radioactively labeled. An IRMA requires the production of a multivalent antigen conjugate; by techniques such as conjugation to a protein e.g., rabbit serum albumin (RSA). The multivalent antigen conjugate must have at least 2 antigen residues per molecule and the antigen residues must be of sufficient distance apart to allow binding by at least two antibodies to the antigen. For example, in an IRMA the multivalent antigen conjugate can be attached to a solid surface such as a plastic sphere. Unlabeled "sample" antigen and antibody to antigen which is radioactively labeled are added to a test tube containing the multivalent antigen conjugate coated sphere. The antigen in the sample competes with the multivalent antigen conjugate for antigen antibody binding sites. After an appropriate incubation period, the unbound reactants are removed by washing and the amount of radioactivity on the solid phase is determined. The amount of bound radioactive antibody is inversely proportional to the concentration of antigen in the sample.

Other techniques can be used to detect Psap and Tsp-1 in the tissue samples obtained in a biopsy, according to a practitioner's preference, and based upon the present disclosure. One such technique is Western blotting (Towbin et al., Proc. Nat. Acad. Sci. 76:4350 (1979)), wherein a suitably treated sample is run on an SDS-PAGE gel before being transferred to a solid support, such as a nitrocellulose filter. Detectably labeled anti-enzyme antibodies can then be used to assess enzyme levels, where the intensity of the signal from the detectable label corresponds to the amount of enzyme present. Levels can be quantified, for example by densitometry.

In one embodiment, Psap and Tsp-1, and/or their mRNA levels in the tissue sample can be determined by mass spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.). See for example, U.S. Patent Application Nos: 20030199001, 20030134304, and 20030077616, which are herein incorporated by reference.

Mass spectrometry methods are well known in the art and have been used to quantify and/or identify biomolecules, such as proteins (see, e.g., Li et al., (2000) Tibtech 18:151-160; Rowley et al., (2000) Methods 20: 383-397; and Kuster and Mann (1998) Curr. Opin. Structural Biol. 8: 393-400). Further, mass spectrometric techniques have been developed that permit at least partial de novo sequencing of isolated proteins. Chait et al., Science 262:89-92 (1993); Keough et al., Proc. Natl. Acad. Sci. USA. 96:7131-6 (1999); reviewed in Bergman, EXS 88:133-44 (2000).

In certain embodiments, a gas phase ion spectrophotometer is used. In other embodiments, laser-desorption/ionization mass spectrometry is used to analyze the sample. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. See, e.g., U.S. Pat. Nos. 5,118,937 and 5,045,694.

In SELDI, the substrate surface is modified so that it is an active participant in the desorption process. In one variant, the surface is derivatized with adsorbent and/or capture reagents that selectively bind the protein of interest. In another variant, the surface is derivatized with energy absorbing molecules that are not desorbed when struck with the laser. In another variant, the surface is derivatized with molecules that bind the protein of interest and that contain a photolytic bond that is broken upon application of the laser. In each of these methods, the derivatizing agent generally is localized to a specific location on the substrate surface where the sample is applied. See, e.g., U.S. Pat. No. 5,719,060 and WO 98/59361. The two methods can be combined by, for example, using a SELDI affinity surface to capture an analyte and adding matrix-containing liquid to the captured analyte to provide the energy absorbing material.

For additional information regarding mass spectrometers, see, e.g., Principles of Instrumental Analysis, 3rd edition., Skoog, Saunders College Publishing, Philadelphia, 1985; and Kirk-Othmer Encyclopedia of Chemical Technology, 4.sup.th ed. Vol. 15 (John Wiley & Sons, New York 1995), pp. 1071-1094.

Detection of the presence of Psap or Tsp-1 mRNA or protein will typically depend on the detection of signal intensity. This, in turn, can reflect the quantity and character of a polypeptide bound to the substrate. For example, in certain embodiments, the signal strength of peak values from spectra of a first sample and a second sample can be compared (e.g., visually, by computer analysis etc.), to determine the relative amounts of particular biomolecules. Software programs such as the Biomarker Wizard program (Ciphergen Biosystems, Inc., Fremont, Calif.) can be used to aid in analyzing mass spectra. The mass spectrometers and their techniques are well known to those of skill in the art.

Antibodies or Antisera Against Psap and Tsp-1 Proteins

In one embodiment, the diagnostic method of the invention uses antibodies or anti-sera for determining the expression levels of Psap and Tsp-1. The antibodies for use in the present invention can be obtained from a commercial source such as Novus Biologicals (anti-prosaposin, Clone 1D1-C12, catalog #H00005660-M01), Santa Cruz Biotechnology (Anti-saposin B (E-15), catalog #sc-27014; anti-Tsp-1, Clone CSI 002-65, catalog #sc-59888), and Labvision (anti-Tsp-1, clone Ab-2, catalog #MS-419-B). The antibodies can be polyclonal or monoclonal antibodies. Alternatively, antibodies can be raised against Psap protein (Genbank Accession No. NM_002778) or Tsp-1 (Genbank Accession No. NM_003246). Methods for the production of enzyme antibodies are disclosed in PCT publication WO 97/40072 or U.S. Application. No. 2002/0182702, which are herein incorporated by reference.

Antibodies for use in the present invention can be produced using standard methods to produce antibodies, for example, by monoclonal antibody production (Campbell, A. M., Monoclonal Antibodies Technology Laboratory Techniques in Biochemistry and Molecular Biology, Elsevier Science Publishers, Amsterdam, the Netherlands (1984); St. Groth et al., J. Immunology, (1990) 35: 1-21; and Kozbor et al., Immunology Today (1983) 4:72). Antibodies can also be readily obtained by using antigenic portions of the protein to screen an antibody library, such as a phage display library by methods well known in the art. For example, U.S. Pat. No. 5,702,892 and WO 01/18058 disclose bacteriophage display libraries and selection methods for producing antibody binding domain fragments.

Detection of Psap and Tsp-1 antibodies can be achieved by direct labeling of the antibodies themselves, with labels including a radioactive label such as $^3H$, $^{14}C$, $^{35}S$, $^{125}I$, or $^{131}I$, a fluorescent label, a hapten label such as biotin, or an enzyme such as horse radish peroxidase or alkaline phosphatase. Alternatively, unlabeled primary antibody is used in conjunction with labeled secondary antibody, comprising antisera, polyclonal antisera or a monoclonal antibody specific for the primary antibody. In one embodiment, the primary antibody or antisera is unlabeled, the secondary antisera or antibody is conjugated with biotin and enzyme-linked strepavidin is used to produce visible staining for histochemical analysis.

The present invention can be defined in any of the following alphabetized paragraphs:

[A] An isolated peptide consisting essentially of at least ten consecutive amino acid residues fragment derived from the sequence LEKTCDWLPKPNMSASCKEI (SEQ. ID. No. 29) or a conservative substitutive variant thereof, wherein the peptide is flanked by 0-4 amino acid residues on either terminus or both termini.

[B] An isolated peptide consisting essentially of the sequence CDWLPKPNMSASC (SEQ. ID. No. 37) or a conservative substitutive variant thereof, wherein the peptide is flanked by 0-4 amino acid residues on either terminus or both termini.

[C] An isolated peptide consisting essentially of the sequence LEKTCDWLPKPNMSASCKEI (SEQ. ID. No. 29) or a conservative substitutive variant thereof, wherein the peptide is flanked by 0-4 amino acid residues on either terminus or both termini.

[D] The isolated peptide of any of paragraphs [A]-[C], wherein the peptide is capable of activating p53 and inducing Tsp-1 expression.

[E] The isolated peptide of any of paragraphs [A]-[C], wherein the peptide is fused/conjugated to a therapeutic molecule.

[F] The isolated peptide of any of paragraphs [A]-[C], wherein the peptide has 0-5 conservative amino acid substitution.

[G] An isolated chimeric polypeptide comprising a first portion and a second portion, wherein the first portion is a peptide of any one of paragraphs [A]-[F], and wherein said second portion is not a Psap protein.

[H] The isolated chimeric polypeptide of paragraph [G], wherein the second portion comprises an amino acid sequence or a polymer that enhances the serum half life of said first portion.

[I] The isolated chimeric polypeptide of paragraph [G], wherein the second portion is a therapeutic molecule.

[J] A composition comprising of a peptide of any one of paragraphs [A]-[F], or an isolated chimeric polypeptide of any one of paragraphs [G]-[I], and a pharmaceutically acceptable carrier.

[K] Use of a peptide of any one of paragraphs [A]-[F] or an isolated chimeric polypeptide of any one of paragraphs [G]-[I] for the treatment of an angiogenesis-dependent disease or disorder.

[L] Use of a peptide of any one of paragraphs [A]-[F] or an isolated chimeric polypeptide of any one of paragraphs [G]-[I] for inhibiting the recurrence of an angiogenesis-dependent disease or disorder in a subject.

[M] Use of a peptide of any one of paragraphs [A]-[F] or an isolated chimeric polypeptide of any one of paragraphs [G]-[I] for inhibiting metastasis of cancer in a subject diagnosed with cancer.

[N] Use of a peptide of any one of paragraphs [A]-[F] or an isolated chimeric polypeptide of any one of paragraphs [G]-[I] for the manufacture of medicament for the treatment of an angiogenesis-dependent disease or disorder.

[O] Use of a peptide of any one of paragraphs [A]-[G] or an isolated chimeric polypeptide of any one of paragraphs [G]-[I] for the manufacture of medicament for inhibiting the recurrence of an angiogenesis-dependent disease or disorder.

[P] Use of a peptide of any one of paragraphs [A]-[F] or an isolated chimeric polypeptide of any one of paragraphs [G]-[I] for the manufacture of medicament for inhibiting metastasis of cancer in a subject diagnosed with cancer.

[Q] Uses of any one of paragraphs [K], [L], [N] and [O], wherein the angiogenesis-dependent disease or disorder is selected from a group consisting of cancer, psoriasis, age-related macular degeneration, thyroid hyperplasia, preeclampsia, rheumatoid arthritis and osteoarthritis, Alzheimer's disease, obesity, pleural effusion, atherosclerosis, endometriosis, diabetic/other retinopathies, neovascular glaucoma, age-related macular degeneration, hemangiomas, and corneal neovascularization.

[R] Uses of any one of paragraphs [K]-[Q], wherein the peptide or polypeptide is administered in conjunction with chemotherapy, radiation therapy, a cytostatic agent, an anti-VEGF agent, an anti-angiogenesis factor, and/or a p53 reactivation agent.

[S] A method of treating an angiogenesis-dependent disease or disorder, comprising administering to a subject in need thereof a therapeutically effective amount of a composition of paragraph [J].

[T] A method of inhibiting the recurrence of an angiogenesis-dependent disease or disorder, the method comprising administering to a subject in need thereof a therapeutically effective amount of a composition of paragraph [J].

[U] A method of inhibiting metastasis of cancer in a subject diagnosed with cancer, the method comprising administering to the subject a therapeutically effective amount of a composition of paragraph [J].

[V] A method of treating an individual diagnosed with cancer comprising:
  a. determining a level of Psap in a tumor sample from said individual;
  b. comparing the Psap level determined in (a) with a reference Psap level; and
  c. wherein said Psap level determined in (a) is lower than 95% of said reference Psap level, administering a therapeutically effective amount of a composition of paragraph [J].

[W] The method of paragraph [S] or [T], wherein the angiogenesis-dependent disease or disorder is selected from a group consisting of cancer, psoriasis, age-related macular degeneration, thyroid hyperplasia, preeclampsia, rheumatoid arthritis and osteoarthritis, Alzheimer's disease, obesity, pleural effusion, atherosclerosis, endometriosis, diabetic/other retinopathies, neovascular glaucoma, age-related macular degeneration, hemangiomas, and corneal neovascularization.

[X] The method of any one of paragraphs [S]-[W], wherein the composition is administered in conjunction with chemotherapy, radiation therapy, a cytostatic agent, an anti-VEGF agent, an anti-angiogenesis factor, and/or a p53 reactivation agent.

Unless otherwise stated, the present invention was performed using standard procedures that are well known to one skilled in the art, for example, in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); Methods in Enzymology: Guide to Molecular Cloning Techniques Vol. 152, S. L. Berger and A. R. Kimmerl Eds., Academic Press Inc., San Diego, USA (1987); Current Protocols in Molecular Biology (CPMB) (Fred M. Ausubel, et al., ed., John Wiley and Sons, Inc.); Current Protocols in Protein Science (CPPS) (John E. Coligan, et al., ed., John Wiley and Sons, Inc.); Current Protocols in Cell Biology (CPCB) (Juan S. Bonifacino et al., ed., John Wiley and Sons, Inc.); Culture of Animal Cells: A Manual of Basic Technique by R. Ian Freshney, Publisher: Wiley-Liss; 5th edition (2005); and Animal Cell Culture Methods (Methods in Cell Biology, Vol 57, Jennie P. Mather and David Barnes editors, Academic Press, 1st edition, 1998), which are all incorporated herein by reference in their entireties.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

Definitions of common terms in molecular biology are found in Benjamin Lewin, Genes IX, published by Jones & Bartlett Publishing, 2007 (ISBN-13: 9780763740634); Kendrew et al., (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages may mean±1%.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

This invention is further illustrated by the following examples which should not be construed as limiting. The contents of all references cited throughout this application, as well as the figures and tables are incorporated herein by reference in their entirety.

EXAMPLES

Experimental Procedures
Cell Lines

The cell lines PC3 was obtained from the American Type Culture Collection (ATCC, Manassas, Va.). PC3M-LN4 was the generous gift of Dr. Isaiah Fidler (MD Anderson Cancer Center, Houston, Tex.). The prostate cancer cell lines were grown in RPMI medium containing 10% fetal bovine serum (FBS). The prostate fibroblasts were grown in DMEM medium with 10% FBS. The WI 38 and MRC 5 lung fibroblasts were also obtained from the ATCC and were grown in MEM medium with 10% FBS.

Animal Studies

All animal work was done in accordance with a protocol approved by the Institutional Animal Care and Use Committee. Male SCID mice 6-8 weeks old were injected with $2 \times 10^6$ viable cells in the prostate gland. The cells were washed and harvested in PBS prior to injection into the prostate glands of anaesthetized mice (2% avertin, 0.5 ml per mouse) in a volume of 0.8 ml. Endpoint assays were conducted at 5 weeks after injection unless significant morbidity required that the mouse be euthanized earlier.

In vitro Conditioned Media Assays and Co-culture Assays

For the conditioned media assay, $1.5 \times 10^6$ tumor cells and fibroblasts cells were grown in the tumor cell media containing 0.1% FBS for 12 hours at which point the conditioned media from the tumor cells was centrifuged to remove any cells or cell debris and transferred to the fibroblasts subsequent to removal of the low serum fibroblast growth media. All assays were performed a minimum of five times and representative samples depicted. The fibroblasts and media were harvested after 12 to 16 hours after addition of the tumor cell conditioned media and lysed for the western blot analysis while the conditioned media was collected for ELISA analysis. For the co-culture assays, $1 \times 10^6$ fibroblasts were seeded in the bottom chamber of transwell tissue culture plates (Corning Inc., Corning, N.Y.) and $1 \times 10^6$ tumor cells were seeded on the membrane in the top chamber of the plates. The two cell types were co-cultured for 40 to 44 hours in tumor cell media containing 0.1% FBS before harvesting and lysing the fibroblasts for western blot analysis and collecting the media for ELISA analysis.

Western Blot Analyses and ELISA Analysis

For Western blotting, cells were harvested by mechanical scraping into 4° C. PBS, cell pellets were obtained by removing PBS after centrifugation at 13,000 rpm in a Heraeus Biofuge Fresco (Thermo Electron, Asheville, N.C.) for 2 min. Cells were then lysed in 50 mM Tris-HCl (pH 7.4), 150 mM NaCl, 1% NP40, 1 mM sodium orthovanadate, 5 mM NaF, 20 mM β-glycerophosphate, and complete protease inhibitor (Roche, Indianapolis, Ind.) and protein concentrations were determined by the BioRad protein assay (BioRad, Hercules, Calif.). Fifty micrograms of protein were loaded per well onto a 4-12% pre-cast Bis-Tris gel (BioRad, Hercules, Calif.). The protein extracts were electrophoresed and transferred to an immobilon-P membrane (Millipore, Bedford, Mass.). The membranes were blocked in 5% nonfat milk and incubated in primary antibody to Tsp-1 (Ab-11, LabVision, Fremont, Calif.), c-Myc and phospho-Myc (Cell Signaling Technology, Beverly, Mass.), Prosaposin (Santa Cruz Biotechnology, Santa Cruz, Calif.), β-actin (AbCam, Cambridge, UK). The membranes were then washed in PBS+0.1% Tween-20 and incubated with either HRP-conjugated goat anti-mouse or anti-rabbit secondary antibody (Jackson Immunoresearch Laboratories, West Grove, Pa.) followed by another wash. The membrane was then developed with ECL reagent (Pierce, Rockford, Ill.) and exposed on film. Protein volume intensity was determined using a Bio-Rad Chemi-Doc XRS system (Bio-Rad, CA).

For ELISA analysis, the conditioned media were centrifuged to remove cell debris and the supernatant retained to measure VEGF levels using an ELISA kit that was specific for human VEGF (R & D, Minneapolis, Minn.). VEGF levels were normalized against total protein from the cells used in the assay. Xenograft tumors and tissue samples were homogenized and suspended in PBS and murine VEGF levels were determined using an ELISA kit that was specific for murine VEGF (R & D, Minneapolis, Minn.) results were normalized against the mass of the tumors. All error bars included in the graphical depiction of ELISA data represent SEM (Standard Error of Mean).

Immunohistochemistry

Thin paraffin sections (5 μm) from formalin fixed and paraffin embedded prostate tumors and lung tissue were dewaxed with xylene/ethanol before heat induced microwave epitope retrieval in Tris-HCL (pH 1.0) for 15 minutes. Immunostaining of tissue sections was performed on the DAKO Autostainer with the DAKO ARK (animal research kit) peroxidase (Dako Cytomation, Copenhagen, Denmark) as detection system. The slides were incubated with a mouse monoclonal thrombospondin antibody (TSP-Ab-4, clone A6.1) (Neomarkers, CA), diluted 1:50 for 60 minutes at room temperature. Antigen localization was achieved using the DAB diaminobenzidine peroxidase reaction, counterstained with hematoxylin. Sections incubated with isotypic mouse IgG1 (Dako Cytomation, Denmark) served as negative controls. Thrombospondin expression was evaluated subjectively by estimating the staining intensity and percentage positivity. A staining index (values 0-9), obtained as a product of staining intensity (0-3) and proportion of immunopositive tumor cells (≤10%=1, 10-50%=2, >50%=3), was calculated. Cases with a TSP staining index<2 were defined as weak/negative.

Regarding p53, sections were stained with a mouse monoclonal antibody (p53-PAB1802; Santa Cruz Biotechnology, CA, USA), incubated overnight (4° C.), dilution 1:10, after heat induced microwave epitope retrieval in TRS (pH 6.0) for 15 minutes. For p53, only nuclear staining was considered, and staining intensity was recorded as either negative/weak or moderate/strong. For both antibodies, immunostaining of tissue sections was performed on the DAKO Autostainer with the DAKO ARK (animal research kit) peroxidase (Dako Cytomation, Copenhagen, Denmark) as detection system. Antigen localization was achieved using the DAB diaminobenzidine peroxidase reaction, counterstained with hematoxylin.

Fractionation of Conditioned Media and Identification of Prosaposin

Volumes of 500 mL were collected of PC3 and PC3M-LN4 conditioned media from cells grown in serum free RPMI media for 16 hours. The conditioned media was centrifuged to remove any cells or cell debris for 5 minutes at 3,000 rpm in a Sorvall SS-34 rotor. Conditioned media was then loaded onto a 10 mL Heparin-$Cu^{2+}$ sepharose column at 1 ml/min. The column was washed with 100 mL 10 mM $NaPO_4$, 150 mM NaCl, pH 7.4. The column was subsequently washed with 50 mL 10 mM $NaPO_4$, 2M NaCl, pH 7.4; 50 mL 10 mM $NaPO_4$, 150 mM NaCl, pH 7.4; 50 mM 10 mM $NaPO_4$, 150 mL NaCl, 10 mM imidazole, pH 7.4, and finally 50 mL 10 mM $NaPO_4$, 150 mM NaCl, pH 7.4. Following these wash steps, the remaining bound proteins were eluted at 1 mL/min in 10 mM $NaPO_4$, 10 mM imidazole, pH 7.4 with a linear gradient of NaCl ranging from 0.3M to 2M with fractions collected in 0.05M NaCl increments. The fractions were then dialyzed against 10 mM $NaPO_4$, 150 mL NaCl, pHII 7.4 to remove excess NaCl and imidazole.

The fractions were then tested for activity by adding 1 mL to serum starved prostate or lung fibroblasts in 9 mL of DMEM containing 0.1% FBS for 12 hours. The fibroblasts were then prepped for western blot analysis as described above. Fractions containing Tsp-1 stimulating activity were concentrated using centriplus-10 columns (Millipore, Mass., USA) and submitted to the Children's Hospital Proteomics Center for tandem liquid chromatography/mass spectroscopy analysis. The lists of proteins present in all the active fractions was then cross compared to identify proteins present in all active fractions.

Prosaposin Purification

Prosaposin was cloned into pLNCX acceptor vector (Clontech) including a C-terminal 6x-HN tag. PC3M-LN4 cells were then retrovirally transduced with this construct and subsequent to selection using G418 were serum starved cells for 12 hours and collected 500 mL of conditioned media. The conditioned media was then incubated with 5 mL Talon metal affinity resin (Clontech) for 1 hr at 4° C. The solution was then centrifuged at 2,000×G in an SS-34 rotor for 10 minutes and the supernatant removed. The beads were then resuspended in 10 mM $NaPO_4$, 150 mM NaCl, pH8.0 and loaded into a 10 mL Econo-column (Bio-Rad). The column was then washed first with 100 mL 10 mM $NaPO_4$, 150 mM NaCl, pH8.0 and subsequently with 10 mM $NaPO_4$, 150 mM NaCl, 25 mM imidazole pH8.0. The remaining bound proteins were then eluted from the column with a step gradient of 50-500 mM imidazole in 10 mM $NaPO_4$, 150 mM NaCl, pH 7.4. Fractions were analyzed for Prosaposin expression and purity by western blot and SYPRO Ruby staining, respectively. Prosaposin containing fractions were then dialyzed against 10 mM $NaPO_4$, 150 mM NaCl, pH 7.4 and concentrated as described above.

Tail Vein Metastasis

Wild-type and Tsp-1−/− C57BL/6J mice were pretreated with 500 µL of serum-free conditioned media from PC3 or PC3shPsap cells or serum-free RPMI media for 10 days via intraperitoneal (i.p.) injection. On the 10th day mice were injected via tail vein, with $1 \times 10^6$ Lewis Lung Carcinoma cells. Subsequently, i.p. injections of serum-free tumor cell conditioned media or control RPMI were performed for 19 additional days, at which point the animals were sacrificed. The lungs were photographed and the number of visible metastatic nodules was counted by eye.

Example 1

Tsp-1 Expression is Inversely Related to Metastatic Potential

The initial step of metastasis is dependent on access to the vasculature or lymphatic system. Metastatic human tumors may differ in the relative of expression of pro- and anti-angiogenic proteins compared to non-metastatic tumors. Thus, the level of VEGF secretion by the weakly metastatic prostate cancer cell line PC3 and a metastatic derivative PC3M-LN4 as well as by the breast cancer cell line MDA-MB-231 and a bone-specific metastatic derivative MDA-MET were measured. PC3M-LN4 cells have been documented to metastasize to multiple organs, including lymph node, liver, lung and bone, while MDA-MET was derived to metastasize only to bone via intra-cardiac injection (Bendre et al., 2002; Pettaway et al., 1996).

Highly metastatic PC3M-LN4 cells and MDA-MET cells secreted lower levels of VEGF than their parental counterparts, as measured by ELISA (FIG. 1A). Even under hypoxic conditions (1% O2), the relative levels remained unchanged with the parental cells secreting more VEGF than their more metastatic derivatives (FIG. 1A). The levels of other angiogenic proteins such as bFGF, TGF□, and PDGF secreted by the tumor cells were analyzed but no significant differences was found between the metastatic and non-metastatic cells (data not shown).

Next, an endogenous inhibitor of angiogenesis, Tsp-1, was determined to ascertain whether metastatic tumor cells express lower levels of Tsp-1 than their non-metastatic counterparts. As determined by western blot analysis, Tsp-1 levels decreased as the metastatic potential of the cell lines increased (FIG. 1B). The non-metastatic PC3 cells expressed high levels of Tsp-1 while their metastatic PC3M-LN4 derivatives expressed no detectable Tsp-1. This analysis was extended to the breast cancer cell lines MDA-MB-231 and MDA-MET. Consistent with the expression levels in the prostate cancer cells, the weakly metastatic MDA-MB-231 breast cancer cell line also expressed higher levels of Tsp-1 than its bone-specific metastatic derivative MDA-MET (FIG. 1B). This indicated an inverse relationship between metastatic potential and Tsp-1 expression.

Example 2

Myc Expression is Directly Related to Metastatic Potential

It has been demonstrated that c-myc is often amplified or overexpressed in several types of human cancer, including prostate and breast cancer (Escot et al., 1986; Nag and Smith, 1989). Furthermore, c-Myc represses the expression of Tsp-1 (Janz et al., 2000; Ngo et al., 2000; Tikhonenko et al., 1996; Watnick et al., 2003). Therefore, the levels of c-Myc were analyzed to determine whether the levels of c-Myc increase as tumors progress to the metastatic phenotype. The levels of c-Myc increase with the metastatic potential of both prostate and breast cancer cells were examined. Protein expression of c-Myc was significantly increased in the highly metastatic PC3M-LN4 and MDA-MET cells as compared to the parental PC3 and MDA-MB- 231 cells (FIG. 1B). Furthermore, levels of phosphorylated c-Myc, which have been shown to be directly involved in Tsp-1 repression (Watnick et al., 2003), were also significantly increased in the metastatic cell lines (FIG. 1C). Hence, the levels of Tsp-1 could be attributable to the effects of Myc protein expression.

Example 3

Expression of Tsp-1 in Primary Tumors

Figure 8:
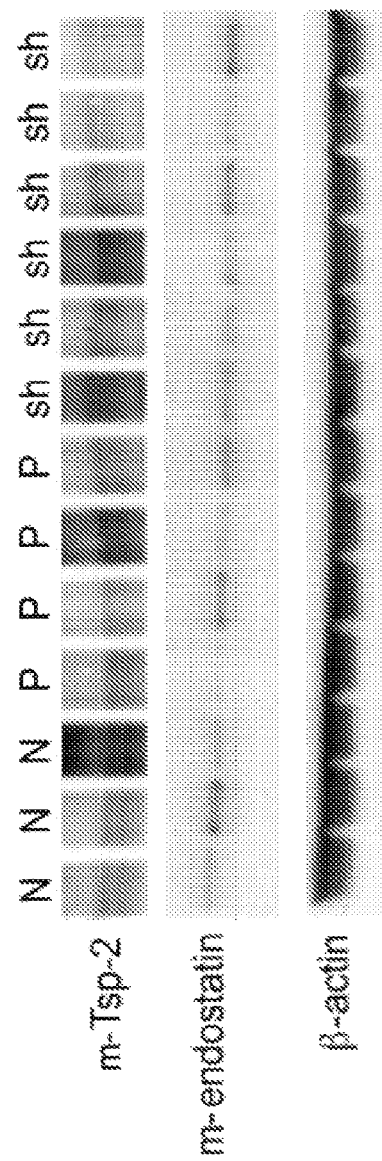
FIG. 8. Western blot analysis of the expression levels of Thrombospondin-2 (Tsp-2), murine endostatin (m-endostatin) and β-actin protein in normal mouse prostate (N) tumors formed by PC3 cells (P), and tumor formed by PC3shPsap cells (sh).

In order to determine whether levels of Tsp-1 observed in in vitro culture conditions were representative of their expression levels in vivo, 2×106 PC3 and their metastatic derivatives, PC3M-LN4 cells, were injected orthotopically into the prostate glands of SCID mice. Five weeks after injection the tumors and surrounding tissue were analyzed for Tsp-1 expression via western blot analysis and immunohistochemistry. The prostate tumors formed by both PC3 and PC3M-LN4 cells were histologically characterized by significant nuclear atypia and a diffuse infiltrating growth pattern, i.e., poorly differentiated, often surrounding benign prostate glands. Strong Tsp-1 staining was observed in fibrous stroma surrounding the invading tumor cells in 14 out of 17 PC3 tumors (FIG. 1F) but in only one out of 16 PC3M-LN4 prostate tumors (FIG. 1F). Conversely, undetectable Tsp-1 staining was observed in the fibrous stroma surrounding the remaining tumors (3/17 PC3 and 15/16 PC3M-LN4 tumors (FIG. 1F). Significantly, analysis of Thrombospondin-2 (Tsp-2) and Endostatin expression by western blot analysis revealed no elevation in PC3 primary tumors relative to normal tissue (FIG. 8).

Consistent with the immunohistochemistry results, four of five PC3 tumors examined expressed high levels of Tsp-1 and low/undetectable, levels of c-Myc by western blot (FIG. 1D). Conversely, western blot analyses revealed that four out of four representative PC3M-LN4 tumors expressed low levels of Tsp-1 and high levels of c-Myc (FIG. 1D). However, one of the PC3 tumors analyzed by western blot expressed low levels of Tsp-1 and high levels of c-Myc (FIG. 1D, P5). Strikingly, this PC3 tumor was one of only two PC3 tumors that formed lung metastases (data not shown).

The level of VEGF secreted by the host stroma in these tumors was analyzed using a murine specific VEGF ELISA that does not recognize the human form of the protein secreted by the tumor cells themselves. Surprisingly, but in keeping with the in vitro observations, 4 out of 5 PC3 tumors sampled contained higher levels of stromal (murine) VEGF than the 4 sampled tumors formed by the PC3M-LN4 cells (FIG. 1E). Significantly, the one metastatic PC3 tumor that did not express higher levels of VEGF also expressed low levels of Tsp-1 as determined by immunohistochemistry and western blot (FIG. 1D), thus indicating that repression of Tsp-1 obviates the requirements for high levels of VEGF in tumor metastasis.

Example 4

Expression of Tsp-1 in Metastases

Having determined that reduced Tsp-1 expression favored primary growth, the expression of Tsp-1 in distant tissue sites was determine to ascertain if similar reduction of expression of Tsp-1 in distant tissue sites was correlated with the growth of metastases. The lungs from mice injected orthotopically with PC3 and PC3M-LN4 cells were analyzed. The lung metastases were distributed in both central and peripheral lung tissues, and in a few cases as small subpleural tumor cell clusters. The lung metastases harbored only a minimal amount of stroma compared with corresponding prostate tumors, but scattered stromal cells were identified within the metastases.

As determined by immunohistochemical analyses, metastatic colonies formed by the PC3 and PC3M-LN4 cells contained undetectable to very low levels of Tsp-1 in the infiltrating stroma (data not shown). Moreover, the PC3M-LN4 cells formed metastases with much greater efficiency than the parental PC3 cells, 10/16 mice injected with PC3M-LN4 cells had detectable metastatic colonies in their lungs while only 2/17 mice injected with PC3 cells had detectable metastatic colonies in their lungs. The frequency of lymph node metastases was virtually identical. Large lymph node metastases were detected in 12/16 mice injected with PC3M-LN4 cells and the two PC3 tumors that metastasized to lung also metastasized to lymph node (FIG. 1F, table 1).

Significantly, the metastatic colonies formed by the two cell types were almost identical with respect to their expression levels of Tsp-1. We observed that the two mice with lung metastases from PC3 tumors were in the group of three mice that harbored primary tumors with low levels of stromal Tsp-1 expression (FIG. 1F, PC3-5). Furthermore, 10/15 PC3M-LN4 tumors that expressed low levels of stromal Tsp-1 gave rise to metastatic colonies. Strikingly, of the fifteen primary tumors that expressed high levels of Tsp-1 (14 PC3 tumors and 1 PC3M-LN4 tumor, designated #9) none gave rise to metastatic colonies, suggesting that stromal Tsp-1 expression at the primary site is an indicator of metastatic potential (FIGS. 1D and F, table 1). Moreover, all metastases that formed showed low levels of Tsp-1 expression in the metastasis-associated stroma. Indeed, the few metastases formed by the generally non-metastatic PC3 cells also lacked stromal Tsp-1 expression.

Example 5

Effects of Tumor Cells on Fibroblasts in vitro

The regulation of stromal Tsp-1 by human tumor cells could be the result of a unidirectional paracrine signaling event or a reciprocal signaling system involving both tumor cells and nearby stromal fibroblasts. In order to determine which signaling system was involved, it was necessary to create an in vitro tissue culture system that recapitulates the in vivo observations. To that end, human prostate (PrF) and mammary fibroblasts (a gift of Dr. Korneli a Polyak, Dana Farber Cancer Institute, Boston, Mass.) was treated with conditioned media from metastatic and non-metastatic prostate and breast cancer cell lines, respectively.

Treatment of fibroblasts with conditioned media from non-metastatic PC3 prostate and MDA-MB-231 breast cancer cell lines stimulated Tsp-1 expression 4-fold (as determined by band volume density) (FIGS. 2A and B). Conversely, treatment of prostate fibroblasts with conditioned media from the metastastic PC3M-LN4 line resulted in a 3-fold suppression of Tsp-1 protein expression (FIG. 2A). Hence, non-metastatic PC-3 cells actively induced Tsp-1 expression above its normal basal levels, while metastatic PC3M-LN4 actively suppressed Tsp-1 below its normal levels.

Figure 2B:
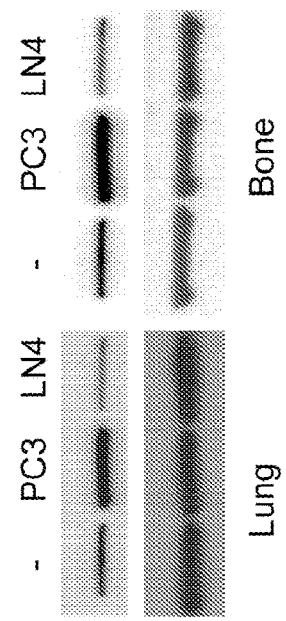
FIG. 2B. Western blot analyses of Tsp-1 and β-Actin expression in normal human mammary fibroblasts that were treated with the conditioned media (CM) from MDA-MB-231 (231) and MDA-MET (MET) cells or co-cultured in transwell apparati (TW) with MDA-MB-231 (231) and MDA-MET (MET) cells.

The conditioned media from MDA-MET cells stimulated Tsp-1 expression in mammary fibroblasts. Furthermore, when these tumor cells were co-cultured with mammary fibroblasts in a transwell apparatus, the level of Tsp-1 expression in the fibroblasts was still not repressed by MDA-MET cells (FIG. 2B). While the MDA-MET cells are portrayed as being metastatic, in fact they do not metastasize from orthotopic sites of injection and instead do so only following intracardiac injection. Thus, in consonance with the fact that MDA-MET cells do not metastasize when injected into the mammary fat pad, these cells are unable to repress Tsp-1 expression in mammary fibroblasts.

Figure 2C:
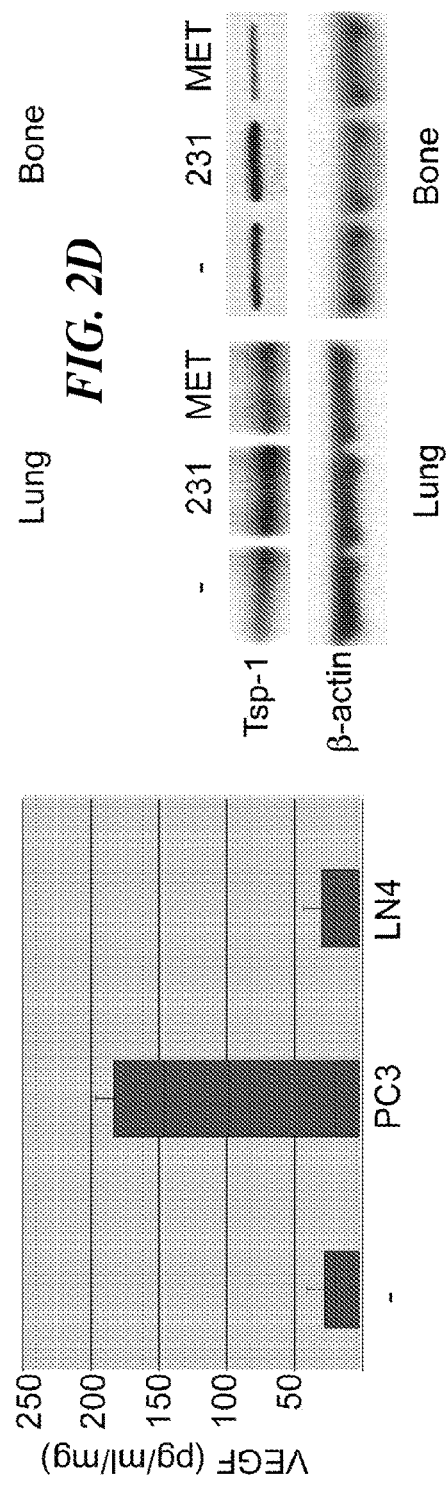
FIG. 2C. Western blot analyses of ELISA of VEGF secretion from prostate fibroblasts treated with the conditioned media from PC3, PC3M-LN4 (LN4) cells. Error bars represent SEM (Standard Error of Mean) of 3 independent experiments performed in triplicate.

The role of stromal Tsp-1 repression was strengthened by the observation that the level of VEGF secretion induced in PrFs by the conditioned media from the PC3M-LN4 tumor cells was lower than that induced by the conditioned media from the PC3 cells (FIG. 2C). These data recapitulate the in vivo observations and suggest that repression of Tsp-1 at both the primary and metastatic sites may be a more critical event for tumor growth than the stimulation of VEGF secretion. Furthermore, the stimulation of stromal Tsp-1 by PC3 cells, despite the concomitant stimulation of VEGF, suggests that Tsp-1 is a potent inhibitor of metastasis even in such cases when the tumor itself is angiogenic.

Figure 2D:
FIG. 2D. Western blot analyses of Tsp-1 and β-Actin expression in WI38 lung fibroblasts and bone marrow stromal cells that were untreated (−) or treated with the conditioned media from PC or PC3M-LN4 (LN4) cells.
Figure 2E:
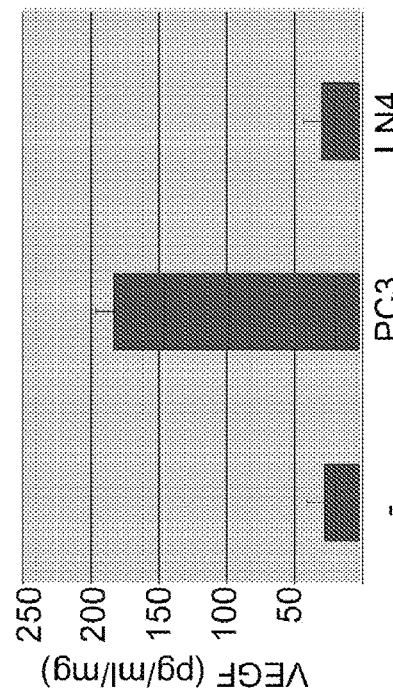
FIG. 2E. Western blot analyses of Tsp-1 and β-Actin expression in WI38 lung fibroblasts and bone marrow stromal cells that were untreated (−) or treated with the conditioned media from MDA-MB-231 (231) or MDA-MET (MET) cells.
Figure 9:
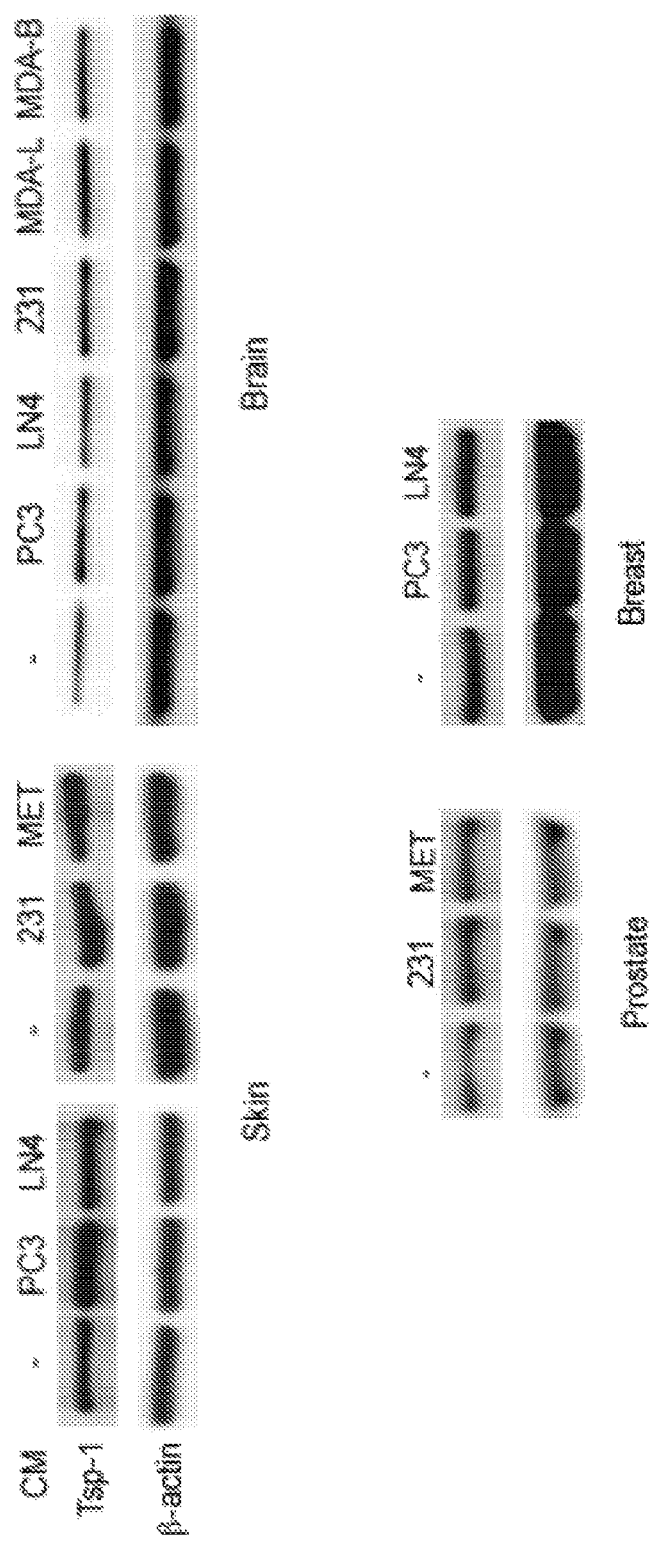
FIG. 9. Western blot analysis of Tsp-1 and β-Actin expression in normal human dermal fibroblasts (NHDF), normal human astrocytes (NHA), normal human prostate fibroblasts (prostate) and normal human mammary fibroblasts that were untreated (−) or treated with the conditioned media from PC3, PC3M-LN4 (LN4), MDA-MB-231 (231), MDA-MB-231-4175 (MDA-L), MDA-MB-1833 (MDA-B) or MDA-MET (MET) cells as denoted.

In addition to repressing stromal Tsp-1 production in the primary tumor, it was demonstrated that Tsp-1 expression was also suppressed in sites of pulmonary metastasis formation. The ability of metastasizing cancer cells to also repress Tsp-1 production in the fibroblasts forming the stroma was determined in two favored sites of metastasis—the lungs and the bone marrow. Human lung and bone marrow derived fibroblasts were treated with conditioned media from PC3, PC3M-LN4, MDA-MB-231 and MDA-MET cells. Consistent with their ability to metastasize to both lung and bone, western blot analysis revealed that PC3M-LN4 cells repressed Tsp-1 expression in both types of fibroblasts (FIG. 2D). Also, consistent with their bone-specific metastatic potential, MDA-MET cells only repressed Tsp-1 in bone marrow-derived fibroblasts and not in lung fibroblasts (FIG. 2E). Strikingly, rather than repressing Tsp-1 expression, the non-metastatic PC3 and MDA-MB-231 cells stimulated Tsp-1 expression in both lung and bone marrow-derived fibroblasts (FIGS. 2D and E). Finally, neither PC3M-LN4 nor MDA-MET was able to repress Tsp-1 in fibroblasts from tissues to which they do not metastasize, such as skin, brain, and in the case of PC3M-LN4, breast (FIG. 9). These observations held two implications. First, cancer cells can successfully repress Tsp-1 expression in the stromal fibroblasts of tissues in which they succeed in forming metastases. Second, the fibroblasts in different tissues, although superficially similar, are biologically heterogeneous, in that some are and some are not responsive to these Tsp-1-repressing signals.

Example 6

Identification of a Prosaposin as a Tsp-1 Stimulating Protein

In order to determine the mechanism by which PC3 cells were able to stimulate the expression of p53 and consequently Tsp-1 in stromal fibroblasts, a proteomic analysis of the proteins secreted by PC3 cells was undertaken. The first step was to fractionate the conditioned media over a heparin-Cu2+ sepharose column with increasing concentrations of NaCl in the presence of imidazole (Shing, 1988). Subsequently, we treated both prostate and lung fibroblasts with the fractionated media and analyzed Tsp-1 expression by western blot analysis. Three fractions, eluting between 0.7 and 0.9M NaCl in the presence of 10 mM imidazole contained an activity that stimulated Tsp-1 expression in prostate and lung fibroblasts (FIGS. 3A and B).

The Tsp-1-inducing fractions were concentrated and submitted them for tandem liquid chromatography/mass spectrometry (LC/MS) analysis. The LC/MS analysis revealed that only two proteins were present in all of the active fractions, Prosaposin and Fetuin A (Table 3). Western blot analysis of cell lysates and conditioned media from both PC3 and PC3M-LN4 cells revealed that Prosaposin (Psap), was expressed at ~10-fold higher levels in PC3 cells than in PC3M-LN4 cells (FIG. 3C), while there was no significant difference between the two cell populations in Fetuin A expression (data not shown). Significantly, it was observed that metastatic derivatives of the MDA-MB-231 cell line also expressed significantly lower levels of Psap (FIG. 3D) than the parental, weakly metastatic, MDA-MB-231 cells To determine whether Prosaposin was the protein responsible for stimulating Tsp-1 expression in stromal fibroblasts, PC3 cells were transduced with lentiviral constructs specifying five different shRNAs targeted to Psap. It was confirmed via western blot analysis that four of these hairpin sequences suppressed the expression of Psap expressed by PC3 cells (FIG. 3E, #1, 2, 4, and 5). Significantly, suppression of Psap expression had no effect on the expression of Tsp-1 by PC3 cells themselves (FIG. 3E). Normal human prostate and WI-38 lung fibroblasts were subsequently treated with the conditioned media from the five cell populations expressing the various Psap shRNA sequences and assessed Tsp-1 expression. Western blot analysis revealed that the conditioned media from the four cell populations in which Psap had been suppressed no longer stimulated Tsp-1 in PrF and WI-38 cells (FIGS. 3F and G). In contrast, treatment of prostate and lung fibroblasts with conditioned media from PC3 cells with the weakest knockdown of Prosaposin (#3) still stimulated Tsp-1 expression (FIGS. 3F and G).

Figure 3B:
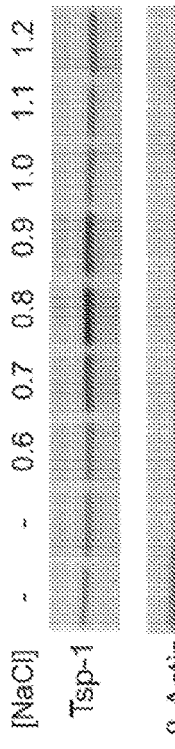
FIG. 3B. Western blot analyses of Tsp-1 and β-actin expression in WI 38 lung fibroblasts treated with fractions of conditioned media from PC3 cells eluted from a $Cu^{2+}$-heparin column.
Figure 3D:
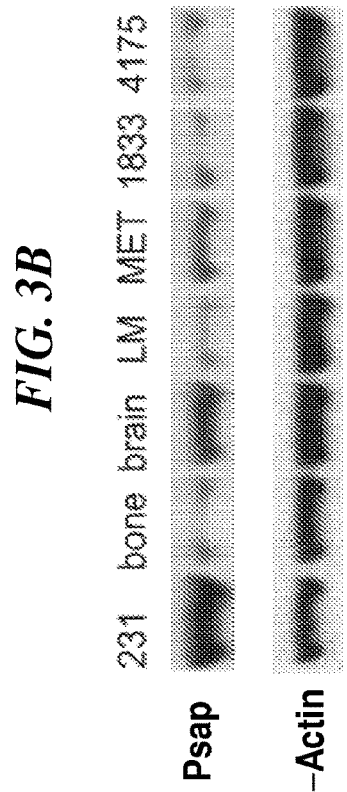
FIG. 3D. Western blot analyses of Psap and β-actin expression in MDA-MB-231 (231), MDA-Bone (Bone), MDA-Brain (Brain), MDA-MB-LM2-4 (LM), MDA-MET (MET), MDA-MB-231-1833 (1833) and MDA-MB-231-4175 (4175) cells.
Figure 3F:
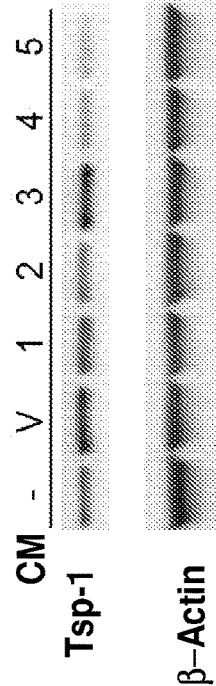
FIG. 3F. Western blot analyses of Tsp-1 and β-actin expression in prostate fibroblasts treated with conditioned media (CM) from pLKO vector transduced PC3, and PC3 cells transduced with 5 shRNA sequences specific for Psap.
Figure 3A:
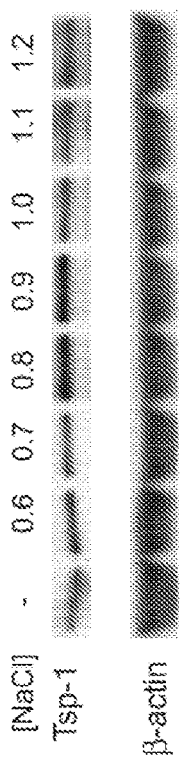
FIG. 3A. Western blot analyses of Tsp-1 and β-actin expression in prostate fibroblasts treated with fractions of conditioned media from PC3 cells eluted from a Cu2+- heparin column.
Figure 3C:
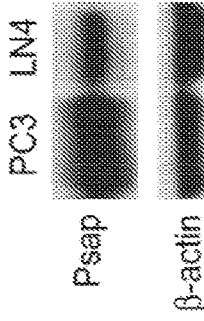
FIG. 3C. Western blot analyses of Psap and β-actin expression in PC3 and PC3M-LN4 (LN4) cells.
Figure 3E:
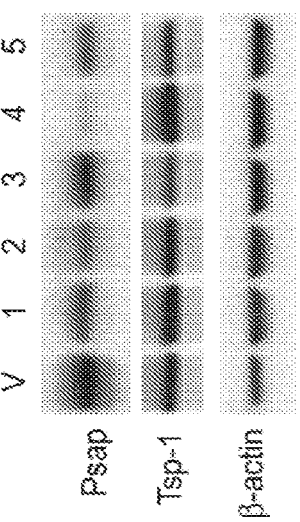
FIG. 3E. Western blot analyses of Psap, Tsp-1 and β-actin expression in PC3 cells that were transduced with five shRNA constructs for Psap or an empty pLKO vector (V).

In order to confirm the role of Psap as a stimulator of Tsp-1, the PC3M-LN4 cells, which normally do not express significant levels of Psap, was transduced with a retroviral construct specifying Psap (FIG. 3H). Treatment of normal human prostate fibroblasts with conditioned media from these Psap-overexpressing PC3M-LN4 cells reversed their normal ability to repress Tsp-1 (FIG. 3I). Finally, a 6x-HN-tagged version of prosaposin was purified using a Talon metal affinity resin. Treatment of prostate fibroblasts with purified prosaposin resulted in the stimulation of Tsp-1 expression (~5-fold), confirming that Prosaposin sufficed, on its own, to elicit the previously observed increase in Tsp-1 expression (FIG. 3J).

Example 7

Role of p53 in Stromal Tsp-1 Regulation

In order to determine the mechanism by which tumor cells regulate Tsp-1, the tumor suppressor p53 was studied. It has been demonstrated that the tumor suppressor p53 is a transcriptional activator of Tsp-1 in human fibroblasts (Dameron et al., 1994). Thus, the relative p53 expression levels in the stroma of PC3 and PC3M-LN4 tumors were determined via western blot analysis. Both PC3 and PC3M-LN4 contain deletion mutations in the p53 gene (Isaacs et al., 1991), resulting in the absence of detectable p53 protein in both cell types. The immunohistochemical analysis of p53 tumor expression is therefore simplified by the lack of contribution from the tumor cells themselves.

The analyses of PC3 and PC3M-LN4 tumors revealed a significant association between p53 and Tsp-1 expression levels in tumor-associated stromal cells. Of 7 cases with strong Tsp-1 staining, 6 cases had strong p53 staining. Correspondingly, of 7 cases with weak or negative Tsp-1 staining, 6 cases had negative/weak p53 staining (Fisher's exact test, one-sided: p=0.015) (data not shown). Consistent with the immunohistochemical observations, western blot analysis revealed that p53 expression was markedly elevated in the tumor stroma of PC3 primary tumors but undetectable in PC3M-LN4 tumors (FIG. 4A). Hence, the non-metastasizing PC3 tumors could induce both p53 and Tsp-1 expression in the tumor-associated stroma, while the metastasizing PC3M-LN4 cells had no such effect.

Significantly, the p53 expression was stimulated in the proximal lumbar lymph nodes from mice bearing PC3 tumors despite the fact that there were no lymph node metastases. In contrast, lymph nodes from mice bearing PC3M-LN4 tumors expressed p53 at levels similar to normal lymph nodes (FIG. 4B). These observations provided the first suggestion that PC3 tumors secrete a protein that not only stimulates p53 in a paracrine fashion in the stroma of the primary tumor but also stimulates p53 expression in distal tissues via some type of endocrine signaling, a mechanism that is described in more detail below.

Having determined that p53 protein levels were elevated in the stroma of PC3 tumors, the inventors determined if p53 stimulation could be responsible for the increased expression of Tsp-1. Cultured prostate fibroblasts (PrFs) were treated with conditioned media from either the PC3 or PC3M-LN4 cells and assessed the change in p53 protein levels via western blot analysis. Consistent with the immunohistochemical and western blot results of the tumor-associated stroma, PC3-conditioned media stimulated p53 protein levels in PrFs, while PC3M-LN4-conditioned media induced a modest repression of p53 in PrF's (FIG. 4C). Hence, in parallel with earlier analyses of Tsp-1 expression, non-metastatic cells induced p53 levels while metastatic cells caused their repression.

The p53 expression was silenced in both prostate and lung fibroblasts via lentiviral transduction of a short-hairpin RNA (shRNA) sequence targeted to p53 (Brummelkamp et al., 2002). As expected, treatment of these cells with conditioned media from PC3 cells failed to stimulate p53 (FIGS. 4D and E). More significantly conditioned media from PC3 cells failed to stimulate Tsp-1 expression in fibroblasts in which p53 had been silenced (FIGS. 4D and E). These results demonstrate that stimulation of Tsp-1 in fibroblasts by PC3 cells is p53-dependent.

Figure 4F:
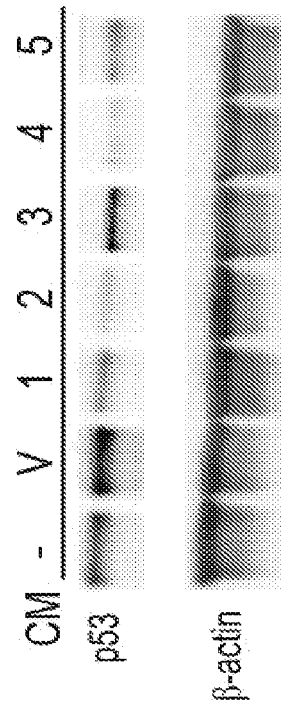
FIG. 4F. Western blot analyses of p53 and β-actin expression in prostate fibroblasts treated with conditioned media (CM) from pLKO vector transduced PC3, and PC3 cells transduced with 5 shRNA sequences specific for Psap.
Figure 4G:
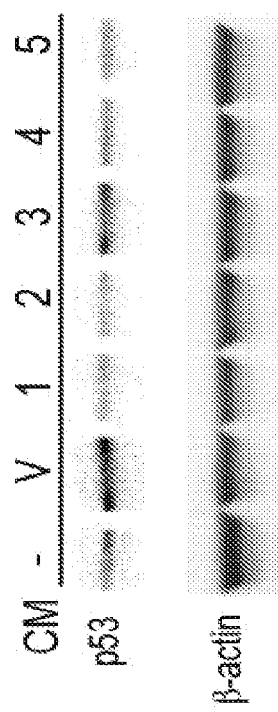
FIG. 4G. Western blot analyses of p53 and β-actin expression in WI 38 lung fibroblasts treated with conditioned media (CM) from pLKO vector transduced PC3, and PC3 cells transduced with 5 shRNA sequences specific for Psap.
Figure 4E:
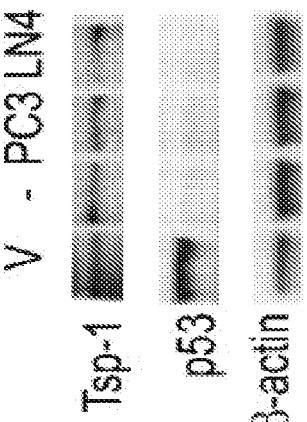
FIG. 4E. Western blot analyses of Tsp-1, p53 and β-Actin expression in WI38 lung fibroblasts containing empty pLKO vector (V) or p53 shRNA that were untreated (−) or treated with the conditioned media from PC3 or PC3M-LN4 (LN4).
Figure 4I:
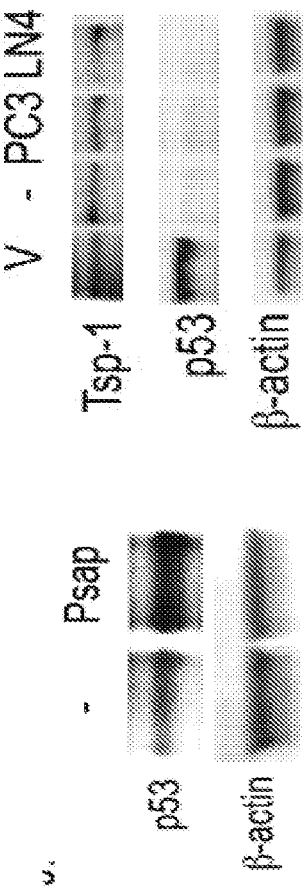
FIG. 4I. Western blot analyses of p53 and β-actin expression in untreated prostate fibroblasts (−), or treated with 5 μg of purified recombinant human Psap.
Figure 4H:
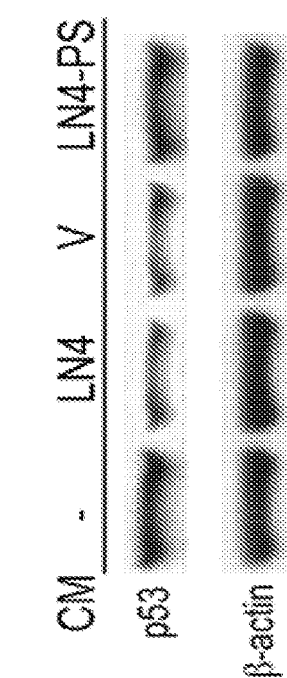
FIG. 4H. Western blot analyses of p53 and β-actin expression in untreated prostate fibroblasts (−) or treated with conditioned media from PC3M-LN4 (LN4), PC3M-LN4-pLNCX (V) or PC3M-LN4-Psap (Psap) cells.

Could Prosaposin also function as a p53-stimulating protein? Prostate and lung fibroblasts were treated with conditioned media from the five populations of PC3shPsap cells described above. As observed for Tsp-1 expression, silencing of Psap also reversed the ability of PC3 to stimulate p53 expression (FIGS. 4F and G). Of note is the observation that the one shRNA sequence that did not suppress Psap in PC3 cells (#3) still stimulated p53 in both prostate and lung fibroblasts (FIGS. 4F and G). Moreover, overexpression of Psap in PC3M-LN4 cells reversed the ability to repress p53 in prostate fibroblasts (FIG. 4H) and treatment of prostate fibroblasts with purified recombinant Psap stimulated p53 expression (FIG. 4I). These data confirm that Psap stimulates p53 expression and as a result induces the stimulation of Tsp-1 expression.

Example 8

Prosaposin Expression is Negatively Regulated by Myc

The metastatic PC3M-LN4 cells express lower levels of Psap than the non-metastatic parental PC3 cells. In addition, the PC3 cells express lower levels of Myc than their metastatic derivative PC3M-LN4, indicating that Psap expression might be negatively regulated by Myc. To examine this possibility, PC3 cells were transduced with a retroviral construct specifying a Myc-Estrogen Receptor (ER) fusion protein, which is activated upon administration of 4-hydroxy-tamoxifen (4-HT) (Littlewood et al., 1995). Upon treatment of PC3-MycER cells with 4-HT and resulting induction of Myc function, there was a significant reduction (4-fold) in Psap levels (FIG. 5A). Furthermore, conditioned media from the 4-HT-treated PC3MycER cells failed to stimulate the expression of either p53 or Tsp-1 in lung or prostate fibroblasts, while conditioned media from untreated PC3MycER cells stimulated both p53 and Tsp-1 expression in these two cell types (FIG. 5B).

To further explored the connection between Myc and Psap expression, Myc expression in PC3M-LN4 cells were silenced via lentiviral transduction of an shRNA construct that specifically antagonizes c-Myc expression. Two shRNA sequences directed against Myc that were able to achieve significant knockdown of Myc protein expression were identified (4- and 8-fold, respectively) (FIG. 5C). Indeed, these two cell lines expressed higher levels (>3- and 6-fold, respectively) of Psap than PC3M-LN4 cells, as determined via western blot analysis (FIG. 5D). Consistent with Psap overexpression, conditioned media from the PC3M-LN4shMyc cells no longer repressed Tsp-1 expression in lung and prostate fibroblasts (FIG. 5E). Taken together these data indicate that Myc is a negative regulator of Psap expression in these tumor cells.

Example 9

Loss of Prosaposin Stimulates Tumor Metastasis

Given Psap's ability to stimulate p53 and Tsp-1 expression in prostate and lung fibroblasts, it was speculated that it might also inhibit the metastatic potential of PC3 cells in vivo. To test this hypothesis, 2×106 PC3shPsap cells that demonstrated the greatest knockdown of Psap expression (FIG. 3E: #4) and PC3pLKO control cells were injected, independently, into the prostate glands of SCID mice. It was observed that six of seven tumors formed by PC3shPsap cells gave rise to large lymph node metastases whereas none of the eight tumors generated from PC3pLKO vector controls cells gave rise to metastases (data not shown). Significantly, the tumors that arose from PC3shPsap cells formed metastases with a similar frequency to PC3M-LN4 cells (6/7 vs. 12/15), albeit with increased latency of 8-9 weeks as compared to 5-6 weeks. Of greater significance is the fact that, although one of the shPsap tumors grew significantly larger than the PC3pLKO tumors, three of the smaller shPsap tumors (FIG. 6A: #4, 5, and 7), which grew to approximately the same size as the PC3pLKO control tumors, formed visible lymph node metastases (data not shown). These data indicated that reduction of Psap expression, achieved in this instance by use of an shRNA, significantly potentiated the ability of otherwise-non-metastatic tumor cells to form lymph nodes metastases.

Could the suppression of Prosaposin expression abrogated the stimulation of p53 and Tsp-1 previously observed in PC3 tumors. Immunohistochemical analysis of p53 and Tsp-1 expression in the primary tumors formed by PC3 and PC3shPsap tumors revealed that p53 expression in the tumor-associated stromal cells of PC3shPsap tumors was completely negative (n=4) (data not shown), in contrast to the behavior of PC3 control tumors in which p53 expression was significantly stimulated. Regarding Tsp-1 staining, most PC3shPsap tumors were weak or negative within the central parts of the tumors, whereas occasional moderate staining was observed in the periphery, corresponding to the invasive border, but independent of p53 expression (n=4/10) (data not shown).

These results were supported by western blot analysis of the tumors formed by PC3shPsap cells, which revealed no stimulation of either p53 or Tsp-1 in the tumor stroma (FIG. 6B). Western blot analysis of 4 representative tumors revealed that PC3shPsap tumors no longer stimulated p53 or Tsp-1 expression in lymph node or lung tissue of mice bearing these tumors (FIGS. 6C and D). Taken together these findings strongly indicate that Psap functions as a repressor of both lymphatic and vascular metastasis by inducing p53 and consequently Tsp-1 expression in stromal fibroblasts via both paracrine and endocrine signaling mechanisms. In addition, when Psap-suppressed cancer cells metastasized to lymph nodes, they were surrounded by stromal cells that similarly lacked p53 and Tsp-1 expression.

Example 10

Tsp-1 Expression is Required for Prosaposin-mediated Suppression of Metastasis

Is Tsp-1 expression required for Prosaposin-mediated suppression of lung metastasis in vivo? Tsp-1−/− mice (Lawler et al., 1998) were used to answer this question. Earlier observations have shwon that Prosaposin could act systemically to influence the levels of both Tsp-1 and p53 in distant organs (FIGS. 6C and D). Both wild-type C57BL/6J and Tsp-1−/− mice from the same genetic background were pretreated with RPMI media or conditioned media from PC3pLKO or PC3shPsap cells for 10 days; these serum-free media were injected at daily intervals into the peritoneal space of these animals. On the tenth day, 1×106 syngeneic Lewis Lung Carcinoma (LLC) cells were injected via tail vein into wild-type and Tsp-1−/− mice that were treated as described above or with control RPMI media alone. Nineteen days after tail vein injection, these mice were sacrificed and examined the lungs, in which many of the LLC cells were presumably trapped.

Figure 7B:
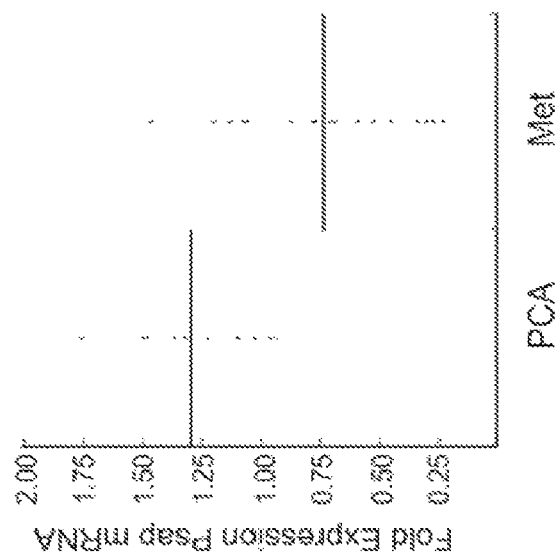
FIG. 7B. Relative mRNA expression levels of Psap in localized human prostate tumors and metastatic human prostate tumors. Each bar represents the mean of each group. The difference in Psap expression between localized and metastatic prostate tumors has a p-value<0.0001 based on one way ANOVA.
Figure 7A:
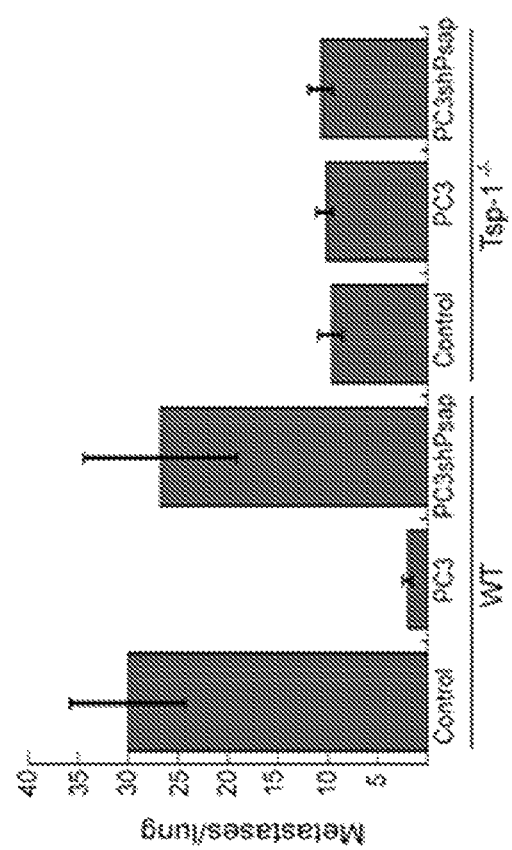
FIG. 7A. Plot of metastases/lung in the mice described in (K), PC3=PC3pLKO.

It was observed that the lungs of wild-type mice treated with RPMI alone were riddled with metastases, containing an average of 30 metastatic colonies per lung (FIG. 7A). Strikingly, it was also observed that the lungs of wild-type mice treated with PC3pLKO-conditioned media contained, on average only 2 metastatic colonies, more than 15-fold fewer than control media-treated mice (FIG. 7A). Conversely, the lungs of mice treated with conditioned media from PC3shPsap cells resembled the control mice with respect to the number of metastases, containing 27 metastatic nodules per lung on average (FIG. 7A). This supported the notion that the PC3 cells released a substance that could actively suppress metastasis formation by these LLC cells.

Figure 10:
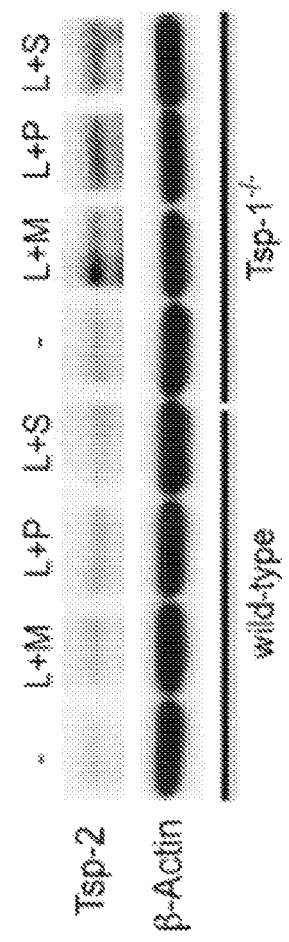
FIG. 10. Western blot analysis of murine Tsp-2 and β-Actin expression in normal lung tissue (−) and lungs of wild-type and tsp-1−/−C57Bl/6J mice injected with 1×10⁶ Lewis Lung Carcinoma cells and treated with serum free RPMI media (L+M), conditioned media from empty vector containing PC3pLKO (L+P) or PC3shPsap cells (L+S).
Figures 11, 12:
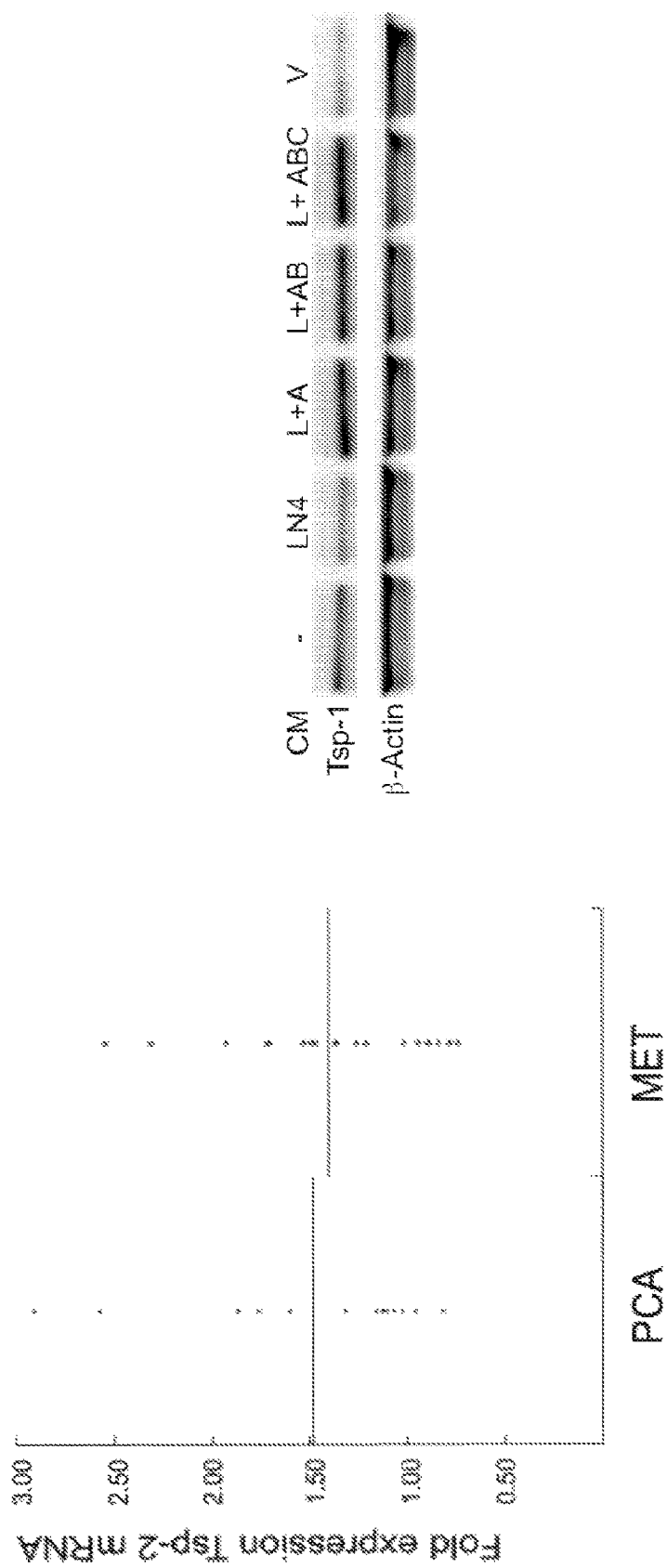
FIG. 11. Relative mRNA expression levels of Tsp-2 in localized human prostate tumors (PCA) and metastatic human prostate tumors (MET). Each bar represents the mean of each group. The difference in Tsp-2 expression between encapsulated and metastatic prostate tumors has a p-value=0.6797 based on one way ANOVA.
FIG. 12. Saposin A stimulates Tsp-1. Western blot of Tsp-1 and β-Actin expression in prostate fibroblasts treated with conditioned media from PC3M-LN4 cells (LN4) or PC3M-LN4 cells transiently transfected with an expression vector (pCMV) specifying Saposin A (L+A), Saposin AB (L+AB), Saposin ABC (L+ABC), or control empty vector.

Consistent with a requirement for Tsp-1, the number of metastases observed in the lungs of tsp-1−/− mice treated with conditioned media from PC3pLKO and PC3shPsap cells was virtually identical (10.25 vs 10.7) compared to 9.7 in the control mice (FIG. 7A). Hence, in the absence of Tsp-1 production by the host, the factor(s) released by PC3 cells failed to suppress metastasis formation by LLC cells. The observed lower numbers of metastases in the Tsp-1 KO mice compared with their wild-type counterparts was apparently related to compensatory Tsp-2 production induced by LLC cells in these mice, a phenomenon not observed in human tumors (FIGS. 10 and 11).

Figure 7C:
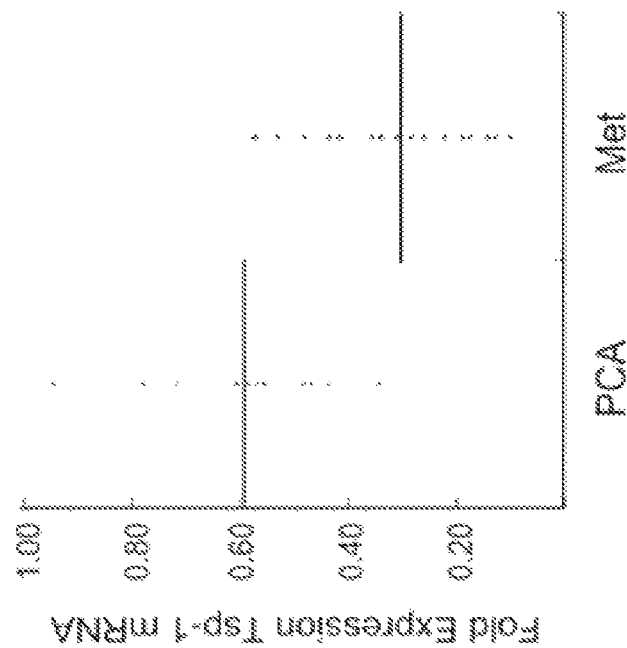
FIG. 7C. Relative mRNA expression levels of Tsp-1 in localized human prostate tumors and metastatic human prostate tumors. Each bar represents the mean of each group. The difference in Tsp-1 expression between localized and metastatic prostate tumors has a p-value<0.0001 based on one way ANOVA.
Figure 7D:
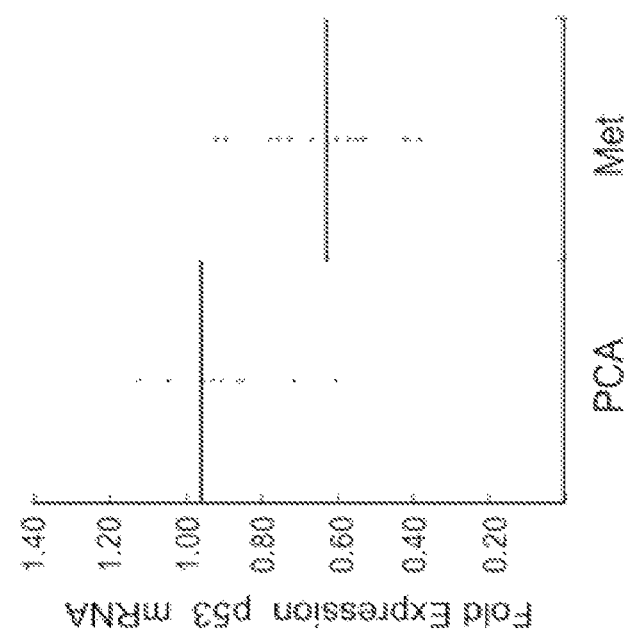
FIG. 7D. Relative mRNA expression levels of p53 in localized human prostate tumors and metastatic human prostate tumors. Each bar represents the mean of each group. The difference in p53 expression between localized and metastatic prostate tumors has a p-value=0.0004 based on one way ANOVA.
Figure 7E:
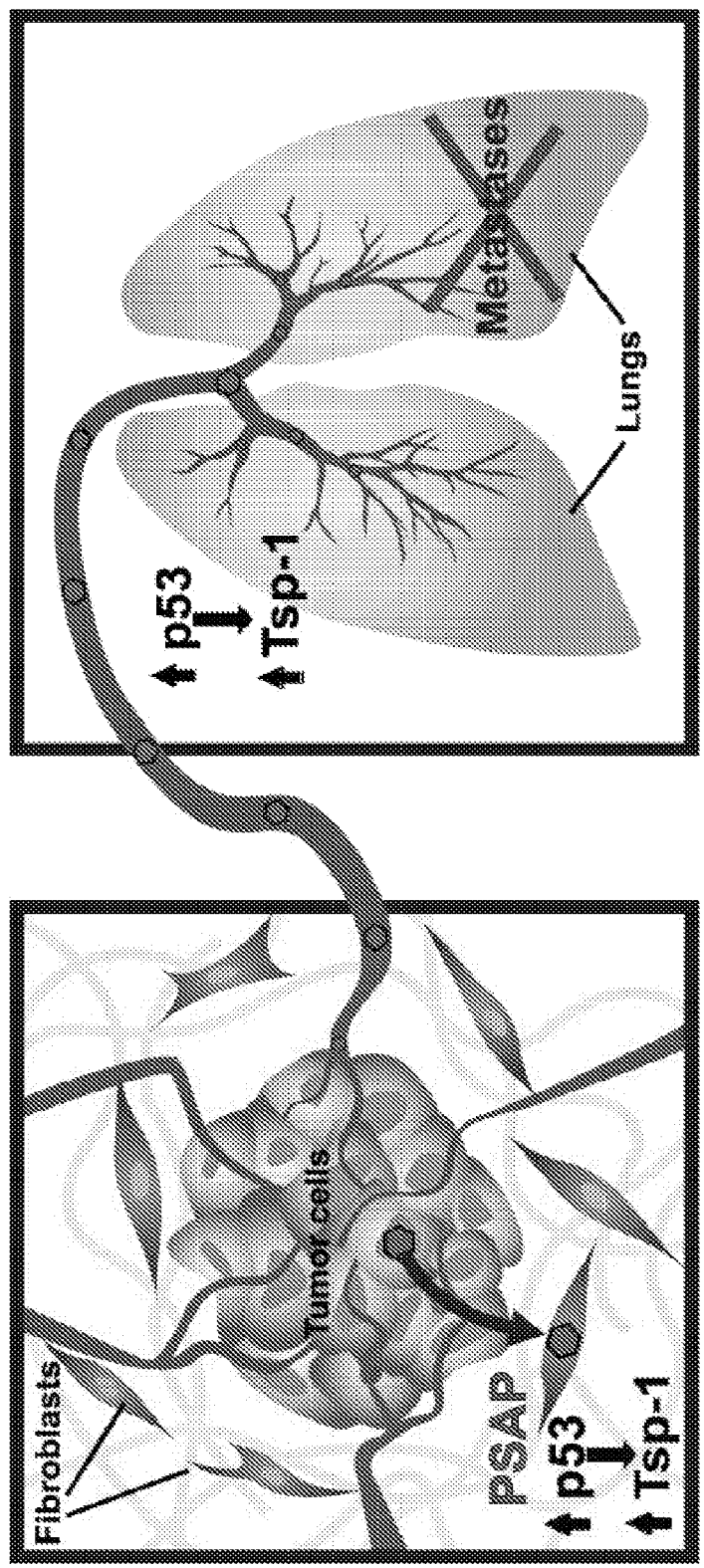
FIG. 7E. Schematic depiction of Prosaposin-mediated inhibition of tumor metastasis (blue hexagons=Prosaposin).

Of interest is whether Prosaposin is differentially expressed in metastatic and localized human prostate cancer. A microarray gene expression data set was gathered from 55 patient samples consisting of normal prostate, benign prostatic hyperplasia (BPII), localized primary prostate tumors and metastatic prostate tumors (Dhanasekaran et al., 2001) and the data were analyzed. Consistent with the xenograft experiments, it was discovered that relative psap mRNA expression (normalized to normal, benign prostate tissue) was ~40% lower, on average, in the metastatic tumors as compared with localized primary tumors with a p value<0.0001 (FIG. 7B). Analysis of this same data set revealed that the relative tsp-1 mRNA expression was, on average, ~50% lower in the metastatic tumors, also with a p value<0.0001 (FIG. 7C). Finally, the relative expression of p53 was ~35% lower in metastatic tumors compared to localized tumors, with a p value of 0.0004 (FIG. 7D). These expression data support the results obtained in the experiments and demonstrate that in metastatic human tumors expression of Prosaposin is suppressed compared to non-metastatic tumors. Taken together these data indicate that Prosaposin functions as a suppressor of tumor metastasis (FIG. 7E).

Example 11

Saposin A Stimulates Tsp-1

Truncation mutants of Prosaposin comprised of SaposinA, SaposinAB, and SaposinABC downstream of the native signal sequence of Prosaposin that mediates secretion of the protein. These mutants were created by PCR of Prosaposin using the following primers: Saposin A: 5' Primer: 5'-ggcggcTCAGTCGACGGTACCGG-3' (SEQ. ID. No. 9) which primes at the 5' region of the pDNR-Dual MCS, the vector where the cDNA of Psap is subcloned into, 3' Primer: 5'-ggcgcctctagaAGAGACTCGCAGAGGTT-GAG-3' (SEQ. ID. No. 10). Saposin AB: 5' Primer: 5'-ggcg-gcTCAGTCGACGGTACCGG-3'(SEQ. ID. No. 9) and 3' Primer: 5'-ggcgcctctagaACCTCATCACAGAACCC-3' (SEQ. ID. No. 11). Saposin ABC: 5' Primer: 5'-ggcggcTCA-GTCGACGGTACCGG-3' (SEQ. ID. No. 9) and 3' Primer: 5'-ggcgcctctagaGCCAGAGCAGAGGTGCAGC-3' (SEQ. ID. No. 12).

The resulting PCR products were cloned into the SalI and XbaI sites of pDNR-dual. The Saposin constructs were then transferred via Cre-recombinase mediated cloning into pCMVneo for transient expression. These pCMVneoSaposin constructs were transiently transfected into the PC3M-LN4 prostate cancer cells. After 48 hours the conditioned media from these cells as well as cells infected with pCMVneo alone were transferred to prostate and lung fibroblasts. After 12 hours the treated fibroblasts were harvested and lysed and Tsp-1 expression assessed by western blot analysis.

It has been demonstrated that Psap inhibits metastasis via stimulation of Tsp-1 expression and this stimulation is via the tumor suppressor p53. In order to determine the active region of the full-length Psap, constructs were created expressing truncation mutants specifying Saposin A, Saposin AR, and Saposin ARC. Following transient transfection of PC3M-LN4 cells with these vectors, prostate and lung fibroblasts were treated with the conditioned media from these cells. It was determined that Saposin A is the minimal domain that is functionally required for the stimulation of Tsp-1 in prostate fibroblasts (FIG. 12).

Example 12

Psap in Platelets and Plasma as Biomarker for Metastasis

Figure 13:
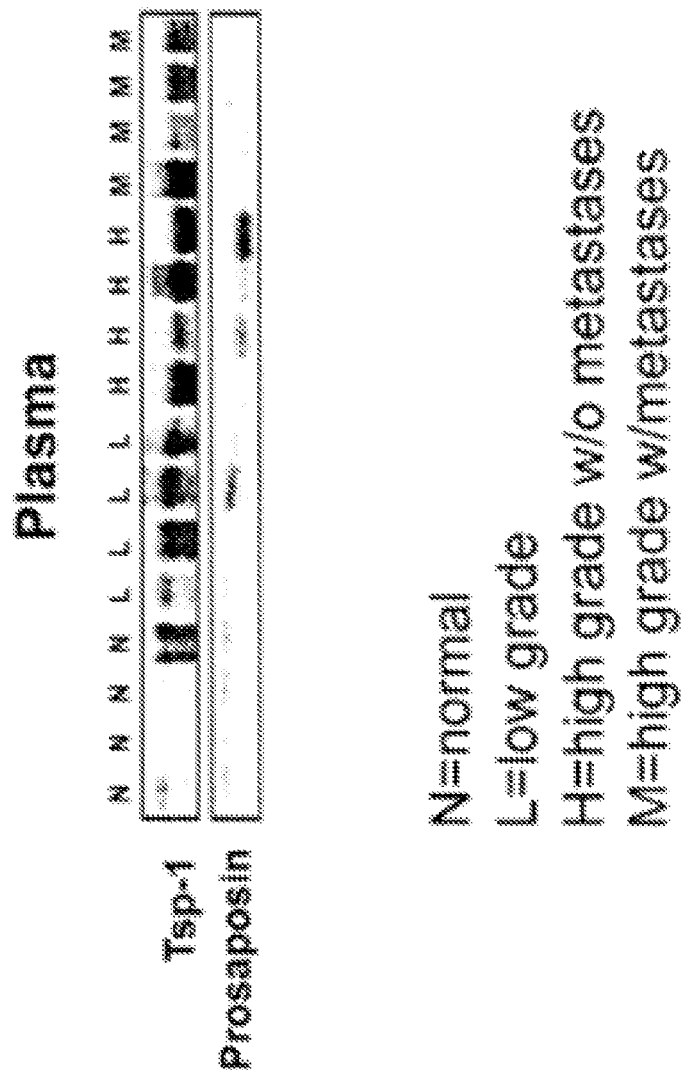
FIG. 13. Psap expression in plasma from colorectal cancer patients. Western blot analysis of prosaposin and Tsp-1 protein levels in plasma samples from normal patients, and colon cancer patients with low grade (T1, N0, M0), high grade without metastases (3T3, 1T4 N0, M0) and high grade with metastasis (3T3, 1T4, N1, M1).

Since the amount of Psap secreted by tumors depended on whether the tumor was metastatic or non-metastatic, the Psap in platelets and plasma were determined for patients with either tumor type. There was also a strong correlation between metastasis and the Psap level in the plasma and/or platelets of patients with non-metastatic and metastatic cancers. Both plasma and platelets of patients with non-metastatic cancers contained elevated levels of Psap compared to normal individuals with no diagnosed cancers. Conversely, the plasma and platelets of patients with metastatic cancers contain Psap levels that are comparable to normal individuals with no diagnosed cancers (FIG. 13).

Figures 14A, 14B:
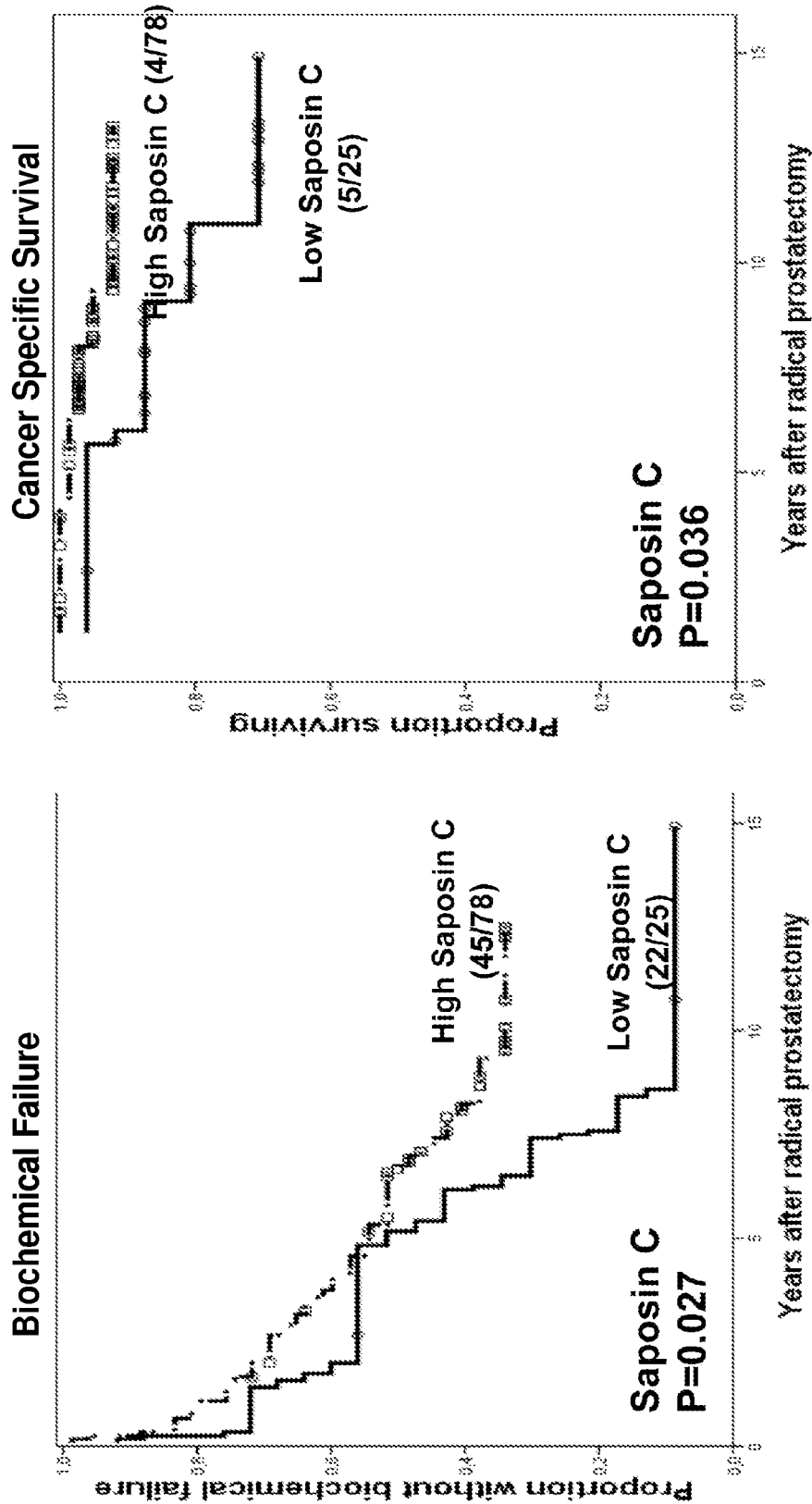
FIG. 14A. Correlation of endogenous expression of Prosaposin and biochemical failure in patients after radical prostatectomy.
FIG. 14B. Kaplan Meyer plot of survival of patients from the series of men described above as a function of time elapsed subsequent to radical prostatectomy and endogenous expression of Prosaposin.

Moreover, high protein levels of endogenously expressed prosaposin in human prostate cancer patients, as determined by immunohistochemical analysis significantly correlated with increased survival and delayed time to cancer recurrence after radical prostatectomy (FIGS. 14A and B).

Representative tumor areas from a tissue microarray were identified on HE slides, and three tissue cylinders (diameter of 0.6 mm) were punched from the donor block and mounted into a recipient paraffin block. Sections were stained for expression of Prosaposin using the antibody from Santa Cruz Biotechnology described above. The tissue microarray was assembled from a consecutive series of 104 men treated by radical prostatectomy for clinically localized prostate cancer during 1988-1994, with long and complete follow-up, was included. Clinical stage T1/T2 disease, negative bone scan and generally good health were the prerequisites for radical retropubic prostatectomy. The majority of cancers in this series is clinical stage T2 and presented before the PSA era started in Norway in the mid-1990s. Consequently, the prevalence of adverse prognostic factors like capsular penetration, seminal vesicle invasion and positive surgical margins is rather high compared with most contemporary series. No patients treated by radical prostatectomy received radiotherapy prior to biochemical failure or clinical recurrence.

Postoperatively, s-PSA, loco-regional tumor recurrences, distant metastases, and patient survival were recorded. Time from surgery until biochemical failure (defined as persistent or rising s-PSA level of >0.5 ng/ml in two consecutive blood samples) was noted. Further, a tumor in the prostatic fossa or evidence of distant metastasis on bone scan, X-ray or MRI was recorded as clinical recurrence. The last time of follow-up was December 2001. Median follow-up time was 95 months (7.9 yrs). No patients were lost because of insufficient data. 67 patients experienced biochemical failure, 31 patients had clinical recurrence, and 9 patients died of prostate cancer.

Over 100 years ago Stephen Paget published his "seed and soil" hypothesis, in which he noted that tumors from certain organs tend to preferentially metastasize to specific organs due to the compatibility between 'seed and soil' (Paget, 1889). The tissue specificity, or homing, of tumor cells to their metastatic destination has since been demonstrated to be mediated in part by discrete chemokine ligand-receptor interactions (Muller et al., 2001). However, the contributions of the tumor stroma at both the primary and metastatic sites that regulate the growth of metastases subsequent to colonization has not been as well documented.

It has been previously demonstrated that, at the primary site, tumor growth beyond the microscopic size is regulated by the levels of Tsp-1 expressed by the epithelial tumor cells (Watnick et al., 2003). Metastatic human tumor cells should be more angiogenic than their non/weakly metastatic counterparts in the primary site, so as to have better access to their conduit, the vasculature and lymphatics, as well as at metastatic sites to allow their growth beyond the microscopic size. Described herein 14 of 17 tumors formed by the weakly metastatic PC3 cell line expressed high levels of Tsp-1. Of the three PC3 tumors that expressed low levels of Tsp-1 two formed lung metastases. Furthermore, 15 of 16 tumors formed by the highly metastatic PC3M-LN4 cell line expressed low levels of Tsp-1. Of the fifteen PC3M-LN4 tumors that expressed low levels of Tsp-1 ten, or two-thirds, developed lung metastases. Finally, no primary tumors that expressed high levels of Tsp-1 (0/15 combined) formed lung metastases. Thus, high levels of Tsp-1 in the stroma of primary tumors are a potent barrier to metastasis.

Described herein is a novel suppressor of tumor metastasis. It was demonstrated that secretion of Psap by tumor cells inhibits metastasis by stimulating the expression of p53 and, consequently, Tsp-1 in stromal fibroblasts. Significantly, Psap, secreted by the primary tumor, also was able to stimulate the expression of p53 in distal tissues, such as lymph node and lung. Furthermore, the Psap-mediated stimulation of Tsp-1 was a direct function of p53 activation as shRNA knockdown of p53 abolishes this stimulation. Additionally, it was determined that expression of Psap was not only repressed in metastatic prostate cancer cells, but in several independently derived metastatic versions of the MDA-MB-231 cell line. These lines were derived to metastasize specifically to bone and lung, however they all share the common trait of reduced expression of Psap. These observations indicate that repression of Psap expression can be a common mechanism to enhance tumor metastasis, and can be a component of a "metastatic switch".

Additionally, by culturing tumor cells and fibroblasts from various tissues in a trans-well tissue culture apparatus, it was possible to recapitulate our in vivo observations and extend them to demonstrate that the ability to repress Tsp-1 in stromal fibroblasts strictly correlates with the ability to metastasize to the tissue from which the fibroblasts were derived. Specifically, PC3M-LN4 cells, which have been reported to be able to metastasize to both lung and bone (Pettaway et al., 1996), can repress Tsp-1 in both lung fibroblasts and bone marrow derived stromal cells, while they are unable to repress Tsp-1 in mammary or dermal fibroblasts, or astrocytes. Coordinately, MDA-MET cells, which were selected to metastasize solely to the bone (Bendre et al., 2002), are only able to repress Tsp-1 in bone marrow-derived stromal cells. These observations indicate that while repression of Tsp-1 in the stroma of the primary tumor is necessary for metastasis, repression of Tsp-1 at the distal site determines tissue specificity.

The role of Psap in the inhibition of metastases is confirmed by the formation of metastases by tumors in which Psap expression has been suppressed via shRNA. Significantly, shPsap tumors, with the exception of one, did not grow substantially larger than the parental PC3 tumors.

These findings indicate that Psap functions as an inhibitor of tumor metastasis and not of primary tumor growth. The observation that repression of Psap expression also results in the formation of lymph node metastases, accompanied by decreased Tsp-1 expression in the node itself, is somewhat surprising as lymph-angiogenesis and lymph node metastases have been demonstrated not to be affected by Tsp-1 in a murine model of skin cancer (Hawighorst et al., 2002).

It was demonstrated here that escape from the primary site and growth at the metastatic site is not only a function of tumor-secreted Tsp-1 but also of the level of Tsp-1 secreted by the tumor-associated stromal fibroblasts.

Example 13

Clinical Correlation of Psap, Tsp-1 and p53 Expression with Metastasis

Figures 15, 16A, 16B:
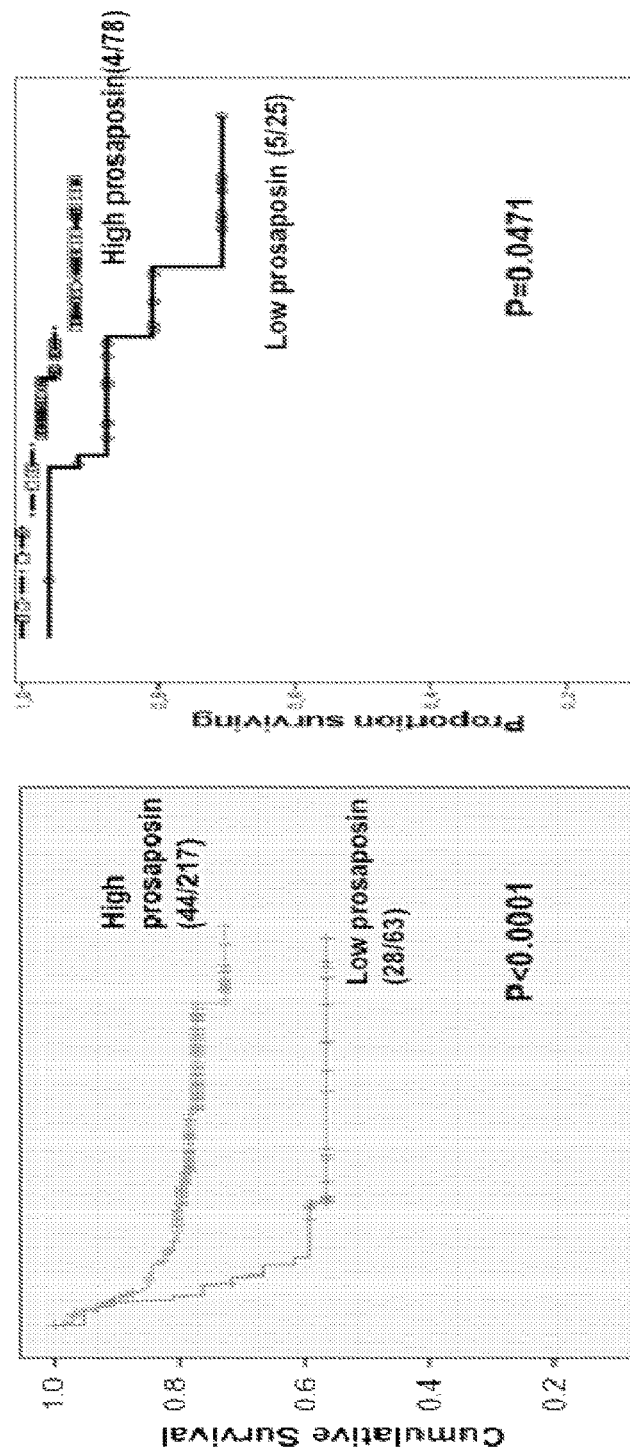
FIG. 15. Western blot analysis of prosaposin in serum of normal patients (N) and colon cancer patients with low grade carcinoma (L), high grade carcinoma without metastases (H) and high grade carcinoma with metastases (M), loading was normalized to total protein.
FIG. 16A. Survival curves for endometrial cancer patients with high and low prosaposin expression.
FIG. 16B. Survival curves for prostate cancer patients with high and low prosaposin expression.

The investigators analyzed the prosaposin protein levels in the serum of normal subjects and colon cancer patients of varying stages. The prosaposin levels increased with grade T1-T4 and then decreased back to normal levels in patients with metastasis (FIG. 15). Interestingly, patient H3 was originally diagnosed as stage T4 with no mets (N0M0) yet subsequently developed both lymph node and lung metastases and was reclassified as N2M1, which is consistent with the hypothesis that prosaposin levels inversely correlate with metastatic progression. The fact that colon cancer is not a hormone responsive cancer, like breast and prostate, strongly indicates that repression of prosaposin is a more widespread event in metastatic disease.

A study consisting of 104 men who were treated by radical prostatectomy for prostate cancer (Haukeland University Hospital, Bergen, Norway) and 290 women who were treated with complete hysterectomy for endometrial cancer was conducted. The study consisted of both with long and complete follow-up. Immunohistochemical analysis of the prosaposin protein expression in a tissue microarray revealed an association between low prosaposin and cancer specific survival (P=0.0471 by log rank for prostate cancer and P<0.0001 by log rank for endometrial cancer) (FIGS. 16A and 16B).

Example 14

Figures 17A, 17B:
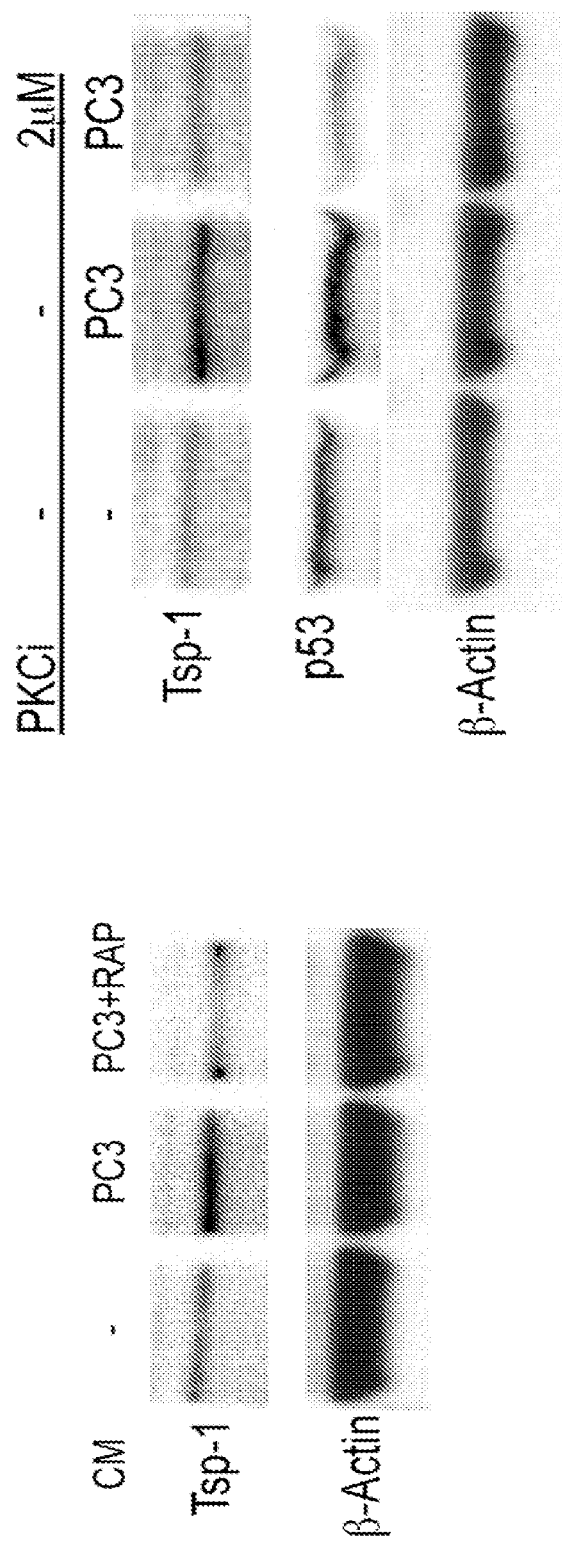
FIG. 17A. Western blot analysis of Tsp-1 and β-actin expression in prostate fibroblasts that were untreated (−) or treated with conditioned media from PC3 cells alone or in combination with RAP.
FIG. 17B. Western blot analysis of Tsp-1, p53 and β-actin expression in prostate fibroblasts that were untreated (−) or treated with conditioned media from PC3 cells alone or in combination with the PKC inhibitor Gö 6983 (PKCi).

Prosaposin Stimulates Tsp-1 and p53 Via LRP-1 and PKC Mediated Signaling Mechanisms It has been demonstrated that Low Density Lipoprotein Receptor Related Protein (LRP) can mediate the uptake of Prosaposin. Thus, in order to determine how prosaposin stimulates the expression of Tsp-1 and p53 prostate fibroblasts were treated with PC3 conditioned media (CM) in the presence and absence of Receptor Associate Protein (RAP) a competitive inhibitor or LRP binding. Western blot analysis revealed that in the presence of RAP PC3 CM no longer stimulated Tsp-1 (FIG. 17A). It has also been demonstrated that ligation of LRP releases intracellular Ca2+ stores. To determine whether prosaposin activated this pathway prostate fibroblasts were treated with CM from PC3 cells in the presence and absence of the PKC inhibitor Gö 6983. It was observed, via western blot analysis, that inhibition of PKC abolished the stimulation of Tsp-1 and p53 (FIG. 17B). Thus, it demonstrates that prosaposin functions via the binding to an LRP family member.

Figure 18:
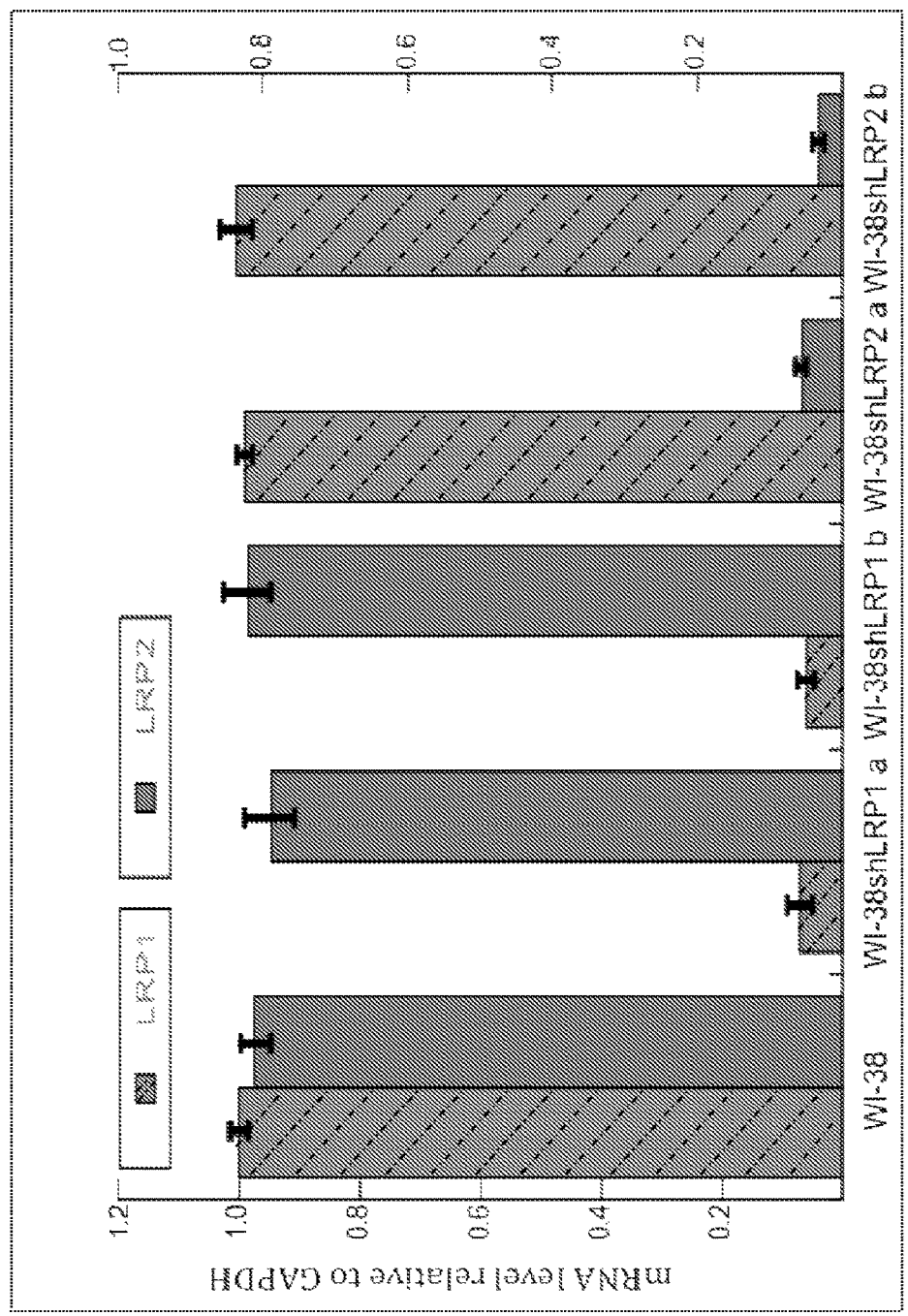
FIG. 18. Plot of mRNA levels of LRP1 and LRP2 (relative to GAPDH) in WI-38 lung fibroblasts and WI-38 lung fibroblasts transduced with lentiviral constructs specifying 2 shRNA sequences specific for LRP1 (LRP1a and LRP1b) and LRP2 (LRP2a and LRP2b).

The expression of LRP1 and LRP2 was then silenced, independently in WI-38 lung fibroblasts, to determine the requirement for LRP1 in mediating prosaposin functions and whether the closely related protein LRP2 could substitute. As shown in FIG. 18, over 95% suppression of LRP1 and LRP2 mRNA with 2 different shRNA sequences were obtained and, importantly, knockdown of one did not affect expression of the other.

Figures 19, 20:
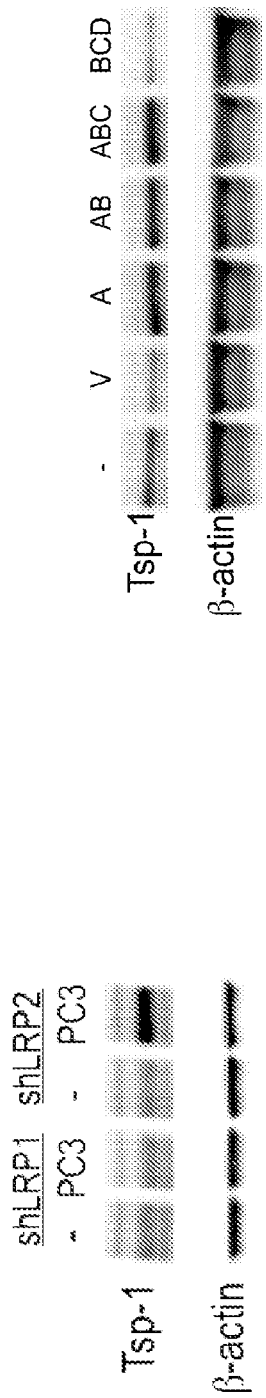
FIG. 19. Western blot analysis of Tsp-1 and actin in WI-38 lung fibroblasts silenced for LRP1 (shLRP1) or LRP2 (shLRP2) that were untreated (−) or treated with PC3 conditioned media.
FIG. 20. Western blot analysis of Tsp-1 expression in WI-38 lung fibroblasts treated with CM from PC3M-LN4 transduced with empty pLNCX (V) or with pLNCX-saposin A (A), pLNCX-saposin AR (AR), pLNCX-saposin ARC (ARC), and pLNCX-saposin BCD (BCD).

The cells were then treated with CM from PC3 cells and it was observed that the silencing of LRP1 blocked the stimulation of Tsp-1 expression while silencing of LRP2 had no effect on Tsp-1 stimulation by PC3 conditioned media (FIG. 19).

Example 15

A Peptide within Saposin A is Sufficient to Stimulate Tsp-1

In order to determine the domain of prosaposin that was required for the stimulation of Tsp-1 in fibroblasts PC3M-LN4 cells were transduced with retroviral vectors expressing truncated mutants of prosaposin containing saposin A, saposin AB, saposin ABC, or saposin BCD. The lung fibroblasts were then treated with the CM from these cells and it was observed that all of the constructs containing saposin A, including the construct that only expressed saposin A, were sufficient to stimulate Tsp-1 expression in lung fibroblasts, while the construct specifying saposin BCD was unable to stimulate Tsp-1 (FIG. 20). Thus, it was concluded that saposin A is sufficient to stimulate Tsp-1 in fibroblasts.

Figure 21A:
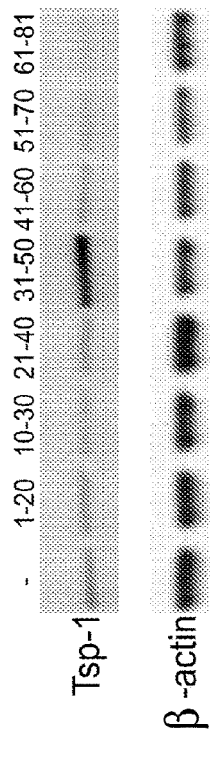
FIG. 21A. Western blot analysis of Tsp-1 and actin expression in WI-38 fibroblasts treated with 7 overlapping 20-amino acid peptides spanning the length of saposin A.

Seven 20-amino acid (20-mer) peptides derived from saposin A were tested for ability to stimulate Tsp-1 expression in fibroblasts. These 20-mers spanned the 81 amino acid sequence of saposin A, their ranges are as follows: amino acid 1-20, 10-30, 21-40, 31-50, 41-60, 51-70 and 61-81. WI-38 lung fibroblasts were treated with these peptides overnight and the Tsp-1 expression was analyzed by Western blot analysis. It was observed that only the peptide comprising amino acids 31-50 of saposin A was able to stimulate Tsp-1 expression (FIG. 21A). This 20-mer has the sequence LEKTCDWLPKPNMSASCKEI (SEQ. ID. No. 29).

Figure 21B:
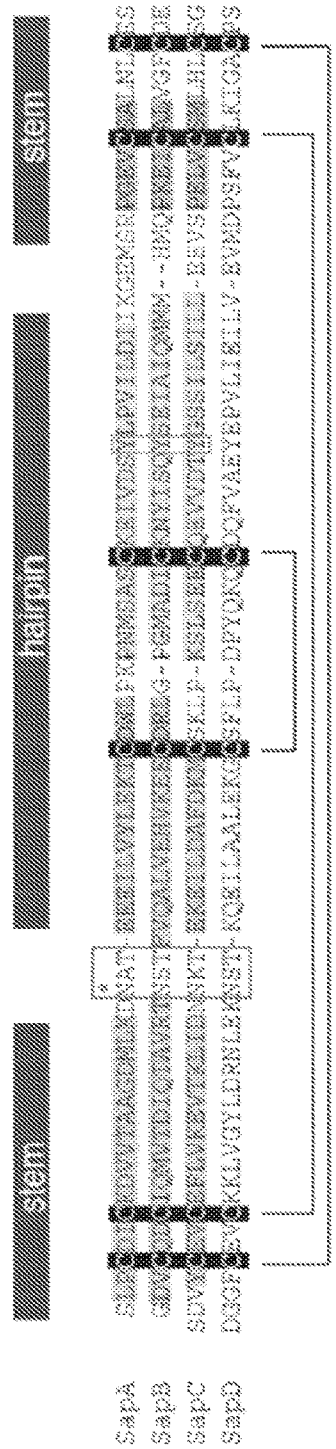
FIG. 21B. Sequence alignment of saposin A, B, C and D (SEQ. ID. Nos. 33-36, respectively, in order of appearance).
Figure 21C:
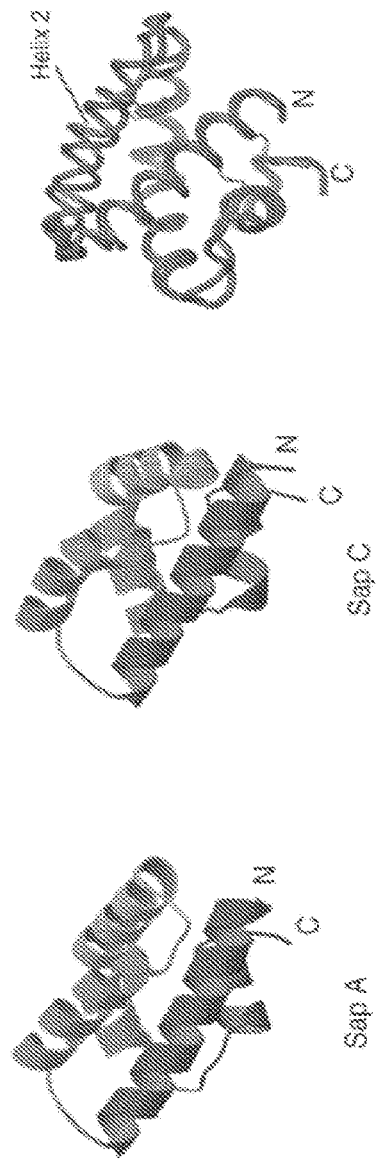
FIG. 21C. Crystal structures of saposin A (Sap A), saposin C (Sap C) and the superimposition of the two.
Figure 22:
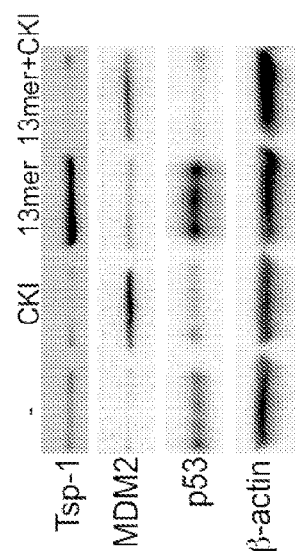
FIG. 22. Western blot analysis of Tsp-1, MDM2, p53 and actin in WI-38 fibroblasts that were untreated (−) treated with D4476, an inhibitor of casein kinase 1, (CKI) a 13 amino acid cyclic peptide comprising residues 35-47 of saposin A (13mer) (CDWLPKPNMSASC; SEQ. ID. No. 37) and the 13 amino acid peptide plus D4476 (13mer+CKI).

Based on the sequence and crystal structure of saposin A and saposin C (FIG. 21B) a cyclic 13 amino acid peptide was synthesized and tested. The cyclic 13-mer comprises amino acid residues 35-47 of saposin A and is flanked at the N- and C-terminus by cysteines which form a disulfide bond (CDWLPKPNMSASC, SEQ. ID. No. 37). It was determined that this peptide was sufficient to stimulate Tsp-1 and p53 (FIG. 22). It has been demonstrated that PKC can phosphorylate ck1 (casein kinase 1) and that ck1 can regulate the interaction of p53 with MDM2 by phosphorylating MDM2. Thus, WI-38 fibroblasts were treated with the cyclic 13-mer in the presence and absence of the casein kinase inhibitor D4476. Western blot analysis revealed that the 13-mer induced the stimulation of p53 and Tsp-1 and the concomitant down regulation of MDM2, and inhibition of CKI by D4476 resulted in the reduction of Tsp-1 and p53 and increase in MDM2 protein levels (FIG. 22). Thus, the data indicate that saposin A binds to LRP1 through this 13 amino acid motif resulting in activation of a signal transduction pathway leading from PKC to CKI culminating in a reduction of MDM2 levels and resultant increase in p53 and Tsp-1 protein levels.

Example 16

Prosaposin Inhibits Lymphatic Endothelial Cells Migration

Figure 23:
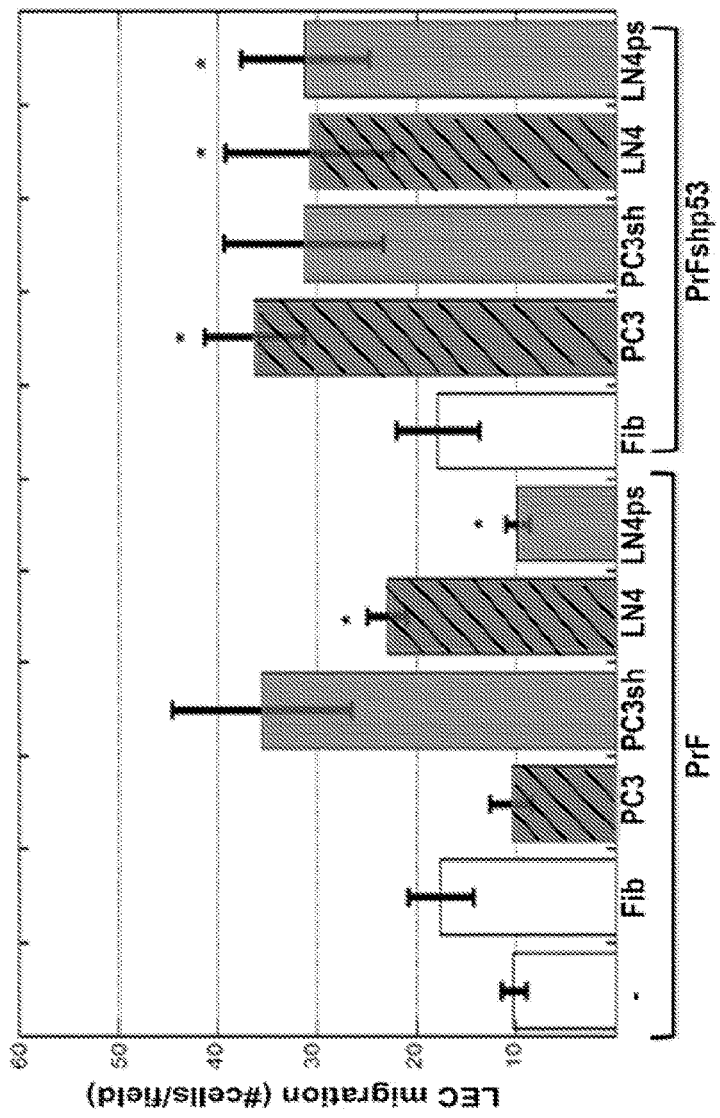
FIG. 23. Migration of lymphatic endothelial cells (LEC) in the absence (−) or presence of wild-type or prostate fibroblasts in which p53 was silenced via shRNA, that were untreated (Fib) or treated with conditioned media from PC3, PC3M-LN4 (LN4), PC3 cells in which Prosaposin was silenced via shRNA (PC3sh), or PC3M-LN4 cells ectopically expressing prosaposin (LN4ps). The asterisk * denotes statistically significant differences with p values<0.001 as determined by one way ANOVA.

It was demonstrated that silencing of prosaposin in PC3 cells enabled lymph node metastasis. Thus, in vitro migration assays were performed in which lymphatic endothelial cells (LEC) were plated on an 8 mm pore membrane in the upper chamber of a transwell tissue culture apparatus. In the bottom chamber prostate fibroblasts were plated alone or in combination with PC3, PC3shPsap, PC3M-LN4 and PC3M-LN4-Psap cells. After 8 hours the bottom of the membrane were stained with DAPI and the number of LECs per high-powered field that migrated across the membrane were counted. It was observed that PC3 cells inhibited the migration of LECs by 2-fold, while silencing of Psap in these cells resulted in a 1.5-fold increase in LEC migration. Similarly, PC3M-LN4 cells induced the migration of 2-fold more LECs/field, while ectopic expression of Prosaposin in these cells virtually abolished the stimulation of migration in a p53-dependent manner (FIG. 23).

Figures 24A, 24B:
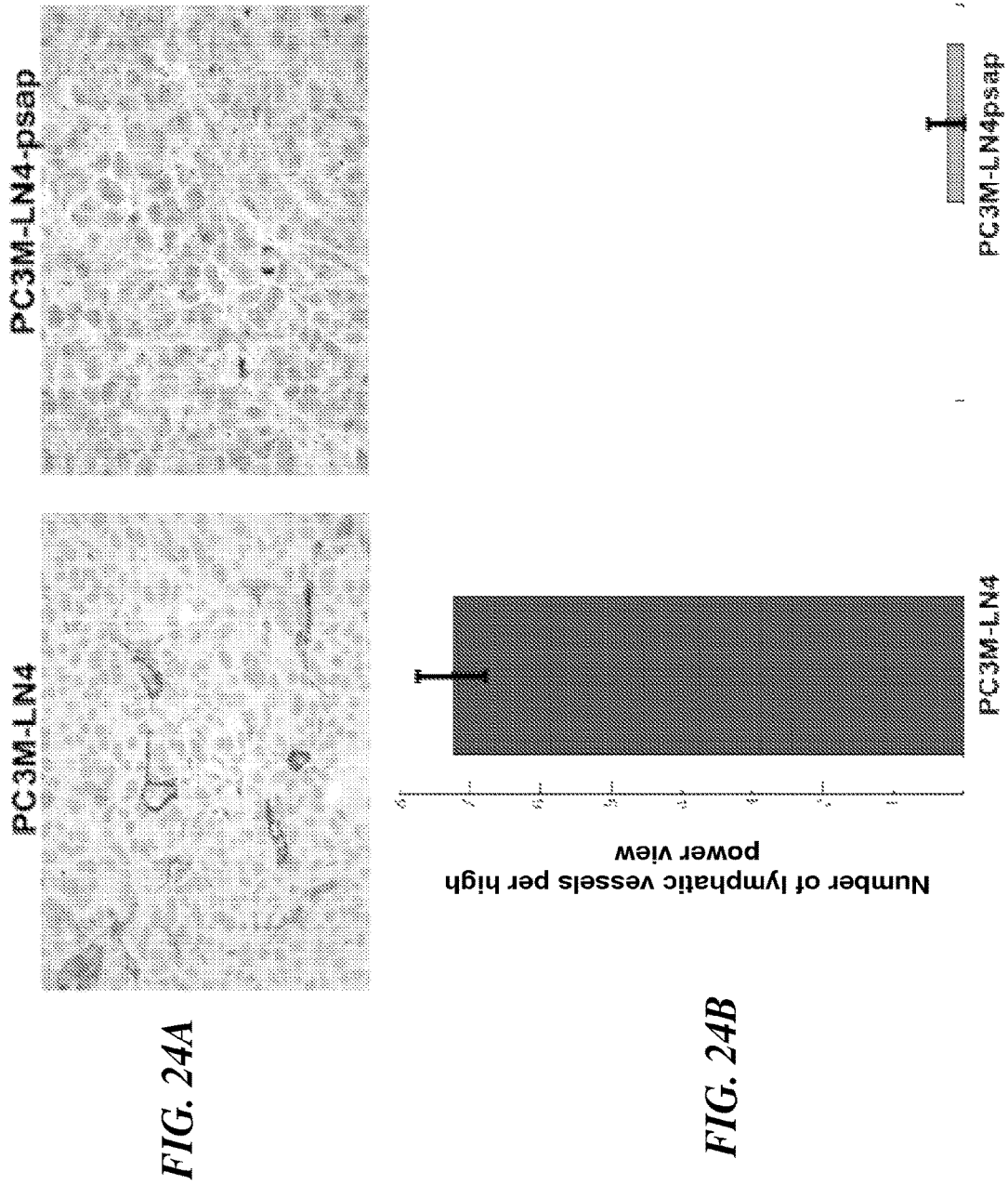
FIG. 24A. Immunohistochemistry of podoplanin expression in PC3M-LN4 and PC3M-LN4-psap tumors.
FIG. 24B. Graphical depiction of the number of podoplanin positive lymphatic vessels in each tumor type.

Next, primary prostate tumor xenografts were stained for podoplanin expression, a marker for lymphatic vessels. It was found that tumors formed by PC3M-LN4 cells contained ~15-fold more intratumoral lymphatic vessels than tumors formed by PC3M-LN4-psap cells (FIGS. 24A and 24B).

Figure 25:
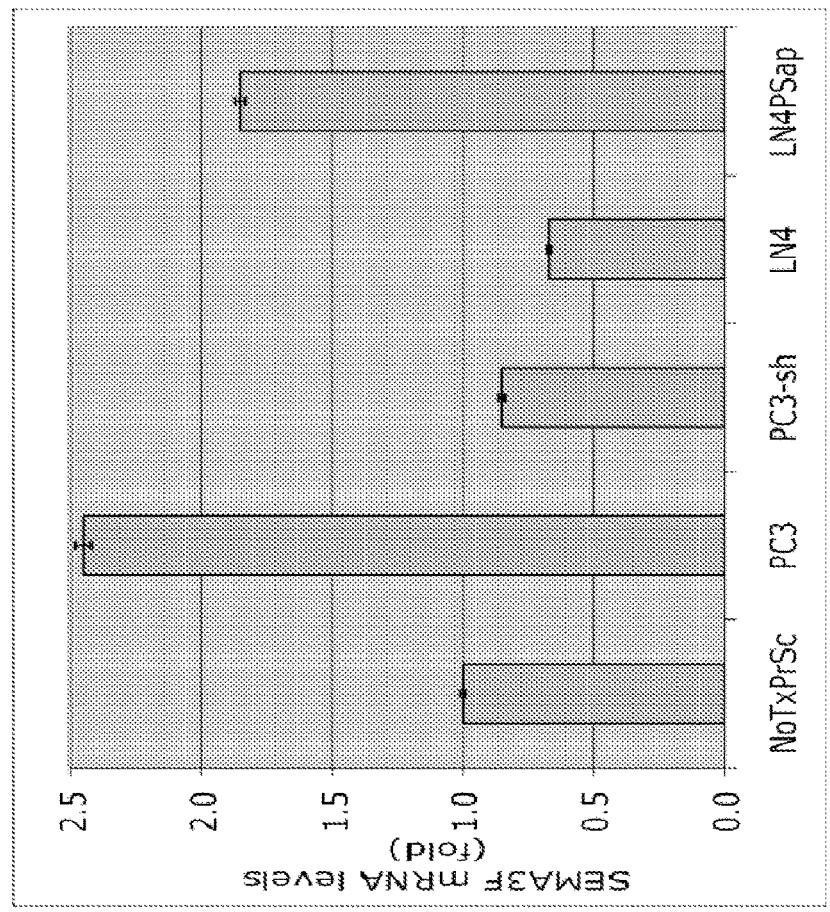
FIG. 25. mRNA levels of semaphorin 3F, relative to GAPDH, in WI-38 fibroblasts that were untreated (NoTx-PrSc) treated with conditioned media from PC3, PC3-sh prosaposin (PC3-sh), PC3M-LN4 (LN4) and PC3M-LN4 cells ectopically expressing prosaposin (LN4Psap) as determined by real time RT-PCR.

Finally, it was determined that prosaposin stimulates the expression of semaphorin 3F, a transcriptional target of p53 and an inhibitor of metastasis and lymphangiogenesis, at the mRNA level (FIG. 25).

Example 17

A 20-mer Peptide Derived from Saposin A Stimulates Tsp-1 Production in vivo

Treatment of Mice with Peptides:

The 20-mer LEKTCDWLPKPNMSASCKEI (SEQ. ID. No. 29) was tested in vivo in mice for their ability to induce Tsp-1 expression. Four mice were treated with the 20-amino acid peptide (residues 31-50 of saposin A) at a dose of 30 mg/kg/day in combination with 200 uL of conditioned media (CM) from the metastatic prostate cancer cell line PC3M-LN4. The peptide was co-treated with CM to mimic a tumor bearing mice, since PC3M-LN4 tumors have been shown to secrete a factor that represses Tsp-1 in the lungs of mice. Another four mice were treated with CM from PC3M-LN4 alone, and a control group of four mice with treated with vehicle (PBS) alone. As a positive control, mice were also treated with conditioned media from the non-metastatic prostate cancer cell line PC3, which has been shown to express high levels of the full-length prosaposin protein. Mice were treated for 9 days after which they were sacrificed and the lungs and livers were harvested and lysed. Tissue lysates were then run on a 4-12% gradient bis-tris polyacrylamide gel and transferred to a nitrocellulose membrane for western blotting with antibodies specific for thrombospondin-1 (Tsp-1) and β-actin.

Figure 26:
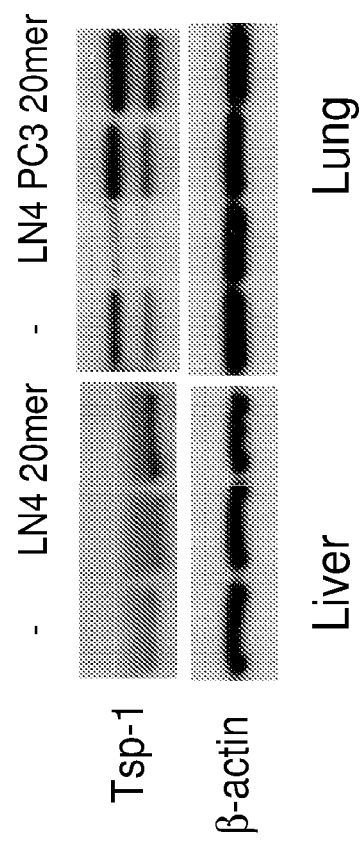
FIG. 26. Western blot analysis showing a 20-mer peptide derived from Saposin A stimulates Tsp-1 expression in the lungs and liver of mice in vivo.

FIG. 26 shows that the 20-mer stimulated Tsp-1 expression over control in the liver and lung tissues. Treatment with PC3M-LN4 CM reduced the expression of Tsp-1 in both the lungs of mice but had no effect on the Tsp-1 expression in the liver. Conversely, treatment with the 20-amino acid peptide stimulated the expression of Tsp-1 in the lung and liver by 6- and 4-fold, respectively compared to PC3M-LN4 CM. Moreover, the level of stimulation was greater than that of the weakly metastatic pancreatic cancer cell line PC3. These data validate the in vivo administration of the functional peptides of Saposin A for inducing Tsp-1 increased expression in vivo.

The references cited herein and throughout the specification are incorporated herein by reference.

REFERENCES

Bendre, M. S., et al., (2002) Cancer Res 62, 5571-5579.
Brown, L. F., et al., (1999) Clinical Cancer Research 5:1041-1056.
Brummelkamp, T. R., et al., (2002) Science 296:550-553.
Bykov V J, and Wiman K G. (2003) Ann Med. 35(7):458-65.
Campana W M, et al., (1996) Biochem Biophys Res Commun; 229(3): 706-712.
Campana W M, et al., (1998) FASEB J; 12(3): 307-314.
Campana W M, et al., (1999) Biochim Biophys Acta; 1427(3): 392-400.
Dameron, K. M., et al., (1994) Science 265:1582-1584.
Dong, J., et al., (2004) EMBO J; 23:2800-2810.
Ebba Bråkenhielm, et al., (2004) Circulation Research; 94:1579
Elenbaas, B., et al., (2001) Genes Dev 15, 50-65.
Escot, C., et al., (1986) Proc Natl Acad Sci USA; 83:4834-4838.
Espinoza-Fonseca L M. (2005) Theor Biol Med Model. September 20; 2:38.
Gurova, K. V., et al., (2004) Cancer Res. 64:1951-1958.
Fidler, I. J. (2003). Nat Rev Cancer 3:453-458.
Folkman, J. (1971). N Engl J Med 285:1182-1186.
Fukumura, D., et al., (1998) Cell 94:715-725.
Grammas P, et al., (1999) Am. J. Path., 154(2):337-42
Gopalakrishnan, M. M., et al., (2004) Biochem J. November 1; 383(Pt 3): 507-515.
Hawighorst, T., et al., (2002). Oncogene 21, 7945-7956.
Healy D L, et al., (1998) Human Reproduction Update, 4:736-740.
Hiraiwa M, et al., (1997) Biochem Biophys Res Commun; 240(2): 415-418.
Hiraiwa M, et al., (1997) Proc Natl Acad Sci USA; 94(9): 4778-4781.
Ho C K and Li G. (2005) Br J Dermatol. November; 153(5):900-10.
Issaeva N, et al., (2004) Nat Med. 10(12):1321-8.
Janz, A., et al., (2000) Nucleic Acids Res 28:2268-2275.
Kalas, W., et al., (2005) Cancer Res 65:8878-8886.
Kang, Y., et al., (2003) Cancer Cell 3:537-549.
Kishimoto Y, et al., (1992) J Lipid Res; 33(9): 1255-1267.
Koch, A. E., (2000) Ann. Rheum. Dis.; 59(Suppl 1):i65-i71
Koochekpour S. Atlas Genet Cytogenet Oncol Haematol. March 2006.
Koochekpour S. Atlas Genet Cytogenet Oncol Haematol. September 2006
Kotani Y, et al., (1996) J Neurochem; 66(5): 2197-2200.
Littlewood, T. D., et al., (1995) Nucleic Acids Res 23, 1686-1690.
MacDougall, J. R., and Matrisian, L. M. (1995). Cancer Metastasis Rev 14:351-362.
Martins, C. P., et al., (2006). Cell 127:1323-1334.
Minn, A. J., et al., (2005) Nature 436:518-524.
Misasi R, et al., (2001) FASEB J; 15(2): 467-474.
Morales, C R. (1998), 51:156-166.
Morales, C R, (2003) Asian J Androl; 5(1): 57-63.
Muller, A., et al., (2001). Nature 410:50-56.
Nag, A., and Smith, R. G. (1989) Prostate 15:115-122.
Naumov, G. N., et al., (2002) Cancer Res 62:2162-2168.
Ngo, C. V., et al., (2000) Cell Growth Differ 11.
O'Brien J S, et al., (1994) Proc Natl Acad Sci USA.; 91(20): 9593-9596.
O'Brien J S, et al., (1995) FASEB J; 9(8): 681-685.

Paget, S. (1889) Lancet 1:571-573.
Paleolog, E. M., (2002) Arthritis Res, 4(Suppl 3):S81-S90)
Pettaway, C. A., et al., (1996) Clinical Cancer Research 2:1627-1636.
Rehman Abdur, et al., Breast Cancer Research 2005, 7:R765-R774.
Roth, J., et al., (2003) Can. Res. 63: 3904-3908.
Schultheiss C, et al., (2006) Angiogenesis. 9(2):59-65.
Shing, Y. (1988). J Biol Chem 263:9059-9062.
Tanner S, Barberis A. (2004). J Negat Results Biomed. 3:5.
Tikhonenko, et al., (1996) J Biol. Chem. 271:30741-30747.
Vassilev, et al., (2004) Science 303:844-848.
Ventura, A., et al., (2007) Nature 445:661-665.
Vagnucci A H, Li W W, (2003) Lancet, 361(9357):605-8.
Watnick, R., et al., (2003) Cancer Cell 3.
Wiman, K. G., (2006) Cell Death and Differentiation 13:921-926.
Xue, W., et al., (2007) Nature 445:656-660.
Savagner, P., et al., (2004) Cell 117:927-939.

TABLE 2

Summary of thrombospondin-1 expression induced in stromal cells by metastatic and non-metastatic tumor cells.

| Tumor cells | Prostate | Lung | Bone Marrow | Breast | Skin |
| --- | --- | --- | --- | --- | --- |
| PC3 | ↑↑↑ | ↑↑↑ | ↑↑↑ | ↑ | ↑ |
| PC3M-LN4 | ↓↓ | ↓↓ | ↓↓ | ↑ | ↑ |
| MDA-MB-231 | ↑↑ | ↑↑ | ↑↑ | ↑↑↑ | ↑ |
| MDA-MET | — | ↑ | ↓↓ | — | ↑ |

TABLE 3

List of human proteins secreted from metastatic and non-metastatic tumors as analyzed by tandem LC/MS analysis. The Tsp-1 stimulating fractions of Heparin/$Cu^{2+}$ fractionated PC3 or LN4 conditioned media are the salt elution fractions at 0.7M and 0.9M NaCl respectively. Proteins present in all active fractions are highlighted in bold.

| PC3 0.7M | PC3 0.9M | LN4 0.7M | LN4 0.9M |
| --- | --- | --- | --- |
| Actin, cytoplasmic 1 | Actin, cytoplasmic 1 | Ribonucleases P/MRP protein subunit POP1 | Actin, cytoplasmic 1 |
| HSP 90-beta | HSP 90-beta | Splice Isoform 1 of 106 kDa O-GlcNAc transferase-interacting protein | Splice Isoform 1 of Fibronectin precursor |
| Splice Isoform Sap-mu-0 of Proactivator polypeptide precursor | Splice Isoform Sap-mu-0 of Proactivator polypeptide precursor | Splice Isoform Sap-mu-0 of Proactivator polypeptide precursor | Splice Isoform Sap-mu-0 of Proactivator polypeptide precursor |
| HSP 90-alpha 2 | HSP 90-alpha 2 | Lumican precursor | Pyruvate kinase 3 isoform 2 |
| Elongation factor 2 | Elongation factor 2 |  | Peroxiredoxin 1 |
| Cathepsin D precursor | Cathepsin D precursor |  | Nucleoside diphosphate kinase B |
| Alpha-2-HS-glycoprotein precursor | Alpha-2-HS-glycoprotein precursor | Alpha-2-HS-glycoprotein precursor | Alpha-2-HS-glycoprotein precursor |
| Splice Isoform 1 of Nucleophosmin | Quiescin Q6, isoform a |  | Quiescin Q6, isoform a |
| 29 kDa protein | 58 kDa protein | Serotransferrin precursor | Serotransferrin precursor |
| Hypothetical protein FLJ45525 | Hypothetical protein FLJ45525 |  | Alcadein alpha-1 |
| Importin beta-1 subunit | Fructose-bisphosphate aldolase A | Importin beta-1 subunit | Fructose-bisphosphate aldolase A |
| Alpha-fetoprotein precursor |  | Alpha-fetoprotein precursor | Alpha-fetoprotein precursor |
| DNA-(apurinic or apyrimidinic site) lyase | Complement C3 precursor | Rab proteins geranylgeranyltransferase component A 1 | Complement C3 precursor |
| Annexin A5 | Thrombospondin 1 precursor | Heparin cofactor II precursor | Thrombospondin 1 precursor |
| Transitional endoplasmic reticulum ATPase | Alpha 2 macroglobulin variant | Eukaryotic translation initiation factor 2C, 2 | Alpha 2 macroglobulin variant |
| Metalloproteinase inhibitor 1 precursor | Metalloproteinase inhibitor 1 precursor | Uveal autoantigen | Urokinase-type plasminogen activator precursor |
| Protein disulfide-isomerase A3 precursor | Splice Isoform APP770 of Amyloid beta A4 protein precursor |  | Splice Isoform APP770 of Amyloid beta A4 protein precursor |
| PREDICTED: similar to ATP-dependent DNA helicase II, 70 kDa subunit | EEF1A1 protein |  | EEF1A1 protein |
| Hypothetical protein LOC345651 | Keratin, type II cytoskeletal 1 |  | Keratin, type II cytoskeletal 1 |
| Splice Isoform 1 of Heat shock cognate 71 kDa protein | ALB protein | ALB protein | ALB protein |
| Pentraxin-related protein PTX3 precursor | Pentraxin-related protein PTX3 precursor |  | Lactotransferrin precursor |
| Tubulin beta-3 chain | Tubulin beta-3 chain |  | Tubulin beta-3 chain |
|  | Tubulin alpha-6 chain |  | Tubulin alpha-6 chain |
|  | Alpha enolase |  | Splice Isoform 1 of Solute carrier family 12 member 7 |

TABLE 3-continued

List of human proteins secreted from metastatic and non-metastatic tumors as analyzed by tandem LC/MS analysis. The Tsp-1 stimulating fractions of Heparin/$Cu^{2+}$ fractionated PC3 or LN4 conditioned media are the salt elution fractions at 0.7M and 0.9M NaCl respectively. Proteins present in all active fractions are highlighted in bold.

| PC3 0.7M | PC3 0.9M | LN4 0.7M | LN4 0.9M |
|---|---|---|---|
| | Alpha-actinin 1<br>Peptidyl-prolyl cis-trans<br>isomerase A | | Alpha-actinin 1<br>Glia derived nexin precursor |

```
NP_002769
                                                       (SEQ. ID. No. 1)
MYALFLLASLLGAALAGPVLGLKCTRGSAVWCQNVKTASDCGAVKHCLQTVWNKPTVKSLPC

DICKDVVTAAGDMLKDNATILVYLKTCDWLPKPNMSASCKIVDSYLPVILDIIKGMSRPGVCSA

LNLCSLQKHLALNHQKQLSNKIPLDMTVVAPFMANIPLLLYPQDGPRSKPQPKDNGDVCQDCIQ

MVTDIQTAVRTNSTFVQALVHVKCDRLGPGMADICKNYISQYSIAIQMMMHMQPKICALVGFC

DVKMPMQTLVPAKVASKNVIPALLVPIKKHVPAKSDVYCVCFLVKVTKLIDNNKTKILDAFDK

MCSKLPKSLSCQVVDTYGSSILSILLVSPLVCSMLHLCSGTRLPALTVHVTQPKDGGFCVCKKLV

GYLDRNLKNSTKQILAALKGCSFLPDPYQKQCDQFVAYPVLIILVVMDPSFVCLKIGACPSAHKP

LLGTKCIWGPSYWCQNTTAAQCNAVHCKRHVWN

NM_002778
                                                       (SEQ. ID. No. 2)
5'GGGGTTAGCGCCTGCGCTCTGGACGGCTTTGGGGCAGGGCAGATTTATATCTGCGGGGA

TCAGCTGACGCTCCGCATTGCAGACTGCGGAGTCAGACGGCGCTATGTACGCCCTCTTCCTC

CTGGCCAGCCTCCTGGGCGCGGCTCTAGCCGGCCCGGTCCTTGGACTGAAAGAATGCACCA

GGGGCTCGGCAGTGTGGTGCCAGAATGTGAAGACGGCGTCCGACTGCGGGGCAGTGAAGCA

CTGCCTGCAGACCGTTTGGAACAAGCCAACAGTGAAATCCCTTCCCTGCGACATATGCAAA

GACGTTGTCACCGCAGCTGGTGATATGCTGAAGGACAATGCCACTGAGGAGGAGATCCTTG

TTTACTTGGAGAAGACCTGTGACTGGCTTCCGAAACCGAACATGTCTGCTTCATGCAAGGAG

ATAGTGGACTCCTACCTCCCTGTCATCCTGGACATCATTAAAGGAGAAATGAGCCGTCCTGG

GGAGGTGTGCTCTGCTCTCAACCTCTGCGAGTCTCTCCAGAAGCACCTAGCAGAGCTGAATC

ACCAGAAGCAGCTGGAGTCCAATAAGATCCCAGAGCTGGACATGACTGAGGTGGTGGCCCC

CTTCATGGCCAACATCCCTCTCCTCCTCTACCCTCAGGACGGCCCCCGCAGCAAGCCCCAGC

CAAAGGATAATGGGGACGTTTGCCAGGACTGCATTCAGATGGTGACTGACATCCAGACTGC

TGTACGGACCAACTCCACCTTTGTCCAGGCCTTGGTGGAACATGTCAAGGAGGAGTGTGACC

GCCTGGGCCCTGGCATGGCCGACATATGCAAGAACTATATCAGCCAGTATTCTGAAATTGCT

ATCCAGATGATGATGCACATGCAACCCAAGGAGATCTGTGCGCTGGTTGGGTTCTGTGATGA

GGTGAAAGAGATGCCCATGCAGACTCTGGTCCCCGCCAAAGTGGCCTCCAAGAATGTCATC

CCTGCCCTGGAACTGGTGGAGCCCATTAAGAAGCACGAGGTCCCAGCAAAGTCTGATGTTT

ACTGTGAGGTGTGTGAATTCCTGGTGAAGGAGGTGACCAAGCTGATTGACAACAACAAGAC

TGAGAAAGAAATACTCGACGCTTTTGACAAAATGTGCTCGAAGCTGCCGAAGTCCCTGTCG

GAAGAGTGCCAGGAGGTGGTGGACACGTACGGCAGCTCCATCCTGTCCATCCTGCTGGAGG

AGGTCAGCCCTGAGCTGGTGTGCAGCATGCTGCACCTCTGCTCTGGCACGCGGCTGCCTGCA

CTGACCGTTCACGTGACTCAGCCAAAGGACGGTGGCTTCTGCGAAGTGTGCAAGAAGCTGG

TGGGTTATTTGGATCGCAACCTGGAGAAAAACAGCACCAAGCAGGAGATCCTGGCTGCTCT
```

-continued

```
TGAGAAAGGCTGCAGCTTCCTGCCAGACCCTTACCAGAAGCAGTGTGATCAGTTTGTGGCA

GAGTACGAGCCCGTGCTGATCGAGATCCTGGTGGAGGTGATGGATCCTTCCTTCGTGTGCTT

GAAAATTGGAGCCTGCCCCTCGGCCCATAAGCCCTTGTTGGGAACTGAGAAGTGTATATGG

GGCCCAAGCTACTGGTGCCAGAACACAGAGACAGCAGCCCAGTGCAATGCTGTCGAGCATT

GCAAACGCCATGTGTGGAACTAGGAGGAGGAATATTCCATCTTGGCAGAAACCACAGCATT

GGTTTTTTTCTACTTGTGTGTCTGGGGGAATGAACGCACAGATCTGTTTGACTTTGTTATAAA

AATAGGGCTCCCCCACCTCCCCCATTTCTGTGTCCTTTATTGTAGCATTGCTGTCTGCAAGGG

AGCCCCTAGCCCCTGGCAGACATAGCTGCTTCAGTGCCCCTTTTCTCTCTGCTAGATGGATGT

TGATGCACTGGAGGTCTTTTAGCCTGCCCTTGCATGGCGCCTGCTGGAGGAGGAGAGAGCTC

TGCTGGCATGAGCCACAGTTTCTTGACTGGAGGCCATCAACCCTCTTGGTTGAGGCCTTGTT

CTGAGCCCTGACATGTGCTTGGGCACTGGTGGGCCTGGGCTTCTGAGGTGGCCTCCTGCCCT

GATCAGGGACCCTCCCCGCTTTCCTGGGCCTCTCAGTTGAACAAAGCAGCAAAACAAAGGC

AGTTTTATATGAAAGATTAGAAGCCTGGAATAATCAGGCTTTTTAAATGATGTAATTCCCAC

TGTAATAGCATAGGGATTTTGGAAGCAGCTGCTGGTGGCTTGGGACATCAGTGGGGCCAAG

GGTTCTCTGTCCCTGGTTCAACTGTGATTTGGCTTTCCCGTGTCTTTCCTGGTGATGCCTTGTT

TGGGGTTCTGTGGGTTTGGGTGGGAAGAGGGCCATCTGCCTGAATGTAACCTGCTAGCTCTC

CGAAGGCCCTGCGGGCCTGGCTTGTGTGAGCGTGTGGACAGTGGTGGCCGCGCTGTGCCTG

CTCGTGTTGCCTACATGTCCCTGGCTGTTGAGGCGCTGCTTCAGCCTGCACCCCTCCCTTGTC

TCATAGATGCTCCTTTTGACCTTTTCAAATAAATATGGATGGCGAGCTCCTAGGCCTCTGGCT

TCCTGGTAGAGGGCGGCATGCCGAAGGGTCTGCTGGGTGTGGATTGGATGCTGGGGTGTGG

GGGTTGGAAGCTGTCTGTGGCCCACTTGGGCACCCACGCTTCTGTCCACTTCTGGTTGCCAG

GAGACAGCAAGCAAAGCCAGCAGGACATGAAGTTGCTATTAAATGGACTTCGTGATTTTTG

TTTTGCACTAAAGTTTCTGTGATTTAACAATAAAATTCTGTTAGCCAGAAAAAAAAAAAAAA

AAAA-3'
```

NP_001035930
(SEQ. ID. No. 3)
```
MYALFLLASLLGAALAGPVLGLKCTRGSAVWCQNVKTASDCGAVKHCLQTVWNKPTVKSLPC

DICKDVVTAAGDMLKDNATILVYLKTCDWLPKPNMSASCKIVDSYLPVILDIIKGMSRPGVCSA

LNLCSLQKHLALNHQKQLSNKIPLDMTVVAPFMANIPLLLYPQDGPRSKPQPKDNGDVCQDCIQ

MVTDIQTAVRTNSTFVQALVHVKCDRLGPGMADICKNYISQYSIAIQMMMHMQDQQPKICALV

GFCDVKMPMQTLVPAKVASKNVIPALLVPIKKHVPAKSDVYCVCFLVKVTKLIDNNKTKILDAF

DKMCSKLPKSLSCQVVDTYGSSILSILLVSPLVCSMLHLCSGTRLPALTVHVTQPKDGGFCVCKK

LVGYLDRNLKNSTKQILAALKGCSFLPDPYQKQCDQFVAYPVLIILVVMDPSFVCLKIGACPSAH

KPLLGTKCIWGPSYWCQNTTAAQCNAVHCKRHVWN
```

NM_001042465
(SEQ. ID. No. 4)
```
5'GGGGTTAGCGCCTGCGCTCTGGACGGCTTTGGGGCAGGGCAGATTTATATCTGCGGGGA

TCAGCTGACGCTCCGCATTGCAGACTGCGGAGTCAGACGGCGCTATGTACGCCCTCTTCCTC

CTGGCCAGCCTCCTGGGCGCGGCTCTAGCCGGCCCGGTCCTTGGACTGAAAGAATGCACCA

GGGGCTCGGCAGTGTGGTGCCAGAATGTGAAGACGGCGTCCGACTGCGGGGCAGTGAAGCA

CTGCCTGCAGACCGTTTGGAACAAGCCAACAGTGAAATCCCTTCCCTGCGACATATGCAAA

GACGTTGTCACCGCAGCTGGTGATATGCTGAAGGACAATGCCACTGAGGAGGAGATCCTTG
```

-continued

```
TTTACTTGGAGAAGACCTGTGACTGGCTTCCGAAACCGAACATGTCTGCTTCATGCAAGGAG

ATAGTGGACTCCTACCTCCCTGTCATCCTGGACATCATTAAAGGAGAAATGAGCCGTCCTGG

GGAGGTGTGCTCTGCTCTCAACCTCTGCGAGTCTCTCCAGAAGCACCTAGCAGAGCTGAATC

ACCAGAAGCAGCTGGAGTCCAATAAGATCCCAGAGCTGGACATGACTGAGGTGGTGGCCCC

CTTCATGGCCAACATCCCTCTCCTCCTCTACCCTCAGGACGGCCCCCGCAGCAAGCCCCAGC

CAAAGGATAATGGGGACGTTTGCCAGGACTGCATTCAGATGGTGACTGACATCCAGACTGC

TGTACGGACCAACTCCACCTTTGTCCAGGCCTTGGTGGAACATGTCAAGGAGGAGTGTGACC

GCCTGGGCCCTGGCATGGCCGACATATGCAAGAACTATATCAGCCAGTATTCTGAAATTGCT

ATCCAGATGATGATGCACATGCAGGATCAGCAACCCAAGGAGATCTGTGCGCTGGTTGGGT

TCTGTGATGAGGTGAAAGAGATGCCCATGCAGACTCTGGTCCCCGCCAAAGTGGCCTCCAA

GAATGTCATCCCTGCCCTGGAACTGGTGGAGCCCATTAAGAAGCACGAGGTCCCAGCAAAG

TCTGATGTTTACTGTGAGGTGTGTGAATTCCTGGTGAAGGAGGTGACCAAGCTGATTGACAA

CAACAAGACTGAGAAAGAAATACTCGACGCTTTTGACAAAATGTGCTCGAAGCTGCCGAAG

TCCCTGTCGGAAGAGTGCCAGGAGGTGGTGGACACGTACGGCAGCTCCATCCTGTCCATCCT

GCTGGAGGAGGTCAGCCCTGAGCTGGTGTGCAGCATGCTGCACCTCTGCTCTGGCACGCGG

CTGCCTGCACTGACCGTTCACGTGACTCAGCCAAAGGACGGTGGCTTCTGCGAAGTGTGCAA

GAAGCTGGTGGGTTATTTGGATCGCAACCTGGAGAAAAACAGCACCAAGCAGGAGATCCTG

GCTGCTCTTGAGAAAGGCTGCAGCTTCCTGCCAGACCCTTACCAGAAGCAGTGTGATCAGTT

TGTGGCAGAGTACGAGCCCGTGCTGATCGAGATCCTGGTGGAGGTGATGGATCCTTCCTTCG

TGTGCTTGAAAATTGGAGCCTGCCCCTCGGCCCATAAGCCCTTGTTGGGAACTGAGAAGTGT

ATATGGGCCCAAGCTACTGGTGCCAGAACACAGAGACAGCAGCCCAGTGCAATGCTGTCG

AGCATTGCAAACGCCATGTGTGGAACTAGGAGGAGGAATATTCCATCTTGGCAGAAACCAC

AGCATTGGTTTTTTTCTACTTGTGTGTCTGGGGGAATGAACGCACAGATCTGTTTGACTTTGT

TATAAAAATAGGGCTCCCCCACCTCCCCCATTTCTGTGTCCTTTATTGTAGCATTGCTGTCTG

CAAGGGAGCCCCTAGCCCCTGGCAGACATAGCTGCTTCAGTGCCCCTTTTCTCTCTGCTAGA

TGGATGTTGATGCACTGGAGGTCTTTTAGCCTGCCCTTGCATGGCGCCTGCTGGAGGAGGAG

AGAGCTCTGCTGGCATGAGCCACAGTTTCTTGACTGGAGGCCATCAACCCTCTTGGTTGAGG

CCTTGTTCTGAGCCCTGACATGTGCTTGGGCACTGGTGGGCCTGGGCTTCTGAGGTGGCCTC

CTGCCCTGATCAGGGACCCTCCCCGCTTTCCTGGGCCTCTCAGTTGAACAAAGCAGCAAAC

AAAGGCAGTTTTATATGAAAGATTAGAAGCCTGGAATAATCAGGCTTTTTAAATGATGTAAT

TCCCACTGTAATAGCATAGGGATTTTGGAAGCAGCTGCTGGTGGCTTGGGACATCAGTGGG

GCCAAGGGTTCTCTGTCCCTGGTTCAACTGTGATTTGGCTTTCCCGTGTCTTTCCTGGTGATG

CCTTGTTTGGGGTTCTGTGGGTTTGGGTGGGAAGAGGGCCATCTGCCTGAATGTAACCTGCT

AGCTCTCCGAAGGCCCTGCGGGCCTGGCTTGTGTGAGCGTGTGGACAGTGGTGGCCGCGCT

GTGCCTGCTCGTGTTGCCTACATGTCCCTGGCTGTTGAGGCGCTGCTTCAGCCTGCACCCCTC

CCTTGTCTCATAGATGCTCCTTTTGACCTTTTCAAATAAATATGGATGGCGAGCTCCTAGGCC

TCTGGCTTCCTGGTAGAGGGCGGCATGCCGAAGGGTCTGCTGGGTGTGGATTGGATGCTGG

GGTGTGGGGGTTGGAAGCTGTCTGTGGCCCACTTGGGCACCCACGCTTCTGTCCACTTCTGG

TTGCCAGGAGACAGCAAGCAAAGCCAGCAGGACATGAAGTTGCTATTAAATGGACTTCGTG

ATTTTTGTTTTGCACTAAAGTTTCTGTGATTTAACAATAAAATTCTGTTAGCCAGAAAAAAA

AAAAAAAAAA-3'
```

NP_001035931

(SEQ. ID. No. 5)

MYALFLLASLLGAALAGPVLGLKCTRGSAVWCQNVKTASDCGAVKHCLQTVWNKPTVKSLPC

DICKDVVTAAGDMLKDNATILVYLKTCDWLPKPNMSASCKIVDSYLPVILDIIKGMSRPGVCSA

LNLCSLQKHLALNHQKQLSNKIPLDMTVVAPFMANIPLLLYPQDGPRSKPQPKDNGDVCQDCIQ

MYTDIQTAVRTNSTFVQALVHVKCDRLGPGMADICKNYISQYSIAIQMMMHMDQQPKICALVG

FCDVKMPMQTLVPAKVASKNVIPALLVPIKKHVPAKSDVYCVCFLVKVTKLIDNNKTKILDAFD

KMCSKLPKSLSCQVVDTYGSSILSILLVSPLVCSMLHLCSGTRLPALTVHVTQPKDGGFCVCKKL

VGYLDRNLKNSTKQIIAALKGCSFLPDPYQKQCDQFVAYPVLIILVVMDPSFVCLKIGACPSAHK

PLLGTKCIWGPSYWCQNTTAAQCNAVHCKRHVWN

NM_001042466

(SEQ. ID. No. 6)

5'GGGGTTAGCGCCTGCGCTCTGGACGGCTTTGGGGCAGGGCAGATTTATATCTGCGGGGGA

TCAGCTGACGCTCCGCATTGCAGACTGCGGAGTCAGACGGCGCTATGTACGCCCTCTTCCTC

CTGGCCAGCCTCCTGGGCGCGGCTCTAGCCGGCCCGGTCCTTGGACTGAAAGAATGCACCA

GGGGCTCGGCAGTGTGGTGCCAGAATGTGAAGACGGCGTCCGACTGCGGGGCAGTGAAGCA

CTGCCTGCAGACCGTTTGGAACAAGCCAACAGTGAAATCCCTTCCCTGCGACATATGCAAA

GACGTTGTCACCGCAGCTGGTGATATGCTGAAGGACAATGCCACTGAGGAGGAGATCCTTG

TTTACTTGGAGAAGACCTGTGACTGGCTTCCGAAACCGAACATGTCTGCTTCATGCAAGGAG

ATAGTGGACTCCTACCTCCCTGTCATCCTGGACATCATTAAAGGAGAAATGAGCCGTCCTGG

GGAGGTGTGCTCTGCTCTCAACCTCTGCGAGTCTCTCCAGAAGCACCTAGCAGAGCTGAATC

ACCAGAAGCAGCTGGAGTCCAATAAGATCCCAGAGCTGGACATGACTGAGGTGGTGGCCCC

CTTCATGGCCAACATCCCTCTCCTCCTCTACCCTCAGGACGGCCCCCGCAGCAAGCCCCAGC

CAAAGGATAATGGGGACGTTTGCCAGGACTGCATTCAGATGGTGACTGACATCCAGACTGC

TGTACGGACCAACTCCACCTTTGTCCAGGCCTTGGTGGAACATGTCAAGGAGGAGTGTGACC

GCCTGGGCCCTGGCATGGCCGACATATGCAAGAACTATATCAGCCAGTATTCTGAAATTGCT

ATCCAGATGATGATGCACATGGATCAGCAACCCAAGGAGATCTGTGCGCTGGTTGGGTTCT

GTGATGAGGTGAAAGAGATGCCCATGCAGACTCTGGTCCCCGCCAAAGTGGCCTCCAAGAA

TGTCATCCCTGCCCTGGAACTGGTGGAGCCCATTAAGAAGCACGAGGTCCCAGCAAAGTCT

GATGTTTACTGTGAGGTGTGTGAATTCCTGGTGAAGGAGGTGACCAAGCTGATTGACAACA

ACAAGACTGAGAAAGAAATACTCGACGCTTTTGACAAAATGTGCTCGAAGCTGCCGAAGTC

CCTGTCGGAAGAGTGCCAGGAGGTGGTGGACACGTACGGCAGCTCCATCCTGTCCATCCTG

CTGGAGGAGGTCAGCCCTGAGCTGGTGTGCAGCATGCTGCACCTCTGCTCTGGCACGCGGCT

GCCTGCACTGACCGTTCACGTGACTCAGCCAAAGGACGGTGGCTTCTGCGAAGTGTGCAAG

AAGCTGGTGGGTTATTTGGATCGCAACCTGGAGAAAAACAGCACCAAGCAGGAGATCCTGG

CTGCTCTTGAGAAAGGCTGCAGCTTCCTGCCAGACCCTTACCAGAAGCAGTGTGATCAGTTT

GTGGCAGAGTACAGAGCCCGTGCTGATCGAGATCCTGGTGGAGGTGATGGATCCTTCCTTCGT

GTGCTTGAAAATTGGAGCCTGCCCCTCGGCCCATAAGCCCTTGTTGGGAACTGAGAAGTGTA

TATGGGGCCCAAGCTACTGGTGCCAGAACACAGAGACAGCAGCCCAGTGCAATGCTGTCGA

GCATTGCAAACGCCATGTGTGGAACTAGGAGGAGGAATATTCCATCTTGGCAGAAACCACA

GCATTGGTTTTTTTCTACTTGTGTGTCTGGGGAATGAACGCACAGATCTGTTTGACTTTGTT

ATAAAAATAGGGCTCCCCCACCTCCCCCATTTCTGTGTCCTTTATTGTAGCATTGCTGTCTGC

-continued

```
AAGGGAGCCCCTAGCCCCTGGCAGACATAGCTGCTTCAGTGCCCCTTTTCTCTCTGCTAGAT

GGATGTTGATGCACTGGAGGTCTTTTAGCCTGCCCTTGCATGGCGCCTGCTGGAGGAGGAGA

GAGCTCTGCTGGCATGAGCCACAGTTTCTTGACTGGAGGCCATCAACCCTCTTGGTTGAGGC

CTTGTTCTGAGCCCTGACATGTGCTTGGGCACTGGTGGGCCTGGGCTTCTGAGGTGGCCTCC

TGCCCTGATCAGGGACCCTCCCCGCTTTCCTGGGCCTCTCAGTTGAACAAAGCAGCAAAACA

AAGGCAGTTTTATATGAAAGATTAGAAGCCTGGAATAATCAGGCTTTTTAAATGATGTAATT

CCCACTGTAATAGCATAGGGATTTTGGAAGCAGCTGCTGGTGGCTTGGGACATCAGTGGGG

CCAAGGGTTCTCTGTCCCTGGTTCAACTGTGATTTGGCTTTCCCGTGTCTTTCCTGGTGATGC

CTTGTTTGGGGTTCTGTGGGTTTGGGTGGGAAGAGGGCCATCTGCCTGAATGTAACCTGCTA

GCTCTCCGAAGGCCCTGCGGGCCTGGCTTGTGTGAGCGTGTGGACAGTGGTGGCCGCGCTGT

GCCTGCTCGTGTTGCCTACATGTCCCTGGCTGTTGAGGCGCTGCTTCAGCCTGCACCCCTCCC

TTGTCTCATAGATGCTCCTTTTGACCTTTTCAAATAAATATGGATGGCGAGCTCCTAGGCCTC

TGGCTTCCTGGTAGAGGGCGGCATGCCGAAGGGTCTGCTGGGTGTGGATTGGATGCTGGGG

TGTGGGGGTTGGAAGCTGTCTGTGGCCCACTTGGGCACCCACGCTTCTGTCCACTTCTGGTT

GCCAGGAGACAGCAAGCAAAGCCAGCAGGACATGAAGTTGCTATTAAATGGACTTCGTGAT

TTTTGTTTTGCACTAAAGTTTCTGTGATTTAACAATAAAATTCTGTTAGCCAGAAAAAAAAA

AAAAAAAAA-3'
```

---

What is claimed:

1. An isolated peptide consisting of the amino acid sequence CDWLPKPNMSASC (SEQ ID NO: 37), wherein the peptide is:
   (a) cyclic;
   (b) N-terminal acetylated or thioglycolic acid amidated;
   (c) C-terminal carboxylamidated;
   (d) pegylated; or
   (e) conjugated to a polymer that enhances the serum half-life of the peptide.

2. An isolated chimeric polypeptide comprising a first portion and a second portion, wherein said first portion is the peptide of claim 1, and wherein said second portion is not a Psap peptide.

3. A composition comprising the peptide of claim 1, and a pharmaceutically acceptable carrier.

4. A method for treatment of an angiogenesis-dependent disease or disorder, comprising: administering to a subject in need thereof a therapeutically effective amount of the peptide of claim 1.

5. A method of inhibiting the recurrence of an angiogenesis-dependent disease or disorder, the method comprising administering to a subject in need thereof a therapeutically effective amount of the peptide of claim 1.

6. A method of inhibiting metastasis of cancer in a subject diagnosed with cancer, the method comprising administering to the subject a therapeutically effective amount of the peptide of claim 1.

7. The method of claim 4, wherein the angiogenesis-dependent disease or disorder is selected from a group consisting of cancer, psoriasis, age-related macular degeneration, thyroid hyperplasia, preeclampsia, rheumatoid arthritis and osteoarthritis, Alzheimer's disease, obesity, pleural effusion, atherosclerosis, endometriosis, diabetic/other retinopathies, neovascular glaucoma, age-related macular degeneration, hemangiomas, and corneal neovascularization.

8. The method of claim 4, wherein the peptide is administered in conjunction with chemotherapy, radiation therapy, a cytostatic agent, an anti-VEGF agent, an anti-angiogenesis factor, and/or a p53 reactivation agent.

9. A method of treating an angiogenesis-dependent disease or disorder, comprising administering to a subject in need thereof a therapeutically effective amount of the composition of claim 3.

10. A method of inhibiting the recurrence of an angiogenesis-dependent disease or disorder, the method comprising administering to a subject in need thereof a therapeutically effective amount of the composition of claim 3.

11. A method of inhibiting metastasis of cancer in a subject diagnosed with cancer, the method comprising administering to the subject a therapeutically effective amount of the composition of claim 3.

12. A method of treating an individual diagnosed with cancer comprising:
  a) determining a level of Psap in a tumor sample from said individual;
  b) comparing the Psap level determined in a) with a reference Psap level; and
  c) wherein said Psap level determined in a) is lower than 95% of said reference Psap level,
  administering a therapeutically effective amount of a composition of claim 3.

13. The method of claim 9, wherein the angiogenesis-dependent disease or disorder is selected from a group consisting of cancer, psoriasis, age-related macular degeneration, thyroid hyperplasia, preeclampsia, rheumatoid arthritis and osteoarthritis, Alzheimer's disease, obesity, pleural effusion, atherosclerosis, endometriosis, diabetic/other retinopathies, neovascular glaucoma, age-related macular degeneration, hemangiomas, and corneal neovascularization.

14. The method of claim 9, wherein the composition is administered in conjunction with chemotherapy, radiation therapy, a cytostatic, an anti-VEGF agent, an antiangiogenesis factor, and/or a p53 reactivation agent.

15. The isolated peptide of claim 1, wherein the peptide is capable of activating p53 and inducing Tsp-1 expression.

16. The isolated peptide of claim 1, wherein the peptide is fused/conjugated to a therapeutic molecule.

17. The isolated peptide of claim 1, wherein the cyclization comprises cyclization of the amino and the carboxyl termini of the peptide by a disulfide bond or a covalent bond.

18. The isolated peptide of claim 1, wherein the linker is (Gly$_4$Ser)$_3$ (SEQ ID NO: 82).

19. The isolated peptide of claim 17, wherein the covalent bond is a peptide bond.

* * * * *

UNITED STATES PATENT AND TRADEMARK OFFICE
CERTIFICATE OF CORRECTION

PATENT NO. : 10,267,799 B2
APPLICATION NO. : 13/516511
DATED : April 23, 2019
INVENTOR(S) : Randolph Watnick It is certified that error appears in the above-identified patent and that said Letters Patent is hereby corrected as shown below:

In the Claims

Claim 1, Column 143, Line 57 replace "the peptide is:" with -- the peptide is --

Claim 1, Column 143, Line 63 replace "half-life of the peptide." with -- half life of the peptide. --

Claim 3, Column 144, Line 54 replace "A composition comprising the peptide of claim 1, and" with -- A composition comprising of the peptide of claim 1, and --

Claim 12, Column 146, Line 3 replace "administering a therapeutically effective amount of a" with -- administering a therapeutically effective amount of the --

Claim 14, Column 146, Line 16 replace "therapy, a cytostatic, an anti-VEGF agent, an antiangiogen" with -- therapy, a cytostatic agent, an anti-VEGF agent, an antiangiogen --

Signed and Sealed this
Fifth Day of November, 2019

Andrei Iancu
*Director of the United States Patent and Trademark Office*

SEQUENCE LISTING

<160> NUMBER OF SEQ ID NOS: 82

<210> SEQ ID NO 1
<211> LENGTH: 479
<212> TYPE: PRT
<213> ORGANISM: Homo sapiens

<400> SEQUENCE: 1

```
Met Tyr Ala Leu Phe Leu Leu Ala Ser Leu Leu Gly Ala Ala Leu Ala
1               5                   10                  15

Gly Pro Val Leu Gly Leu Lys Cys Thr Arg Gly Ser Ala Val Trp Cys
            20                  25                  30

Gln Asn Val Lys Thr Ala Ser Asp Cys Gly Ala Val Lys His Cys Leu
        35                  40                  45

Gln Thr Val Trp Asn Lys Pro Thr Val Lys Ser Leu Pro Cys Asp Ile
    50                  55                  60

Cys Lys Asp Val Val Thr Ala Ala Gly Asp Met Leu Lys Asp Asn Ala
65                  70                  75                  80

Thr Ile Leu Val Tyr Leu Lys Thr Cys Asp Trp Leu Pro Lys Pro Asn
                85                  90                  95

Met Ser Ala Ser Cys Lys Ile Val Asp Ser Tyr Leu Pro Val Ile Leu
            100                 105                 110

Asp Ile Ile Lys Gly Met Ser Arg Pro Gly Val Cys Ser Ala Leu Asn
        115                 120                 125

Leu Cys Ser Leu Gln Lys His Leu Ala Leu Asn His Gln Lys Gln Leu
    130                 135                 140

Ser Asn Lys Ile Pro Leu Asp Met Thr Val Val Ala Pro Phe Met Ala
145                 150                 155                 160

Asn Ile Pro Leu Leu Leu Tyr Pro Gln Asp Gly Pro Arg Ser Lys Pro
                165                 170                 175
```

```
Gln Pro Lys Asp Asn Gly Asp Val Cys Gln Asp Cys Ile Gln Met Val
                180                 185                 190
Thr Asp Ile Gln Thr Ala Val Arg Thr Asn Ser Thr Phe Val Gln Ala
            195                 200                 205
Leu Val His Val Lys Cys Asp Arg Leu Gly Pro Gly Met Ala Asp Ile
        210                 215                 220
Cys Lys Asn Tyr Ile Ser Gln Tyr Ser Ile Ala Ile Gln Met Met Met
225                 230                 235                 240
His Met Gln Pro Lys Ile Cys Ala Leu Val Gly Phe Cys Asp Val Lys
                245                 250                 255
Met Pro Met Gln Thr Leu Val Pro Ala Lys Val Ala Ser Lys Asn Val
            260                 265                 270
Ile Pro Ala Leu Leu Val Pro Ile Lys Lys His Val Pro Ala Lys Ser
        275                 280                 285
Asp Val Tyr Cys Val Cys Phe Leu Val Lys Val Thr Lys Leu Ile Asp
    290                 295                 300
Asn Asn Lys Thr Lys Ile Leu Asp Ala Phe Asp Lys Met Cys Ser Lys
305                 310                 315                 320
Leu Pro Lys Ser Leu Ser Cys Gln Val Val Asp Thr Tyr Gly Ser Ser
                325                 330                 335
Ile Leu Ser Ile Leu Leu Val Ser Pro Leu Val Cys Ser Met Leu His
            340                 345                 350
Leu Cys Ser Gly Thr Arg Leu Pro Ala Leu Thr Val His Val Thr Gln
        355                 360                 365
Pro Lys Asp Gly Gly Phe Cys Val Cys Lys Lys Leu Val Gly Tyr Leu
    370                 375                 380
Asp Arg Asn Leu Lys Asn Ser Thr Lys Gln Ile Leu Ala Ala Leu Lys
385                 390                 395                 400
Gly Cys Ser Phe Leu Pro Asp Pro Tyr Gln Lys Gln Cys Asp Gln Phe
                405                 410                 415
Val Ala Tyr Pro Val Leu Ile Ile Leu Val Val Met Asp Pro Ser Phe
            420                 425                 430
Val Cys Leu Lys Ile Gly Ala Cys Pro Ser Ala His Lys Pro Leu Leu
        435                 440                 445
Gly Thr Lys Cys Ile Trp Gly Pro Ser Tyr Trp Cys Gln Asn Thr Thr
    450                 455                 460
Ala Ala Gln Cys Asn Ala Val His Cys Lys Arg His Val Trp Asn
465                 470                 475

<210> SEQ ID NO 2
<211> LENGTH: 2839
<212> TYPE: DNA
<213> ORGANISM: Homo sapiens

<400> SEQUENCE: 2
ggggttagcg cctgcgctct ggacggcttt ggggcagggc agatttatat ctgcggggga      60
tcagctgacg ctccgcattg cagactgcgg agtcagacgg cgctatgtac gccctcttcc     120
tcctggccag cctcctgggc gcggctctag ccggcccggt ccttggactg aaagaatgca     180 ccagggctc ggcagtgtgg tgccagaatg tgaagacggc gtccgactgc ggggcagtga     240
agcactgcct gcagaccgtt tggaacaagc aacagtgaa atcccttccc tgcgacatat     300
gcaaagacgt tgtcaccgca gctggtgata tgctgaagga caatgccact gaggaggaga     360
tccttgttta cttggagaag acctgtgact ggcttccgaa accgaacatg tctgcttcat     420
```

-continued

```
gcaaggagat agtggactcc tacctccctg tcatcctgga catcattaaa ggagaaatga      480
gccgtcctgg ggaggtgtgc tctgctctca acctctgcga gtctctccag aagcacctag      540
cagagctgaa tcaccagaag cagctggagt ccaataagat cccagagctg acatgactg       600
aggtggtggc cccttcatg gccaacatcc ctctcctcct ctaccctcag gacggccccc       660
gcagcaagcc ccagccaaag gataatgggg acgtttgcca ggactgcatt cagatggtga     720
ctgacatcca gactgctgta cggaccaact ccacctttgt ccaggccttg gtggaacatg     780
tcaaggagga gtgtgaccgc ctgggccctg gcatggccga catatgcaag aactatatca     840
gccagtattc tgaaattgct atccagatga tgatgcacat gcaacccaag gagatctgtg     900
cgctggttgg gttctgtgat gaggtgaaag agatgcccat gcagactctg gtccccgcca     960
aagtggcctc caagaatgtc atccctgccc tggaactggt ggagcccatt aagaagcacg    1020
aggtcccagc aaagtctgat gtttactgtg aggtgtgtga attcctggtg aaggaggtga    1080
ccaagctgat tgacaacaac aagactgaga agaaatact cgacgctttt gacaaaatgt     1140
gctcgaagct gccgaagtcc ctgtcggaag agtgccagga ggtggtggac acgtacggca    1200
gctccatcct gtccatcctg ctggaggagg tcagccctga gctggtgtgc agcatgctgc    1260
acctctgctc tggcacgcgg ctgcctgcac tgaccgttca cgtgactcag ccaaaggacg    1320
gtggcttctg cgaagtgtgc aagaagctgg tgggttattt ggatcgcaac ctggagaaaa    1380
acagcaccaa gcaggagatc ctggctgctc ttgagaaagg ctgcagcttc ctgccagacc    1440
cttaccagaa gcagtgtgat cagtttgtgg cagagtacga gcccgtgctg atcgagatcc    1500
tggtggaggt gatggatcct tccttcgtgt gcttgaaaat tggagcctgc ccctcggccc    1560
ataagccctt gttgggaact gagaagtgta tatgggccc aagctactgg tgccagaaca    1620
cagagacagc agcccagtgc aatgctgtcg agcattgcaa acgccatgtg tggaactagg    1680
aggaggaata ttccatcttg gcagaaacca cagcattggt ttttttctac ttgtgtgtct    1740
gggggaatga acgcacagat ctgtttgact ttgttataaa aatagggctc ccccacctcc    1800
cccatttctg tgtcctttat tgtagcattg ctgtctgcaa gggagcccct agccctggc    1860
agacatagct gcttcagtgc ccctttctc tctgctagat ggatgttgat gcactggagg    1920
tcttttagcc tgcccttgca tggcgcctgc tggaggagga gagagctctg ctggcatgag    1980
ccacagtttc ttgactggag gccatcaacc ctccttggttg aggccttgtt ctgagccctg    2040
acatgtgctt gggcactggt gggcctgggc ttctgaggtg gcctcctgcc ctgatcaggg    2100
accctccccg ctttcctggg cctctcagtt gaacaaagca gcaaaacaaa ggcagtttta    2160
tatgaaagat tagaagcctg gaataatcag gctttttaaa tgatgtaatt cccactgtaa    2220
tagcataggg attttggaag cagctgctgg tggcttggga catcagtggg gccaagggtt    2280
ctctgtccct ggttcaactg tgatttggct ttcccgtgtc tttcctggtg atgccttgtt    2340
tggggttctg tgggtttggg tgggaagagg gccatctgcc tgaatgtaac ctgctagctc    2400
tccgaaggcc ctgcgggcct ggcttgtgtg agcgtgtgga cagtggtggc cgcgctgtgc    2460
ctgctcgtgt tgcctacatg tccctggctg ttgaggcgct gcttcagcct gcacccctcc    2520
cttgtctcat agatgctcct tttgaccttt tcaaataaat atggatggcg agctcctagg    2580
cctctggctt cctggtagag ggcggcatgc cgaagggtct gctgggtgtg gattggatgc    2640
tggggtgtgg gggttggaag ctgtctgtgg cccacttggg cacccacgct tctgtccact    2700
tctggttgcc aggagacagc aagcaaagcc agcaggacat gaagttgcta ttaaatggac    2760
```

```
ttcgtgattt ttgttttgca ctaaagtttc tgtgatttaa caataaaatt ctgttagcca    2820
gaaaaaaaaa aaaaaaaaa                                                 2839
```

<210> SEQ ID NO 3
<211> LENGTH: 482
<212> TYPE: PRT
<213> ORGANISM: Homo sapiens

<400> SEQUENCE: 3

```
Met Tyr Ala Leu Phe Leu Leu Ala Ser Leu Leu Gly Ala Ala Leu Ala
1               5                   10                  15

Gly Pro Val Leu Gly Leu Lys Cys Thr Arg Gly Ser Ala Val Trp Cys
            20                  25                  30

Gln Asn Val Lys Thr Ala Ser Asp Cys Gly Ala Val Lys His Cys Leu
        35                  40                  45

Gln Thr Val Trp Asn Lys Pro Thr Val Lys Ser Leu Pro Cys Asp Ile
    50                  55                  60

Cys Lys Asp Val Val Thr Ala Ala Gly Asp Met Leu Lys Asp Asn Ala
65                  70                  75                  80

Thr Ile Leu Val Tyr Leu Lys Thr Cys Asp Trp Leu Pro Lys Pro Asn
                85                  90                  95

Met Ser Ala Ser Cys Lys Ile Val Asp Ser Tyr Leu Pro Val Ile Leu
            100                 105                 110

Asp Ile Ile Lys Gly Met Ser Arg Pro Gly Val Cys Ser Ala Leu Asn
        115                 120                 125

Leu Cys Ser Leu Gln Lys His Leu Ala Leu Asn His Gln Lys Gln Leu
130                 135                 140

Ser Asn Lys Ile Pro Leu Asp Met Thr Val Val Ala Pro Phe Met Ala
145                 150                 155                 160

Asn Ile Pro Leu Leu Leu Tyr Pro Gln Asp Gly Pro Arg Ser Lys Pro
                165                 170                 175

Gln Pro Lys Asp Asn Gly Asp Val Cys Gln Asp Cys Ile Gln Met Val
            180                 185                 190

Thr Asp Ile Gln Thr Ala Val Arg Thr Asn Ser Thr Phe Val Gln Ala
        195                 200                 205

Leu Val His Val Lys Cys Asp Arg Leu Gly Pro Gly Met Ala Asp Ile
210                 215                 220

Cys Lys Asn Tyr Ile Ser Gln Tyr Ser Ile Ala Ile Gln Met Met Met
225                 230                 235                 240

His Met Gln Asp Gln Gln Pro Lys Ile Cys Ala Leu Val Gly Phe Cys
                245                 250                 255

Asp Val Lys Met Pro Met Gln Thr Leu Val Pro Ala Lys Val Ala Ser
            260                 265                 270

Lys Asn Val Ile Pro Ala Leu Leu Val Pro Ile Lys Lys His Val Pro
        275                 280                 285

Ala Lys Ser Asp Val Tyr Cys Val Cys Phe Leu Val Lys Val Thr Lys
    290                 295                 300

Leu Ile Asp Asn Asn Lys Thr Lys Ile Leu Asp Ala Phe Asp Lys Met
305                 310                 315                 320

Cys Ser Lys Leu Pro Lys Ser Leu Ser Cys Gln Val Val Asp Thr Tyr
                325                 330                 335

Gly Ser Ser Ile Leu Ser Ile Leu Leu Val Ser Pro Leu Val Cys Ser
            340                 345                 350

Met Leu His Leu Cys Ser Gly Thr Arg Leu Pro Ala Leu Thr Val His
```

```
            355                 360                 365
Val Thr Gln Pro Lys Asp Gly Phe Cys Val Cys Lys Lys Leu Val
    370                 375                 380

Gly Tyr Leu Asp Arg Asn Leu Lys Asn Ser Thr Lys Gln Ile Leu Ala
385                 390                 395                 400

Ala Leu Lys Gly Cys Ser Phe Leu Pro Asp Pro Tyr Gln Lys Gln Cys
                405                 410                 415

Asp Gln Phe Val Ala Tyr Pro Val Leu Ile Ile Leu Val Val Met Asp
            420                 425                 430

Pro Ser Phe Val Cys Leu Lys Ile Gly Ala Cys Pro Ser Ala His Lys
        435                 440                 445

Pro Leu Leu Gly Thr Lys Cys Ile Trp Gly Pro Ser Tyr Trp Cys Gln
    450                 455                 460

Asn Thr Thr Ala Ala Gln Cys Asn Ala Val His Cys Lys Arg His Val
465                 470                 475                 480

Trp Asn
```

<210> SEQ ID NO 4
<211> LENGTH: 2848
<212> TYPE: DNA
<213> ORGANISM: Homo sapiens

<400> SEQUENCE: 4

```
ggggttagcg cctgcgctct ggacggcttt ggggcagggc agatttatat ctgcggggga      60
tcagctgacg ctccgcattg cagactgcgg agtcagacgg cgctatgtac gccctcttcc     120
tcctggccag cctcctgggc gcggctctag ccggcccggt ccttggactg aaagaatgca     180
ccagggctc ggcagtgtgg tgccagaatg tgaagacggc gtccgactgc ggggcagtga     240
agcactgcct gcagaccgtt tggaacaagc caacagtgaa atcccttccc tgcgacatat     300
gcaaagacgt tgtcaccgca gctggtgata tgctgaagga caatgccact gaggaggaga     360
tccttgttta cttggagaag acctgtgact ggcttccgaa accgaacatg tctgcttcat     420
gcaaggagat agtggactcc tacctccctg tcatcctgga catcattaaa ggagaaatga     480
gccgtcctgg ggaggtgtgc tctgctctca acctctgcga gtctctccag aagcacctag     540
cagagctgaa tcaccagaag cagctggagt ccaataagat cccagagctg acatgactg      600
aggtggtggc ccccttcatg gccaacatcc ctctcctcct ctaccctcag gacggccccc     660
gcagcaagcc ccagccaaag gataatgggg acgtttgcca ggactgcatt cagatggtga     720
ctgacatcca gactgctgta cggaccaact ccaccttgt ccaggccttg gtggaacatg      780
tcaaggagga gtgtgaccgc tgggccctg gcatggccga catatgcaag aactatatca     840
gccagtattc tgaaattgct atccagatga tgatgcacat gcaggatcag caacccaagg     900
agatctgtgc gctggttggg ttctgtgatg aggtgaaaga gatgcccatg cagactctgg     960
tccccgccaa agtggcctcc aagaatgtca tccctgccct ggaactggtg gagcccatta    1020
agaagcacga ggtcccagca aagtctgatg tttactgtga ggtgtgtgaa ttcctggtga    1080
aggaggtgac caagctgatt gacaacaaca gactgagaa agaaatactc gacgcttttg    1140
acaaaatgtg ctcgaagctg ccgaagtccc tgtcggaaga gtgccaggag gtggtggaca    1200
cgtacggcag ctccatcctg tccatcctgc tggaggaggt cagccctgag ctggtgtgca    1260
gcatgctgca cctctgctct ggcacgcggg tgcctgcact gaccgttcac gtgactcagc    1320
caaaggacgg tggcttctgc gaagtgtgca agaagctggt gggttatttg gatcgcaacc    1380
```

```
tggagaaaaa cagcaccaag caggagatcc tggctgctct tgagaaaggc tgcagcttcc  1440
tgccagaccc ttaccagaag cagtgtgatc agtttgtggc agagtacgag cccgtgctga  1500
tcgagatcct ggtggaggtg atggatcctt ccttcgtgtg cttgaaaatt ggagcctgcc  1560
cctcggccca taagcccttg ttgggaactg agaagtgtat atggggccca agctactggt  1620
gccagaacac agagacagca gcccagtgca atgctgtcga gcattgcaaa cgccatgtgt  1680
ggaactagga ggaggaatat tccatcttgg cagaaaccac agcattggtt ttttctact  1740 tgtgtgtctg ggggaatgaa cgcacagatc tgtttgactt tgttataaaa atagggctcc  1800
cccacctccc ccatttctgt gtcctttatt gtagcattgc tgtctgcaag ggagccccta  1860
gcccctggca gacatagctg cttcagtgcc ccttttctct ctgctagatg gatgttgatg  1920
cactggaggt cttttagcct gcccttgcat ggcgcctgct ggaggaggag agagctctgc  1980
tggcatgagc cacagtttct tgactggagg ccatcaaccc tcttggttga ggccttgttc  2040
tgagccctga catgtgcttg ggcactggtg ggcctgggct tctgaggtgg cctcctgccc  2100
tgatcaggga ccctccccgc tttcctgggc tctcagttg aacaaagcag caaaacaaag  2160
gcagttttat atgaaagatt agaagcctgg aataatcagg ctttttaaat gatgtaattc  2220
ccactgtaat agcataggga ttttggaagc agctgctggt ggcttgggac atcagtgggg  2280
ccaagggttc tctgtccctg gttcaactgt gatttggctt tcccgtgtct ttcctggtga  2340
tgccttgttt ggggttctgt gggtttgggt gggaagaggg ccatctgcct gaatgtaacc  2400
tgctagctct ccgaaggccc tgcgggcctg gcttgtgtga gcgtgtggac agtggtggcc  2460
gcgctgtgcc tgctcgtgtt gcctacatgt ccctggctgt tgaggcgctg cttcagcctg  2520 caccctcc ttgtctcata gatgctcctt ttgacctttt caaataaata tggatggcga  2580
gctcctaggc ctctggcttc ctggtagagg gcggcatgcc gaagggtctg ctgggtgtgg  2640
attggatgct ggggtgtggg ggttggaagc tgtctgtggc ccacttgggc acccacgctt  2700
ctgtccactt ctggttgcca ggagacagca agcaaagcca gcaggacatg aagttgctat  2760
taaatggact tcgtgatttt tgttttgcac taaagtttct gtgatttaac aataaaattc  2820
tgttagccag aaaaaaaaaa aaaaaaaa                                   2848
```

```
<210> SEQ ID NO 5
<211> LENGTH: 481
<212> TYPE: PRT
<213> ORGANISM: Homo sapiens

<400> SEQUENCE: 5

Met Tyr Ala Leu Phe Leu Leu Ala Ser Leu Leu Gly Ala Ala Leu Ala
1               5                   10                  15

Gly Pro Val Leu Gly Leu Lys Cys Thr Arg Gly Ser Ala Val Trp Cys
            20                  25                  30

Gln Asn Val Lys Thr Ala Ser Asp Cys Gly Ala Val Lys His Cys Leu
        35                  40                  45

Gln Thr Val Trp Asn Lys Pro Thr Val Lys Ser Leu Pro Cys Asp Ile
    50                  55                  60

Cys Lys Asp Val Val Thr Ala Ala Gly Asp Met Leu Lys Asp Asn Ala
65                  70                  75                  80

Thr Ile Leu Val Tyr Leu Lys Thr Cys Asp Trp Leu Pro Lys Pro Asn
                85                  90                  95

Met Ser Ala Ser Cys Lys Ile Val Asp Ser Tyr Leu Pro Val Ile Leu
            100                 105                 110
```

```
Asp Ile Ile Lys Gly Met Ser Pro Gly Val Cys Ser Ala Leu Asn
            115                 120                 125
Leu Cys Ser Leu Gln Lys His Leu Ala Leu Asn His Gln Lys Gln Leu
130                 135                 140
Ser Asn Lys Ile Pro Leu Asp Met Thr Val Val Ala Pro Phe Met Ala
145                 150                 155                 160
Asn Ile Pro Leu Leu Leu Tyr Pro Gln Asp Gly Pro Arg Ser Lys Pro
                165                 170                 175
Gln Pro Lys Asp Asn Gly Asp Val Cys Gln Asp Cys Ile Gln Met Val
            180                 185                 190
Thr Asp Ile Gln Thr Ala Val Arg Thr Asn Ser Thr Phe Val Gln Ala
        195                 200                 205
Leu Val His Val Lys Cys Asp Arg Leu Gly Pro Gly Met Ala Asp Ile
    210                 215                 220
Cys Lys Asn Tyr Ile Ser Gln Tyr Ser Ile Ala Ile Gln Met Met Met
225                 230                 235                 240
His Met Asp Gln Gln Pro Lys Ile Cys Ala Leu Val Gly Phe Cys Asp
                245                 250                 255
Val Lys Met Pro Met Gln Thr Leu Val Pro Ala Lys Val Ala Ser Lys
            260                 265                 270
Asn Val Ile Pro Ala Leu Leu Val Pro Ile Lys Lys His Val Pro Ala
        275                 280                 285
Lys Ser Asp Val Tyr Cys Val Cys Phe Leu Val Lys Val Thr Lys Leu
    290                 295                 300
Ile Asp Asn Asn Lys Thr Lys Ile Leu Asp Ala Phe Asp Lys Met Cys
305                 310                 315                 320
Ser Lys Leu Pro Lys Ser Leu Ser Cys Gln Val Val Asp Thr Tyr Gly
                325                 330                 335
Ser Ser Ile Leu Ser Ile Leu Val Ser Pro Leu Val Cys Ser Met
            340                 345                 350
Leu His Leu Cys Ser Gly Thr Arg Leu Pro Ala Leu Thr Val His Val
    355                 360                 365
Thr Gln Pro Lys Asp Gly Gly Phe Cys Val Cys Lys Lys Leu Val Gly
370                 375                 380
Tyr Leu Asp Arg Asn Leu Lys Asn Ser Thr Lys Gln Ile Leu Ala Ala
385                 390                 395                 400
Leu Lys Gly Cys Ser Phe Leu Pro Asp Pro Tyr Gln Lys Gln Cys Asp
                405                 410                 415
Gln Phe Val Ala Tyr Pro Val Leu Ile Ile Leu Val Met Asp Pro
            420                 425                 430
Ser Phe Val Cys Leu Lys Ile Gly Ala Cys Pro Ser Ala His Lys Pro
        435                 440                 445
Leu Leu Gly Thr Lys Cys Ile Trp Gly Pro Ser Tyr Trp Cys Gln Asn
    450                 455                 460
Thr Thr Ala Ala Gln Cys Asn Ala Val His Cys Lys Arg His Val Trp
465                 470                 475                 480
Asn

<210> SEQ ID NO 6
<211> LENGTH: 2845
<212> TYPE: DNA
<213> ORGANISM: Homo sapiens

<400> SEQUENCE: 6
```

| | | | | |
|---|---|---|---|---|
| ggggttagcg | cctgcgctct | ggacggcttt | ggggcagggc | agatttatat | ctgcggggga | 60 |
| tcagctgacg | ctccgcattg | cagactgcgg | agtcagacgg | cgctatgtac | gccctcttcc | 120 |
| tcctggccag | cctcctgggc | gcggctctag | ccggcccggt | ccttggactg | aaagaatgca | 180 |
| ccaggggctc | ggcagtgtgg | tgccagaatg | tgaagacggc | gtccgactgc | ggggcagtga | 240 |
| agcactgcct | gcagaccgtt | tggaacaagc | caacagtgaa | atcccttccc | tgcgacatat | 300 |
| gcaaagacgt | tgtcaccgca | gctggtgata | tgctgaagga | caatgccact | gaggaggaga | 360 |
| tccttgttta | cttggagaag | acctgtgact | ggcttccgaa | accgaacatg | tctgcttcat | 420 |
| gcaaggagat | agtggactcc | tacctccctg | tcatcctgga | catcattaaa | ggagaaatga | 480 |
| gccgtcctgg | ggaggtgtgc | tctgctctca | acctctgcga | gtctctccag | aagcacctag | 540 |
| cagagctgaa | tcaccagaag | cagctggagt | ccaataagat | cccagagctg | acatgactg | 600 |
| aggtggtggc | ccccttcatg | gccaacatcc | ctctcctcct | ctaccctcag | gacggccccc | 660 |
| gcagcaagcc | ccagccaaag | gataatgggg | acgtttgcca | ggactgcatt | cagatggtga | 720 |
| ctgacatcca | gactgctgta | cggaccaact | ccacctttgt | ccaggccttg | gtggaacatg | 780 |
| tcaaggagga | gtgtgaccgc | tgggccctg | gcatggccga | catatgcaag | aactatatca | 840 |
| gccagtattc | tgaaattgct | atccagatga | tgatgcacat | ggatcagcaa | cccaaggaga | 900 |
| tctgtgcgct | ggttgggttc | tgtgatgagg | tgaaagagat | gcccatgcag | actctggtcc | 960 |
| ccgccaaagt | ggcctccaag | aatgtcatcc | ctgccctgga | actggtggag | cccattaaga | 1020 |
| agcacgaggt | cccagcaaag | tctgatgttt | actgtgaggt | gtgtgaattc | ctggtgaagg | 1080 |
| aggtgaccaa | gctgattgac | aacaacaaga | ctgagaaaga | aatactcgac | gcttttgaca | 1140 |
| aaatgtgctc | gaagctgccg | aagtccctgt | cggaagagtg | ccaggaggtg | gtggacacgt | 1200 |
| acggcagctc | catcctgtcc | atcctgctgg | aggaggtcag | ccctgagctg | gtgtgcagca | 1260 |
| tgctgcacct | ctgctctggc | acgcggctgc | ctgcactgac | cgttcacgtg | actcagccaa | 1320 |
| aggacggtgg | cttctgcgaa | gtgtgcaaga | agctggtggg | ttatttggat | cgcaacctgg | 1380 |
| agaaaaacag | caccaagcag | gagatcctgg | ctgctcttga | gaaaggctgc | agcttcctgc | 1440 |
| cagacccta | ccagaagcag | tgtgatcagt | tgtggcaga | gtacgagccc | gtgctgatcg | 1500 |
| agatcctggt | ggaggtgatg | gatccttcct | tcgtgtgctt | gaaaattgga | gcctgcccct | 1560 |
| cggcccataa | gccccttgttg | ggaactgaga | agtgtatatg | gggcccaagc | tactggtgcc | 1620 |
| agaacacaga | gacagcagcc | cagtgcaatg | ctgtcgagca | ttgcaaacgc | catgtgtgga | 1680 |
| actaggagga | ggaatattcc | atcttggcag | aaaccacagc | attggttttt | ttctacttgt | 1740 |
| gtgtctgggg | gaatgaacgc | acagatctgt | ttgactttgt | tataaaaata | gggctccccc | 1800 |
| acctccccca | tttctgtgtc | ctttattgta | gcattgctgt | ctgcaaggga | gccctagcc | 1860 |
| cctggcagac | atagctgctt | cagtgcccct | tttctctctg | ctagatggat | gttgatgcac | 1920 |
| tggaggtctt | ttagcctgcc | cttgcatggc | gcctgctgga | ggaggagaga | gctctgctgg | 1980 |
| catgagccac | agtttcttga | ctggaggcca | tcaaccctct | tggttgaggc | cttgttctga | 2040 |
| gccctgacat | gtgcttgggc | actggtgggc | ctgggcttct | gaggtggcct | cctgccctga | 2100 |
| tcagggaccc | tccccgcttt | cctgggcctc | tcagttgaac | aaagcagcaa | acaaaggca | 2160 |
| gttttatatg | aaagattaga | agcctggaat | aatcaggctt | tttaaatgat | gtaattccca | 2220 |
| ctgtaatagc | atagggattt | tggaagcagc | tgctggtggc | ttgggacatc | agtggggcca | 2280 |
| agggttctct | gtccctggtt | caactgtgat | ttggcttttcc | cgtgtctttc | ctggtgatgc | 2340 |
| cttgtttggg | gttctgtggg | tttgggtggg | aagagggcca | tctgcctgaa | tgtaacctgc | 2400 |

```
tagctctccg aaggccctgc gggcctggct tgtgtgagcg tgtggacagt ggtggccgcg   2460
ctgtgcctgc tcgtgttgcc tacatgtccc tggctgttga ggcgctgctt cagcctgcac   2520
ccctcccttg tctcatagat gctccttttg acctttcaa ataaatatgg atggcgagct    2580
cctaggcctc tggcttcctg gtagagggcg gcatgccgaa gggtctgctg ggtgtggatt   2640
ggatgctggg gtgtgggggt tggaagctgt ctgtggccca cttgggcacc cacgcttctg   2700
tccacttctg gttgccagga gacagcaagc aaagccagca ggacatgaag ttgctattaa   2760
atggacttcg tgattttgt tttgcactaa agtttctgtg atttaacaat aaaattctgt    2820
tagccagaaa aaaaaaaaaa aaaaa                                         2845
```

<210> SEQ ID NO 7  
<211> LENGTH: 33  
<212> TYPE: DNA  
<213> ORGANISM: Artificial Sequence  
<220> FEATURE:  
<223> OTHER INFORMATION: Description of Artificial Sequence: Synthetic oligonucleotide

<400> SEQUENCE: 7

```
cgggctacgt aatgtacgcc ctcttcctcc tgg                                33
```

<210> SEQ ID NO 8  
<211> LENGTH: 30  
<212> TYPE: DNA  
<213> ORGANISM: Artificial Sequence  
<220> FEATURE:  
<223> OTHER INFORMATION: Description of Artificial Sequence: Synthetic oligonucleotide

<400> SEQUENCE: 8

```
ggcggggtcg acctagttcc acacatggcg                                    30
```

<210> SEQ ID NO 9  
<211> LENGTH: 23  
<212> TYPE: DNA  
<213> ORGANISM: Artificial Sequence  
<220> FEATURE:  
<223> OTHER INFORMATION: Description of Artificial Sequence: Synthetic oligonucleotide

<400> SEQUENCE: 9

```
ggcggctcag tcgacggtac cgg                                           23
```

<210> SEQ ID NO 10  
<211> LENGTH: 32  
<212> TYPE: DNA  
<213> ORGANISM: Artificial Sequence  
<220> FEATURE:  
<223> OTHER INFORMATION: Description of Artificial Sequence: Synthetic oligonucleotide

<400> SEQUENCE: 10

```
ggcgcctcta gaagagactc gcagaggttg ag                                 32
```

<210> SEQ ID NO 11  
<211> LENGTH: 29  
<212> TYPE: DNA  
<213> ORGANISM: Artificial Sequence  
<220> FEATURE:  
<223> OTHER INFORMATION: Description of Artificial Sequence: Synthetic oligonucleotide

<400> SEQUENCE: 11
ggcgcctcta gaacctcatc acagaaccc                                           29

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ggcgcctcta gagccagagc agaggtgcag c                                        31

<210> SEQ ID NO 13
<211> LENGTH: 81
<212> TYPE: PRT
<213> ORGANISM: Homo sapiens

<400> SEQUENCE: 13

Ser Leu Pro Cys Asp Ile Cys Lys Asp Val Val Thr Ala Ala Gly Asp
1               5                   10                  15

Met Leu Lys Asp Asn Ala Thr Glu Glu Ile Leu Val Tyr Leu Glu
            20                  25                  30

Lys Thr Cys Asp Trp Leu Pro Lys Pro Asn Met Ser Ala Ser Cys Lys
        35                  40                  45

Glu Ile Val Asp Ser Tyr Leu Pro Val Ile Leu Asp Ile Ile Lys Gly
    50                  55                  60

Glu Met Ser Arg Pro Gly Glu Val Cys Ser Ala Leu Asn Leu Cys Glu
65                  70                  75                  80

Ser

<210> SEQ ID NO 14
<211> LENGTH: 79
<212> TYPE: PRT
<213> ORGANISM: Homo sapiens

<400> SEQUENCE: 14

Gly Asp Val Cys Gln Asp Cys Ile Gln Met Val Thr Asp Ile Gln Thr
1               5                   10                  15

Ala Val Arg Thr Asn Ser Thr Phe Val Gln Ala Leu Val Glu His Val
            20                  25                  30

Lys Glu Glu Cys Asp Arg Leu Gly Pro Gly Met Ala Asp Ile Cys Lys
        35                  40                  45

Asn Tyr Ile Ser Gln Tyr Ser Glu Ile Ala Ile Gln Met Met Met His
    50                  55                  60

Met Gln Pro Lys Glu Ile Cys Ala Leu Val Gly Phe Cys Asp Glu
65                  70                  75

<210> SEQ ID NO 15
<211> LENGTH: 80
<212> TYPE: PRT
<213> ORGANISM: Homo sapiens

<400> SEQUENCE: 15

Ser Asp Val Tyr Cys Glu Val Cys Glu Phe Leu Val Lys Glu Val Thr
1               5                   10                  15

Lys Leu Ile Asp Asn Asn Lys Thr Glu Lys Glu Ile Leu Asp Ala Phe
            20                  25                  30

Asp Lys Met Cys Ser Lys Leu Pro Lys Ser Leu Ser Glu Glu Cys Gln

```
                35                  40                  45
Glu Val Val Asp Thr Tyr Gly Ser Ser Ile Leu Ser Ile Leu Leu Glu
            50                  55                  60
Glu Val Ser Pro Glu Leu Val Cys Ser Met Leu His Leu Cys Ser Gly
65                  70                  75                  80

<210> SEQ ID NO 16
<211> LENGTH: 80
<212> TYPE: PRT
<213> ORGANISM: Homo sapiens

<400> SEQUENCE: 16

Asp Gly Gly Phe Cys Glu Val Cys Lys Lys Leu Val Gly Tyr Leu Asp
1               5                   10                  15
Arg Asn Leu Glu Lys Asn Ser Thr Lys Gln Glu Ile Leu Ala Ala Leu
            20                  25                  30
Glu Lys Gly Cys Ser Phe Leu Pro Asp Pro Tyr Gln Lys Gln Cys Asp
        35                  40                  45
Gln Phe Val Ala Glu Tyr Glu Pro Val Leu Ile Glu Ile Leu Val Glu
    50                  55                  60
Val Met Asp Pro Ser Phe Val Cys Leu Lys Ile Gly Ala Cys Pro Ser
65                  70                  75                  80

<210> SEQ ID NO 17
<211> LENGTH: 1575
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
atgtacgccc tcttcctcct ggccagcctc ctgggcgcgg ctctagccgg cccggtcctt      60
ggactgaaag aatgcaccag gggctcggca gtgtggtgcc agaatgtgaa gacggcgtcc     120
gactgcgggg cagtgaagca ctgcctgcag accgtttgga caagccaac agtgaaatcc     180 cttccctgcg acatatgcaa agacgttgtc accgcagctg tgatatgct gaaggacaat     240 gccactgagg aggagatcct tgtttacttg gagaagacct gtgactggct tccgaaaccg     300
aacatgtctg cttcatgcaa ggagatagtg gactcctacc tccctgtcat cctggacatc     360
attaaaggag aaatgagccg tcctggggag gtgtgctctg ctctcaacct ctgcgagtct     420
ctccagaagc acctagcaga gctgaatcac cagaagcagc tggagtccaa taagatccca     480
gagctggaca tgactgaggt ggtggccccc ttcatggcca acatccctct cctcctctac     540
cctcaggacg cccccgcag caagcccag ccaaaggata tgggacgt ttgccaggac     600 tgcattcaga tggtgactga catccagact gctgtacgga ccaactccac ctttgtccag     660
gccttggtgg aacatgtcaa ggaggagtgt gaccgcctgg ccctggcat ggccgacata     720 tgcaagaact atatcagcca gtattctgaa attgctatcc agatgatgat gcacatgcaa     780
cccaaggaga tctgtgcgct ggttgggttc tgtgatgagg tgaaagagat gcccatgcag     840
actctggtcc ccgccaaagt ggcctccaag aatgtcatcc ctgccctgga actggtggag     900
cccattaaga agcacgaggt cccagcaaag tctgatgttt actgtgaggt gtgtgaattc     960
ctggtgaagg aggtgaccaa gctgattgac aacaacaaga ctgagaaaga aatactcgac    1020
gcttttgaca aaatgtgctc gaagctgcg aagtccctgt cggaagagtg ccaggaggtg    1080
gtggacacgt acggcagctc catcctgtcc atcctgctgg aggaggtcag ccctgagctg    1140
```

```
gtgtgcagca tgctgcacct ctgctctggc acgcggctgc ctgcactgac cgttcacgtg   1200
actcagccaa aggacggtgg cttctgcgaa gtgtgcaaga agctggtggg ttatttggat   1260
cgcaacctgg agaaaaacag caccaagcag gagatcctgg ctgctcttga gaaaggctgc   1320
agcttcctgc cagaccctta ccagaagcag tgtgatcagt ttgtggcaga gtacgagccc   1380
gtgctgatcg agatcctggt ggaggtgatg gatccttcct tcgtgtgctt gaaaattgga   1440
gcctgcccct cggcccataa gcccttgttg ggaactgaga agtgtatatg gggcccaagc   1500
tactggtgcc agaacacaga gacagcagcc cagtgcaatg ctgtcgagca ttgcaaacgc   1560
catgtgtgga actag                                                    1575
```

```

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Leu Pro Cys Asp Ile Cys Lys Asp Val Val Thr Ala Ala Gly
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Val Thr Ala Ala Gly Asp Met Leu Lys Asp Asn Ala Thr Glu Glu
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asn Ala Thr Glu Glu Glu Ile Leu Val Tyr Leu Glu Lys Thr Cys
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Glu Lys Thr Cys Asp Trp Leu Pro Lys Pro Asn Met Ser Ala
1               5                   10                  15

<210> SEQ ID NO 22
<211> LENGTH: 15
<212> TYPE: PRT
<213> ORGANISM: Artificial Sequence
<220> FEATURE:

```

```
<223> OTHER INFORMATION: Description of Artificial Sequence: Synthetic
      peptide

<400> SEQUENCE: 22

Pro Asn Met Ser Ala Ser Cys Lys Glu Ile Val Asp Ser Tyr Leu
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Val Asp Ser Tyr Leu Pro Val Ile Leu Asp Ile Ile Lys Gly Glu
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ile Ile Lys Gly Glu Met Ser Arg Pro Gly Glu Val Cys Ser Ala
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Arg Pro Gly Glu Val Cys Ser Ala Leu Asn Leu Cys Glu Ser
1               5                   10                  15

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Leu Pro Cys Asp Ile Cys Lys Asp Val Val Thr Ala Ala Gly Asp
1               5                   10                  15

Met Leu Lys Asp
            20

<210> SEQ ID NO 27
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Val Thr Ala Ala Gly Asp Met Leu Lys Asp Asn Ala Thr Glu Glu Glu
```

```
1               5                   10                  15

Ile Leu Val Tyr
            20

<210> SEQ ID NO 28
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asn Ala Thr Glu Glu Glu Ile Leu Val Tyr Leu Glu Lys Thr Cys Asp
1               5                   10                  15

Trp Leu Pro Lys
            20

<210> SEQ ID NO 29
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Leu Glu Lys Thr Cys Asp Trp Leu Pro Lys Pro Asn Met Ser Ala Ser
1               5                   10                  15

Cys Lys Glu Ile
            20

<210> SEQ ID NO 30
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Pro Asn Met Ser Ala Ser Cys Lys Glu Ile Val Asp Ser Tyr Leu Pro
1               5                   10                  15

Val Ile Leu Asp
            20

<210> SEQ ID NO 31
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Val Asp Ser Tyr Leu Pro Val Ile Leu Asp Ile Ile Lys Gly Glu Met
1               5                   10                  15

Ser Arg Pro Gly
            20

<210> SEQ ID NO 32
<211> LENGTH: 21
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 32

Ile Ile Lys Gly Glu Met Ser Arg Pro Gly Glu Val Cys Ser Ala Leu
1               5                   10                  15

Asn Leu Cys Glu Ser
            20

<210> SEQ ID NO 33
<211> LENGTH: 81
<212> TYPE: PRT
<213> ORGANISM: Homo sapiens

<400> SEQUENCE: 33

Ser Leu Pro Cys Asp Ile Cys Lys Asp Val Val Thr Ala Ala Gly Asp
1               5                   10                  15

Met Leu Lys Asp Asn Ala Thr Glu Glu Ile Leu Val Tyr Leu Glu
            20                  25                  30

Lys Thr Cys Asp Trp Leu Pro Lys Pro Asn Met Ser Ala Ser Cys Lys
            35                  40                  45

Glu Ile Val Asp Ser Tyr Leu Pro Val Ile Leu Asp Ile Ile Lys Gly
    50                  55                  60

Glu Met Ser Arg Pro Gly Glu Val Cys Ser Ala Leu Asn Leu Cys Glu
65                  70                  75                  80

Ser

<210> SEQ ID NO 34
<211> LENGTH: 79
<212> TYPE: PRT
<213> ORGANISM: Homo sapiens

<400> SEQUENCE: 34

Gly Asp Val Cys Gln Asp Cys Ile Gln Met Val Thr Asp Ile Gln Thr
1               5                   10                  15

Ala Val Arg Thr Asn Ser Thr Phe Val Gln Ala Leu Val Glu His Val
            20                  25                  30

Lys Glu Glu Cys Asp Arg Leu Gly Pro Gly Met Ala Asp Ile Cys Lys
            35                  40                  45

Asn Tyr Ile Ser Gln Tyr Ser Glu Ile Ala Ile Gln Met Met Met His
    50                  55                  60

Met Gln Pro Lys Glu Ile Cys Ala Leu Val Gly Phe Cys Asp Glu
65                  70                  75

<210> SEQ ID NO 35
<211> LENGTH: 80
<212> TYPE: PRT
<213> ORGANISM: Homo sapiens

<400> SEQUENCE: 35

Ser Asp Val Tyr Cys Glu Val Cys Glu Phe Leu Val Lys Glu Val Thr
1               5                   10                  15

Lys Leu Ile Asp Asn Asn Lys Thr Glu Lys Glu Ile Leu Asp Ala Phe
            20                  25                  30

Asp Lys Met Cys Ser Lys Leu Pro Lys Ser Leu Ser Glu Glu Cys Gln
            35                  40                  45

Glu Val Val Asp Thr Tyr Gly Ser Ser Ile Leu Ser Ile Leu Leu Glu
    50                  55                  60
```

Glu Val Ser Pro Glu Leu Val Cys Ser Met Leu His Leu Cys Ser Gly
65                  70                  75                  80

<210> SEQ ID NO 36
<211> LENGTH: 80
<212> TYPE: PRT
<213> ORGANISM: Homo sapiens

<400> SEQUENCE: 36

Asp Gly Gly Phe Cys Glu Val Cys Lys Lys Leu Val Gly Tyr Leu Asp
1               5                   10                  15

Arg Asn Leu Glu Lys Asn Ser Thr Lys Gln Glu Ile Leu Ala Ala Leu
            20                  25                  30

Glu Lys Gly Cys Ser Phe Leu Pro Asp Pro Tyr Gln Lys Gln Cys Asp
        35                  40                  45

Gln Phe Val Ala Glu Tyr Glu Pro Val Leu Ile Glu Ile Leu Val Glu
    50                  55                  60

Val Met Asp Pro Ser Phe Val Cys Leu Lys Ile Gly Ala Cys Pro Ser
65                  70                  75                  80

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Cys Asp Trp Leu Pro Lys Pro Asn Met Ser Ala Ser Cys
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asp Trp Leu Pro Lys Pro Asn Met Ser Ala
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Cys Asp Trp Leu Pro Lys Pro Asn Met Ser
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Trp Leu Pro Lys Pro Asn Met Ser Ala Ser
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Leu Gly Gly Gly Gly Ser Gly Gly Gly Gly Ser Ala
1               5                   10

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Glu Ala Ala Ala Lys Glu Ala Ala Ala Lys Glu Ala
1               5                   10

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Leu Glu Lys Thr Cys Asp Trp Leu Pro Lys Pro Asn Met Ser Ala Ser
1               5                   10                  15
Cys

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Leu Glu Lys Thr Cys Asp Trp Leu Pro Lys
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Leu Glu Lys Thr Cys Asp Trp Leu Pro Lys Pro
1               5                   10

<210> SEQ ID NO 46
<211> LENGTH: 12
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 46

Leu Glu Lys Thr Cys Asp Trp Leu Pro Lys Pro Asn
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Leu Glu Lys Thr Cys Asp Trp Leu Pro Lys Pro Asn Met
1               5                   10

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Leu Glu Lys Thr Cys Asp Trp Leu Pro Lys Pro Asn Met Ser
1               5                   10

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Leu Glu Lys Thr Cys Asp Trp Leu Pro Lys Pro Asn Met Ser Ala Ser
1               5                   10                  15

<210> SEQ ID NO 50
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Leu Glu Lys Thr Cys Asp Trp Leu Pro Lys Pro Asn Met Ser Ala Ser
1               5                   10                  15

Cys Lys

<210> SEQ ID NO 51
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51
```

```
Leu Glu Lys Thr Cys Asp Trp Leu Pro Lys Pro Asn Met Ser Ala Ser
1               5                   10                  15

Cys Lys Glu
```

<210> SEQ ID NO 52
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

```
Glu Lys Thr Cys Asp Trp Leu Pro Lys Pro Asn Met Ser Ala Ser Cys
1               5                   10                  15

Lys Glu Ile
```

<210> SEQ ID NO 53
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

```
Lys Thr Cys Asp Trp Leu Pro Lys Pro Asn Met Ser Ala Ser Cys Lys
1               5                   10                  15

Glu Ile
```

<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

```
Thr Cys Asp Trp Leu Pro Lys Pro Asn Met Ser Ala Ser Cys Lys Glu
1               5                   10                  15

Ile
```

<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

```
Cys Asp Trp Leu Pro Lys Pro Asn Met Ser Ala Ser Cys Lys Glu Ile
1               5                   10                  15
```

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

```
Asp Trp Leu Pro Lys Pro Asn Met Ser Ala Ser Cys Lys Glu Ile
```

<210> SEQ ID NO 57
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Trp Leu Pro Lys Pro Asn Met Ser Ala Ser Cys Lys Glu Ile
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Leu Pro Lys Pro Asn Met Ser Ala Ser Cys Lys Glu Ile
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Pro Lys Pro Asn Met Ser Ala Ser Cys Lys Glu Ile
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Lys Pro Asn Met Ser Ala Ser Cys Lys Glu Ile
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Pro Asn Met Ser Ala Ser Cys Lys Glu Ile
1               5                   10

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic

```
                            peptide

<400> SEQUENCE: 62

Lys Thr Cys Asp Trp Leu Pro Lys Pro Asn Met Ser Ala Ser Cys
1               5                   10                  15

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Thr Cys Asp Trp Leu Pro Lys Pro Asn Met Ser Ala
1               5                   10

<210> SEQ ID NO 64
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Cys Asp Trp Leu Pro Lys Pro Asn Met Ser Ala Ser Cys Lys
1               5                   10

<210> SEQ ID NO 65
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Leu Asp Lys Thr Cys Asp Trp Leu Pro Lys Pro Asn Met Ser Ala Ser
1               5                   10                  15

Cys Lys Asp Ile
            20

<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Leu Glu Lys Thr Cys Asp Trp Ile Pro Lys Pro Asn Met Ser Ala Ser
1               5                   10                  15

Cys Lys Asp Ile
            20

<210> SEQ ID NO 67
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67
```

```
Leu Glu Lys Thr Cys Asp Trp Leu Pro Lys Pro Asn Met Ser Ala Ser
1               5                   10                  15

Cys Arg Glu Ile
            20

<210> SEQ ID NO 68
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Leu Glu Arg Thr Cys Asp Trp Ile Pro Lys Pro Asn Met Ser Ala Ser
1               5                   10                  15

Cys Lys Asp Ile
            20

<210> SEQ ID NO 69
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Cys Asp Trp Ile Pro Arg Pro Asn Met Ser Ala Ser Cys
1               5                   10

<210> SEQ ID NO 70
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Cys Glu Trp Leu Pro Arg Pro Asn Met Ser Ala Ser Cys
1               5                   10

<210> SEQ ID NO 71
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Cys Asp Trp Ile Pro Lys Pro Asn Met Ser Ala Ser Cys
1               5                   10

<210> SEQ ID NO 72
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Cys Glu Trp Leu Pro Lys Pro Asn Met Ser Gly Ser Cys
1               5                   10
```

<210> SEQ ID NO 73
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Cys Glu Trp Leu Pro His Pro Asn Met Ser Ala Ser Cys
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Pro His Pro Asn Met Ser Gly Ser Cys Lys Glu Leu
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Arg Pro Asn Met Ser Ala Ser Cys Arg Glu Ile
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Pro Asn Met Ser Ala Ser Cys Arg Glu Ile
1               5                   10

<210> SEQ ID NO 77
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Lys Thr Cys Glu Trp Leu Pro His Pro Asn Met Ser Gly Ser Cys
1               5                   10                  15

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 78

Thr Cys Asp Trp Ile Pro Lys Pro Asn Met Ser Ala
1               5                   10

<210> SEQ ID NO 79
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Cys Asp Trp Ile Pro Lys Pro Asn Met Ser Ala Ser Cys Arg
1               5                   10

<210> SEQ ID NO 80
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Cys Asp Trp Leu Pro Lys Pro Asn Met Ser Ala Ser Cys Lys Asp Ile
1               5                   10                  15

<210> SEQ ID NO 81
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Leu Asp Lys Thr Cys Asp Trp Leu Pro Arg Pro Asn Met Ser
1               5                   10

<210> SEQ ID NO 82
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Gly Gly Gly Ser Gly Gly Gly Gly Ser Gly Gly Gly Gly Ser
1               5                   10                  15
```